(12) United States Patent
Taniguchi et al.

(10) Patent No.: US 6,773,394 B2
(45) Date of Patent: Aug. 10, 2004

(54) SYSTEM FOR DETECTING THE SHAPE OF AN ENDOSCOPE USING SOURCE COILS AND SENSE COILS

(75) Inventors: Akira Taniguchi, Hachioji (JP); Chieko Aizawa, Hachioji (JP); Yasuhiro Yoshizawa, Hachioji (JP); Fumiyuki Onoda, Tama (JP); Seiki Toriyama, Hino (JP); Takeshi Kawabata, Sagamihara (JP); Katsuyoshi Sasagawa, Hino (JP); Sumihiro Uchimura, Sagamihara (JP); Masanao Hara, Hino (JP); Kazutaka Tsuji, Hachioji (JP); Takayasu Miyagi, Hachioji (JP); Hiroki Moriyama, Akishima (JP); Hiroshi Ishii, Hino (JP); Yoshinao Oaki, Hino (JP); Tsugio Okazaki, Aizuwakamatsu (JP); Jun Hasegawa, Hino (JP); Yasuo Hirata, Hachioji (JP); Tetsuo Nonami, Hino (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/199,889

(22) Filed: Jul. 17, 2002

(65) Prior Publication Data

US 2003/0055317 A1 Mar. 20, 2003

Related U.S. Application Data

(63) Continuation of application No. 09/387,859, filed on Sep. 1, 1999, now Pat. No. 6,511,417.

(30) Foreign Application Priority Data

Sep. 3, 1998 (JP) .......................................... 10-249906
Sep. 3, 1998 (JP) .......................................... 10-249909
Sep. 4, 1998 (JP) .......................................... 10-251433

(51) Int. Cl.$^7$ ............................................... A61B 1/00
(52) U.S. Cl. ...................................... 600/117; 600/424
(58) Field of Search ................................. 600/101, 102, 600/117, 118, 424, 407; 128/899, 903; 324/219, 246; 340/573.1

(56) References Cited

U.S. PATENT DOCUMENTS

| | | | | | |
|---|---|---|---|---|---|
| 5,042,486 | A | * | 8/1991 | Pfeiler et al. | 600/424 |
| 5,235,243 | A | * | 8/1993 | Tong | 313/479 |
| 5,558,091 | A | * | 9/1996 | Acker et al. | 600/424 |
| 5,568,112 | A | * | 10/1996 | Cure | 335/214 |
| 5,638,819 | A | * | 6/1997 | Manwaring et al. | 600/424 |
| 5,729,129 | A | * | 3/1998 | Acker | 324/207.12 |
| 5,928,248 | A | * | 7/1999 | Acker | 623/1.11 |
| 5,997,473 | A | * | 12/1999 | Taniguchi et al. | 600/117 |
| 6,059,718 | A | * | 5/2000 | Taniguchi et al. | 600/117 |
| 6,175,756 | B1 | * | 1/2001 | Ferre et al. | 600/424 |
| 6,198,963 | B1 | * | 3/2001 | Haim et al. | 600/424 |
| 6,233,476 | B1 | * | 5/2001 | Strommer et al. | 600/424 |

* cited by examiner

*Primary Examiner*—John P. Leubecker
(74) *Attorney, Agent, or Firm*—Ostrolenk, Faber, Gerb & Soffen, LLP

(57) ABSTRACT

An endoscope shape detection system has a CPU included in a control unit. The CPU performs frequency sampling of digital data to calculate coordinates indicating the spatial positions of source coils incorporated in an insertion unit of an endoscope received in a patient and of marker coils placed on a patient. An inserted state of the insertion unit of the endoscope is estimated based on the calculated coordinate data indicating the positions of the source coils. Display data based on the shape of the endoscope is produced from the calculated coordinate data indicating the positions of the source coils, and output to a video RAM. Display data of the marker coils is produced from the calculated coordinate data indicating the positions of the marker coils, and output to the video RAM. Consequently, the positions of the markers are depicted together with the shape of the endoscope. The positional relationship between the insertion unit of the endoscope and a patient's body can therefore be ascertained.

16 Claims, 66 Drawing Sheets

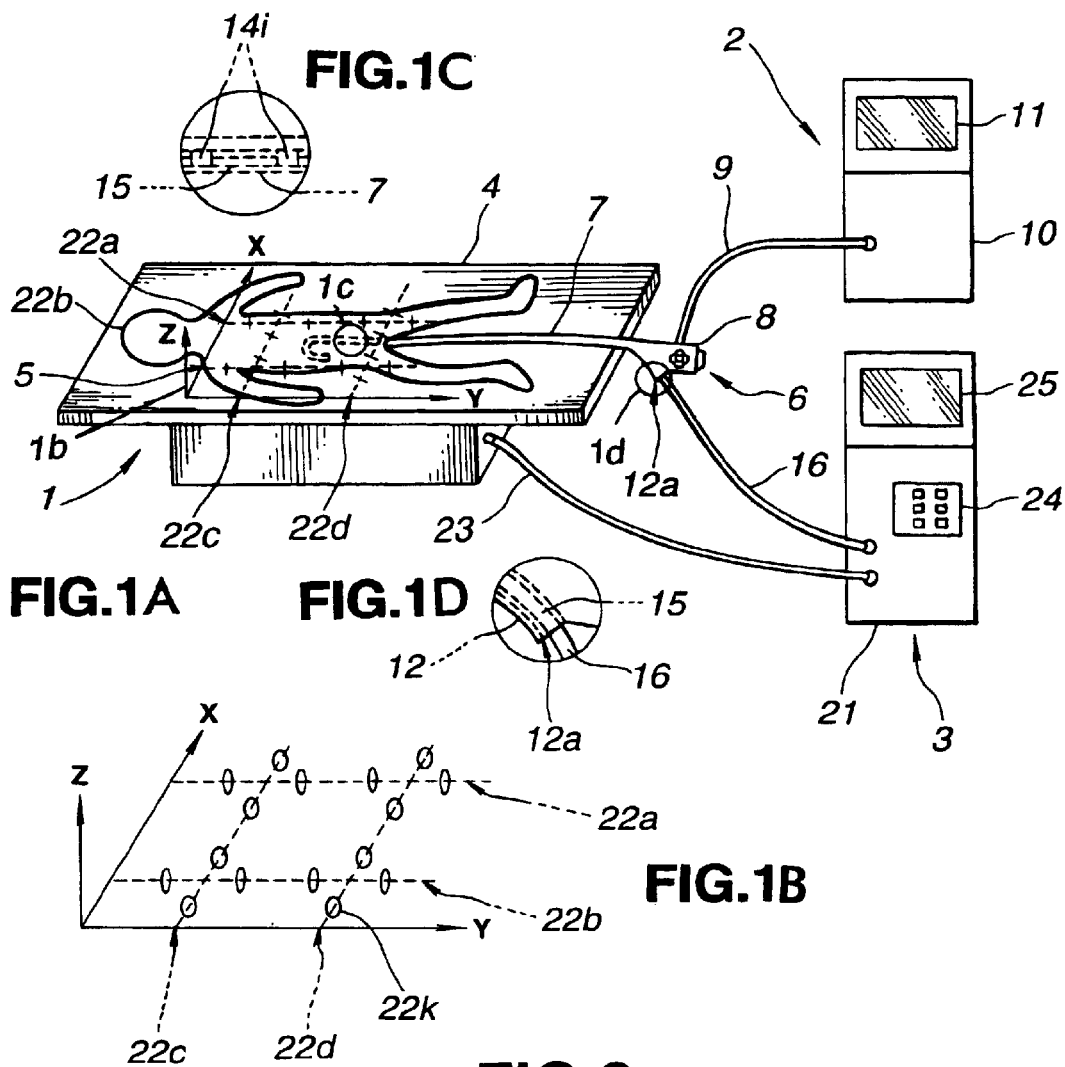
FIG. 1C
FIG. 1A
FIG. 1D
FIG. 1B
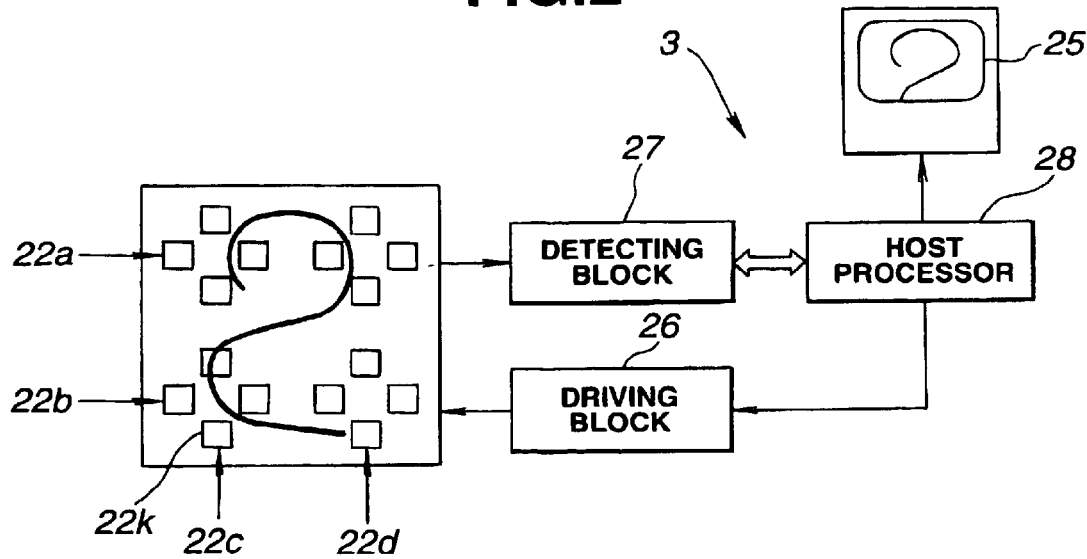
FIG. 2

STRAIGHT LINE m

FIG.43A
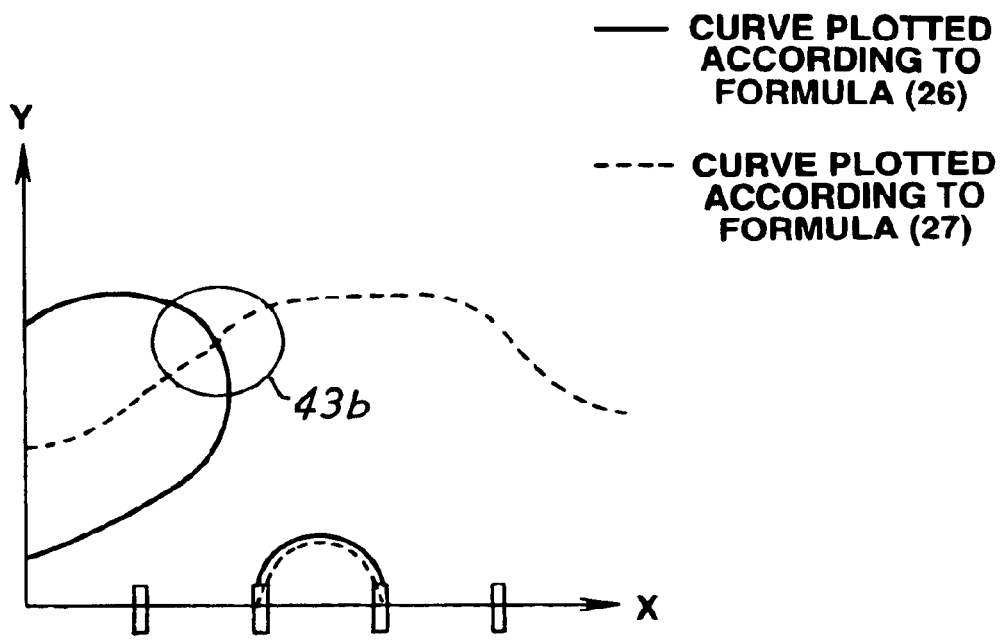
— CURVE PLOTTED ACCORDING TO FORMULA (26)
---- CURVE PLOTTED ACCORDING TO FORMULA (27)
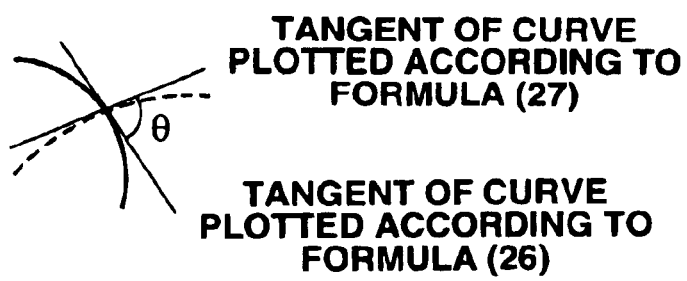
TANGENT OF CURVE PLOTTED ACCORDING TO FORMULA (27)
TANGENT OF CURVE PLOTTED ACCORDING TO FORMULA (26)
FIG.43B

FIG.48B
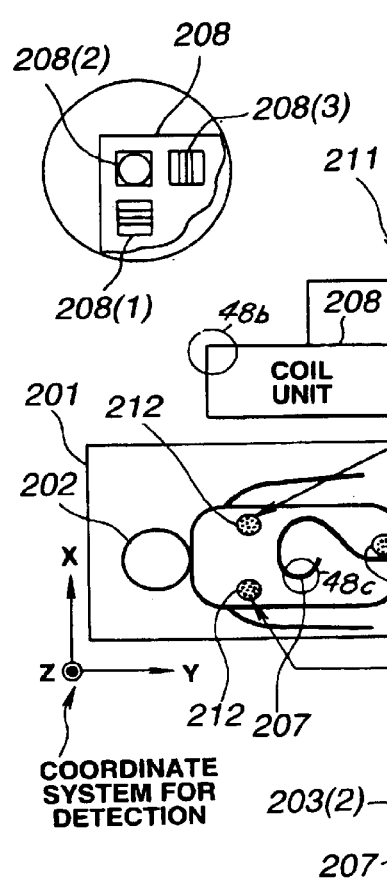
FIG.48A
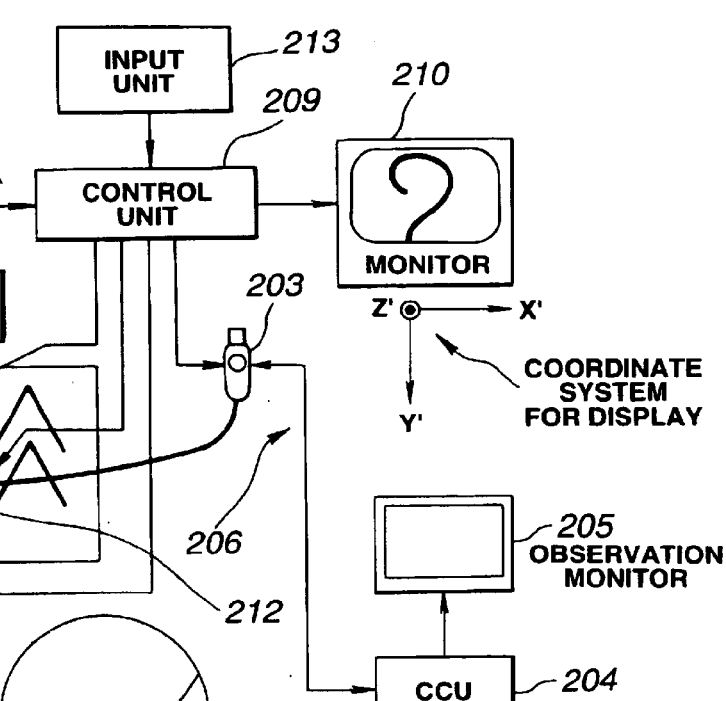
FIG.48C

FIG.50
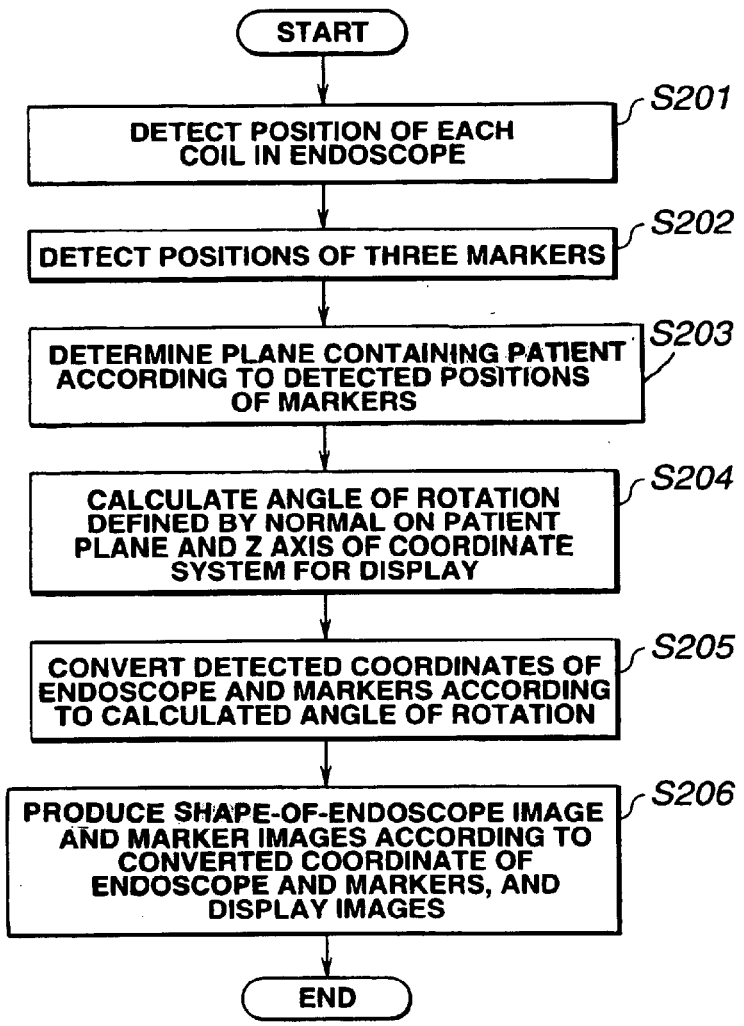
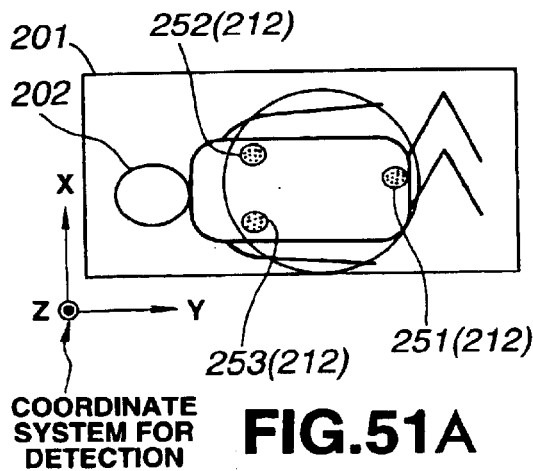
FIG.51A
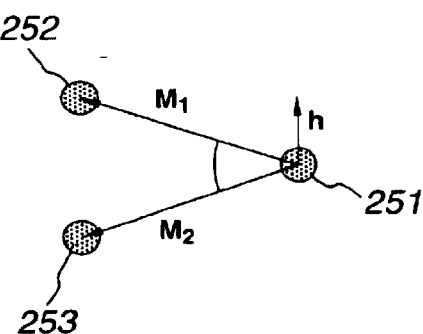
FIG.51B

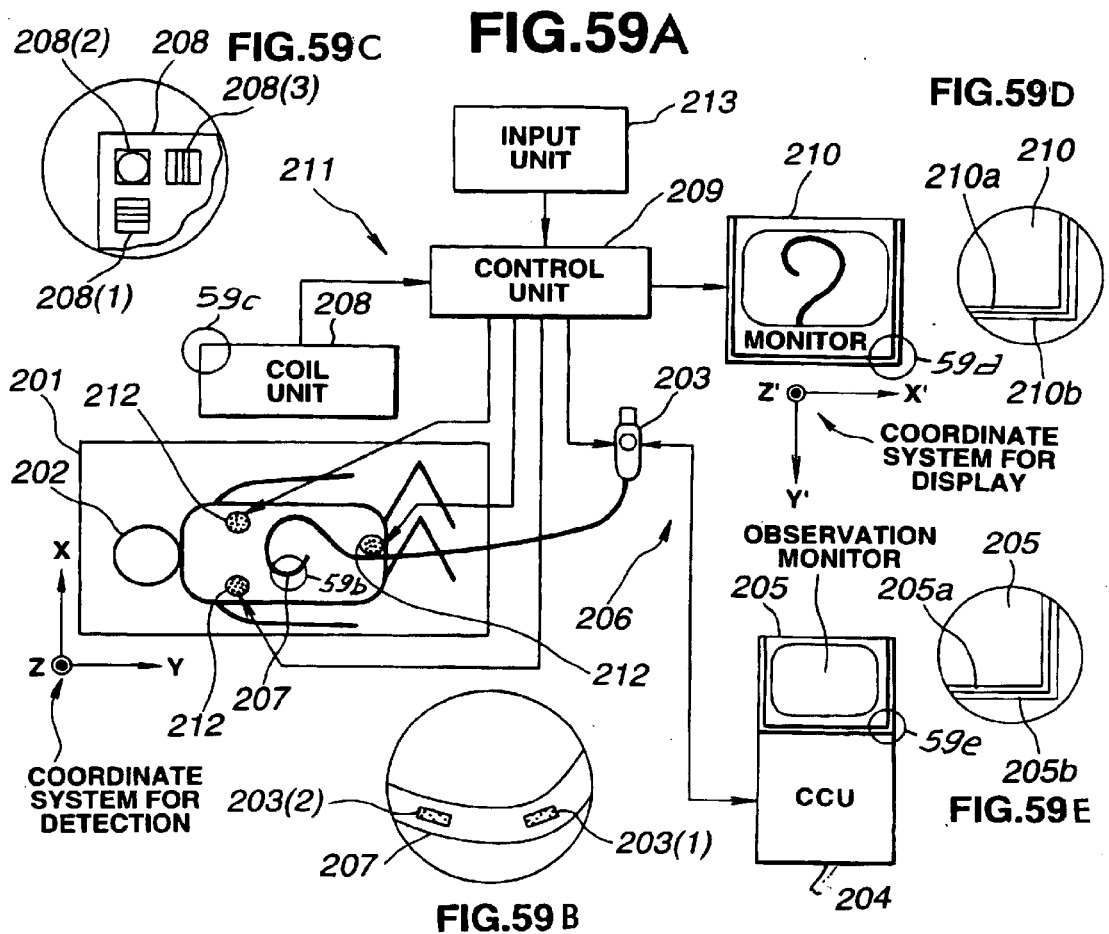
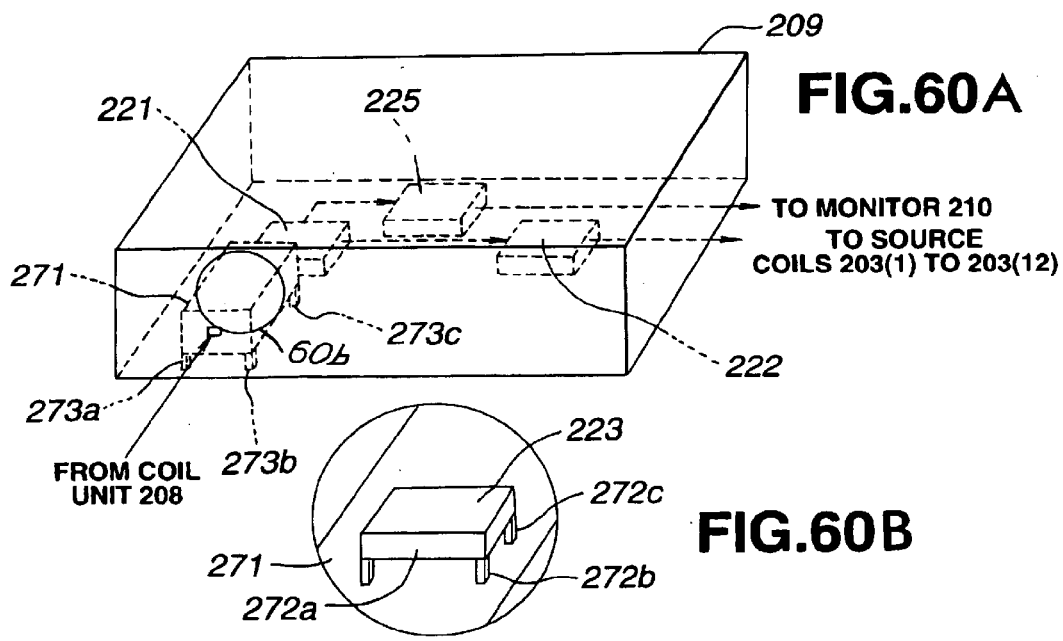

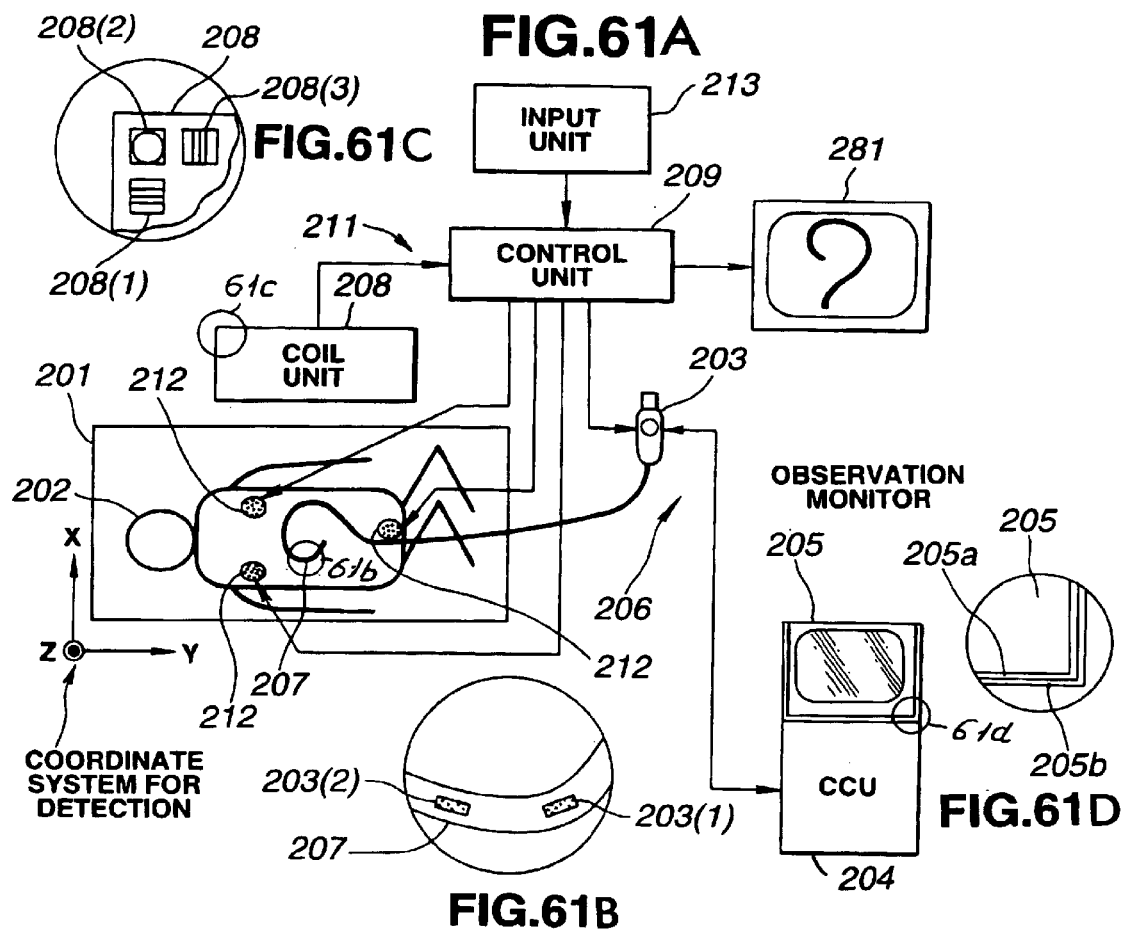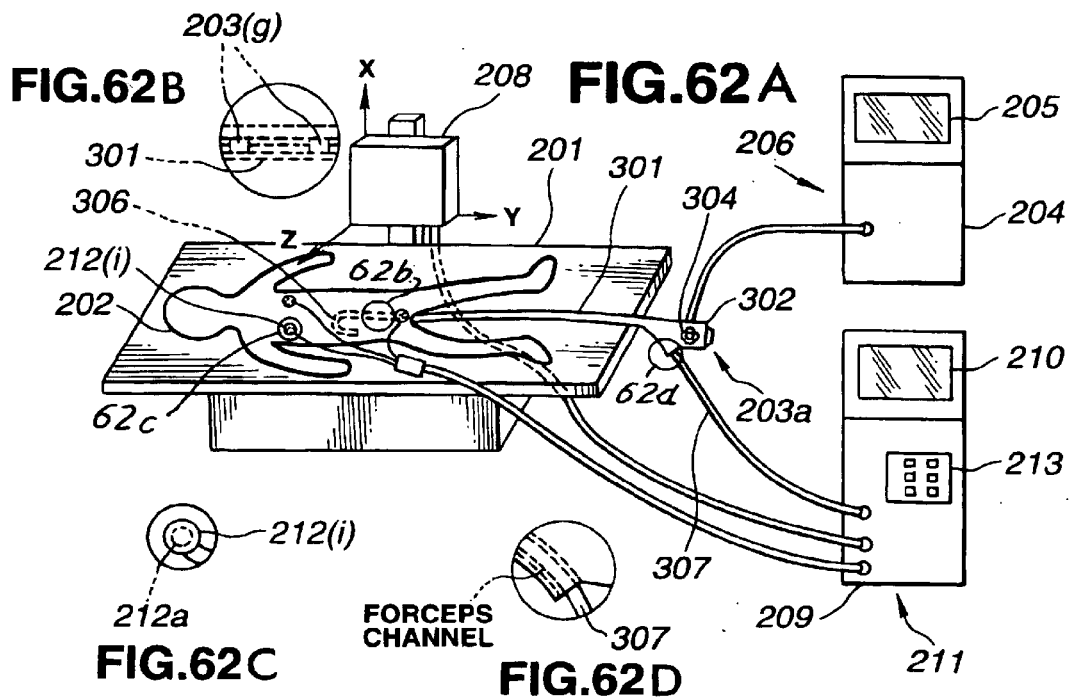

OPERATOR
201
212(2)
202
301(203a)
212(3)  212(4)  212(1)

210

POSITION OF OPERATOR'S HAND

STORE POSITION OF MARKER 212(1) AND DETACH IT FROM PATIENT 505

STORED POSITION OF MARKER 212(1)

SYSTEM FOR DETECTING THE SHAPE OF AN ENDOSCOPE USING SOURCE COILS AND SENSE COILS

This is a continuation of application Ser. No. 09/387,859, filed Sep. 1, 1999 now U.S. Pat. No. 6,511,417.

BACKGROUND OF THE INVENTION

1. Field of the Invention

The present invention relates to a system for detecting the shape of an endoscope inserted into a lumen using source coils and sense coils.

2. Description of the Related Art

In recent years, endoscopes have been widely used in the fields of medicine and industry alike. Endoscopes with a soft insertion unit may be inserted into a tortuous body cavity and thus make it possible to diagnose an organ located in a deep region in a body cavity without the necessity of incision. Moreover, the endoscopes with a soft insertion unit sometimes have, if necessary, a treatment appliance inserted into a channel and thus make it possible to conduct therapeutic treatments including resection of a polyp or the like.

The lumen in a body cavity such as a large intestine or small intestine, is tortuous. It is hard for an operator to see at what position the inserted insertion unit of an endoscope is located or in what form the insertion unit is inserted.

In this case, for example, when the lumen of the inferior alimentary track is examined by inserting the insertion unit through the anus, some expertise is needed for inserting the insertion unit into the tortuous lumen.

During insertion, for smoother insertion, a bendable part of the insertion unit must be bent in conformity with the curve of the lumen. The procedure would be more convenient if the position in a body cavity or if the current bent state of the insertion unit could be understood.

In the past, X rays have been irradiated externally to a subject, into which the insertion unit of an endoscope is inserted, in order to detect an inserted state. The inserted state means a position in a lumen, at which the insertion unit is located, or an inserted form of the insertion unit. However, X rays are harmful to a human body. Besides, a place of irradiation in which X rays are irradiated is limited. Thus, X rays are not a preferable means for detecting the inserted state of the insertion unit of an endoscope.

Various endoscopes and apparatuses have been proposed for detecting the inserted state of an insertion unit of an endoscope in a lumen in a body cavity or the inserted state of a catheter thereof by utilizing magnetic fields without a physiologically adverse effect upon a human body.

However, a technology for indicating the positional relationship of an endoscope to the exterior of a body cavity has not been disclosed. Since the positional relationship between the endoscope and the exterior of the body cavity is unknown, into what region in a patient's body the insertion unit of the endoscope has been inserted cannot be ascertained or in what direction the insertion unit should be inserted cannot be determined. Moreover, since the positional relationship between the insertion unit of the endoscope and an operator's hand is unknown, what region should be compressed manually cannot be determined.

Additionally, a conventional CRT generally adopted as a monitor deflects an electron beam using magnetic fields and therefore generates unwanted magnetic fields. Assuming that the CRT is used as an observation monitor for displaying an endoscopic image or a shape depiction monitor for depicting the shape of an endoscope for a conventional endoscope shape detection system employing magnetic fields, a magnetic detection device detects magnetic fields generated by a magnetic generation device while being affected by the unwanted magnetic fields generated by the CRT. This poses a problem in that the shape of the endoscope cannot be depicted on a stable basis.

According to a conventional display method implemented in a detection system for ascertaining the shape of an endoscope when inserted, if a patient changes his/her position, the positions and angles determining the shape of an endoscope are changed. Consequently, the user would have to re-set his/her line of sight. Moreover, the shape of the entire endoscope is depicted on the display screen, including regions in which the user is not interested, for example, the exterior of a patient's body. The user has to therefore distinguish a region which the user wants to scrutinize, for example, an intracorporeal region of a patient, on the display screen.

According to the display method implemented in the conventional inserted state detection system, an estimated shape of an endoscope is depicted with a reference point in a space of detection aligned with the center of the display area on the monitor. A user must modify the setting of a magnification whenever the user finds it necessary. Showing the shape of an endoscope enlarged is known.

However, although an image showing the shape of an endoscope is not displayed in the center of the display area, if the image of the shape is enlarged, part of the image of the shape comes out of the display area. It is impossible to enlarge the image by making the most of the display area. Even when the image of the shape is enlarged and displayed in an easy-to-see manner, the position of the endoscope changes from one patient to another patient. Consequently, the position of the image of the shape of an endoscope differs and part of the image comes out of the display area. This causes a user to re-set a magnification of the displayed image.

When the insertion unit of an endoscope is inserted into the large intestine or the like, the insertion unit may loop spirally. The insertion of the looping insertion unit pains a patient. Whether an operator recognizes the looping depends conventionally on the operator's skill. This leads to a drawback when looping cannot be recognized readily.

Assuming that the insertion unit of an electronic endoscope is inserted into a body cavity, that a region to be observed is imaged, and that an endoscopic image is viewed through a monitor, it is a matter of common practice that endoscopic images are frozen to produce a still picture which is recorded and viewed for diagnosis. When an image to be frozen appears, a Freeze switch located on an operation unit is pressed. Thus, data of a desired image is recorded in a frame memory or the like in a video processor and then output to the monitor or the like. Eventually, a still picture is displayed.

However, when the Freeze switch is pressed, if the distal part of the insertion unit in which an imaging device is incorporated moves, a color mismatch will be observed in a still picture.

With conventional inserted state detection systems, a user converts images of the shape of an endoscope, which are displayed in the form of a motion picture, into a video signal. The images are then recorded on a video tape for future use in diagnosis or analysis succeeding an examination. The same picture as that viewed during the examination only can be reproduced from the recorded video tape. It is impossible to observe the shape of the endoscope in different directions.

When a conventional endoscope shape detection system is employed, extracorporeal markers are used to mark specified positions on the body surface of a patient for a better understanding of the positional relationship between an endoscope and the patient body. An operator or paramedic must manually affix the extracorporeal markers to the specified positions on the body surface, or fasten them using a tape or the like. The specified positions on the body surface serve as reference positions, for example, such as a position near the anus.

However, according to the foregoing fastening method, if the extracorporeal markers are removed to allow the patient to change his/her position, it is hard to place the markers at the same positions.

SUMMARY OF THE INVENTION

An object of the present invention is to provide an endoscope shape detection system making it possible to readily grasp the positional relationship between the shape of an insertion unit of an endoscope and the exterior of a body cavity.

Another object of the present invention is to provide an endoscope shape detection system capable of suppressing the adverse effect of unwanted magnetic fields generated by a monitor, and depicting the shape of an endoscope in a more stable manner.

Still another object of the present invention is to provide an endoscope shape detection system making it possible to view the shape of an endoscope with a line of sight set in an easy-to-see direction while being unaffected by a change in a patient's position.

Still another object of the present invention is to provide an endoscope shape detection system capable of depicting the shape of an endoscope without causing part of the shape to come out of a display area. Specifically, when the shape of an endoscope is depicted at a size permitting a user to find depiction easy-to-see, even if a subject is changed to another having a different size, no part of the shape will come out of the display area.

Yet another object of the present invention is to provide an endoscope shape detection system making it possible to recognize the looping of an insertion unit, as it is being inserted, in the course of detecting the shape of an endoscope.

Yet another object of the present invention is to provide an endoscope shape detection system capable of producing a desired still picture by freezing images according to a motion made by an insertion unit.

Yet another object of the present invention is to provide an endoscope shape detection system making it possible to observe the shape of an endoscope in an easy-to-see manner all the time even during diagnosis or analysis succeeding an examination.

Yet another object of the present invention is to provide an extracorporeal marker fastening device for an endoscope shape detection system. The extracorporeal marker fastening device makes it possible to set extracorporeal markers at the same positions even when they had to be removed to allow a patient to change his/her position.

An endoscope shape detection system in accordance with the present invention consists mainly of a first coil means, a second coil means, a third coil means, a transmitting and receiving means, and an arithmetic means. The first coil means is inserted into a subject. The second coil means is located at a predetermined position. The third coil means can be located at any position on the subject. The transmitting and receiving means permits transmission and reception of a first magnetic signal between the first coil means and second coil means, and transmission and reception of a second magnetic signal between the third coil means and second coil means. The arithmetic means calculates first position information corresponding to the position of the first coil means relative to the second coil means according to a first detection signal resulting from transmission and reception of the first magnetic signal. The arithmetic means calculates second position information corresponding to the position of the third coil means relative to the second coil means according to a second detection signal resulting from transmission and reception of the second magnetic signal.

In the endoscope shape detection system of the present invention, the arithmetic means calculates the first position information corresponding to the position of the first coil means relative to the second coil means according to the first detection signal resulting from transmission and reception of the first magnetic signal. The arithmetic means also calculates the second position information corresponding to the position of the third coil means relative to the second coil means according to the second detection signal resulting from transmission and reception of the second magnetic signal. Consequently, the endoscope shape detection system makes it possible to readily grasp the positional relationship between the shape of the insertion unit of an endoscope and the exterior of a body cavity.

Other features and advantages of the present invention will become apparent from the description made below.

BRIEF DESCRIPTION OF THE DRAWINGS

The invention is described in detail below with reference to the following figures, throughout which similar reference characters denote corresponding features consistently, wherein:

FIG. 1A to FIG. 39 relate to the first embodiment of the present invention;

FIG. 1A is a schematic view of an endoscopic system constructed according to principles of the invention;

FIG. 1B is a diagrammatic view of the embodiment of FIG. 1A;

FIG. 1C is a partial schematic view, drawn to an enlarged scale, taken along line 1c in FIG. 1A;

FIG. 1D is a partial schematic view, drawn to an enlarged scale, taken along line 1d in FIG. 1A;

FIG. 2 is a block diagram of the endoscope shape detection system shown in FIG. 1A;

FIG. 3 is a block diagram of the endoscope shape detection system shown in FIG. 2;

FIG. 4 is a block diagram of a two-port memory of the endoscope shape detection system shown in FIG. 3;

FIG. 5 is a graphical view of signals and the relative timing thereof with reference to actions made by the two-port memory shown in FIG. 4;

FIG. 6 is a flowchart of operations of the endoscopic system shown in FIG. 1;

FIG. 7 is a flowchart of a sequence of a fast Fourier transform (FFT) of FIG. 6;

FIG. 8 is a graphical view of signals and the relative timing thereof with reference to the timing of parallel processing operations of the endoscopic system of FIG. 6;

FIG. 9 is a diagrammatic view of source coil coordinates used in a coordinates-of-estimated source coil position calculation of FIG. 6;

FIG. 10 is a diagrammatic view of source coil coordinates used in the coordinates-of-estimated source coil position calculation of FIG. 6;

FIG. 11 is a diagrammatic view of source coil coordinates used in the coordinates-of-estimated source coil position calculation of FIG. 6;

FIG. 12 is a diagrammatic view of the coordinates-of-estimated source coil position calculation method of FIG. 6;

FIG. 13 is a diagrammatic view of the coordinates-of-estimated source coil position calculation method of FIG. 6;

FIG. 14 is a diagrammatic view of the coordinates-of-estimated source coil position calculation method of FIG. 6;

FIG. 16 is a diagrammatic view of the coordinates-of-estimated source coil position calculation method of FIG. 6;

FIG. 17 is a diagrammatic view of the coordinates-of-estimated source coil position calculation method of FIG. 6;

FIG. 18 is a diagrammatic view of the coordinates-of-estimated source coil position calculation method of FIG. 6;

FIG. 19 is a diagrammatic view of the coordinates-of-estimated source coil position calculation method of FIG. 6;

FIG. 20 is a flowchart describing a sequence of the coordinates-of-estimated source coil position calculation method of FIG. 6;

FIG. 21 is a flowchart describing a sequence of the coordinates-of-estimated source coil position calculation method of FIG. 6;

FIG. 22 is a flowchart describing a sequence of the position updating control for controlling updating of an estimated position of a source coil determined according to the method of FIG. 20 and FIG. 21;

FIG. 23 is a flowchart describing a sequence of the endoscope shape detection image display of FIG. 6:

FIG. 24 is a display view of a display produced in a normal mode according to the method of FIG. 23;

FIG. 25 is a flowchart describing a sequence in an enlargement mode of FIG. 23;

FIG. 26 is a display view of a display produced in the enlargement mode of FIG, 25;

FIG. 27 is a diagrammatic view of image models of three-dimensional models 1 and 2 produced by the endoscope shape detection image display method of FIG. 6;

FIG. 28 is a flowchart describing an image mode display method for displaying the three-dimensional models 1 and 2 shown in FIG. 27;

FIG. 29 is a diagrammatic view of image models of three-dimensional models 1 and 2 produced by the endoscope detection image display method of FIG. 6;

FIG. 30 is a flowchart describing a sequence of tone correction method of FIG. 29;

FIG. 31 is a diagrammatic view of an effect of the tone correction method of FIG. 30;

FIG. 32 is a flowchart describing a sequence of the tone correction in FIG. 29;

FIG. 33 is a diagrammatic view of an effect of tone correction described in FIG. 30;

FIG. 34 is a flowchart describing an image model display method for displaying a two-dimensional model produced by the endoscope shape detection image display method of FIG. 6;

FIG. 35 is a display view of an image resulting from the endoscope shape detection image display method displayed according to the sequence described in FIG. 34;

FIG. 36 is a flowchart describing an image model display method for displaying a twelve-point model produced by the endoscope shape detection image display method of FIG. 6;

FIG. 37 is a display view of an image resulting from the endoscope shape detection image display method displayed according to the sequence described in FIG. 36;

FIG. 38 is a flowchart describing an image model display method for displaying a linear model produced by the endoscope shape detection image display method of FIG. 6;

FIG. 39 is a display view of an image resulting from the endoscope shape detection image display method displayed according to the sequence described in FIG. 38;

FIG. 40 is a graphical view of a coordinates-of-estimated source coil position calculation method according to the second embodiment of the invention;

FIG. 41 is a flowchart describing a sequence of the coordinates-of-estimated source coil position calculation method of FIG. 40;

FIG. 42 is a flowchart describing the sequence of the coordinates-of-estimated source coil position calculation method of FIG. 40;

FIG. 43A to FIG. 45 relate to the third embodiment of the present invention;

FIG. 43A is a graphical view of a coordinates-of-estimated source coil position calculation method according to the third embodiment of the invention;

FIG. 43B is a partial graphical view, drawn to an enlarged scale, taken along line 43b in FIG. 43A;

FIG. 44 is a flowchart describing a sequence of the coordinates-of-estimated source coil position calculation method performed using two sense coils that define an angle θ, as indicated in FIG. 43, approximate to an angle defined by orthogonal coils;

FIG. 45 is a flowchart describing a sequence of the coordinates-of-estimated source coil position calculation method performed using two sense coils that define an angle θ, as indicated in FIG. 43, approximate to an angle defined by orthogonal coils;

FIG. 46 is a graphical view, in a three-dimensional space, at which a source coil for generating magnetic fields is located;

FIG. 47 is a graphical view of positions of sense coils relative to the position of the source coil shown in FIG. 46 in accordance with the fourth embodiment;

FIG. 48A to FIG. 55 relate to the fifth embodiment of the present invention;

FIG. 48A is a schematic view of an endoscope shape detection system constructed according to the fifth embodiment of the invention;

FIG. 48B is a partial schematic view, drawn to an enlarged scale, taken along line 48b of FIG. 48A;

FIG. 48C is a partial schematic view, drawn to an enlarged scale, taken along line 48c of FIG. 48A;

FIG. 49 is a block diagram of a control unit shown in FIG. 48A;

FIG. 50 is a flowchart describing operations of the endoscope shape detection system shown in FIG. 48A;

FIG. 51A and FIG. 51B are schematic views of the markers shown in FIG. 48A, that is, an anus marker, a left marker, and a right marker;

FIG. 52 is a graphical view of a vector calculated using the anus marker, left marker, and right marker shown in FIG. 51B, and specifying a patient plane on which a patient lies;

FIG. 53 is a graphical view of a vector calculated using the anus marker, left marker and right marker shown in FIG. 51B, and specifying the patient plane;

FIG. 54 is a graphical view of a coordinate transformation to be performed with respect to the vector specifying the patient plane of FIG. 52 and FIG. 53;

FIG. 55 is a graphical view of a coordinate transformation to be performed with respect to the vector specifying the patient plane of FIG. 52 and FIG. 53;

FIG. 56 is a flowchart describing operations of the endoscope shape detection system;

FIG. 57 is a display view of a monitor display produced by the sequences of the flowchart of FIG. 56;

FIG. 58 is a display view of a monitor display produced by the sequences of the flowchart of FIG. 56;

FIG. 59A to FIG. 61 relate to the seventh embodiment of the present invention;

FIG. 59A is a schematic view of an endoscope shape detection system according to the seventh embodiment of the invention;

FIG. 59B is a partial schematic view, drawn to an enlarged scale, taken along line 59b in FIG. 59A;

FIG. 59C is a partial schematic view, drawn to an enlarged scale, taken along line 59c in FIG. 59A;

FIG. 59D is a partial schematic view, drawn to an enlarged scale, taken along line 59d in FIG. 59A;

FIG. 59E is a partial schematic view, drawn to an enlarged scale, taken along line 59e in FIG. 59A;

FIG. 60A is a diagrammatic view of a control unit shown in FIG. 59A;

FIG. 60B is a partial schematic view, drawn to an enlarged scale, taken along line 60b in FIG. 60A;

FIG. 61A is a schematic view of a variant of the endoscope shape detection system shown in FIG. 59A;

FIG. 61B is a partial schematic view, drawn to an enlarged scale, taken along line 61b in FIG. 61A;

FIG. 61C is a partial schematic view, drawn to an enlarged scale, taken along line 61c in FIG. 61A;

FIG. 61D is a partial schematic view, drawn to an enlarged scale, taken along line 61d in FIG. 61A;

FIG. 62 to FIG. 64B relate to the eighth embodiment of the present invention;

FIG. 62A is a schematic view of an endoscope shape detection system according to the eighth embodiment of the invention;

FIG. 62B is a partial schematic view, drawn to an enlarged scale, taken along line 62b in FIG. 62A;

FIG. 62C is a partial schematic view, drawn to an enlarged scale, taken along line 62c in FIG. 62A;

FIG. 62D is a partial schematic view, drawn to an enlarged scale, taken along line 62d in FIG. 61A;

FIG. 63 is a block diagram of a control unit shown in FIG. 62A;

FIG. 64B is a diagrammatic view of the positions of marking on the present endoscope and an operator's hand;

FIG. 65A through FIG. 66 relate to the ninth embodiment of the present invention;

FIG. 65A is a schematic view of operations of the endoscope shape detection system;

FIG. 66 is a diagrammatic view of endoscope shape modeling performed by a variant of the endoscope shape detection system of FIG. 65A;

FIG. 68 is a flowchart describing operations of an endoscope shape detection system according to the eleventh embodiment of the invention;

FIG. 69 is a display view of a display viewed during steps S303 and S304 of FIG. 68;

FIG. 70 is a display view of a display viewed during steps S303 and S304 of FIG. 68;

FIG. 71 is a display view of a display viewed during steps S303 and S304 of FIG. 68;

FIG. 72 is a flowchart describing operations of the endoscope shape detection system according to the twelfth embodiment of the invention;

FIG. 73 is a schematic view of a patient undergoing step S312 of FIG. 72;

FIG. 74 is a diagrammatic view of an endoscope shape during step S316 of FIG. 72;

FIG. 75 and FIG. 76 relate to the thirteenth embodiment of the present invention;

FIG. 75 is a flowchart describing operations of the endoscope shape detection system according to the thirteenth embodiment of the invention;

FIG. 77 is a display view of a display viewed with the endoscope shape detection system according to the fourteenth embodiment of the invention;

FIG. 78 is a display view of a display viewed with the endoscope shape detection system according to the fourteenth embodiment of the invention;

FIG. 79A to FIG. 87 relate to the fifteenth embodiment of the present invention;

FIG. 79A is a schematic view of an endoscopic system according to the fifteenth embodiment of the invention;

FIG. 80 is a partial side elevational view of an endoscope showing the positions of source coils shown in FIG. 79A;

FIG. 81 is a partial side elevational view of a variant of an endoscope showing the positions of the source coils shown in FIG. 79A;

FIGS. 82 to 85 are graphical views of application of principles of detection [based] on which the endoscope shape detection system of FIG. 79 detects the looping of an insertion unit;

FIG. 86 is a flowchart describing a sequence for detecting insertion unit looping by the endoscope shape detection system shown in FIG. 79A;

FIG. 87 is a flowchart describing a sequence for detecting insertion unit looping by the endoscope shape detection system shown in FIG. 79A;

Figure 88:
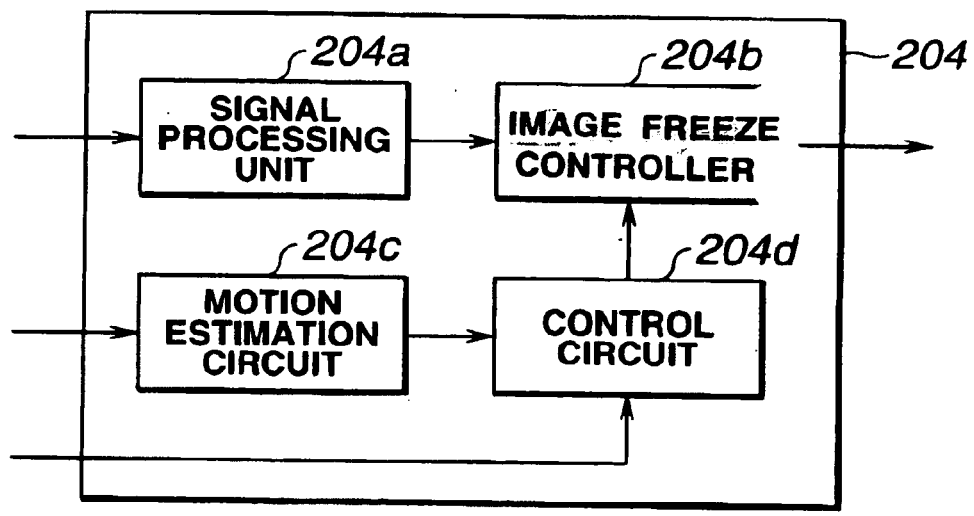
Figure 89:
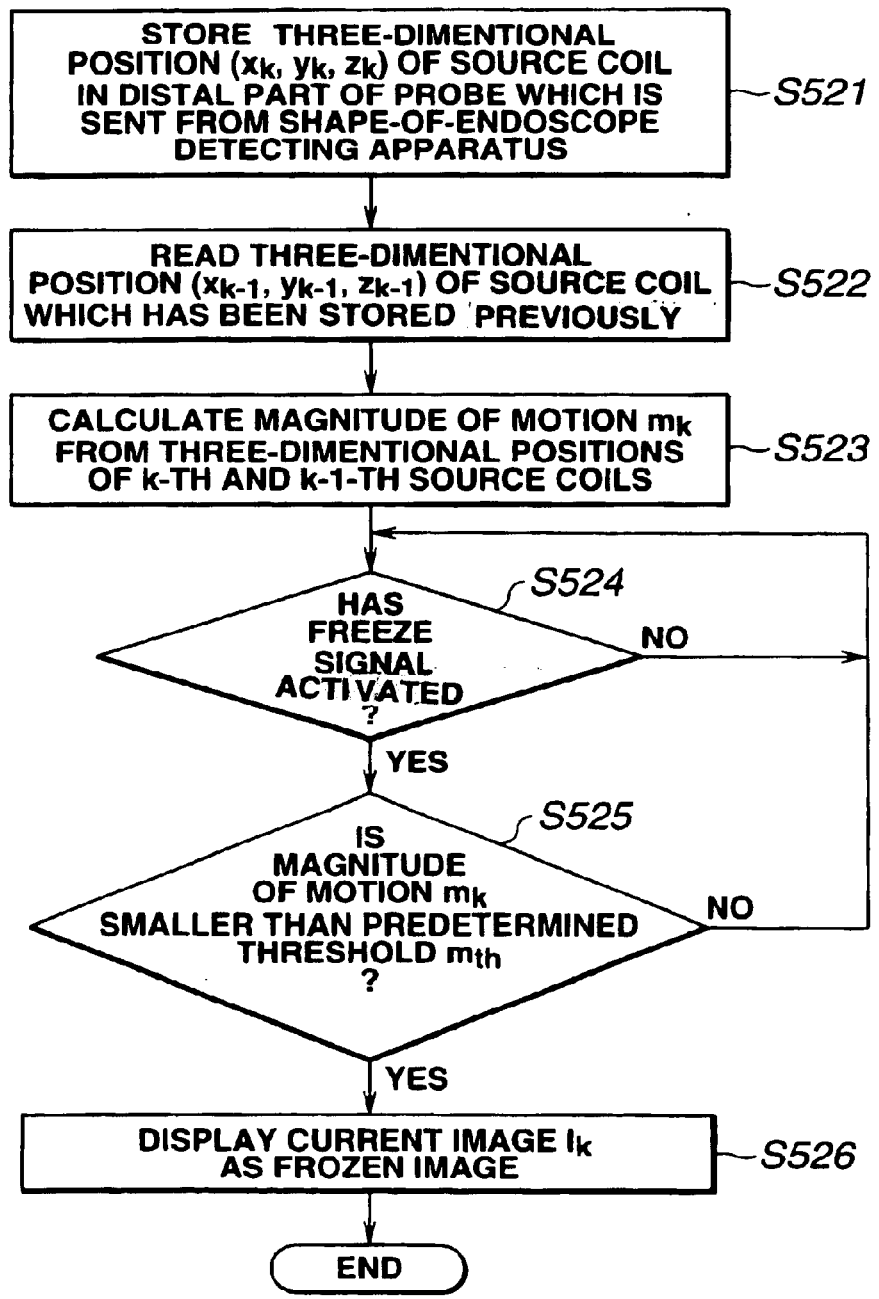
Figure 90:
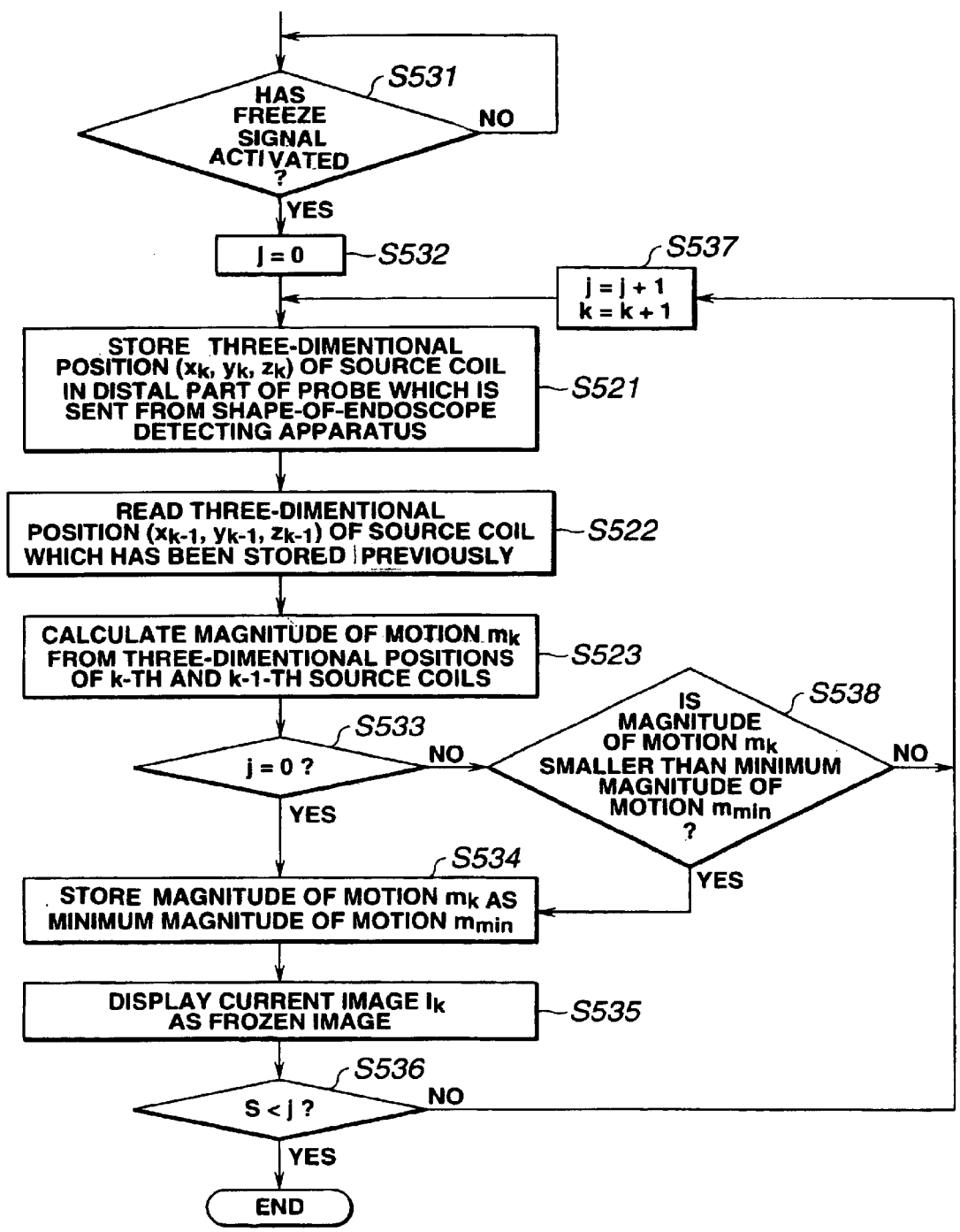
Figure 91:
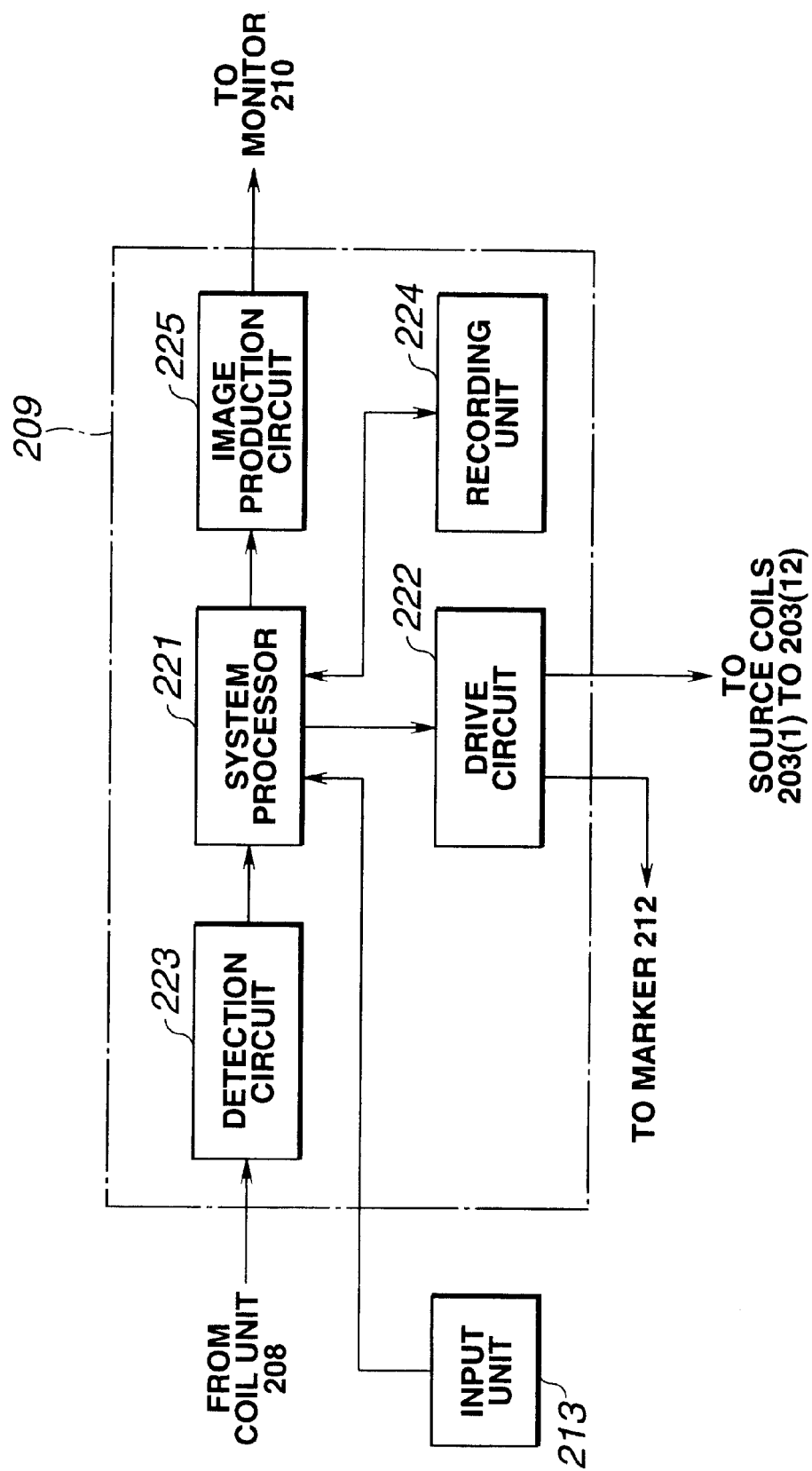
Figure 92:
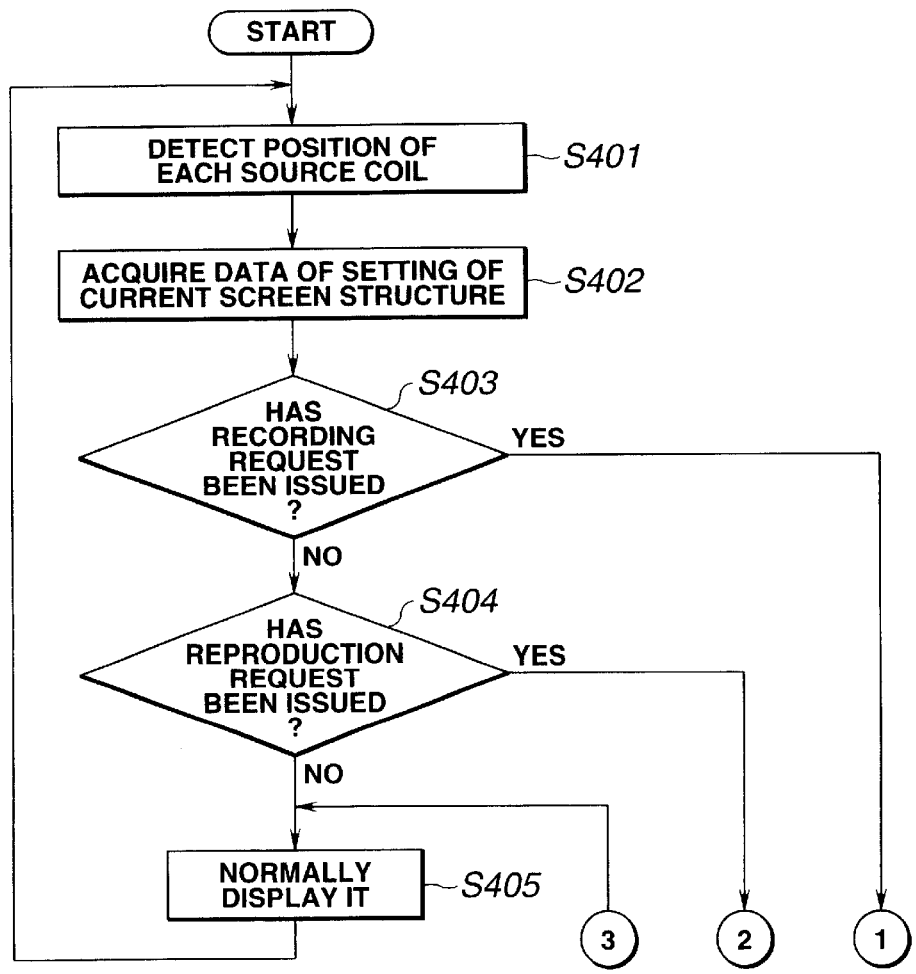
Figure 93:
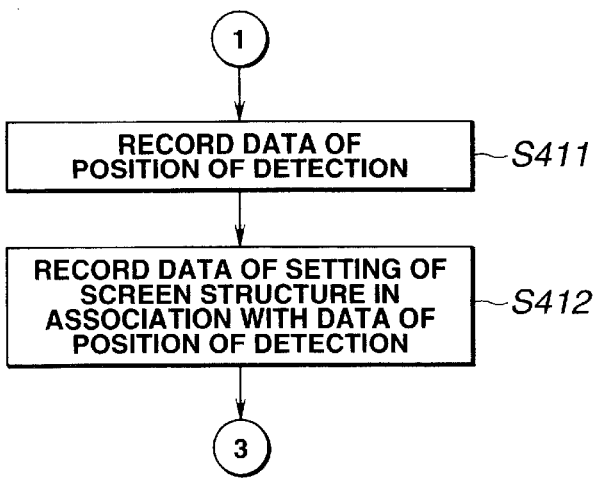
Figure 94:
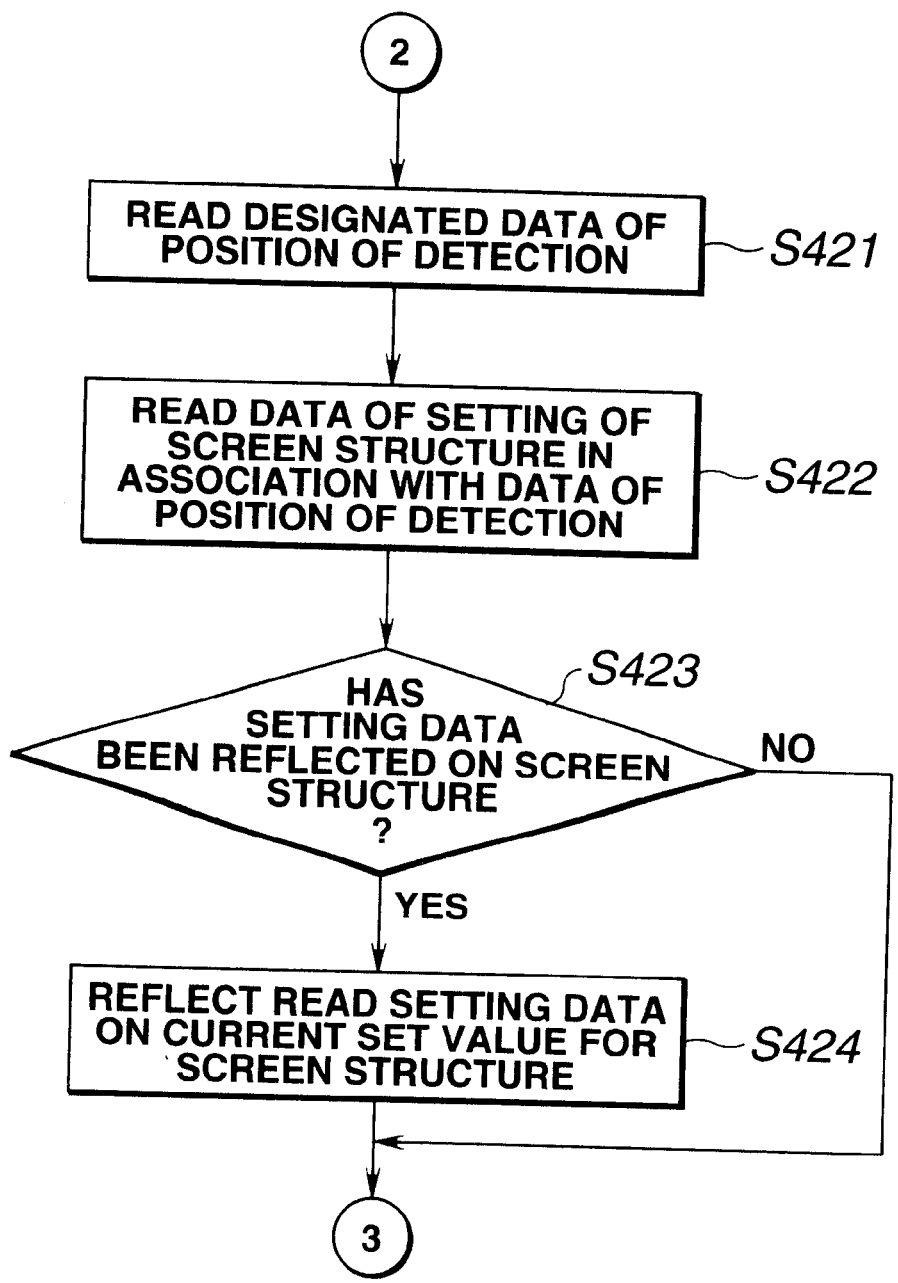
Figure 95:
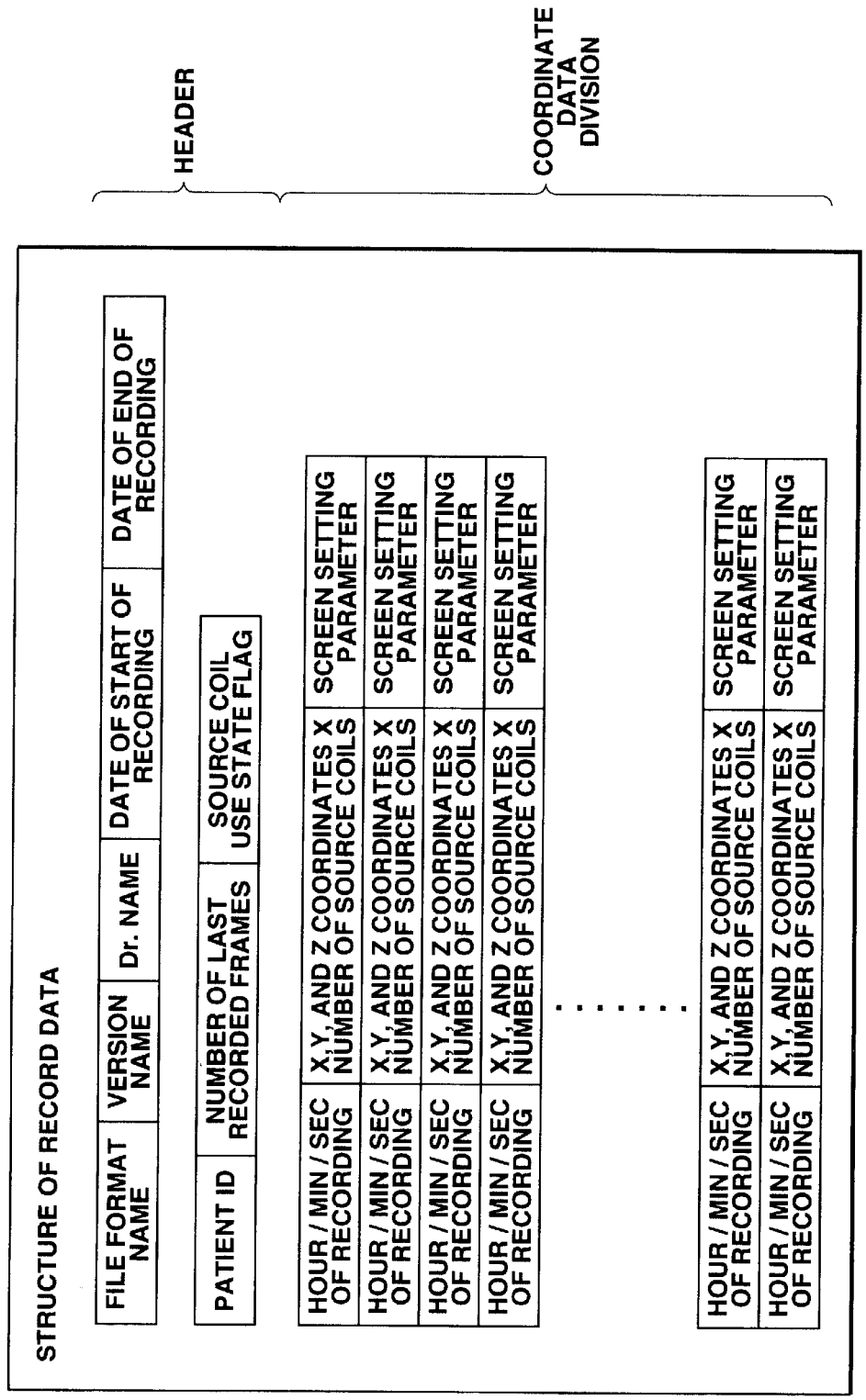
Figure 96:
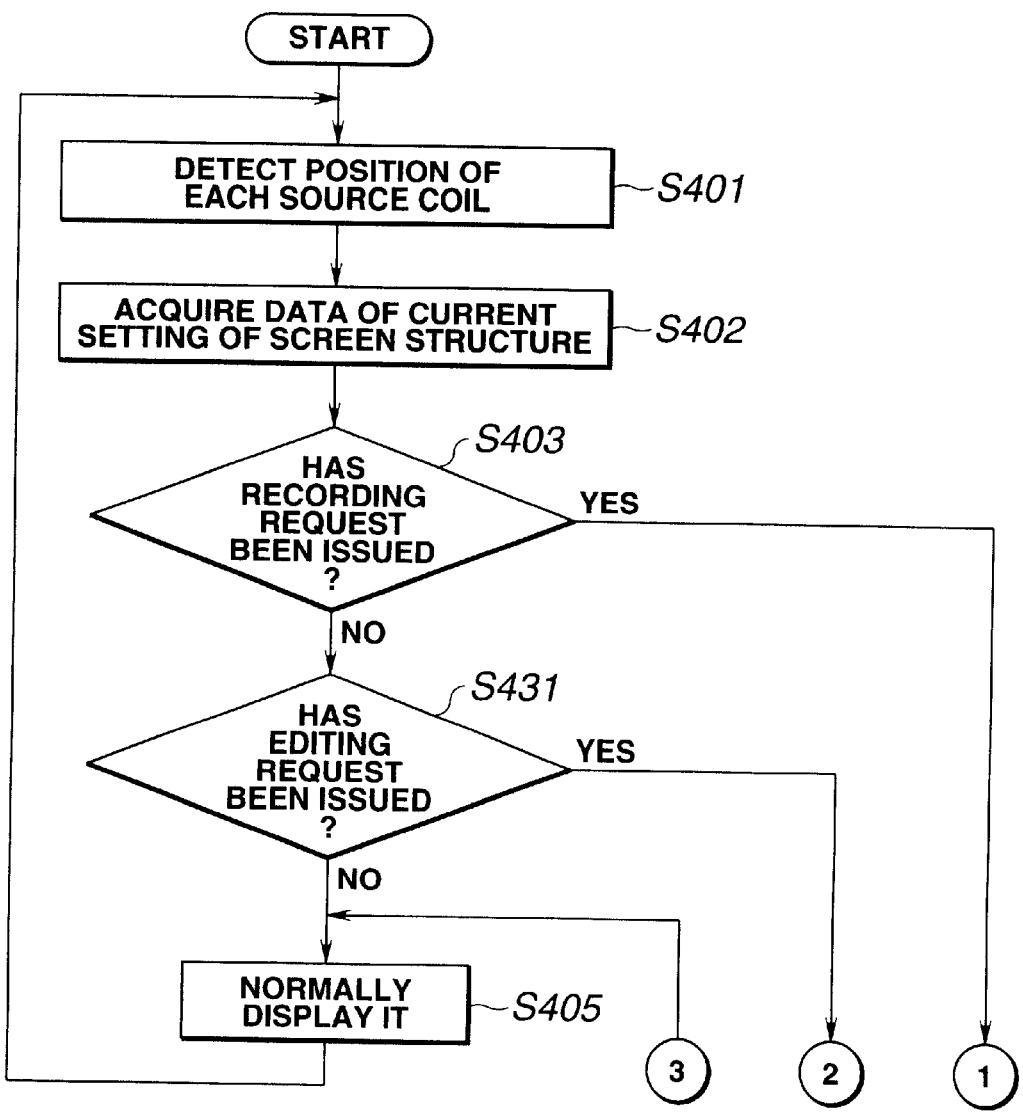
Figure 97:
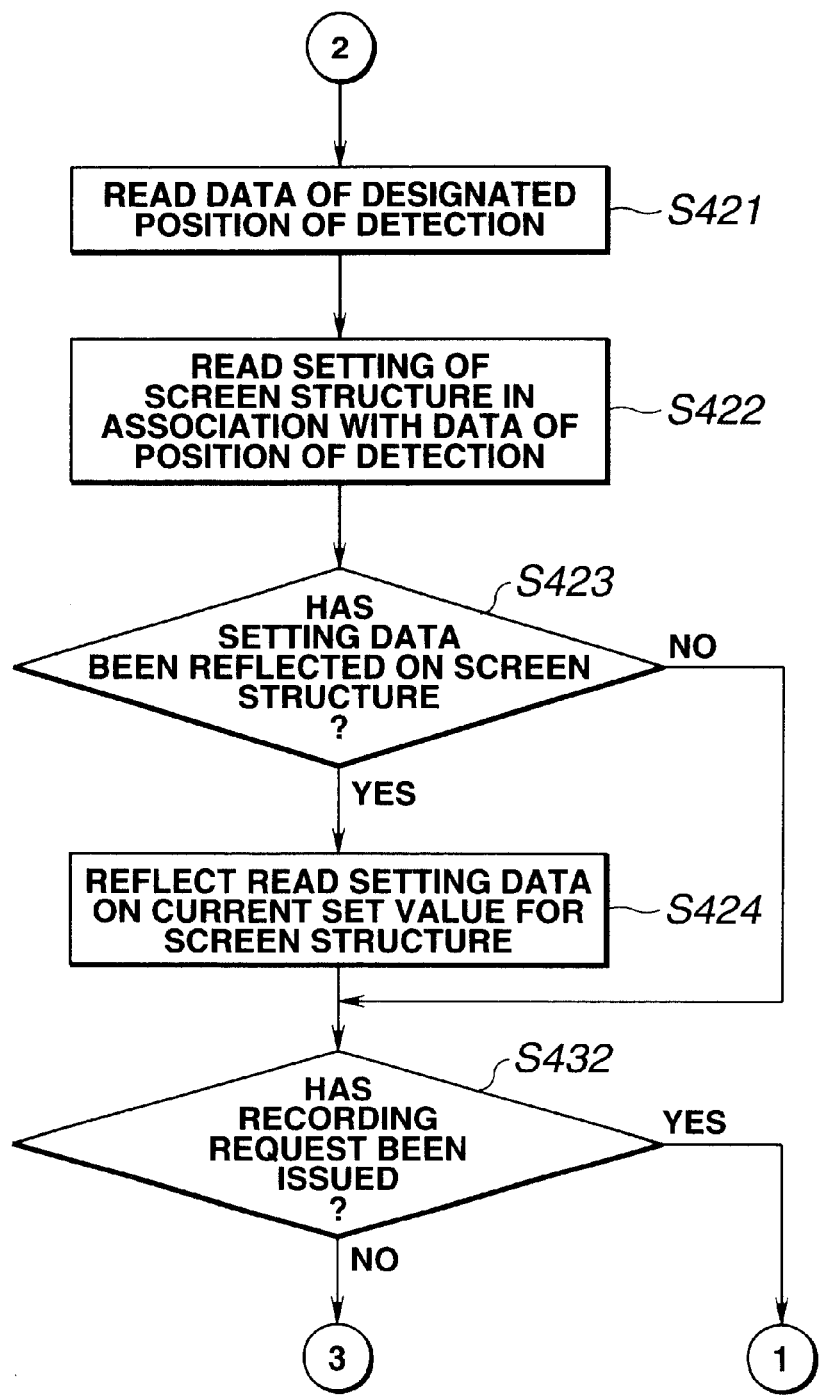
Figure 98:
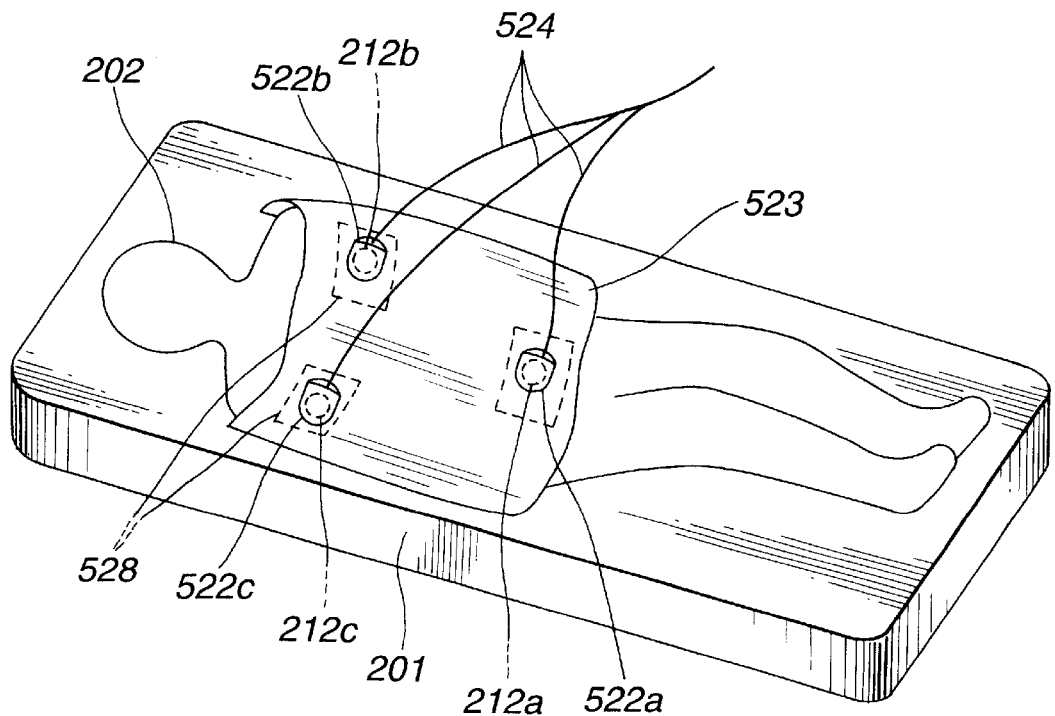
Figure 99:
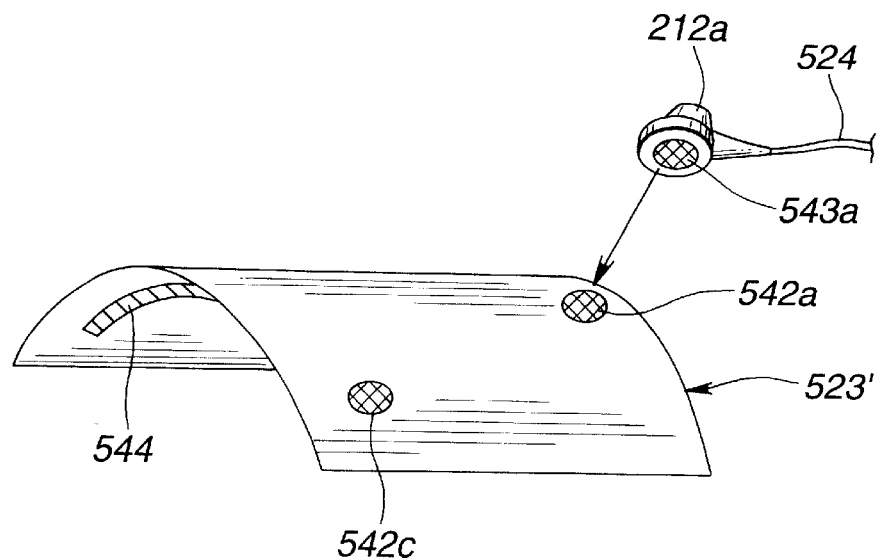
Figure 100:
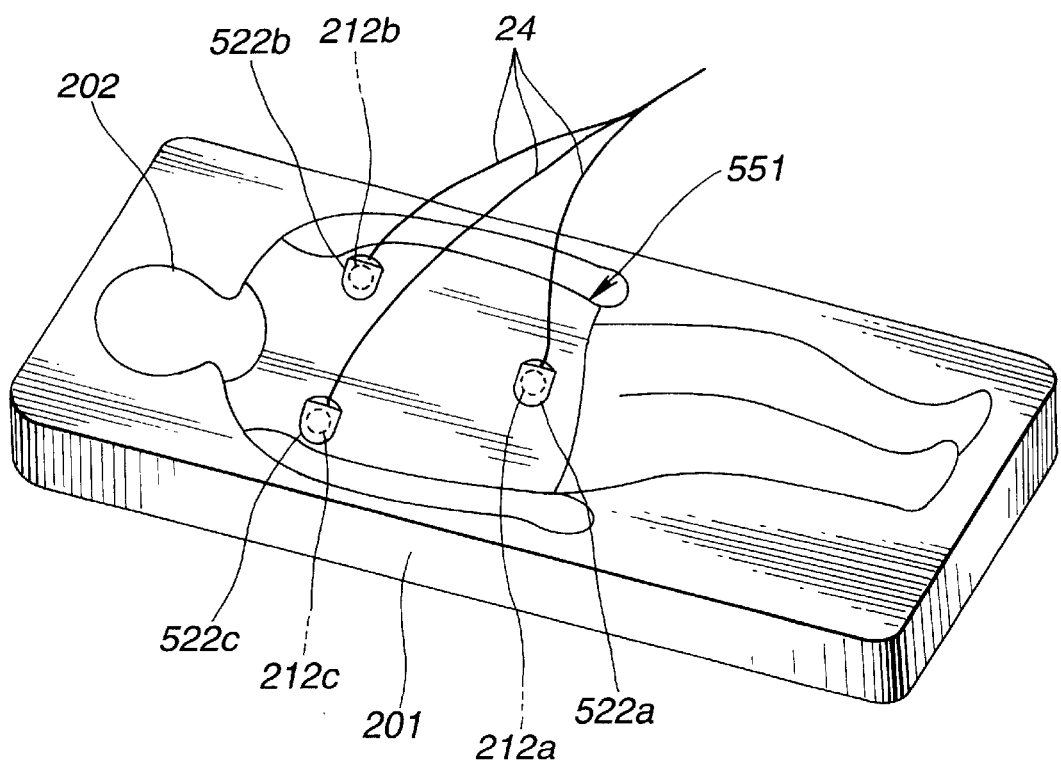
Figure 101:
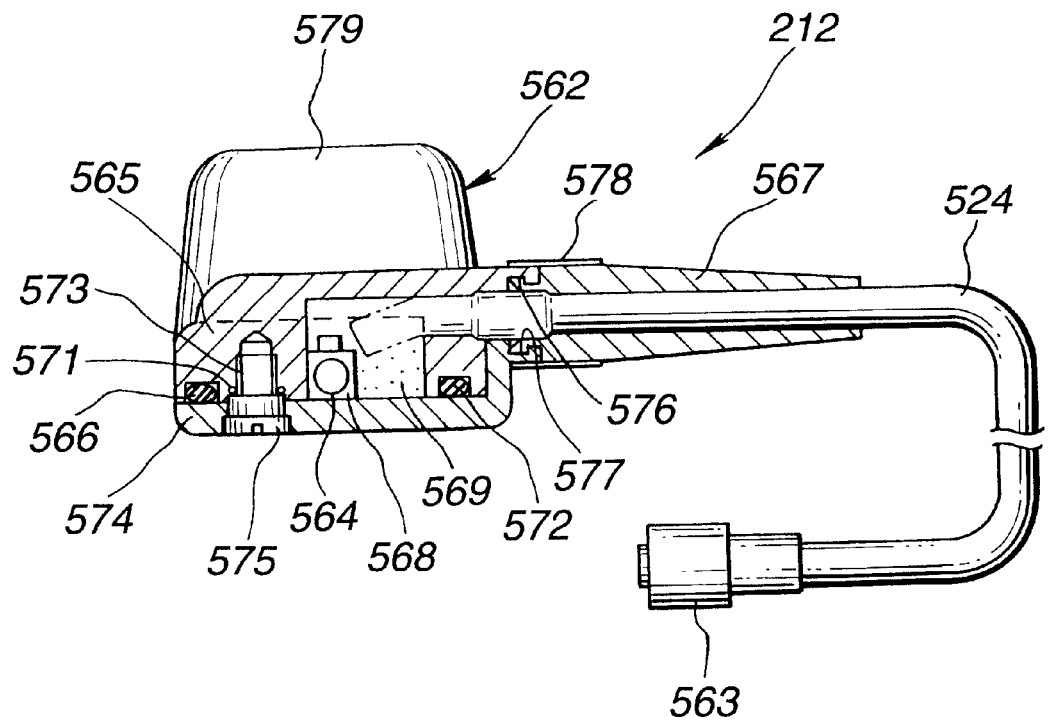
Figure 102:
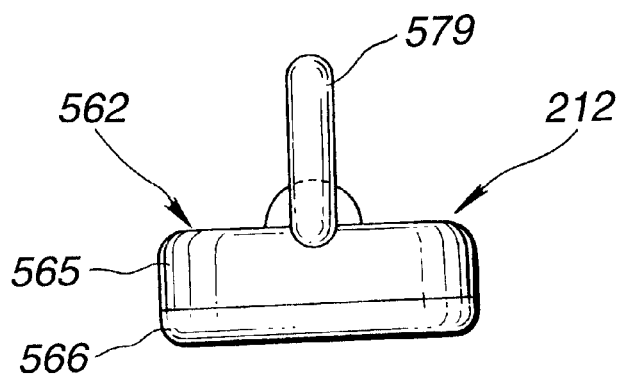
Figure 103:
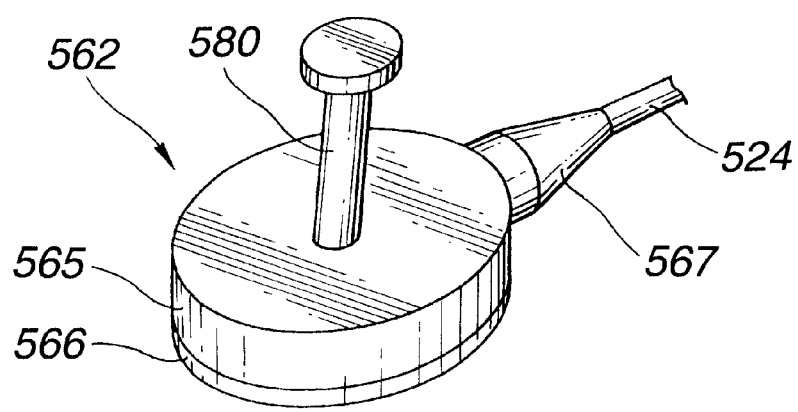
Figure 104:
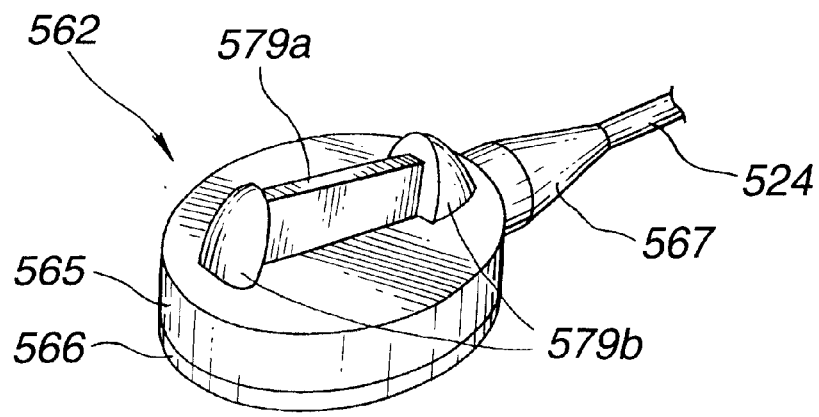
Figure 105:
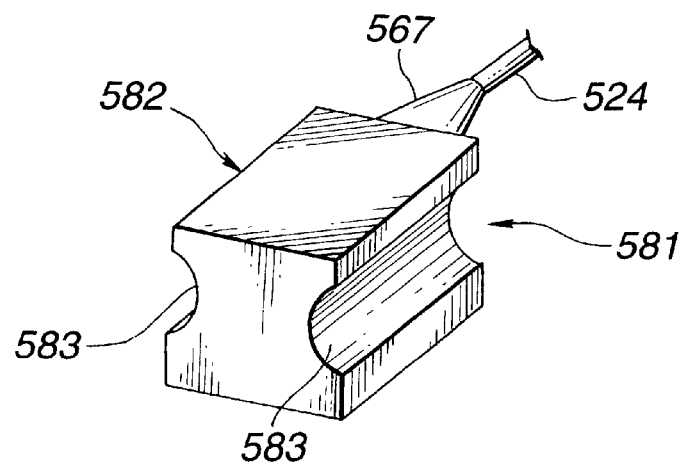
Figure 106:
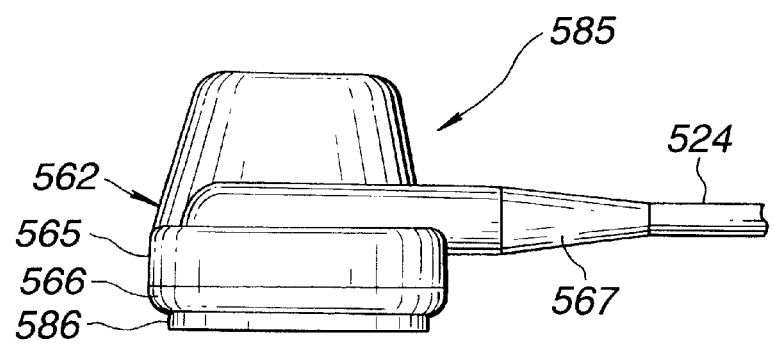
Figure 107:
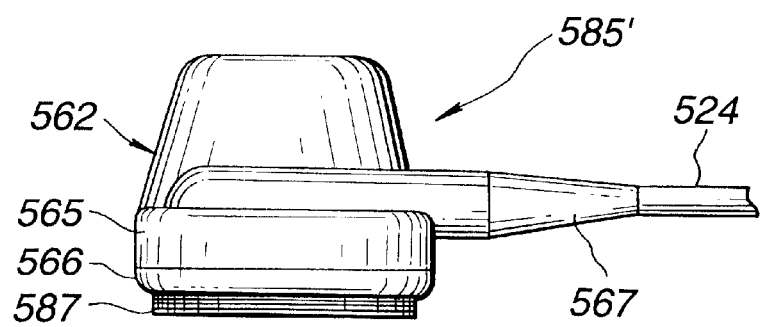
Figure 108:
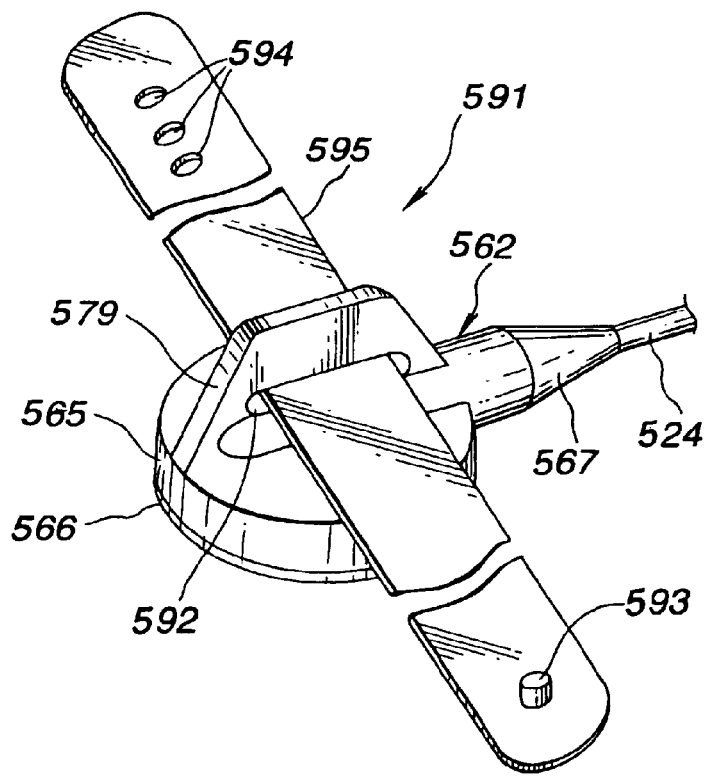
Figure 109:
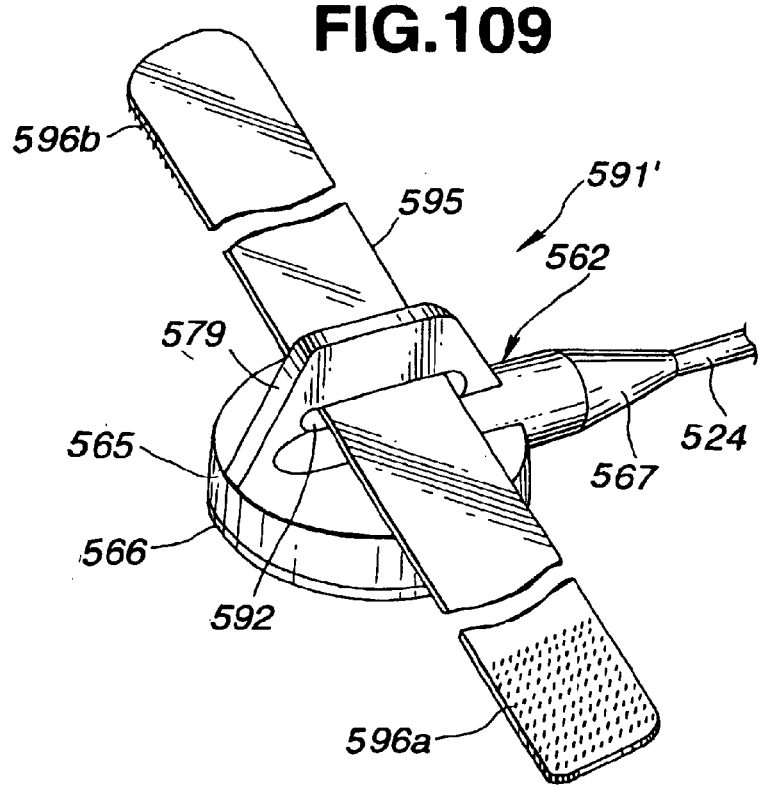

FIG. 88 and FIG. 89 relate to the sixteenth embodiment of the present invention;

FIG. 88 is a schematic view of the configuration of a CCU;

FIG. 89 is a flowchart describing a sequence of freeze control to be performed by the CCU shown in FIG. 88;

FIG. 90 is a flowchart describing a sequence of freeze control to be performed by a CCU in accordance with the seventeenth embodiment of the present invention;

FIG. 91 to FIG. 95 relate to the eighteenth embodiment of the present invention;

FIG. 91 is a schematic view of the configuration of a control unit;

FIG. 92 is a flowchart describing operations of an endoscope shape detection system having the control unit shown in FIG. 91;

FIG. 93 is a flowchart continuous of the flowchart of FIG. 92;

FIG. 94 is a flowchart continuous of the flowchart of FIG. 92;

FIG. 95 is a diagrammatic view of a format with which data is recorded by the control unit according to the flowcharts of FIG. 92 to FIG. 94;

FIG. 96 and FIG. 97 relate to the nineteenth embodiment of the present invention;

FIG. 96 is a flowchart describing operations of the endoscope shape detection system according to the nineteenth embodiment of the invention;

FIG. 97 is a flowchart continuous of the flowchart of FIG. 96;

FIG. 98 and FIG. 99 relate to the twentieth embodiment of the present invention;

FIG. 98 is an environmental view of a marker placement sheet;

FIG. 99 is a schematic view of a variant of the marker placement sheet shown in FIG. 98;

FIG. 100 is an environmental view of a marker placement sheet in accordance with the twenty-first embodiment of the present invention;

FIG. 101 to FIG. 109 relate to an extracorporeal marker employed in the embodiments of the present invention;

FIG. 101 is a partial cross-sectional view of the extracorporeal marker;

FIG. 102 is a side elevational view of the extracorporeal marker shown in FIG. 101;

FIG. 103 is a top right front view of a first variant of the extracorporeal marker shown in FIG. 101;

FIG. 104 is a top right front view of a second variant of the extracorporeal marker shown in FIG. 101;

FIG. 105 is a top right front view of a third variant of the extracorporeal marker shown in FIG. 101;

FIG. 106 is a top right front view of a fourth variant of the extracorporeal marker shown in FIG. 101;

FIG. 107 is a top right front view of a fifth variant of the extracorporeal marker shown in FIG. 101;

FIG. 108 is a top right front view of a sixth variant of the extracorporeal marker shown in FIG. 101;

FIG. 109 is a top right front view of a seventh variant of the extracorporeal marker shown in FIG. 101;

DESCRIPTION OF THE PREFERRED EMBODIMENTS

To begin with, prior to presentation of exemplary embodiments, an algorithm for estimating the three-dimensional positions of source coils using a plurality of pairs of sense coils will be described with reference to the first to seventh embodiments.

According to a related art disclosed in, for example, PCT No. WO094/04938, three coils having mutually orthogonal axes and which are fixed to predetermined positions are used to successively generate alternating gradients, which exhibit mutually orthogonal vectors, in a space. A uniaxial coil having a position in the space is indicated with certain coordinates and is used to measure a voltage induced across itself due to the alternating gradients generated by the coils having three different axes. The spatial coordinates of the uniaxial coil are detected based on the measured data.

However, according to the related art disclosed in the PCT No. W094/04938, unless the frequency of a radiofrequency signal used to generate magnetic fields agrees with that of a frequency component sampled by a frequency sampling means, the frequency component does not exhibit a value, which should be sampled, due to a change in ambient temperature or a time-sequential change. Consequently, the position of an endoscope determined based on the value disagrees with an actual position. This brings about a possibility that an inserted state may not be able to be detected accurately.

Japanese Unexamined Patent Publication No. 9-28661 has proposed an endoscope shape detection system capable of detecting an inserted state of an endoscope. Herein, a frequency adjusting means is included for harmonizing the frequency of a radio-frequency signal with that of a reference signal. Consequently, the frequencies of the radio-frequency signal and reference signal can be harmonized with each other even in such an environment that the frequencies may disagree with each other due to a change in ambient temperature or a time-sequential change. Thus, setting remains unsusceptible to the change.

According to the related art disclosed in the PCT NO. W094/04938, the position of a magnetic generation device is estimated based on output values of a plurality of detection devices. For this purpose, a plurality of triaxial coils, each composed of three orthogonal single-core coils, is needed. This results in a complex configuration.

According to the Japanese Unexamined Patent Publication No. 9-28661, the an endoscope shape detection system is adapted to an endoscopic system. In this case, a plurality of triaxial coils, each composed of three orthogonal single-core coils, is needed for estimating the position of a magnetic generation device according to output values of a plurality of detection devices. This also results in a complex configuration.

According to the Japanese Unexamined Patent Publication No. 9-28661, there is difficulty in strictly harmonizing frequencies of signal components with frequencies observed through Fourier transform or the like in the course of vector analysis. This causes a "leakage" in the frequency domain. A window function or the like must be employed in order to alleviate an adverse effect of the "leakage."

Japanese Unexamined Patent Publication No. 10-332309 has proposed a method of measuring the position of a coil. A detection device (or a magnetic generation device) composed of at least four single-core coils placed at different positions in the same direction along the same straight light is used to estimate a space in which the magnetic generation device (or detection device) exists. The method is characteristic of the decreased number of variables to be estimated.

According to the Japanese Unexamined Patent Publication No. 10-332309, the aforesaid problem can be solved. However, since sense coils each composed of four single-core coils are juxtaposed, errors in circles of magnetic fields, that is, errors in the center and radius of each circle, estimated by the sense coils are observed in the same direction. This poses a problem in that an error in the estimated three-dimensional position of a source coil is observed to be large in a specified direction, thus when the distance between the source coils and sense coils increases, the estimated three-dimensional positions of the source coils become uncertain.

In conjunction with the first to seventh embodiments, a description will be made of an estimation algorithm effective in diminishing an estimation error occurring when the three-dimensional position of a source coil is estimated using sense coils each composed of a plurality of singlecore coils.

As shown in FIG. 1A, an endoscopic system 1 of this embodiment has an endoscope system 2 for use in endoscopic examinations, and an endoscope shape detection system 3 to be used as an aid for the endoscopic examinations. The endoscope shape detection system 3 is used as an insertion aid means when an insertion unit 7 of an electronic endoscope 6 is inserted into a body cavity of a patient 5.

The electronic endoscope 6 has an operation unit 8 formed at the back end of the elongated flexible insertion unit 7. The operation unit 8 has a bending knob. A universal cord 9 extends from the operation unit 8 coupled to a video imaging system (or a video processor) 10.

The electronic endoscope 6 has a light guide passing through it. Illumination light emanating from a light source unit in the video processor 10 is transmitted over the light guide, and irradiated through an illumination window formed on the distal plane of the insertion unit 7. An area of interest of a patient is thus illuminated. Light reflected from an illuminated object, such as a lesion, is converged on an imaging device located on the image plane of an objective locked in an observation window adjacent to the illumination window. The imaging device photoelectrically converts the optical image formed thereon into a data signal.

The signal resulting from photoelectric conversion is processed by a video signal processing unit in the video processor 10, whereby a standard video signal is produced. The images carried by the video signal are displayed on an image observation monitor 11 connected to the video processor 10.

As shown on FIGS. 1C and 1D, the electronic endoscope 6 has a forceps channel 12. A probe 15 having, for example, sixteen magnetic generation devices or source coils 14a, 14b, ..., 14p (hereinafter, generically, 14i) is inserted through an insertion port 12a of the forceps channel 12. Thus, the source coils 14i are placed in the insertion unit 7.

A source cable 16 extends from the back end of the probe 15. A connector attached to the back end of the source cable 16 is coupled to a main unit 21 of the endoscope shape detection system 3 so that it can be uncoupled freely. A radio-frequency signal, or driving signal, is applied from the main unit 21 to the source coils 14i, serving as a magnetic generation means, by way of the source cable 16. serving as a radio-frequency transmitting means. This causes the source coils 11i to radiate electromagnetic waves identifiable with magnetic fields.

Referring also to FIG. 1B, magnetic detection devices, or sense coils, each made by arranging at least four single-core coils $22k$, are coaxial and detect a magnetic field, in the same direction along the same straight line and are incorporated in the examining table 4 on which the patient 5 lies. For example, four sense coils $22a$, $22b$, $22c$, and $22d$ (hereinafter, generically, $22j$) are arranged in two rows and two columns. Specifically, the sense coils $22a$ and $22b$ are parallel to each other, and the sense coils $22c$ and $22d$ are orthogonal to the sense coils $22a$ and $22b$. In this case, the number of single-core coils $22k$ is sixteen.

The sense coils $22j$ are connected to the main unit 21 through a connector attached to the examining table 4 with a sense cable 23 serving as a detection signal transmitting means. The main unit 21 has an operator panel 24 or keyboard to be manipulated by a user for operating the system. A monitor 25 serving as a display means for displaying an image showing the detected shape of an endoscope is connected to the main unit 21.

The configuration of the endoscope shape detection system 3 will be described below. The endoscope shape detection system 3 consists of, as shown in FIG. 2, a driving block 26 for actuating the source coils 14i, a detecting block 27 for detecting signals received by the sense coils $22j$, and a host processor 28 for processing signals detected by the detecting block 27.

Figure 3:
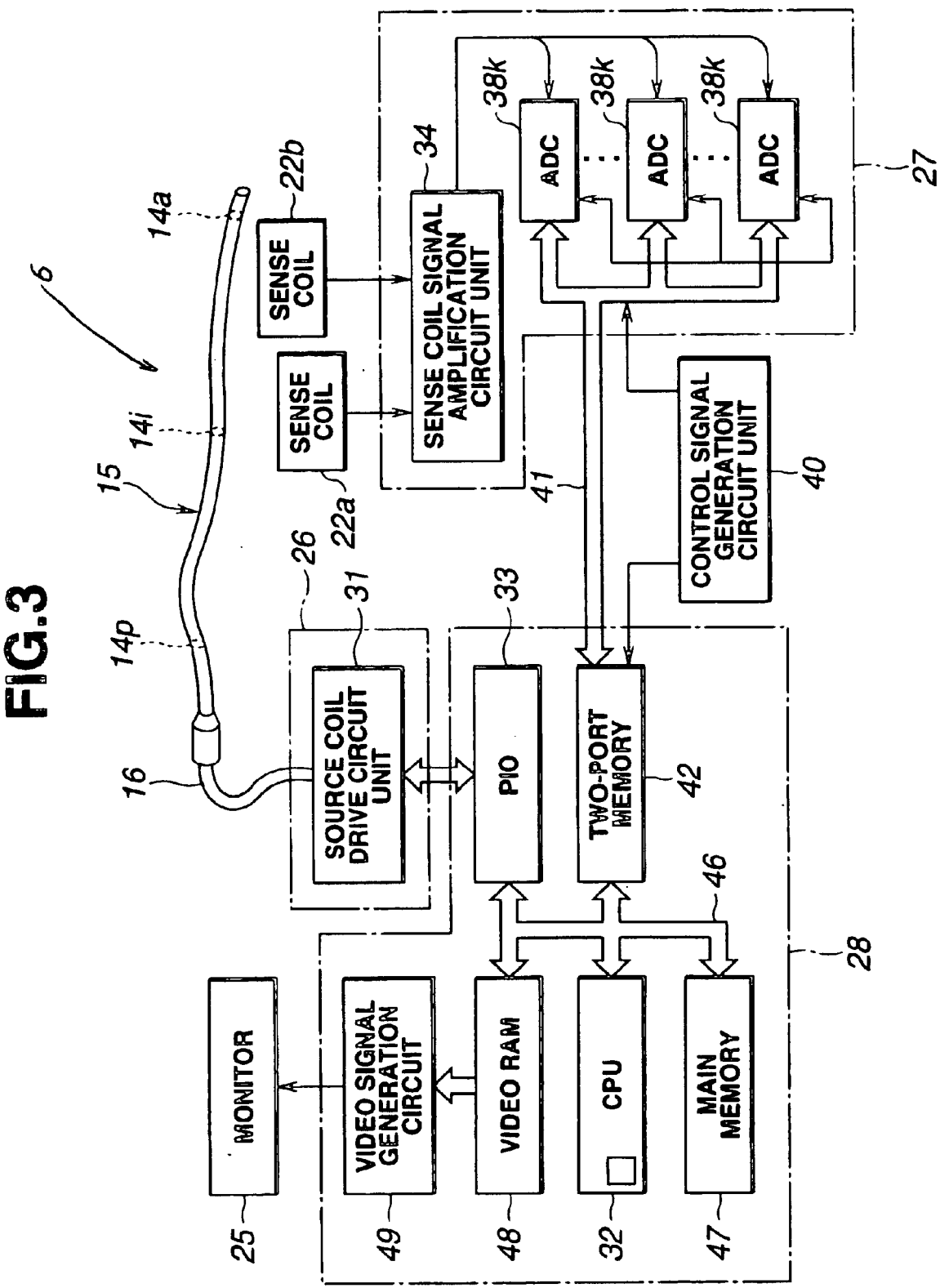

As shown in FIG. 3, the sixteen source coils 14i for generating magnetic fields are arranged in the probe 15 placed at predetermined intervals in the insertion unit 7 of the electronic endoscope 6. The source coils 14i are connected to a source coil drive circuit unit 31 for producing sixteen different radio-frequency driving signals. The source coil drive circuit unit 31 forms the driving block 26.

The source coil drive circuit unit 31 drives the source coils 14i with currents with characteristics of sine waves serving as driving signals of different frequencies. Driving frequencies at which the source coils 14i are driven are specified with driving frequency setting data or driving frequency data. The driving frequency setting data is stored in a driving frequency setting data storage means or a driving frequency setting data memory means (not shown) incorporated in the source coil drive circuit unit 31. The driving frequency data is stored in the driving frequency data storage means (not shown) in the source coil drive circuit unit 31 via a parallel input/output (PIO) circuit 33 under the control of a central processing unit (CPU) 32. The CPU 32 is incorporated in the host processor 28 for performing calculations required for estimating the shape of an endoscope and other processing.

The sixteen single-core coils $22k$ constituting the four sense coils $22j$ are connected to a sense coil signal amplification circuit unit 34 in the detecting block 27.

Figure 4:
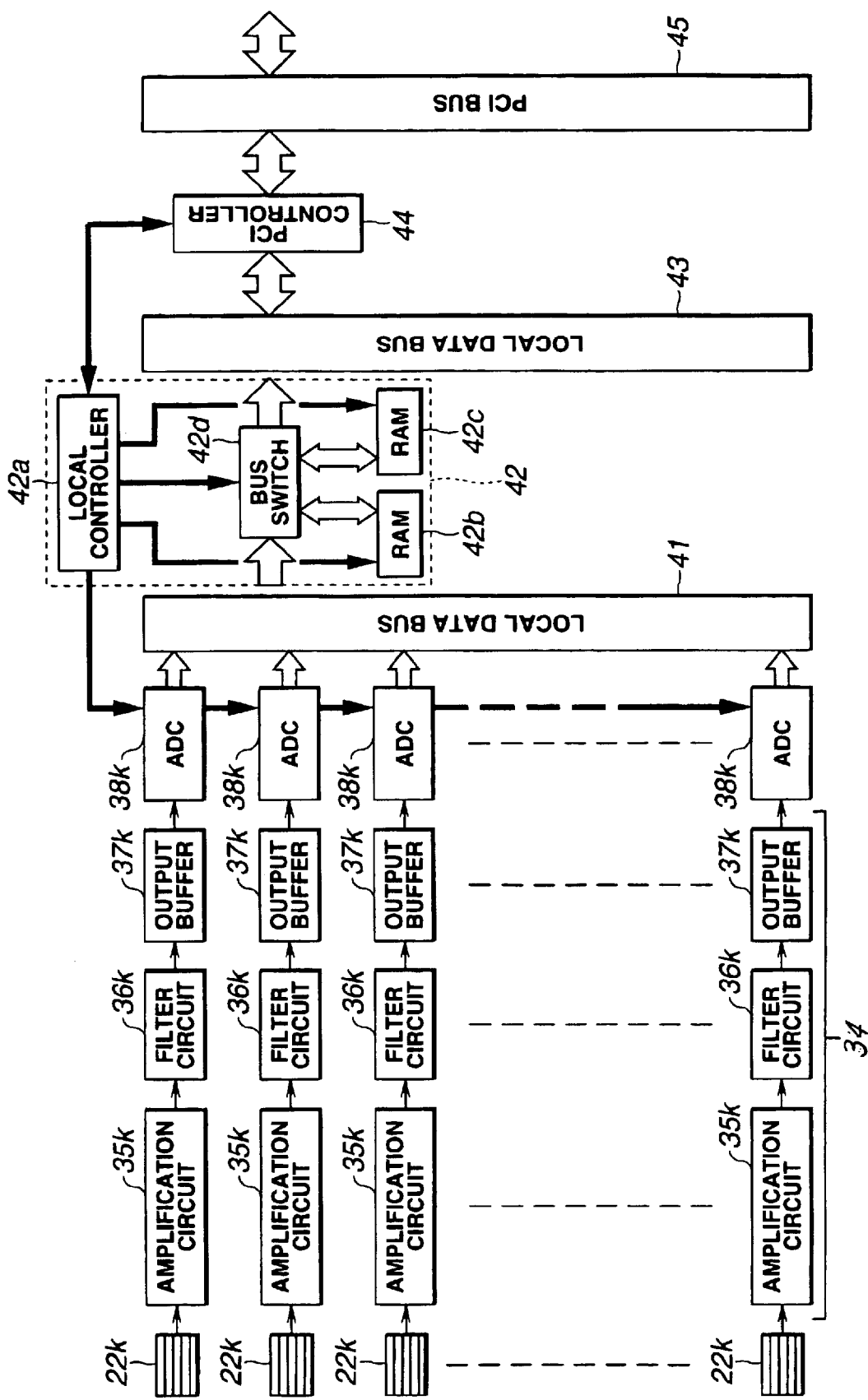

As shown in FIG. 4, in the sense coil signal amplification circuit unit 34, the single-core coils $22k$ are connected to amplification circuits $35k$ on a one-to-one basis. Weak signals detected by the single-core coils 22k are amplified by the amplification circuits 35k. Filter circuits 36k pass a plurality of frequency components generated by the source coils and remove unwanted components of the signals. Thereafter, the signals are converted into digital signals readable by the host processor 28 by analog-to-digital (A/D) converters (ADCs) 38k.

As shown in FIG. 3, the detecting block 27 consists of the sense coil signal amplification circuit unit 24 and A/D converters 38k. As shown in FIG. 4, the sense coil signal amplification circuit unit 34 consists of the amplification circuits 35k, filter circuits 36k, and output buffers 37k.

Referring back to FIG. 3, outputs of the sixteen systems of circuits included in the sense coil signal amplification circuit unit 34 are transmitted to the sixteen A/D converters 38k. The outputs are converted into digital data that are sampled at intervals of a predetermined cycle synchronously with a clock pulse supplied from a control signal generation circuit unit 40. The digital data are written in a two-port memory 42 over a local data bus 41 in response to a control signal sent from the control signal generation circuit unit 40.

The two-port memory 42 is, as shown in FIG. 4, composed functionally of a local controller 42a, a first RAM 42c, a second RAM 42c, and a bus switch 42d. According to the timing of signals illustrated in FIG. 5, the A/D converters 38k start digitization in response to an A/D conversion start signal sent from the local controller 42a. The bus switch 42d switches the RAMs 42b and 42c in response to a switching signal sent from the local controller 42a, and thus uses the RAMs 42b and 42c alternately as a read memory and write memory respectively. After the endoscope shape detection system is energized, data is always acquired in response to a write signal.

Referring back to FIG. 3, the CPU 32 reads digital data written in the two-port memory 42 over an internal bus 46 in response to a control signal sent from the control signal generation circuit unit 40. As shown in FIG. 4, the internal bus 46 is composed of the local bus 43, a PCI controller 44, and a PCI bus 45. The CPU 32 uses a main memory 47 to sample frequencies (fast Fourier transform (FFT)) by processing the digital data as discussed below. Thus, the CPU 32 separates and samples magnetic detection information represented by frequency components having frequencies that correspond to the driving frequencies at which the source coils 14i are driven. The coordinates indicating the spatial positions of the source coils 14i placed in the insertion unit 7 of the electronic endoscope 6 are calculated based on the digital data of the separated magnetic detection information.

An inserted state of the insertion unit 7 of the electronic endoscope 6 is estimated based on the data of the calculated coordinates of the positions. Display data according to which an image of the shape of the endoscope is displayed is produced and output to a video RAM 48. Data written in the video RAM 48 is read by a video signal generation circuit 49, and converted into an analog video signal or a video signal for a computer. The analog video signal is output to the monitor 25. The monitor 25 displays an image of an inserted state of the insertion unit 7 of the electronic endoscope 6 on the display screen according to the analog video signal.

The CPU 32 calculates magnetic detection information associated with the source coils 14i, that is, electromotive forces (amplitudes of sine-wave signals) developed at the four single-core coils 22k constituting each sense coil 22j and phase information. The phase information indicates the positive or negative polarities of the electromotive forces.

A technique for estimating a space, in which source coils are present, from outputs of sense coils, and a technique for estimating the three-dimensional positions of each source coil using two orthogonal sense coils and two parallel sense coils are identical to those described in Japanese Patent Application No. 9-140603.

With respect to the present embodiment, another technique will be described. Specifically, a plurality of sense coils precisely detecting the space in which each source coil exists is selected from among the four sense coils arranged spatially. The three-dimensional position of each source coil is then estimated using the selected sense coils.

Figure 6:
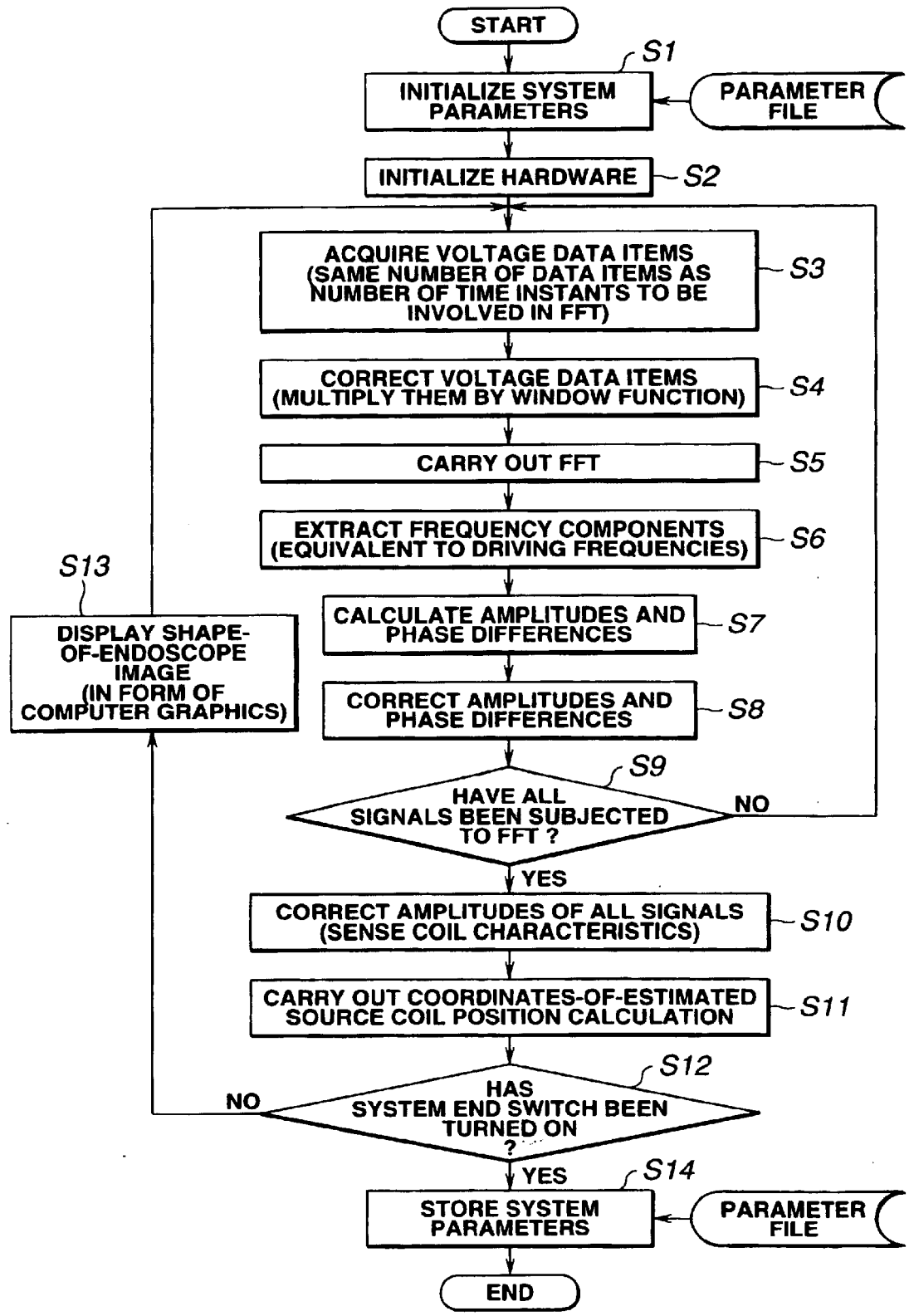

Referring to FIG. 6, after the endoscopic system 1 of the present embodiment is energized, system parameters are initialized based on the data contained in a parameter file at step S1. Hardware is initialized at step S2.

Figure 5:
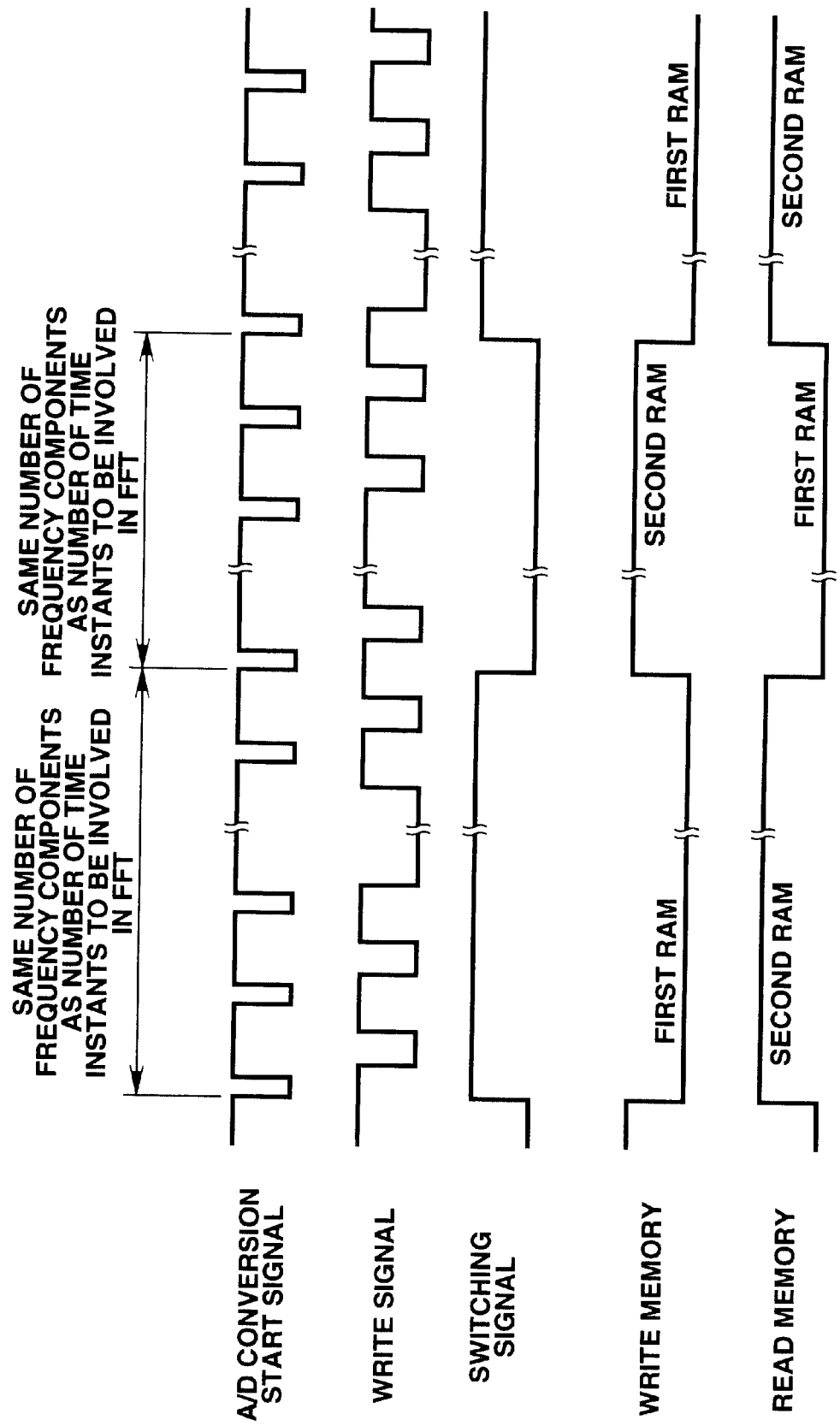

After the endoscopic system is energized, the same number of data as the number of time instants to be involved in FFT is always updated in the two-port memory 42 (see FIG. 5). At step S3, the CPU 32 acquires the same number of data as the number of time instants to be involved in FFT. At step S4, the data are corrected using a window function. The FFT, described below, is carried out at step S5. After the FFT is completed, frequency components having frequencies that correspond to driving frequencies are sampled at step S6. The amplitudes and phase differences of the frequency components are calculated at step S7. The calculated amplitudes and phase differences are corrected at step S8.

At step S9, the CPU 32 determines whether all signals sent from the eight A/D converters 38k have been detected. If the detection has not been completed, control is returned to step S3. If the detection has been completed, the amplitudes of all the signals are corrected according to the characteristics of the sense coils at step S10. At step Sit, the coordinates indicating the estimated positions of the source coils 14i are calculated based on the amplitudes and phase differences of all the signals according to a procedure described [later] below.

Thereafter, at step S12, the CPU 32 determines whether a System End switch of the endoscopic system 1 is turned on. If the switch is not on, endoscope shape detection image display, described below, is carried out at step S13. Control is then returned to step S3. The above processing is repeated. At step S12, if the CPU 32 determines that the System End switch of the endoscopic system 1 is turned on, the system parameters are stored in the parameter file. The system is then de-energized.

Figure 7:
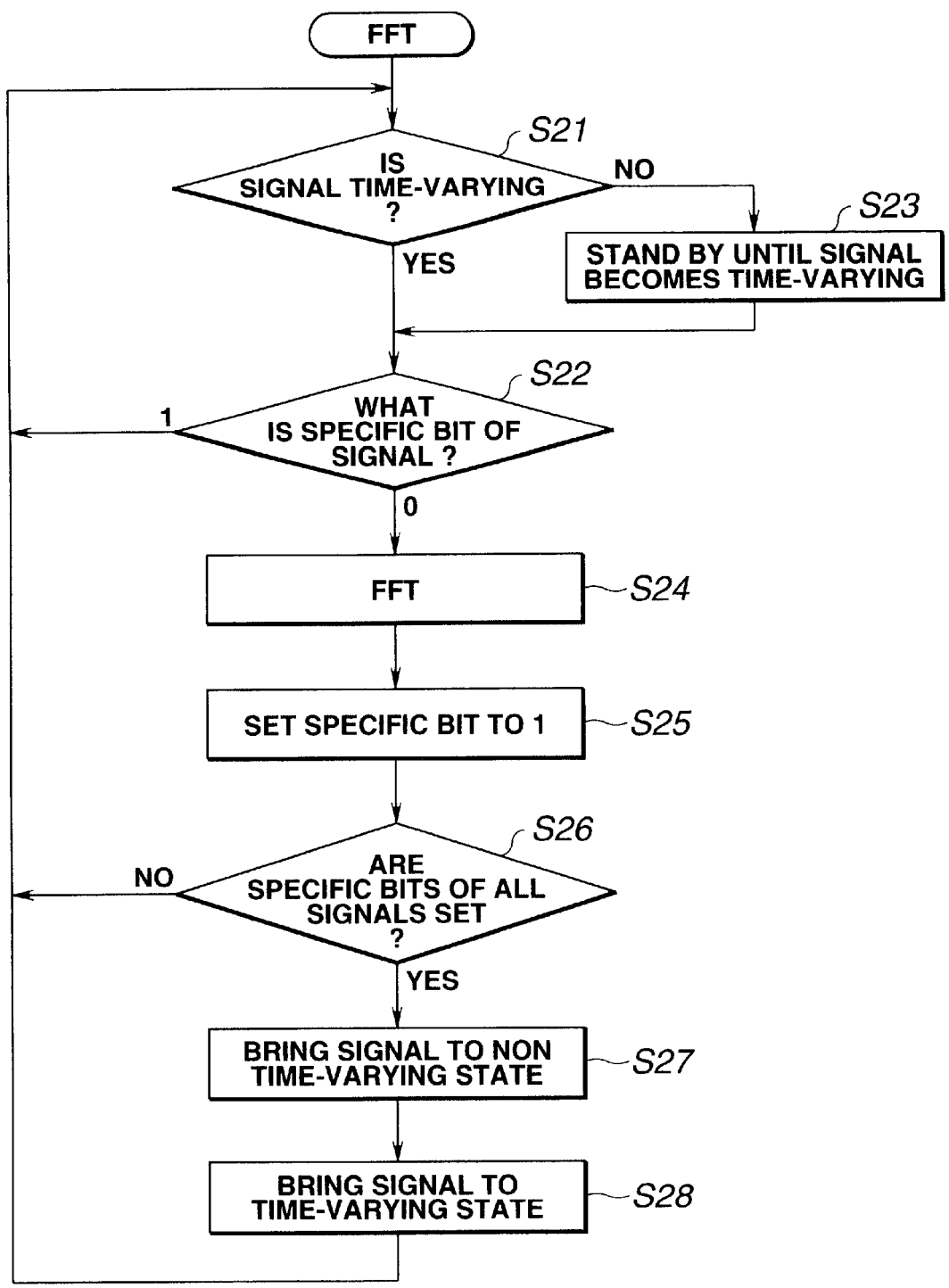

During the FFT of step S5, as described in FIG. 7, the CPU 32 determines whether all the signals are time-varying, that is, whether the signals contain the same number of frequency components as the number of time instants to be involved in FFT. If the signals are time-varying, control is passed to step S22. If the signals are not time-varying, a standby state is established at step S23 and retained until the signals become time-varying. Control is then returned to step S22.

At step S22. the CPU 32 determines specific bits represented by a signal to be subjected to FFT. If the bit is a 0, the signal is processed this time; if the bit is a 1, the signal has already been processed. If the bit is a 0, FFT is carried out at step S24. After the FFT is completed, the bit is set to a 1 at step S25. At step S22, if the CPU 32 determines that the bit is a 1, control is returned to step S21. The processing is repeatedly performed on the subsequent signals. Thus, all signals are subjected to FFT.

At step 26 succeeding step S25, the CPU 32 determines whether specific bits represented by all of the signals are 1s.

If the specific bits of all of the signals are not 1s, control is returned to step S21. Signals representing specific bits that are not 1s are subjected to FFT. At step S26, if the CPU 32 determines that the specific bits represented by all of the signals are 1s, the signals are brought to a non timevarying state at step S27. A standby state is then established. When the signals each come to have the same number of frequency components as the number of time instants to be involved in FFT, the signals are brought to the time-varying state. Control is then returned to step S21.

Figure 8:
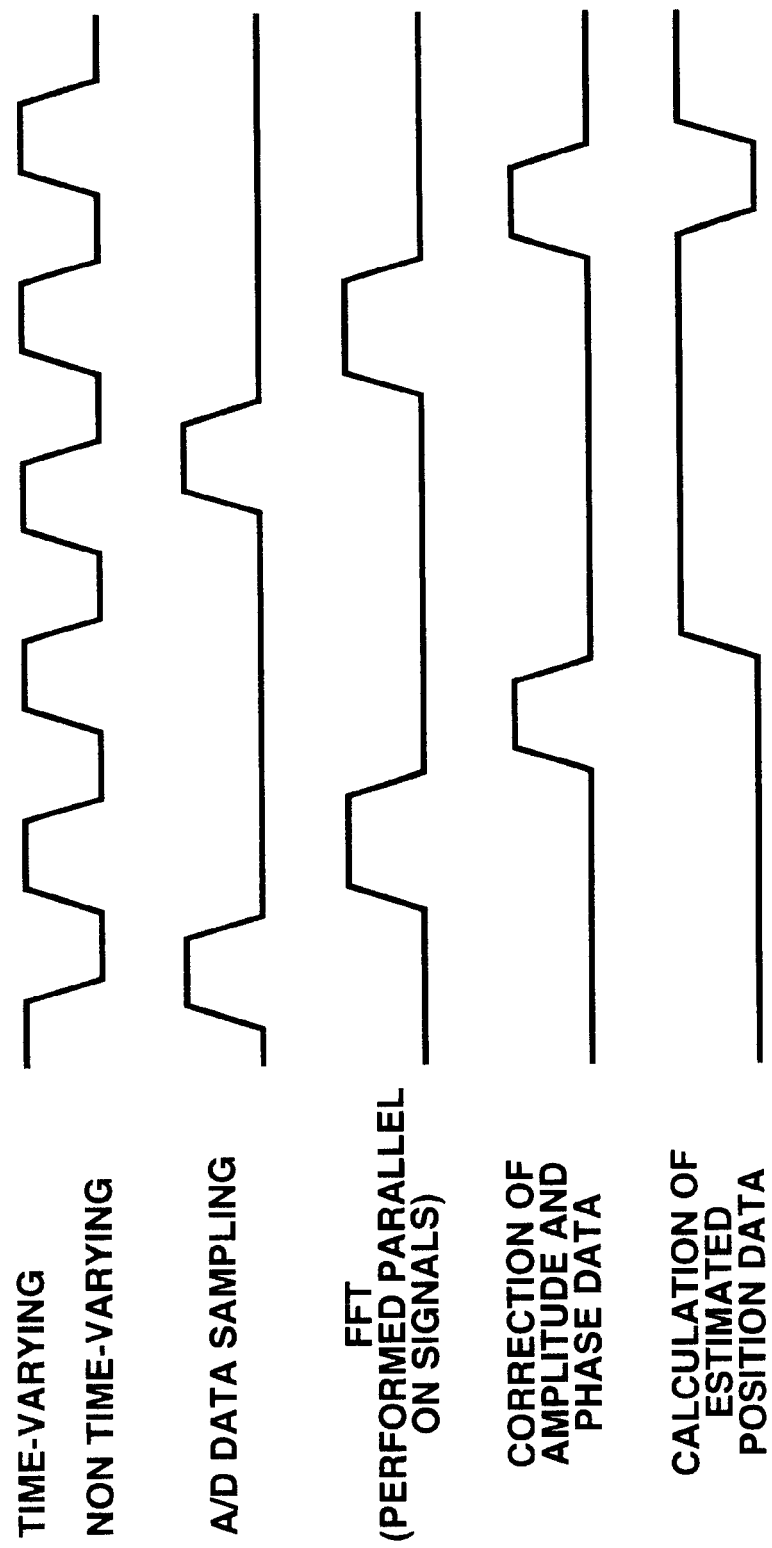

In the processing described in FIG. 6, for attaining a high processing speed, as shown in FIG. 8, each processing unit is carried out as an object of parallel processing. Parallel processing is especially useful in carrying out FFT, an arithmetic operation that requires much processing time repeatedly with processing units having the same contents performing substantially concurrently. By adopting parallel processing, time during which the CPU 32 is available is used effectively in order to attain the high processing speed.

As mentioned above, the CPU 32 carries out frequency sampling based on Fourier transform. What must be overcome is a phenomenon referred to as "leakage" which is dependent on the relationship between the frequencies $f_i$ of sine waves with which the source coils 14$i$ are driven and a width of truncation by which digital data is truncated.

Assuming that a width of truncation by which digital data to be sampled is truncated, which corresponds to the length of a time-varying signal, is equal to integral multiples of all of the driving frequencies $f_i$, the amplitudes and phases of sine waves of frequencies, the amplitude spectrum and phase spectrum, can be calculated accurately. However, if the width of truncation is not equal to an integral multiple of any one of the driving frequencies $f_i$, "leakage" occurs. "Leakage" is reflected as an error in a calculated amplitude and phase. For preventing "leakage," generally, a window function such as a Hamming function is adopted, as discussed in "The Fast Fourier Transform" written by E. Orangbrigham (Sec. 6).

However, the window function is used to merely alleviate an error deriving from "leakage." Moreover, a value minimizing the adverse effect of "leakage" must be adopted as a driving frequency. This may place restrictions on system operations.

Frequency sampling to be performed at step S6 in FIG. 6 will be described below, wherein the adverse effect of the "leakage" is actively corrected by solving a simple algebra of matrices. Consequently, amplitudes and phases can be calculated highly precisely.

For brevity's sake, the discussion following assumes that the results of Fourier transform have already been normalized and multiplied by coefficients according to a window function (rectangular window or the like) and thus compensated for errors.

The Fourier transform, a complex discrete Fourier transform, $F_k$ of a time-varying signal having sine waves of certain frequencies $f_k$ is expressed as follows:

$$F_K = \sum_{n=0}^{N-1} f_n e^{\frac{-j2\pi kn}{N}} \quad (1)$$

where N denotes the length of a sampled discrete signal, and j denotes an imaginary unit. $F_k$ consists of a real part Re$\{F_k\}$ and an imaginary part IM$\{F_k\}$.

The condition that the aforesaid width of truncation by which digital data is truncated is equal to integral multiples of the driving frequencies $f_i$ is equivalent to that frequencies $fs_i$ observed through the discrete Fourier transform are equal to the driving frequencies $f_i$. In other words, the frequencies $f_i$ cannot be observed. If all of the observed frequencies $fs_i$ are equal to each other, the width of truncation corresponds to integral multiples of all the driving frequencies $f_i$. "Leakage" will therefore not occur.

Now, a description will be made of a procedure of defining the Fourier transform $f_i$ that provides frequency components having frequencies that correspond to the driving frequencies $f_i$ that are equal to the observed frequencies $fs_i$ provided by performing the Fourier transform $Fs_i$.

A time-varying signal representing sampled digital data is assumed to be composed of M sine waves having frequencies equal to driving frequencies $f_i$ (i=1, 2, . . . , M). In this case, the relationship between Fourier transforms providing frequency components having frequencies that correspond to the observed frequencies $fs_i$ and driving frequencies $f_i$ respectively can be expressed as follows:

$$\begin{bmatrix} Re\{Fs_1\} \\ Im\{Fs_1\} \\ RE\{Fs_2\} \\ Im\{Fs_2\} \\ \vdots \\ \vdots \\ RE\{Fs_M\} \\ Im\{Fs_M\} \end{bmatrix} = A \cdot \begin{bmatrix} Re\{F_1\} \\ Im\{F_1\} \\ RE\{F_2\} \\ Im\{F_2\} \\ \vdots \\ \vdots \\ RE\{F_M\} \\ Im\{F_M\} \end{bmatrix} \quad (2)$$

wherein A denotes a matrix of 2M×2M in size composed of columns of coefficients defining the magnitudes of leakage occurring depending to the relationship between-each pair of Re$\{F_1\}$ and Im$\{F_1\}$ to Re$\{F_M\}$ and Im$\{F_M\}$ The formula (2) is simplified as follows:

$$Y = A \cdot X \quad (3)$$

where matrices X and Y are matrices of 2M×1 in size consisting of real parts and imaginary parts of the Fourier transforms providing the driving frequencies $f_i$ and observed frequencies $fs_i$ (i=1, 2, [- - -] . . . , M) respectively. When the matrix X is expressed as follows:

$$X = X_1 = [1, 0, 0, 0, \ldots, 0, 0, 0]^t \quad (4)$$

time-varying signal is composed only of sine waves having frequencies that correspond to driving frequencies fl, which are out of phase by π/2, and which have an amplitude 1, thus a cosine wave). "t" denotes transposition. When the matrix X is expressed as follows:

$$X = X_2 = [0, 1, 0, 0, \ldots, 0, 0, 0]^t \quad (5)$$

the time-varying signal is composed only of sine waves having frequencies that correspond to the driving frequencies $f_i$ and have a phase shift of 0. Similarly, when the matrix X is expressed as follows:

$$X = X_3 = [0, 0, 1, 0, \ldots, 0, 0, 0]^t,$$

$$X = X_4 = [0, 0, 0, 1, \ldots, 0, 0, 0]^t,$$

$$\vdots$$

$$\vdots$$

$$X = X_{2M-1} = [0, 0, 0, 0, \ldots, 0, 1, 0]^t,$$

$$X = X_{2m} = [0, 0, 0, 0, \ldots, 0, 0, 1]^t \quad (6)$$

sine waves having frequencies that correspond to the driving frequencies $f_i$ (where i=2, 3, ..., M), which have a phase shift of π/2 or 0, and which have an amplitude 1 are generated as the time-varying signal.

Assuming that when the matrices $X_1$, $X_2$ etc. and $X_{2M}$ are assigned to the formula (3), the matrix Y is expressed as matrices $Y_1$, $Y_2$, etc., and $Y_{2M}$, the matrices $Y_1$, $Y_2$, etc., and $Y_{2M}$ contain "leakage" and express Fourier transforms of digital data represented by time-varying signals having frequency components that are given primarily as the matrices $X_1$, $X_2$, etc. and $X_{2M}$. Herein, "leakage" is construed as such a phenomenon that a matrix X contains a term, which should provide O but actually provides any value other than 0, or that a value that should be a 1 is not actually a 1. The matrices $Y = Y_1$, $Y_2$, etc., and $Y_{2M}$ serve only as terms constituting columns of the matrix A, and are therefore expressed as follows:

$$A = [Y_1, Y_2, Y_3, \ldots, Y_{2M}] \quad (7)$$

Summarily, the matrix X stemming from the Fourier transform $F_1$ that provides the driving frequencies $f_i$, primarily, frequency sampling information used to calculate amplitudes and phases, is expressed as follows:

$$X = A^{-1} \cdot Y \quad (8)$$

The matrix X is calculated as a product of the matrix Y by an inverse matrix $A^{-1}$ of the matrix A. The matrix Y stems from the Fourier transform $Fs_i$ providing the observed frequencies $fs_i$. The matrix A can be, as mentioned above, composed of the matrices $Y = Y_1, Y_2, Y_3, \ldots, Y_{2M}$ stemming from Fourier transforms of time-varying signals having frequency components that are given primarily as the matrices $X = X_1, X_2, X_3$, etc., and $X_{2M}$.

Consequently, the matrix Y stemming from the Fourier transform of a time-varying signal is multiplied by the inverse matrix $A^{-1}$ of the matrix A that is obtained in advance. Frequencies can therefore be sampled more accurately. Eventually, the positions of the source coils $14i$ can be estimated highly precisely.

A matrix Q of 2M×N in size may be defined as a matrix that should stem from Fourier transform and should be multiplied by the inverse matrix $A^{-1}$. Digital data of N×1 long may be multiplied directly by the matrix Q to obtain matrix X.

Thus, the endoscope shape detection system can ensure high precision in estimating the positions of the source coils. This also expands the freedom in selecting driving frequencies.

Next, coordinates-of-estimated source coil position referred to at step S11 in FIG. 6 will be described. To begin with, a procedure of calculating coordinates of the estimated position of each source soil will be described. Thereafter, the contents of processing will be described more particularly.

Figure 9:
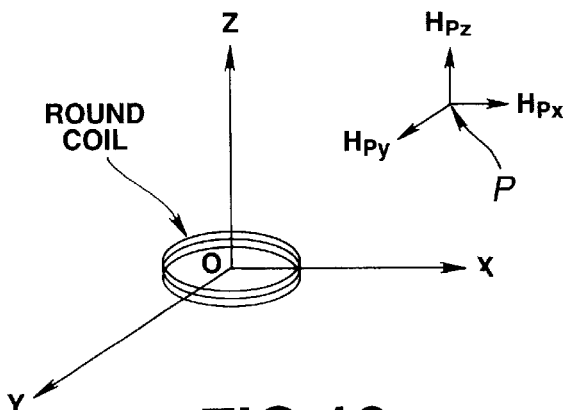

As shown in FIG. 9, a round coil is assumed to have a very small radius and to be very thin. As described in Japanese Unexamined Patent Publication No. 9-84745, when a current flows into the round coil, similarly to when a current flows into a magnetic dipole, a magnetic potential at a point P in a three-dimensional space is expressed as the formula below.

$$U_P \mp \frac{\mu I N_1 \pi a^2}{4\pi\mu} \mp \frac{z}{(x^2+y^2+z^2)^{\frac{3}{2}}} \quad (9)$$

where μ denotes a magnetic permeability, $N_1$ denotes the number of windings of a round coil, a denotes the radius of the round coil, and I denotes a current flowing into the round coil. A magnetic field ($H_{Px}$, $H_{Py}$, $H_{Pz}$) having vectors with the same directions as the X, Y, and Z axes are expressed as follows:

$$H_{Px} = -\frac{\partial U_P}{\partial} = \frac{IN_1 a^2}{4} \frac{3xz}{(x^2+y^2+z^2)^{\frac{5}{2}}} = k_g \frac{3xz}{r^5} \quad (10)$$

$$H_{Py} = -\frac{\partial U_P}{\partial} = \frac{IN_1 a^2}{4} \frac{3yz}{(x^2+y^2+z^2)^{\frac{5}{2}}} = k_g \frac{3yz}{r^5}$$

$$H_{Pz} = -\frac{\partial U_P}{\partial} = \frac{IN_1 a^2}{4} \frac{2z^2-x^2-y^2}{(x^2+y^2+z^2)^{\frac{5}{2}}} = k_g \frac{2z^2-x^2-y^2}{r^5}$$

Figure 10:
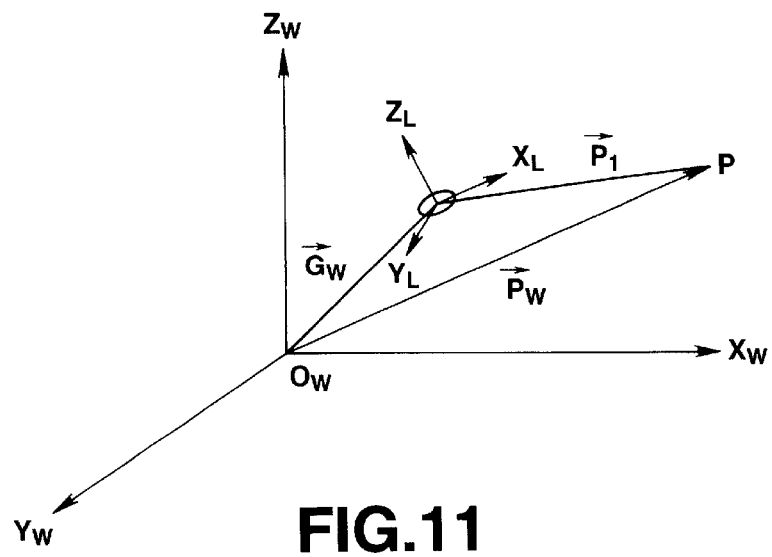

In a three-dimensional space like the one shown in FIG. 10 (hereinafter, a world coordinate system Xw-Yw-Zw), the position of a single-core coil (hereinafter, a source coil) for generating magnetic fields shall be indicated with coordinates ($x_{gw}$, $y_{gw}$, $z_{gw}$). Any position in the three dimensional space shall be point P ($x_{pw}$, $y_{pw}$, $z_{pw}$).

Assuming that a coordinate system defined with the source coil as a reference is a local coordinate system $X_L$-$Y_L$-$Z_L$, the coordinates ($x_{pl}$, $y_{pl}$, $z_{pl}$) indicating the point P in the local coordinate system are expressed as follows:

$$P_1 = R^{-1}(P_W - G_W)$$

$$\begin{pmatrix} x_{Pl} \\ y_{Pl} \\ z_{Pl} \end{pmatrix} = \begin{pmatrix} R_{00} & R_{10} & R_{20} \\ R_{01} & R_{11} & R_{21} \\ R_{02} & R_{12} & R_{22} \end{pmatrix} = \begin{pmatrix} x_{PW} - x_{gW} \\ y_{PW} - y_{gW} \\ z_{PW} - z_{gW} \end{pmatrix} \quad (11)$$

where $P_1$ denotes a vector extending from an origin O to the point P in the local coordinate system, $P_w$ denotes a vector extending from the origin O to the point P in the world coordinate system, $G_w$ denotes a vector oriented towards the position of the source coil in the world coordinate system, and R denotes a rotation matrix.

Figure 11:
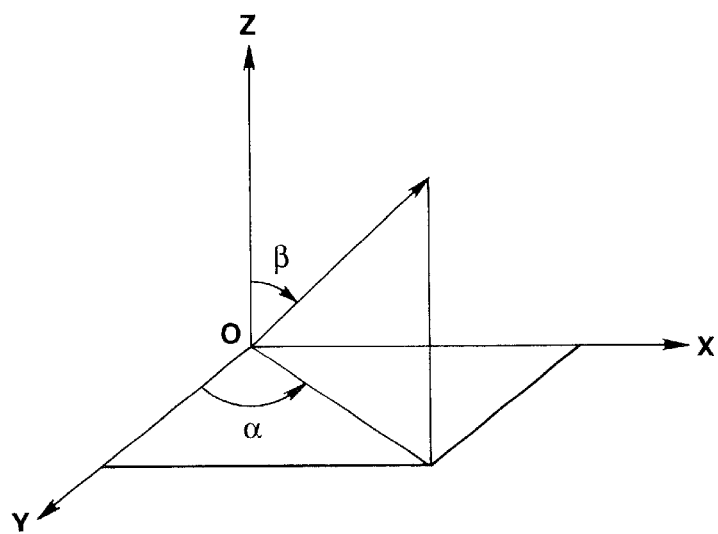

The rotation matrix R in a polar coordinate system shown in FIG. 11 is expressed as follows:

$$R = \begin{pmatrix} R_{00} & R_{10} & R_{02} \\ R_{01} & R_{11} & R_{12} \\ R_{02} & R_{21} & R_{22} \end{pmatrix} = \begin{pmatrix} \cos\alpha & \sin\alpha\cos\beta & \sin\alpha\sin\beta \\ -\sin\alpha & \cos\alpha\cos\beta & \cos\alpha\sin\beta \\ 0 & -\sin\beta & \cos\beta \end{pmatrix} \quad (12)$$

where a denotes a magnitude of rotation with the $Z_w$ axis as a center, and β denotes a magnitude of rotation with the $X_w$ axis as a center. In the local coordinate system with the source coil as a reference, a magnetic field $H_1$ ($H_{pxl}$, $H_{pyl}$, $H_{pzl}$) developed at the point P is expressed based on the formula (10) as follows:

$$H_{Pxl} = \frac{k_g}{r^5} 3 x_{Pl} z_{Pl} \quad (13)$$

$$H_{Pyl} = \frac{k_g}{r^5} 3 y_{Pl} z_{Pl}$$

$$H_{Pzl} = \frac{k_g}{r^5} (2 z_{Pl}^2 - x_{Pl}^2 - y_{Pl}^2)$$

A magnetic field $H_w$ ($H_{PXw}$, $H_{pyw}$, $H_{PZw}$) having components with the same directions as the $X_w$, $Y_w$ and $Z_w$ axes and which is developed at the point P in the world coordinate system is expressed as follows:

$$H_W = RH_l$$

$$H_{PxW} = \frac{k_g}{r^5}[\{2(x_{PW} - x_{gW})^2 - (y_{PW} - y_{gW})^2 - (z_{PW} - z_{gW})^2\}\sin\alpha\sin\beta +$$

$$3(y_{PW} - y_{gW})(x_{PW} - x_{gW})\cos\alpha\sin\beta +$$

$$3(y_{PW} - y_{gW})(x_{PW} - x_{gW})\cos\beta]$$

$$H_{PyW} = \frac{k_g}{r^5}[3(x_{PW} - x_{gW})(y_{PW} - y_{gW})\sin\alpha\sin\beta +$$

$$\{2(y_{PW} - y_{gW})^2 - (z_{PW} - z_{gW})^2 - (x_{PW} - x_{gW})^2\}\cos\alpha\cos\beta +$$

$$3(z_{PW} - z_{gW})(y_{PW} - y_{gW})\cos\beta]$$

$$H_{PzW} = \frac{k_g}{r^5}[3(x_{PW} - x_{gW})(z_{PW} - z_{gW})\sin\alpha\sin\beta + \quad (14)$$

$$3(y_{PW} - y_{gW})(z_{PW} - z_{gW})\cos\alpha\sin\beta +$$

$$\{2(z_{PW} - z_{gW})^2 - (y_{PW} - y_{gW})^2 - (x_{PW} - x_{gW})^2\}\cos\beta]$$

Figure 12:
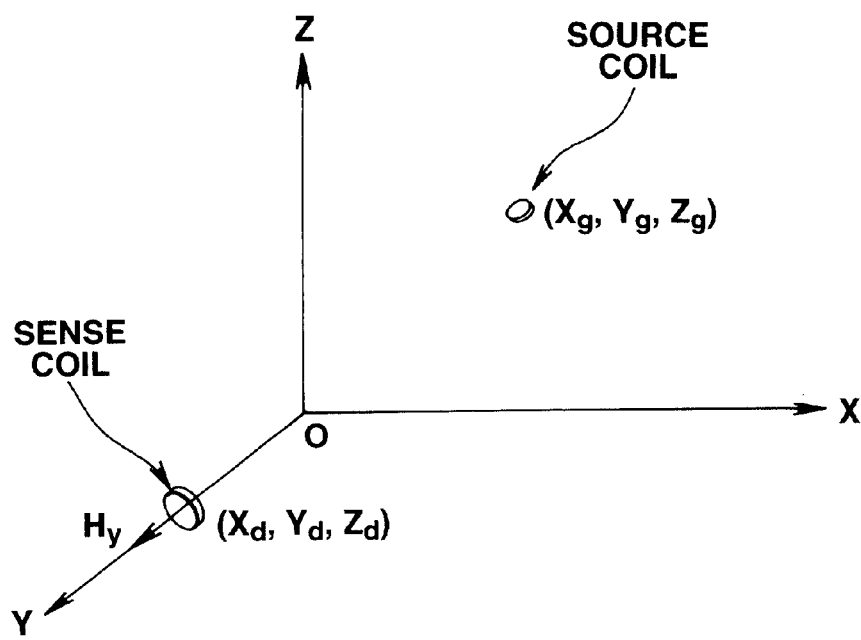

As shown in FIG. 12, assuming that a source coil is placed at a proper position ($X_g$, $Y_g$, $Z_g$) in the three-dimensional space, and that a single-core coil (hereinafter, a sense coil) is placed at a position ($X_d$, $Y_d$, $Z_d$) on the Y axis, the single-core coil has the same direction as the Y axis and detects a magnetic field generated by the source coil as an electromotive force. A magnetic field $H_y$ developed at the position of the sense coil is expressed based on the formula (14) as follows:

$$H_y = \frac{k_g}{r^5}[3(x_d - x_g)(y_d - y_g)\sin\alpha\sin\beta + \quad (15)$$

$$\{2(y_d - y_g)^2 - (z_d - z_g)^2 - (x_d - x_g)^2\}\cos\alpha\sin\beta +$$

$$3(z_d - z_g) - (y_d - y_g)\cos\beta]$$

Furthermore, an electromotive force $V_y$ developed at the sense coil is expressed as a formula below that provides the partial differential of the magnetic field $H_y$ with respect to a time t.

$$V_y = -\mu N_2 \pi b^2 \frac{d}{dt} H_y \quad (16)$$

$$= -\mu N_2 \pi b^2 \frac{\omega I_{max}\cos(\omega + \varphi)N_1 a^2}{4r^5}[3(x_d - x_g)(y_d - y_g)\sin\alpha\sin\beta +$$

$$\{2(y_d - y_g)^2 - (z_d - z_g)^2 - (x_d - x_g)^2\}\cos\alpha\sin\beta +$$

$$3(z_d - z_g)(y_d - y_g)\cos\beta]$$

$$= \frac{k_s}{r^5}[3(x_d - x_g)(y_d - y_g)\sin\alpha\sin\beta + \{2(y_d - y_g)^2 - (z_d - z_g)^2 -$$

$$(x_d - x_g)^2\}\cos\alpha\sin\beta + 3(z_d - z_g)(y_d - y_g)\cos\beta]$$

where $N_2$ denotes the number of windings of the sense coil. Calculating $\omega I_{max}\cos(\omega t+\phi)$ provides a value by differentiating a current $I_{max}\sin(\omega t+\phi)$ flowing into the source coil with respect to the time t.

Figure 13:
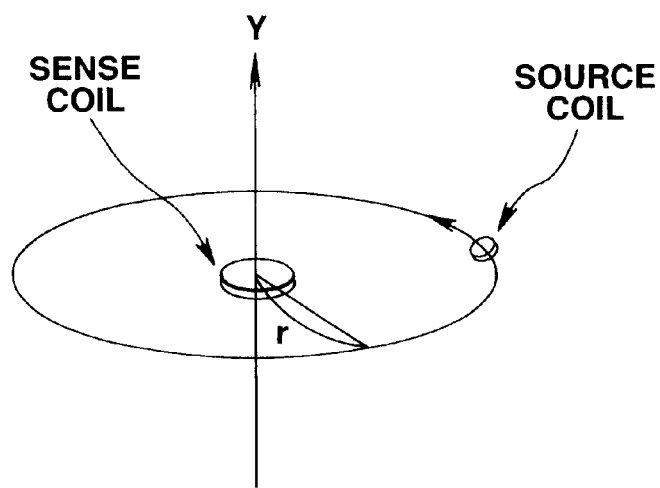

As shown in FIG. 13, assuming that a circle is drawn with the Y axis as a center and that the source coil is moved along the circle, a constant electromotive force is detected at the sense coil all the time. However, the orientation of the sense coil relative to the Y axis remains unchanged.

Therefore, when a plurality of sense coils is lined on the Y axis, a space in which the source coil exists, that is, the circle with the Y axis as a center can be estimated.

Figure 14:
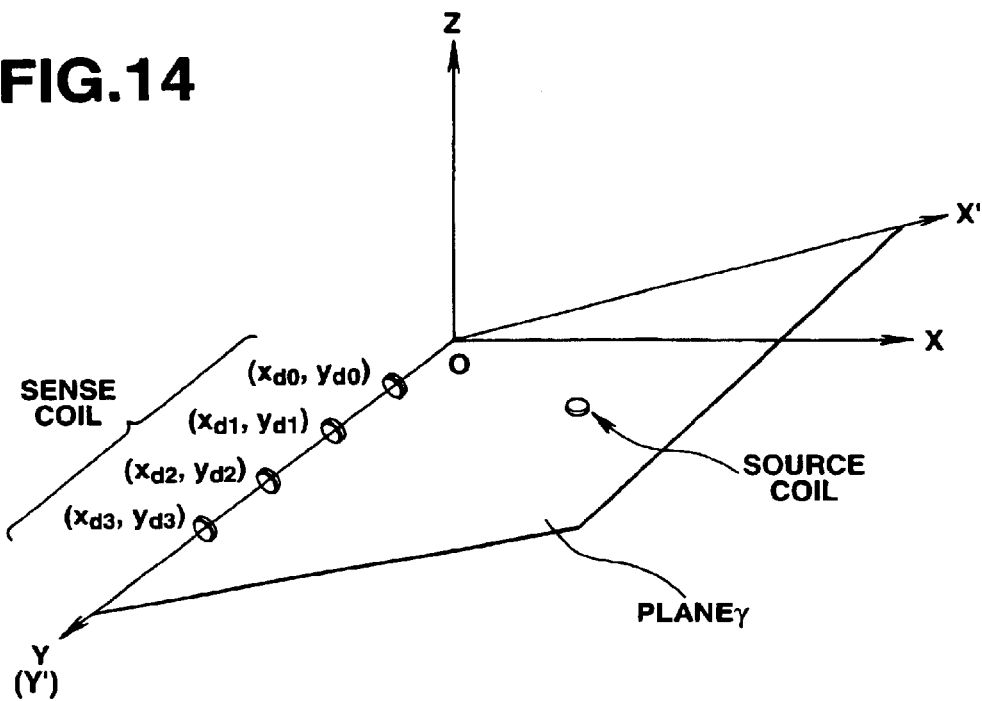

As shown in FIG. 14, assuming that four sense coils are placed on the Y axis and that a coordinate system defined on a plane y determined with the Y axis and the position of the source coil is X'-Y', an electromotive force $V_{yi}$ developed at each sense coil is expressed as follows:

$$V_{yi} = \frac{k_{si}}{r_i^5}[3(x_{di} - x'_g)(y_{di} - y'_g)g_x + \{2(y_{di} - y'_g)^2 - (x_{di} - x'_g)^2\}g_y] \quad (17)$$

where $g_x$ and $g_y$ denote terms specified with the plane y and the orientation of the source coil, $x_{di}$ and $y_{di}$ indicate the position of each sense coil in the coordinate system X'-Y', and $x_g'$ and $y_g'$ indicate the position of the source coil.

The formula (17) includes four unknowns $g_x$, $g_y$, $x_g'$, and $y_g'$. When at least four sense coils are aligned along the Y axis, four equations are defined. The position of the source coil in the coordinate system X'-Y' can be determined by solving the equations.

Figure 15A:
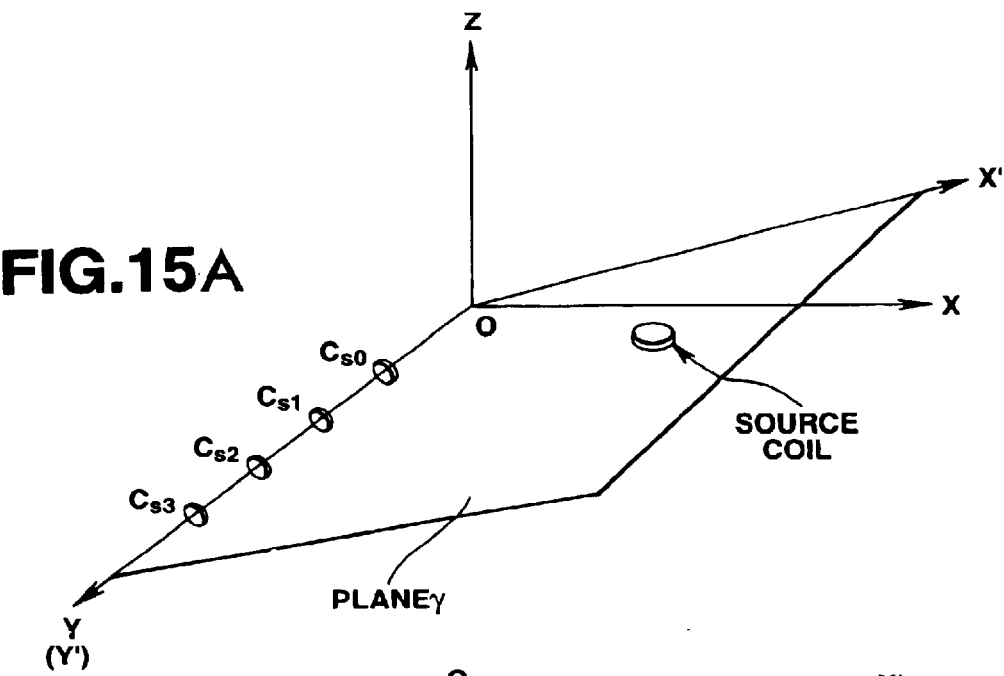
FIGS. 15A and 15B are a diagrammatic views of the coordinates-of-estimated source coil position calculation method of FIG. 6.
Figure 15B:
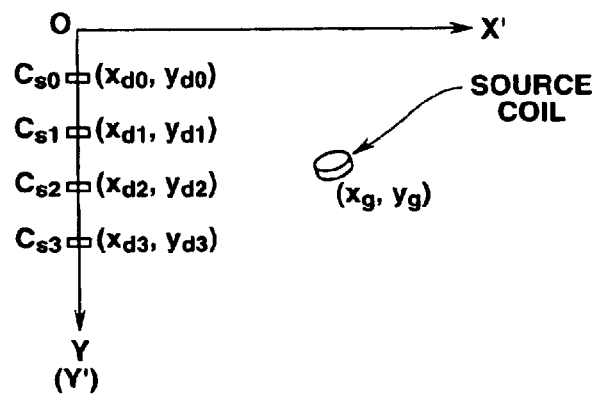

Specifically, as shown in FIGS. 15A and 15B, a source coil for generating magnetic fields is placed at a proper position in a three-dimensional space, and four sense coils are placed along the Y axis. A plane γ determined with the source coil and four sense coils is regarded as an X'-Y' plane. The position of the source coil shall be indicated as ($x_g$, $y_g$), and the positions of the sense coils shall be indicated as ($x_{d0}$, $y_{d0}$), ($x_{d1}$, $y_{d1}$), ($x_{d2}$, $y_{d2}$), and ($x_{d3}$, $y_{d3}$), respectively.

Electromotive forces $V_{y0}$, $V_{y1}$, $V_{y2}$, and $V_{y3}$ developed at the sense coils $C_{s0}$, $C_{s1}$, $C_{s2}$, and $C_{s3}$ are expressed based on the formula (17) as follows:

$$V_{y0} = \frac{k_{s0}}{r_0^5}[3(x_{d0} - x_g)(y_{d0} - y_g)g_x + \{2(y_{d0} - y_g)^2 - (x_{d0} - x_g)^2\}g_y] \quad (18)$$

$$V_{y1} = \frac{k_{s1}}{r_1^5}[3(x_{d1} - x_g)(y_{d1} - y_g)g_x + \{2(y_{d1} - y_g)^2 - (x_{d1} - x_g)^2\}g_y] \quad (19)$$

$$V_{y2} = \frac{k_{s2}}{r_2^5}[3(x_{d2} - x_g)(y_{d2} - y_g)g_x + \{2(y_{d2} - y_g)^2 - (x_{d2} - x_g)^2\}g_y] \quad (20)$$

$$V_{y3} = \frac{k_{s3}}{r_3^5}[3(x_{d3} - x_g)(y_{d3} - y_g)g_x + \{2(y_{d3} - y_g)^2 - (x_{d3} - x_g)^2\}g_y] \quad (21)$$

$k_{si}$ (i=0, 1, 2, 3) denotes a constant determined with a current flowing into the source coil and the number of windings of each sense coil.

The formulas (19) and (20) are rewritten into matrix format as follows:

$$\begin{pmatrix} V_{y1} \\ V_{y2} \end{pmatrix} = \quad (22)$$

$$\begin{pmatrix} \frac{k_{s1}}{r_1^5}3(x_{d1} - x_g)(y_{d1} - y_g) & \frac{k_{s1}}{r_1^5}\{2(y_{d1} - y_g) - (x_{d1} - x_g)^2\} \\ \frac{k_{s2}}{r_2^5}3(x_{d2} - x_g)(y_{d2} - y_g) & \frac{k_{s2}}{r_2^5}\{2(y_{d2} - y_g) - (x_{d2} - x_g)^2\} \end{pmatrix} \begin{pmatrix} g_x \\ g_y \end{pmatrix}$$

The terms specified with the positions of the sense coils and source coil are rewritten as a matrix A as follows:

$$\begin{pmatrix} V_{y1} \\ V_{y2} \end{pmatrix} = \begin{pmatrix} a_{00} & a_{01} \\ a_{10} & a_{11} \end{pmatrix} \begin{pmatrix} g_x \\ g_y \end{pmatrix} \quad (23)$$

$$A = \begin{pmatrix} a_{00} & a_{01} \\ a_{10} & a_{11} \end{pmatrix}$$

An inverse matrix $A^{-1}$ of the matrix A is defined according to Cramer's formula as follows:

$$A^{-1} = \frac{1}{a_{00}a_{11} - a_{00}a_{10}} \begin{pmatrix} a_{11} & -a_{01} \\ -a_{10} & a_{00} \end{pmatrix} \quad (24)$$

Consequently, $g_x$ and $g_y$ are expressed as follows:

$$\begin{pmatrix} g_x \\ g_y \end{pmatrix} = \frac{1}{a_{00}a_{11} - a_{01}a_{10}} \begin{pmatrix} a_{11} & -a_{01} \\ -a_{10} & a_{00} \end{pmatrix} \begin{pmatrix} V_{y1} \\ V_{y2} \end{pmatrix} \quad (25)$$

The determinant of the inverse matrix $A^{-1}$ is solved, and $g_x$ and $g_y$ are assigned to the formulas (18) and (21).

$$V_{y0} = \frac{K_1 R_1 (2Y_{02} + X_{02})(XY_{02} - XY_{20}) - K_2 R_2 (2Y_{01} + X_{01})(XY_{01} - XY_{10})}{R_3 (2Y_{12} + X_{12})(XY_{12} - XY_{21})} \quad (26)$$

$$V_{y3} = \frac{K_3 R_1 (2Y_{32} + X_{32})(XY_{32} - XY_{23}) - K_4 R_2 (2Y_{31} + X_{31})(XY_{31} - XY_{13})}{R_3 (2Y_{12} + X_{12})(XY_{12} - XY_{21})} \quad (27)$$

Thus, $$K_1 = \frac{k_{s0}}{k_{s1}} V_{y1} \quad K_2 = \frac{k_{s0}}{k_{s2}} V_{y2} \quad K_3 = \frac{k_{s3}}{k_{s1}} V_{y1} \quad K_4 = \frac{k_{s3}}{k_{s2}} V_{y2} \quad (28)$$

$$R_0 = r_0^5 \quad R_1 = r_1^5 \quad R_2 = r_2^5 \quad R_3 = r_3^5$$

$$X_{01} = (x_{d0} - x_g)(x_{d1} - x_g) \quad X_{02} = (x_{d0} - x_g)(x_{d2} - x_g)$$

$$X_{31} = (x_{d3} - x_g)(x_{d1} - x_g) \quad X_{32} = (x_{d3} - x_g)(x_{d2} - x_g)$$

$$Y_{01} = (y_{d0} - y_g)(y_{d1} - y_g) \quad Y_{02} = (y_{d0} - y_g)(y_{d2} - y_g)$$

$$Y_{31} = (y_{d3} - y_g)(y_{d1} - y_g) \quad Y_{32} = (y_{d3} - y_g)(y_{d2} - y_g)$$

$$X_{12} = (x_{d1} - x_g)(x_{d2} - x_g) \quad Y_{12} = (y_{d1} - y_g)(y_{d2} - y_g)$$

$$XY_{01} = (x_{d0} - x_g)(y_{d1} - y_g) \quad XY_{10} = (x_{d1} - x_g)(y_{d0} - y_g)$$

$$XY_{02} = (x_{d0} - x_g)(y_{d2} - y_g) \quad XY_{20} = (x_{d2} - x_g)(y_{d0} - y_g)$$

$$XY_{31} = (x_{d3} - x_g)(y_{d1} - y_g) \quad XY_{13} = (x_{d1} - x_g)(y_{d3} - y_g)$$

$$XY_{32} = (x_{d3} - x_g)(y_{d2} - y_g) \quad XY_{23} = (x_{d2} - x_g)(y_{d3} - y_g)$$

$$XY_{12} = (x_{d1} - x_g)(y_{d2} - y_g) \quad XY_{21} = (x_{d2} - x_g)(y_{d1} - y_g)$$

The formulas (26) and (27) are nonlinear equations having unknowns $x_g$ and $y_g$. $x_g$ and $y_g$ are obtained by solving the two equations according to Newton's method.

Assuming that electromotive forces developed at sense coils are $V_{y0}'$ and $V_{y3}'$, respectively, and that $V_{y0}'$ and $V_{y3}'$ given by the formulas (26) and (27) are estimated values, differences are expressed as follows:

$$f_1(X_g, Y_g) = V_{y0} - V_{y0}' \quad (29)$$

$$f_2(X_g, Y_g) = V_{y3} - V_{y3}' \quad (30)$$

Assuming that the electromotive forces $V_{y0}'$ and $V_{y3}'$ developed at the sense coils are measured accurately and that $x_g$ and $y_g$ used to calculate the estimated values $V_{y0}$ and $V_{y3}$ perfectly agree with those indicating the position of the source coil, the right sides of the formulas (29) and (30) sum to 0.

For estimating the position of the source coil, therefore, $x_g$ and $y_g$ with which $f_1=0$ and $f_2=0$ are satisfied should be obtained.

The partial differentials of $f_1$ and $f_2$ are solved with respect to $x_g$ and $y_g$ respectively, whereby a Jacobian determinant J is defined as follows:

$$J = \begin{pmatrix} \frac{\partial f_1}{\partial x_g} & \frac{\partial f_1}{\partial y_g} \\ \frac{\partial f_2}{\partial x_g} & \frac{\partial f_2}{\partial y_g} \end{pmatrix} \quad (31)$$

An inverse matrix $J^{-1}$ of the Jacobian determinant J is defined according to Cramer's formula, and regarded as a matrix C.

$$J^{-1} = \begin{pmatrix} C_{00} & C_{01} \\ C_{10} & C_{11} \end{pmatrix} \quad (32)$$

Newton's method is an iteration of a nonlinear equation $f(X)=0$ and defined as follows:

$$X^{(k+1)} = X^{(k)} - \Delta X^{(k)}$$

A correction value $\Delta X^{(k)}$ is determined while being linearly approximated to the solution of $f(X)$ calculated with $X^{(k)}$ specified as X.

$$\Delta X^{(k)} = J^{-1}(X^{(k)}) f(X^{(k)})$$

Assuming that proper initial values of $x_g$ and $y_g$ are $x_{g0}$ and $y_{g0}$ respectively, the approximate values of $x_g$ and $y_g$ $x_{g1}$ and $y_{g1}$, are obtained according to the following formulas:

$$x_{g1} = x_{g0} - \{C_{00} f_1(x_{g0}, y_{g0}) + C_{01} f_2(x_{g0}, y_{g0})\} \quad (33)$$

$$y_{g1} = y_{g0} - \{C_{10} f_1(x_{g0}, y_{g0}) + C_{11} f_2(x_{g0}, y_{g0})\} \quad (34)$$

$x_{g1}$ and $y_{g1}$ are assigned to the formulas (29) and (30). If $f_1$ and $f_2$ are not equal to 0, $x_{g1}$ and $y_{g1}$ are specified as $x_{g0}$ and $y_{g0}$ in the formulas (33) and (34). This results in xg2 and yg2, respectively. Thereafter, $f_1$ and $f_2$ are obtained again. This operation is repeated, whereby $f_1$ and $f_2$ each are approximated as 0. Consequently, $x_g$ and $y_g$ are obtained.

Newton's method is adopted to solve the nonlinear equations. Alternatively, the least squares method may be adopted.

The position of a source coil on a plane defined with sense coils and the source coil can be estimated from outputs of the sense coils each having at least four single-core coils aligned along the same straight line. In other words, a position of a circle in a three-dimensional space in which the source coil exists can be estimated.

Out of the at least four sense coils aligned along the same straight line, at least two sense coils are arranged in a space to estimate the three-dimensional position of a source coil as a point of intersection between two circles in the space.

Each sense coil 22k consists of four single-core coils. The largest output among the outputs of the four single-core coils is acquired as a maximum output, and two sense coils having maximum outputs that are the largest are selected.

The three-dimensional position of each source coil is estimated according to the condition for placement of the two selected sense coils, that is, whether the two sense coils are placed orthogonally or parallel.

In the present embodiment, a point of intersection between two circles in the space is detected. If the two circles do not intersect, two circumferential points separated by the shortest distance are detected. The two circles may not intersect due to noise or the like.

Figure 16:
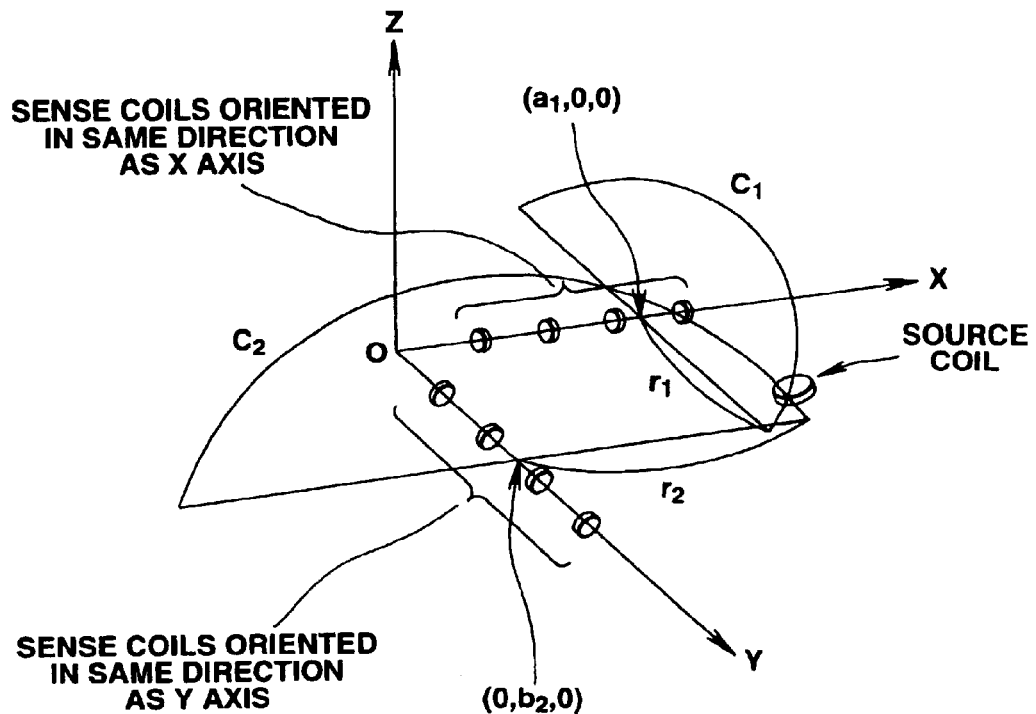

To begin with, a procedure of estimating the three-dimensional position of each source coil will be described on the assumption that two selected sense coils are placed orthogonally. As shown in FIG. 16, a source coil is placed at a proper position, and sense coils are aligned along the X axis and Y axis alike. Circles $C_1$ and $C_2$ on which the source coil exists are determined from the outputs of the sense coils.

Assuming that $C_1$ is a circle lying on a plane $x=a_1$, centered on $(a_1, 0, 0)$, and having a radius $r_1$, and that $C_2$ is a circle lying on a plane $y=b_2$, centered on $(0, b_2, 0)$ and having a radius $r_2$, then:

$$C_1: (x-a_1)^2+y^2+z^2=r_1^2 \qquad (35)$$

$$C_2: x^2+(y-b_2)^2+z^2=r_2^2 \qquad (36)$$

Figure 17:
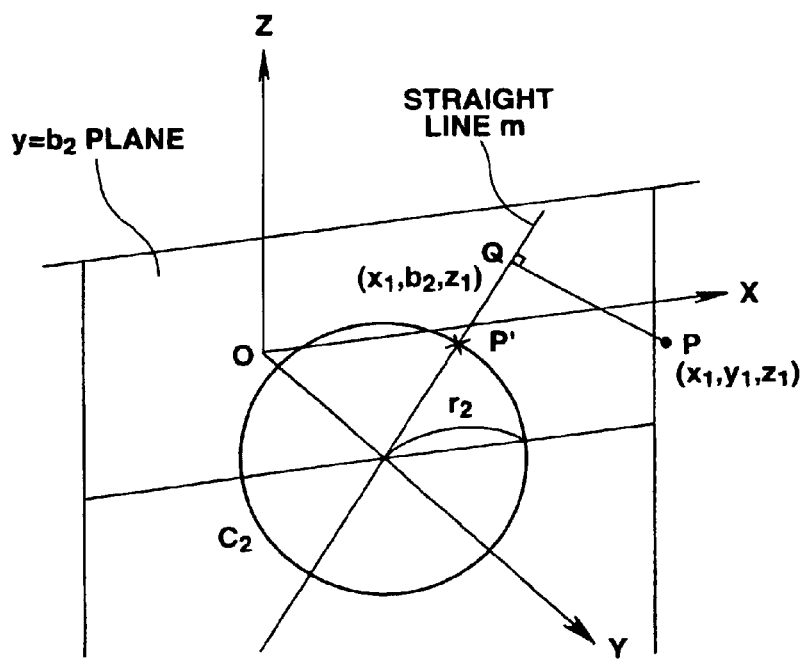

As shown in FIG. 17, the coordinates of a point Q descending perpendicularly from any point $P(x_1, y_1, z_1,)$ to the plane $y=b_2$ are $(x_1, b_2, z_1)$.

A straight line m lying on the plane $y=b_2$ end passing through the point Q and the center $(O. b_2, O)$ of the circle $C_2$ is expressed using a real variable t as follows:

$$x=x_1+tx_1$$
$$y=b_2$$
$$z=z_1+tz_1 \qquad (37)$$

When the formula (35) is assigned to the equation (36) of the circle $C_2$, $$(x_1+tx_1)^2=(z_1+tz_1)^2=r_2^2 \qquad (38)$$

The real variable t is obtained as follows:

$$t = \pm \frac{r_2}{(x_1^2+z_1^2)^{\frac{1}{2}}} - 1 \qquad (39)$$

The straight line m and circle $C_2$ intersect at two points. Herein, $t>0$ shall be satisfied. When the formula (39) is assigned to the formula (37), $$x = \frac{x_1 r_2}{(x_1^2+z_1^2)^{\frac{1}{2}}} \qquad (40)$$
$$y = b_2$$
$$z = \frac{z_1 r_2}{(x_1^2+z_1^2)^{\frac{1}{2}}}$$

The formula (40) expresses, as shown in FIG. 17, a point P' on the circle $C_2$ nearest the point P.

If the point P $(x_1, y_1, z_1)$ lies on the circle $C_1$, $x_1, y_1,$ and $z_1$: are expressed as follows:

$$x_1 = a_1$$
$$y_1 = r_1 \cos\theta$$
$$z_1 = r_1 \sin\theta \qquad (41)$$

The formula (41) is assigned to the formula (40), thus defining the formula (42).

$$x = \frac{a_1 r_2}{(a_1^2 + r_1^2 \sin^2\theta)^{\frac{1}{2}}} \qquad (42)$$
$$y = b_2$$
$$z = \frac{r_1 r_2 \sin\theta}{(a_1^2 + r_1^2 \sin^2\theta)^{\frac{1}{2}}}$$

The square D of the distance between a point on the circle $C_1$ and a point on the circle $C_2$ is expressed as follows:

$$D = \left\{\frac{a_1 r_2}{(a_1^2+r_1^2\sin^2\theta)^{\frac{1}{2}}} - a_1\right\}^2 + (b_2 - r_1\cos\theta)^2 + \qquad (43)$$
$$\left\{\frac{r_1 r_2 \sin\theta}{(a_1^2+r_1^2\sin^2\theta)^{\frac{1}{2}}} - r_1\sin\theta\right\}^2$$
$$= \left\{r_2 - (a_1^2+r_1^2\sin^2\theta)^{\frac{1}{2}}\right\}^2 + (b_2 - r_1\cos\theta)^2$$

When the formula (43) is differentiated with respect to θ, the following formula results:

$$\frac{dD}{dD} = -2\left\{\frac{r_1 r_2 \cos\theta}{(a_1^2+r_1^2\sin^2\theta)^{\frac{1}{2}}} - b_2\right\} r_1 \sin\theta \qquad (44)$$

The condition under which the solution of the formula (44) is 0 is as follows:

$$\sin\theta=0$$

However, the two circles do not intersect at any point, and $r_1<a_1$ and $r_1<b_2$, $r_1<b_2$, or $r_2<a_1$ is established. An alternative condition is expressed as follows:

$$\frac{r_1 r_2 \cos\theta}{(a_1^2+r_1^2\sin^2\theta)^{\frac{1}{2}}} - b_2 = 0 \qquad (45)$$

Solving the formula (45) for θ is as follows:

$$r_1 r_2 \cos\theta = b_2(a_1^2+r_1^2\sin^2\theta)^{\frac{1}{2}} \qquad (46)$$
$$\cos^2\theta = \frac{(b_2^2 a_1^2 + b_2^2 r_1^2)}{(r_1^2 r_2^2 + b_2^2 r_1^2)}$$
$$\theta = \cos^{-1}\left\{\pm\sqrt{\frac{(b_2^2 a_1^2 + b_2^2 r_1^2)}{(r_1^2 r_2^2 + b_2^2 r_1^2)}}\right\}$$

The coordinates of the points on the circumferences of the circles $C_1$ and $C_2$ can be derived from the formulas (46), (40) and (41).

Assuming that the point on the circle $C_1$ has the coordinates $(x_{c1}, y_{c2}, z_{c1})$ and the point on the circle $c_2$ has the coordinates $(x_{c2}, y_{c2}, z_{c2})$, the position $(x_g, y_g, z_g)$ of the source coil can be obtained as averages of the coordinates of the points on the circles as follows:

$$x_g = \frac{x_{c1} + x_{c2}}{2}$$

$$y_g = \frac{y_{c1} + y_{c2}}{2}$$  (47)

$$z_g = \frac{z_{c1} + z_{c2}}{2}$$

Consequently, the spatial position of the source coil can be estimated using two sense coils each having four single-core coils aligned along the same straight line.

Figure 19:
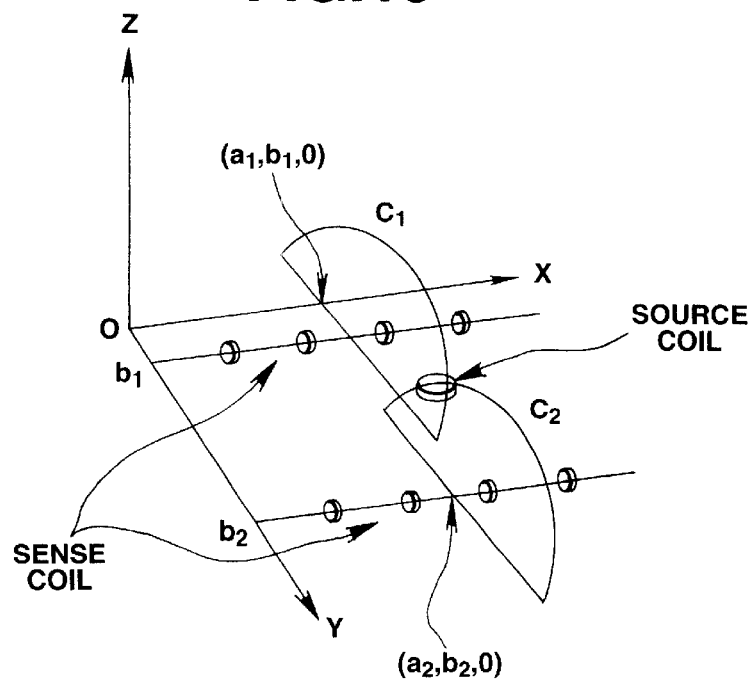

As shown in FIG. 19, sense coils are aligned parallely in order to estimate the position of a source coil. A circle $C_1$ determined using the sense coils is expressed as follows:

$$x = a_1$$

$$y = b_1 + r_1 \cos \theta$$

$$z = r_1 \sin \theta$$  (48)

A circle $C_2$ is expressed as follows:

$$x = a_2$$

$$y = b_2 + r_2 \cos \phi$$

$$z = r_2 \sin \phi$$  (49)

Assuming that a point $P_1$ on the circle $C_1$ has the coordinates $(x_1, y_1, z_1.)$ and a point on the circle $C_2$ has the coordinates $(x_2, y_2, z_2)$, the condition under which the points on the circles $C_1$ and $C_2$ intersect or approach most closely is provided as follows:

$$y_1 = y_2 \text{ and } z_1 = z_2$$  (50)

When the formulas (48) and (49) are solved with the conditional expression (50), the following formulas result:

$$b_1 + r_1 \cos \theta = b_2 + r_2 \cos \theta$$  (51)

$$r_1 \sin \theta = r_2 \sin \phi$$  (52)

When both the sides of the formula (52) are squared, $$r_1^2(1 - \cos^2 \theta) = r_2^2(1 - \cos^2 \phi)$$  (52a)

Solving the formula (51) with this formula, such may be rewritten as:

$$\cos \theta = \frac{r_2^2 - r_1^2 - (b_1 - b_2)^2}{2r_1(b_1 - b_2)}$$  (53)

$$\theta = \cos^{-1}\left\{\frac{r_2^2 - r_1^2 - (b_1 - b_2)^2}{2r_1(b_1 - b_2)}\right\}$$

A point of intersection $(a_1 = a_2)$ between the circles $C_1$ and $C_2$ or two most closely located points can be determined from the formulas (48) and (53), the formulas (49) and (52), and the formula (53).

When the two most closely located points on the circles $C_1$ and $C_2$ are determined, similarly to when the circles intersect, the x coordinates of the points are averaged in order to estimate one x coordinate. One y coordinate and one z coordinate are determined according to the formula (53).

Next, a description will be made of coordinates-of-estimated source coil position calculation carried out by the CPU 32 according to the aforesaid method.

As shown in FIG. 1, four sense coils 22$j$, each having four single-core coils aligned along the same straight line, are incorporated in the couch 4. The probe 15, in which the source coils 14$i$ made by concatenating sixteen single-core coils are placed, is passed through the forceps channel 12 in the electronic endoscope 6.

In the endoscope shape detection system 3, the maximum amplitudes and phases of voltages developed at the sense coils 22$j$ associated with the source coils 14$i$ are measured in order to determine the positive or negative polarities of the voltages, which are attained at the maximum amplitudes, according to the phases.

Figure 20:
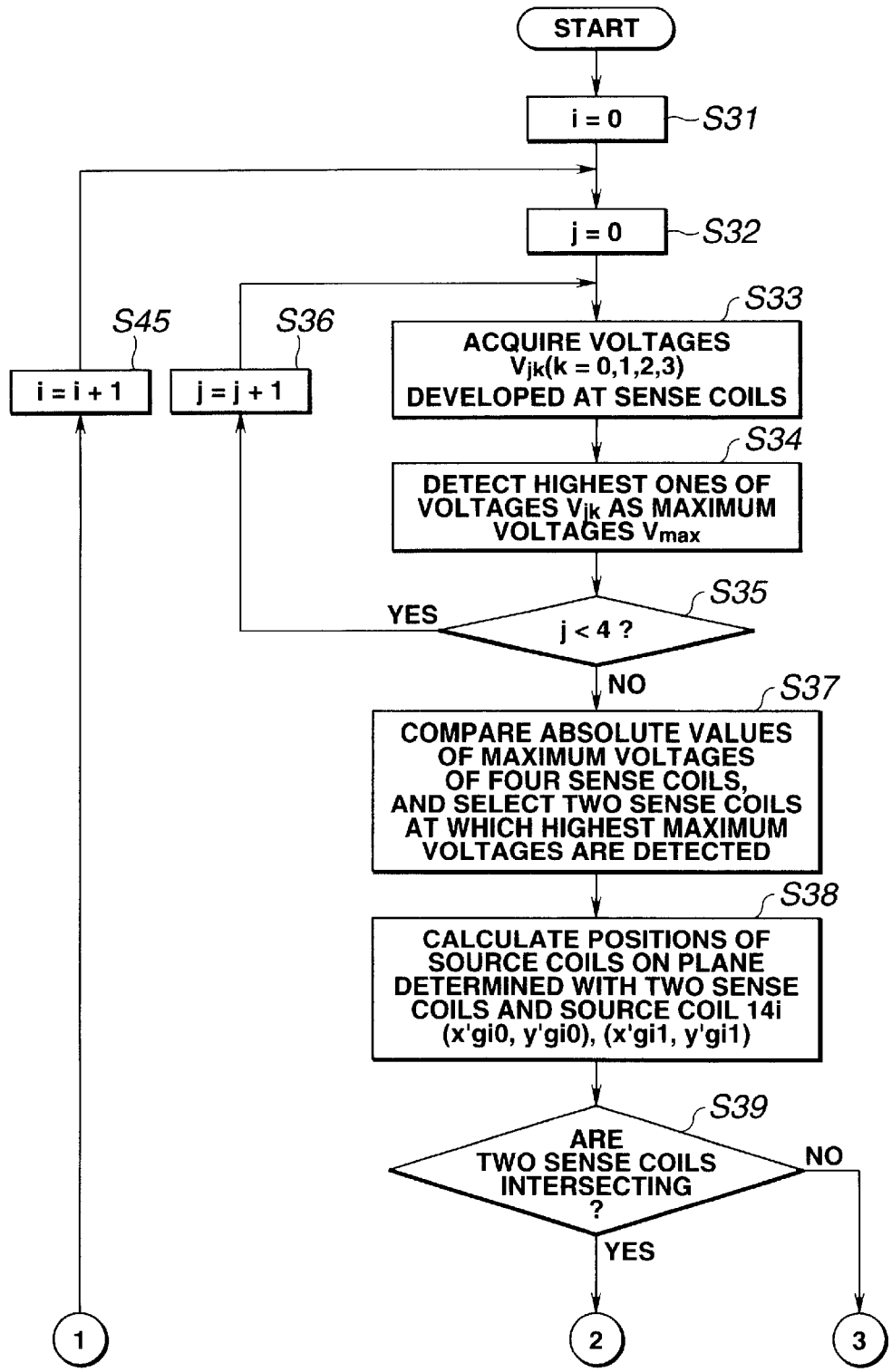

Referring to FIG. 20, the CPU 32 initializes the serial numbers of those of the source coils 14$i$ and sense coils 22$j$, which are treated first, at step S32 and step S32. At step S31, i is reset to 0. At step S32, j is reset to 0.

First, the 0-th source coil and 0-th sense coil are selected. Voltages $V_{00}$, $V_{01}$, $V_{02}$, and $V_{03}$ developed at the four single-core coils of the 0-th sense coil are acquired at step S33. At step S34, the highest one of the four acquired voltages acquired at step S33 is detected as a maximum voltage $V = _{max}[j]$.

At step S35, the CPU 32 determines whether the maximum voltages of all sense coils have been detected. If the detection has not been completed, control is passed to step S36 and j is incremented by one. Control is then returned to step S33.

When step S35 is completed, control is passed to step S37. The absolute values of the maximum voltages detected at the sense coils are compared. Two sense coils at which the highest maximum voltages are detected are selected.

At step S38, the two-dimensional positions $(X'_{g00}, Y'_{g00})$ and $(x'_{g01}, y'_{g01})$ of the 0-th source coil on planes defined with the 0-th source coil and the two sense coils selected at step S37 are obtained.

At step S39, the CPU 32 determines whether the two sense coils selected at step S37 intersect. If so, control is passed to step S40 in FIG. 21. Otherwise, control is passed to step S41 in FIG. 21.

Figure 21:
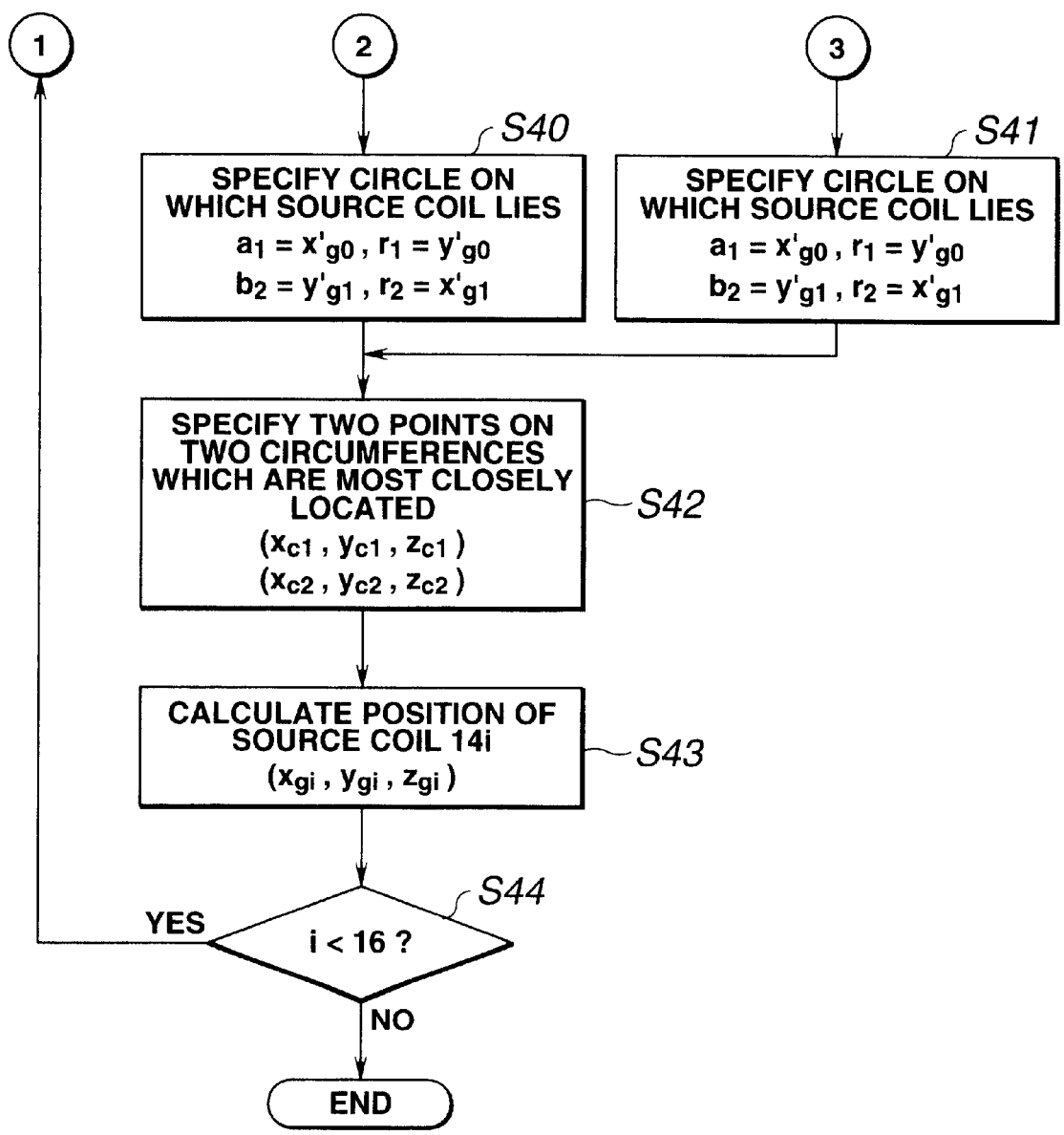

As described in FIG. 21, at step S40, a circle on which the source coil exists and which is determined with two intersecting sense coils is specified. At step S41, a circle on which the source coil exists and which is determined using two sense coils is determined.

At step S42, points most closely located on the circumferences of the two circles determined under the condition for placement of the two sense coils are determined.

At step S43, the three-dimensional position $(x_{g0}, y_{g0}, z_{g0})$ of the O-th source coil is obtained from the two points determined at step S42. At step S44, the CPU 32 determines whether the three-dimensional positions $(x_{gi}, y_{gi}, z_{gi})$ of all of the source coils have been obtained. If the three-dimensional positions of all of the source coils $(x_{gi}, y_{gi}, z_{gi})$ have not been obtained, i is incremented at step S45 in FIG. 20 and control is returned to step S32. The processing is repeated until the three-dimensional positions of all of the source coils $(x_{gi}, y_{gi}, z_{gi})$ have been obtained. The processing is then terminated.

Consequently, the spatial position of each source coil can be estimated using sense coils each having four single-core coils aligned along the same straight line.

In the present embodiment, necessary sense coils are selected based on the absolute values of the maximum voltages detected at the sense coils. Alternatively, the position of each source coil on a plane determined with the four sense coils and the source coil may be estimated, and two sense coils located most closely to the source coil, where the radii of the associated circles are smallest, may be detected. The three-dimensional position of the source coil may then be estimated.

Figure 22:
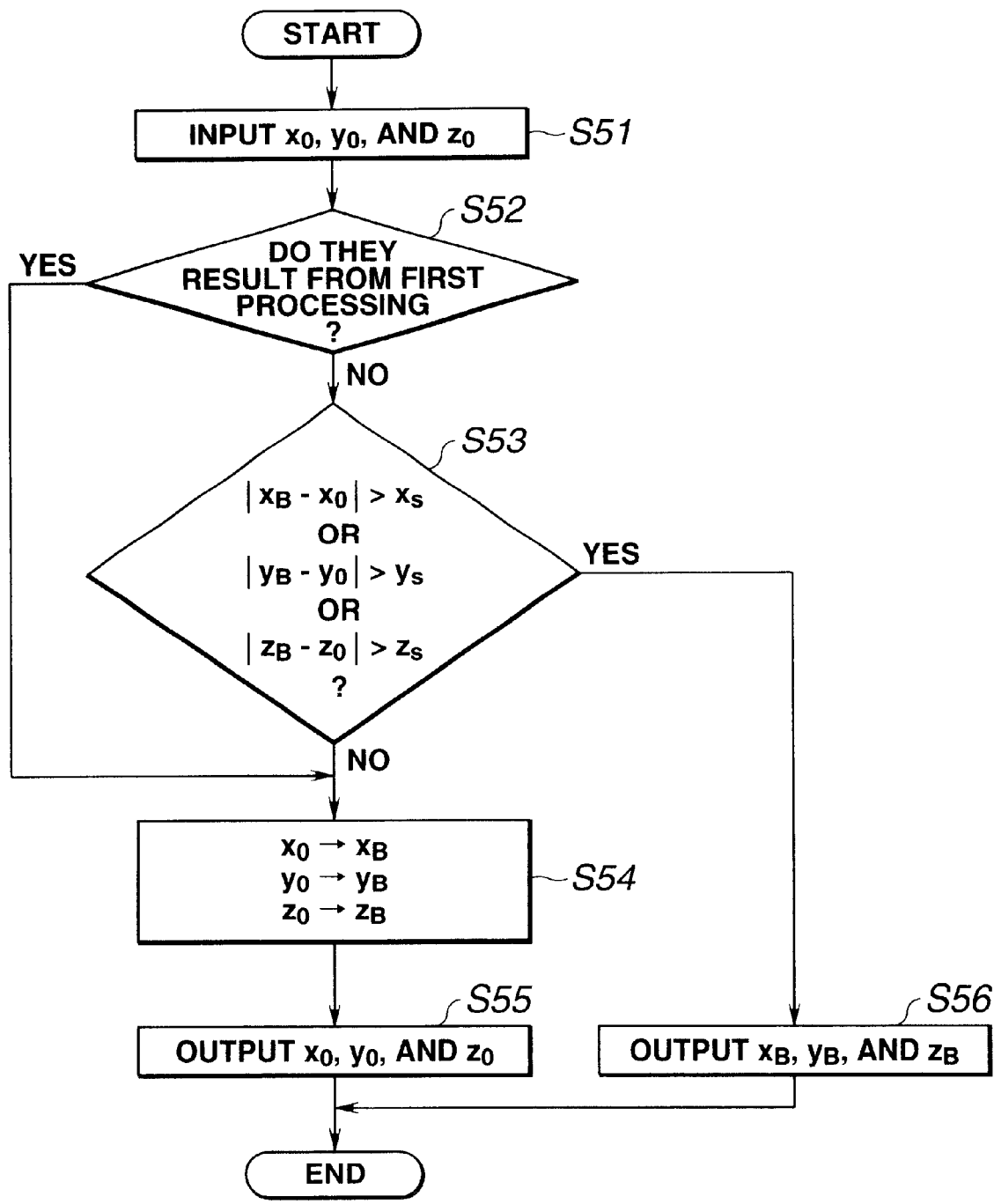

The estimated spatial positions of the source coils are updated continuously. Position update control described in FIG. 22 is extended relative to the position of each source coil. Specifically, as described in FIG. 22, assuming that the spatial (three-dimensional) position of the O-th source coil has coordinates ($x_0$, $y_0$, $z_0$), the three-dimensional estimated coordinates ($x_0$, $y_0$, $z_0$) are entered at step S51. [It is judged at] At step S52 the CPU 32 determines whether the three-dimensional estimated coordinates ($x_0$, $y_0$, $z_0$) were calculated through the first coordinates-of-estimated source coil position calculation. If not, control is passed to step S53. If so, control is passed to step S54.

If the three-dimensional estimated coordinates ($x_0$, $y_0$, $z_0$) are the initial three-dimensional estimated coordinates, the three-dimensional estimated coordinates ($x_0$, $y_0$, $z_0$) are stored as the previous three-dimensional estimated coordinates ($x_B$, $y_B$, $z_B$) at step S54. At step S55, the three-dimensional estimated coordinates ($x_0$, $y_0$, $z_0$) are regarded as resulting from a coordinates-of-estimated source coil position calculation. The processing is then terminated.

The following is based on the assumption that the three-dimensional estimated coordinates are not the initial ones, but the ones calculated through the second processing. At step S51, the three-dimensional estimated coordinates ($x_0$, $y_0$, $z_0$) are entered. At step S52, the CPU 32 determines whether the three-dimensional estimated coordinates ($x_0$, $y_0$, $z_0$) are the initial three-dimensional estimated coordinates calculated through the first coordinates-of-estimated source coil position calculation. Since they are not the initial three-dimensional estimated coordinates, control is passed to step S53. The CPU 32 then determines whether the absolute values of differences between the current three-dimensional estimated coordinates ($x_0$, $y_0$, $z_0$) and the previous three-dimensional estimated coordinates ($x_B$, $y_B$, $z_B$) exceed predetermined variation limits $x_s$, $y_s$, $z_s$) for the x, y, and z coordinates. If not, similarly to the initial three-dimensional estimated coordinates, the three-dimensional estimated coordinates ($x_0$, $y_0$, $z_0$) are stored as the previous ones ($x_B$, $y_B$, $z_B$). At step S55, the three-dimensional estimated coordinates ($x_0$, $y_0$, $z_0$) are regarding as resulting from a coordinates-of-estimated source coil position calculation. The processing is then terminated.

At step S53, if the CPU 32 determines that the absolute values of the differences between the current three-dimensional estimated coordinates ($x_0$, $y_0$, $z_0$) and the previous ones ($x_B$, $y_B$, $z_B$) exceed the predetermined variation limits $x_s$, $y_s$, and zS) for the x, y, and z coordinates, control is passed to step S56. The previous three-dimensional estimated coordinates ($x_B$, $y_B$, $z_B$) are regarded as resulting from coordinates-of-estimated source coil position calculation. The processing is then terminated.

As mentioned above, the position of each source coil is updated based on the predetermined variation limits $x_s$, $y_s$, and $z_s$) for the x, y, and z coordinates.

The foregoing concerned the O-th source coil. The same applies to all of the source coils.

Next, a description will be made of endoscope shape detection image display referred to at step S13 in FIG. 6.

Figure 23:
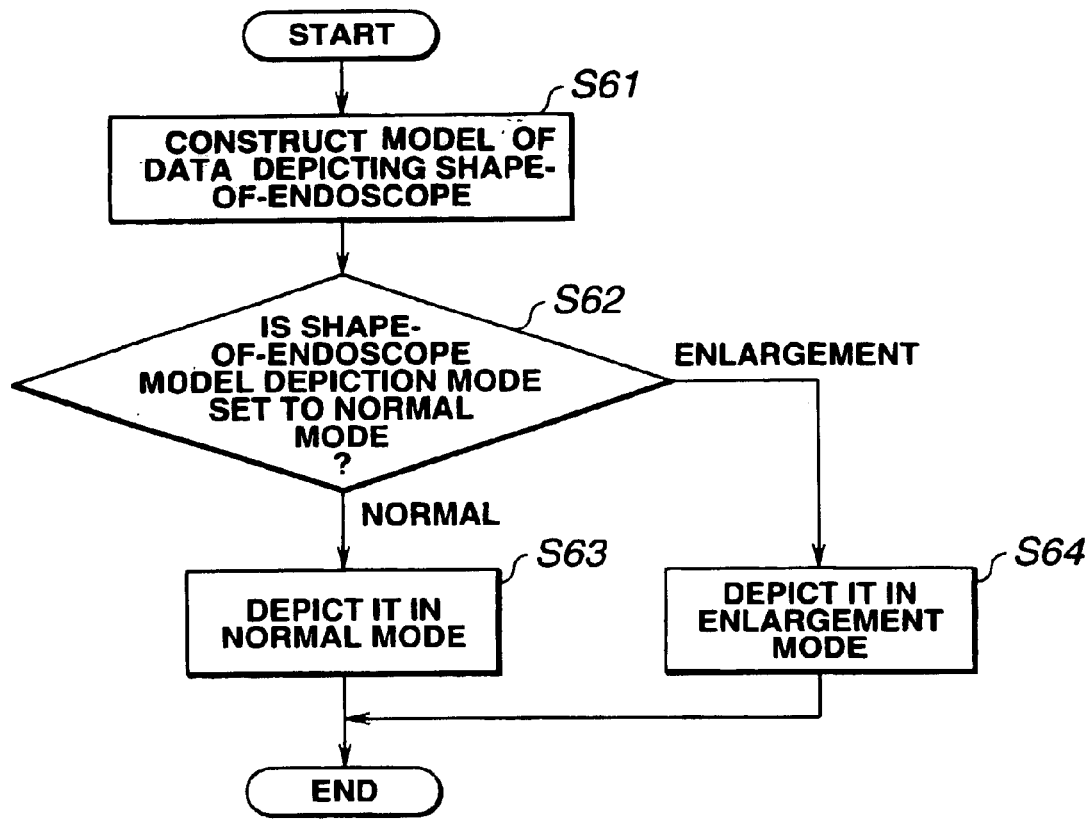

The endoscope shape detection image display is, as described in FIG. 23, at step S61, constructed from data into a model representing the shape of an endoscope according to the coordinates of the position in a space of a source coil resulting from coordinates-of-estimated source coil position calculation. At step S62, the CPU 32 evaluates the depiction mode according to which the model representing the shape of the endoscope is depicted based on the model data pertaining to the shape of the endoscope. If a normal mode is designated, normal-mode processing is carried out at step S63. If an enlargement mode is designated, enlargement-mode processing is carried out at step S64. The processing is then terminated.

Figure 24:
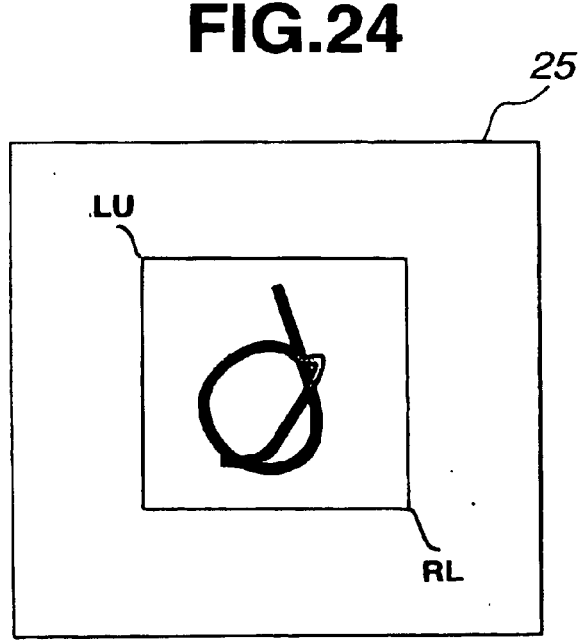

In the normal mode, a model representing the shape of the endoscope like the one shown in FIG. 24 is displayed on the monitor 25 of the endoscope shape detection system 3.

Figure 25:
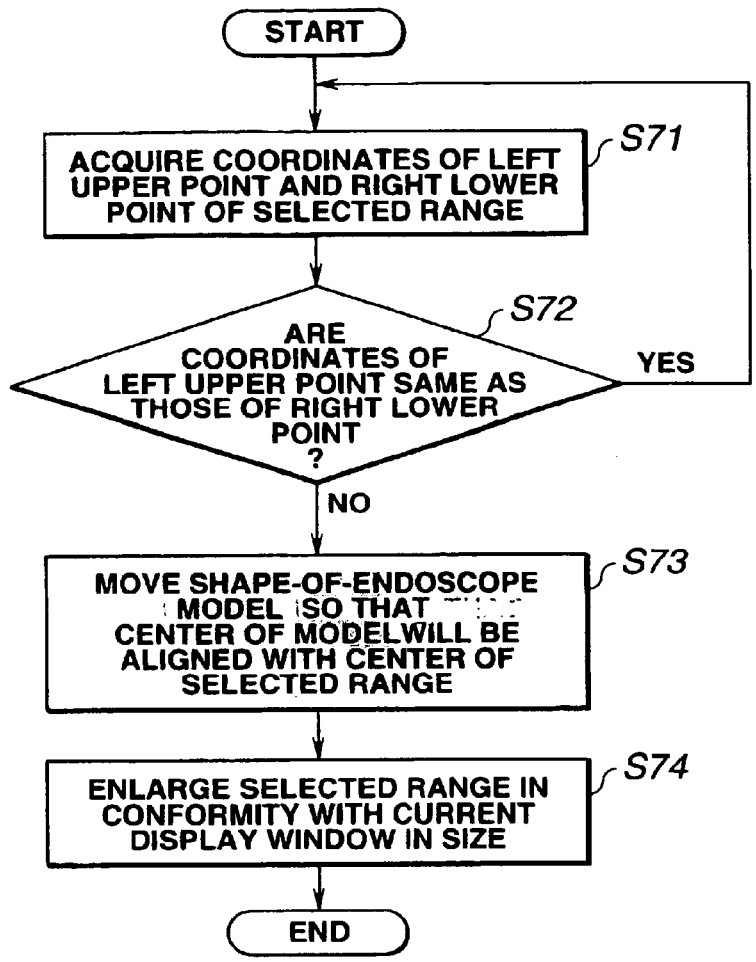

In the enlargement mode, as shown in FIG. 25, the operator panel 24 is used to acquire the coordinates of, for example, the left upper and right lower points LU and RL, respectively, defining a range to be enlarged at step S71. The range is defined with respect to the model representing the shape of the endoscope and displayed on the monitor 25 (see FIG. 24). At step S72, the CPU 32 determines whether the coordinates of the left upper and right lower points are the same. If the coordinates are the same, the range of enlargement cannot be determined. Control is therefore returned to step S71. If the coordinates of the selected left upper and right lower points are not the same, control is passed to step S73.

At step S73, the current model representing the shape of the endoscope is moved so that the center thereof will be aligned with the center of the defined range. At step S74, the defined range is enlarged in conformity with a display window on the monitor 25. The processing is then terminated.

Figure 26:
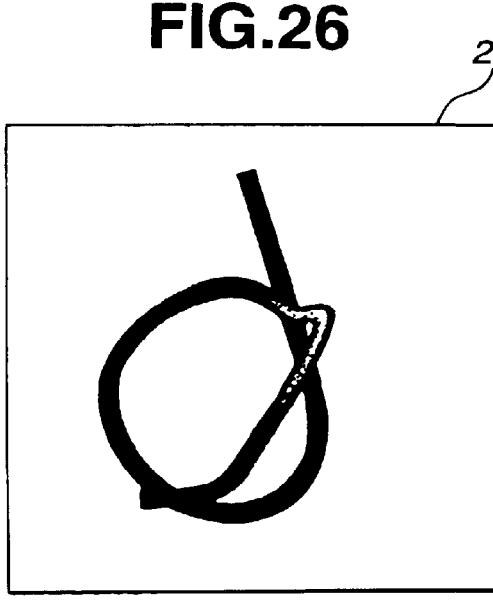

Consequently, the model representing the shape of the endoscope displayed as shown in FIG. 24 on the monitor 25 is enlarged and displayed on the monitor 25 as shown in FIG. 26.

An image showing the shape of the endoscope can be displayed by selecting any of models listed below.

Figure 27:
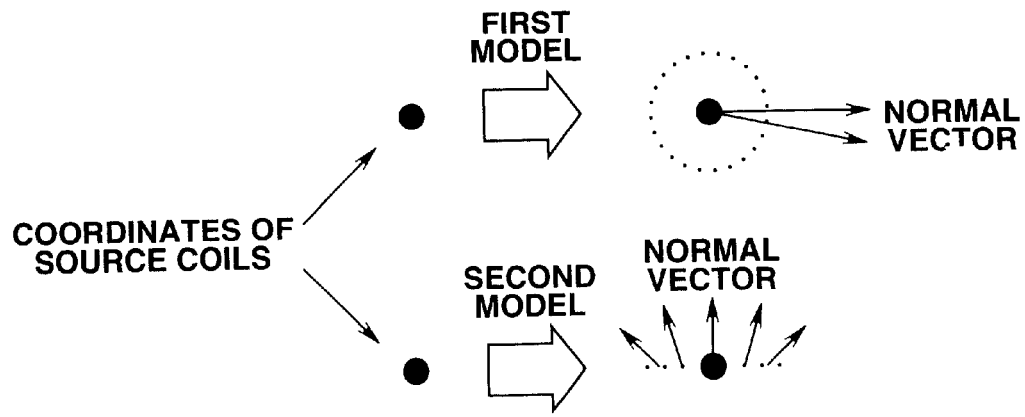

(1) Three-dimensional model 1 and three-dimensional model 2
(2) Two-dimensional model
(3) Twelve-point model
(4) Linear model For depicting the shape of the endoscope using the three-dimensional model 1 or 2, coordinates indicating points on the source coils are, as shown in FIG. 27, interpolated in order to produce a three-dimensional image showing the shape of an endoscope. Then, a combination of cubic function curve approximation and natural line interpolation, a third-order B spline interpolation method, or a second-order B spline interpolation method is adopted. Normal vectors observed at any points on two source coils are then calculated in order to complete the model.

Figure 28:
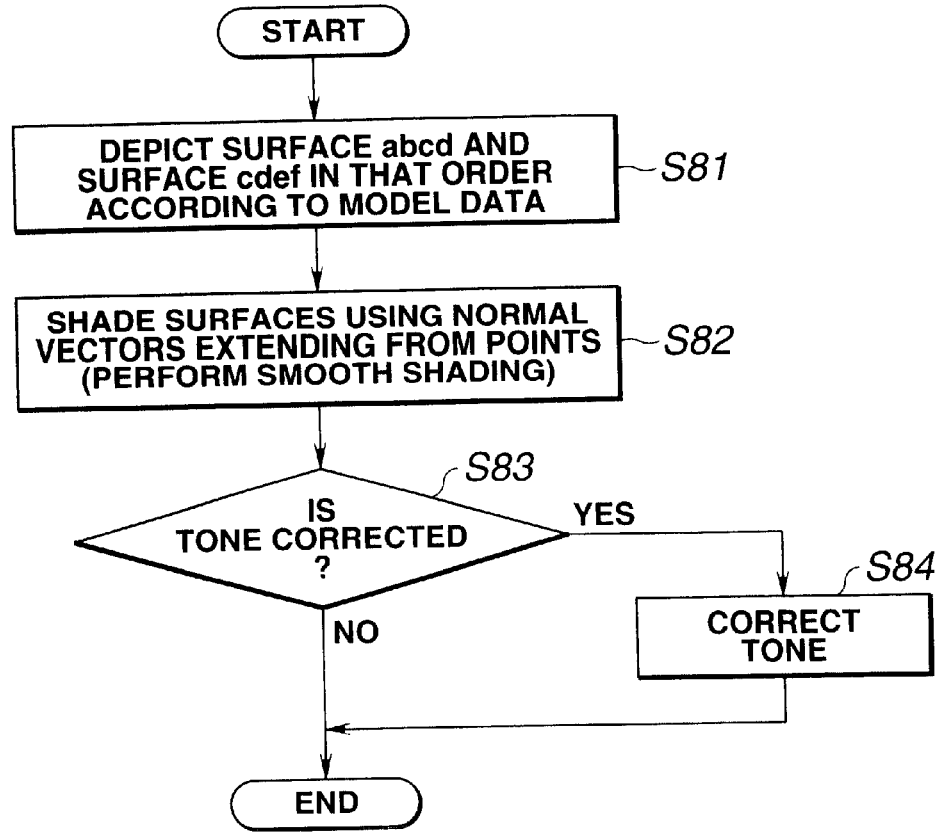
Figure 29:
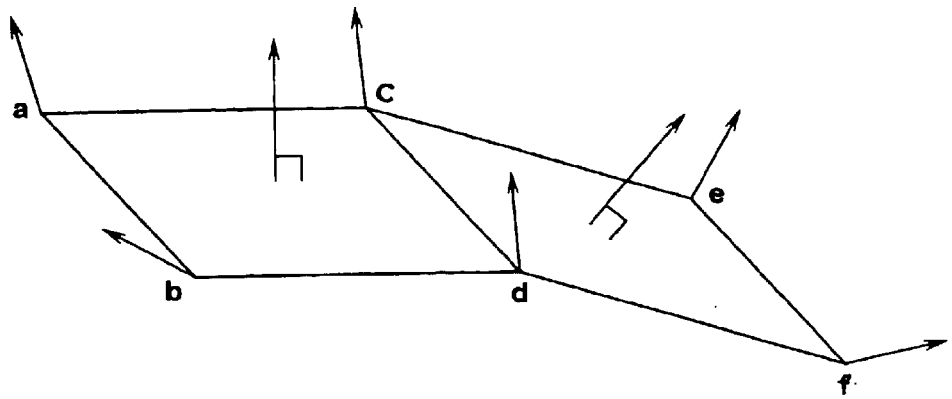

As described in FIG. 28, at step S81, surfaces abcd and cdef shown in FIG. 29 are depicted in that order according to the model data pertaining to the shape of the endoscope. At step S82, the surfaces are shaded based on the normal vectors observed at the points according to a smooth shading method. Consequently, a three-dimensional image showing the shape of the endoscope is displayed.

Thereafter, at step S83, the CPU 32 determines whether tone correction should be carried out to improve a sense of three-dimensionality. For the tone correction, the plane of the monitor 25 is regarded as an XY plane and a depth direction is regarded as the direction of the Z axis. Tone is corrected by assigning proper gray-scale levels to z coordinates. If the CPU 32 determines that tone correction should be carried out, tone correction is carried out at step S84. The processing is then terminated.

The tone correction of step S84 falls into first tone correction and second tone correction. The first tone correction is such that tone is corrected within a range of measurement performed by the endoscope shape detection system 3. The second tone correction is such that tone is corrected within a domain in which the model representing the shape of the endoscope is present.

Figure 30:
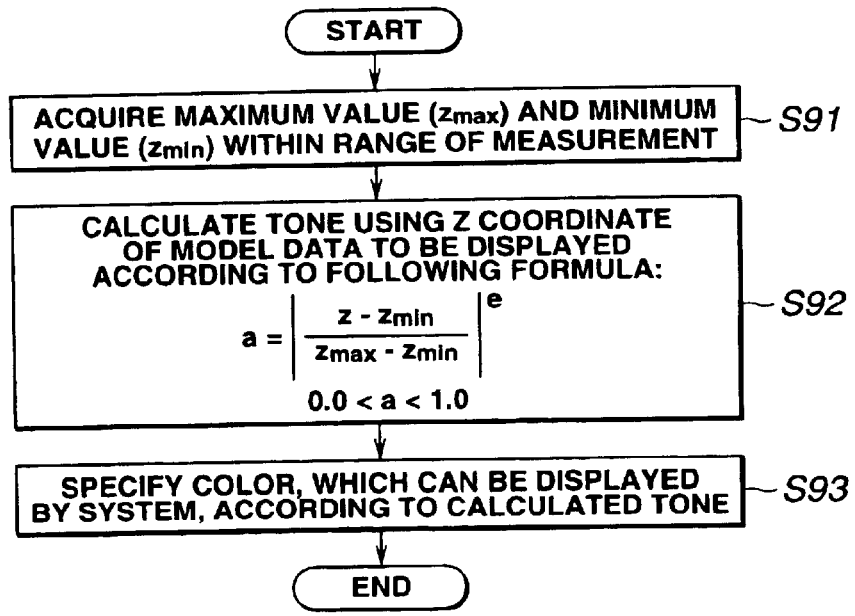
Figure 31:
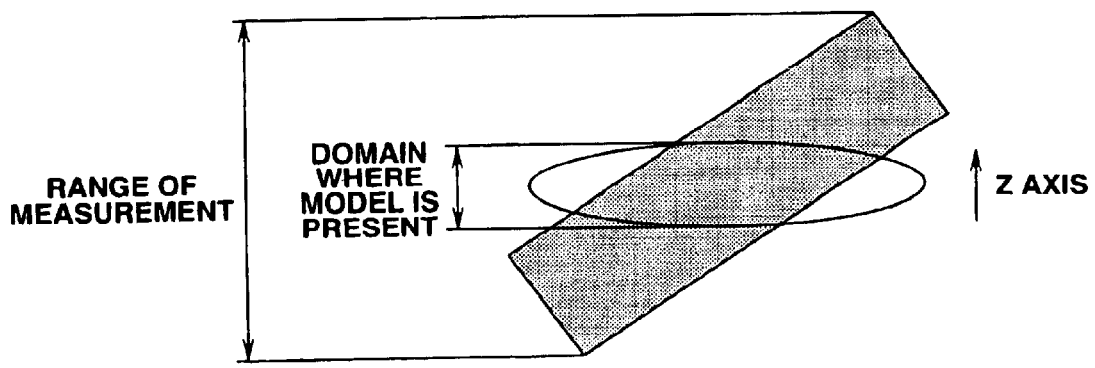

The first tone correction is, as described in FIG. 30, such that maximum and minimum values of z coordinates are acquired from a range of measurement at step S91. Tone is determined from the model data pertaining to the shape of the endoscope at step S92. Colors that can be displayed are selected based on the tone determined at step S93. Consequently, as shown in FIG. 31, the tone is corrected within the range of measurement defined with z coordinates.

Figure 32:
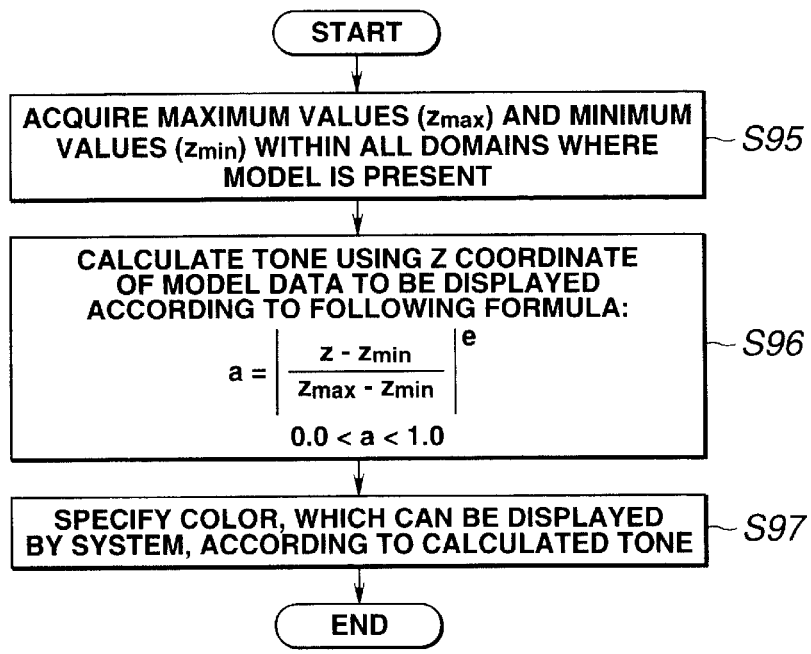
Figure 33:
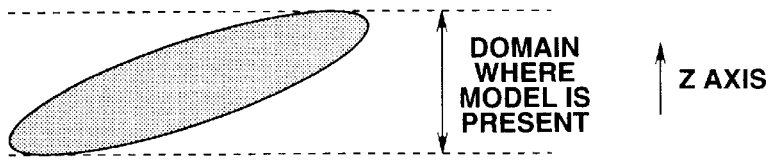

The second tone correction is, as described in FIG. 32, such that maximum and minimum values of z coordinates are acquired from a domain in which the model representing the shape of the endoscope is present at step S95. Tone is determined from the model data pertaining to the shape of the endoscope at step S96. At step S97, colors that can be displayed are selected based on the tone determined at step S97. Consequently, as shown in FIG. 33, the tone is corrected within the domain in which the shape-of-endoscope model is present. The second tone correction ensures finer tone correction for the model representing the shape of the endoscope than the first tone correction.

Figure 34:
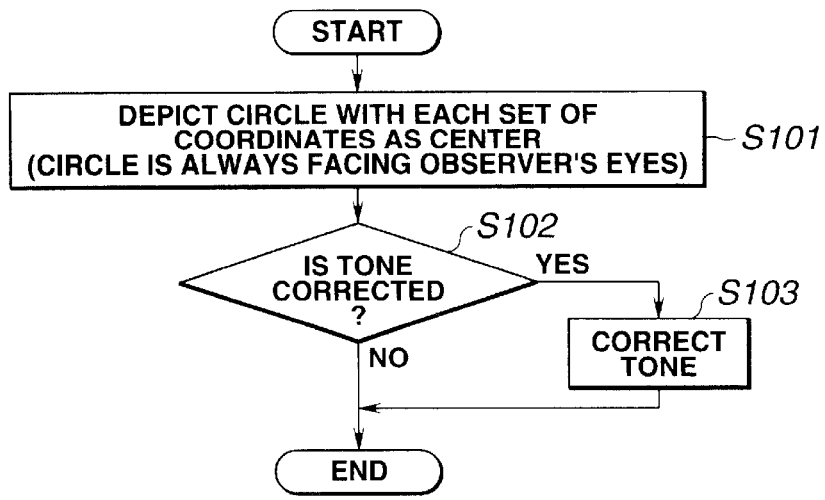
Figure 35:
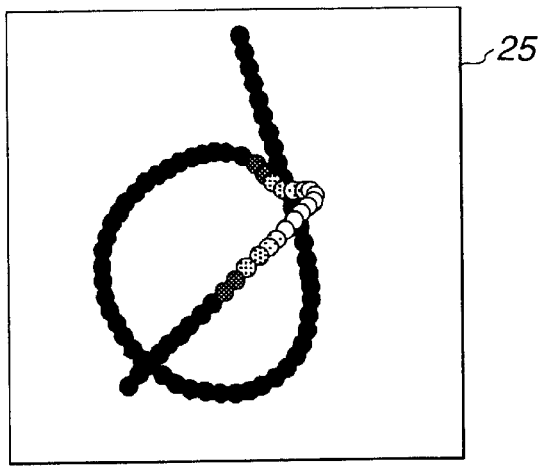

When a two-dimensional model is designated in order to display an image of the shape of the endoscope, a circle is drawn about each of the source coils at step S101 in FIG. 34. Each circle is always oriented in the direction of a line of sight. At step S102, the CPU 32 determines whether tone correction should be carried out. If the CPU 32 determines tone correction should be carried out, tone correction is carried out at step S103. The processing is then terminated. Consequently, an image showing the shape of the endoscope like in FIG. 35 is displayed on the monitor 25.

Figure 36:
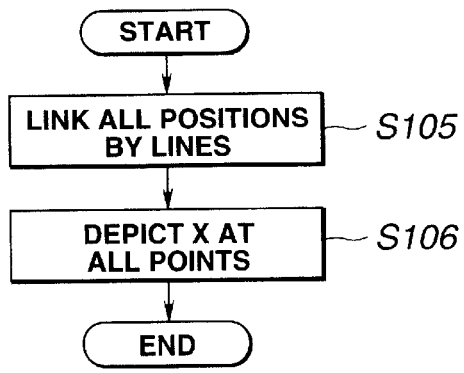
Figure 37:
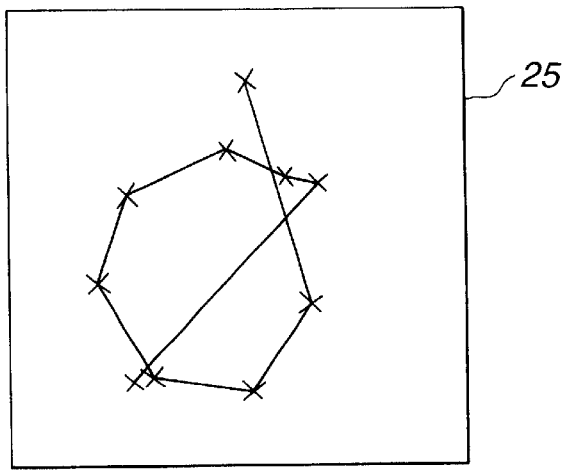

When the twelve-point model is designated to display an image showing the shape of the endoscope, all of the points in a coordinate system indicating the positions of all of the source coils are linked by lines at step S105 in FIG. 36. A cross (x) is drawn at all the points at step S106. The processing is then terminated. Consequently, an image showing the shape of the endoscope like in FIG. 37 is displayed on the monitor 25.

Figure 38:
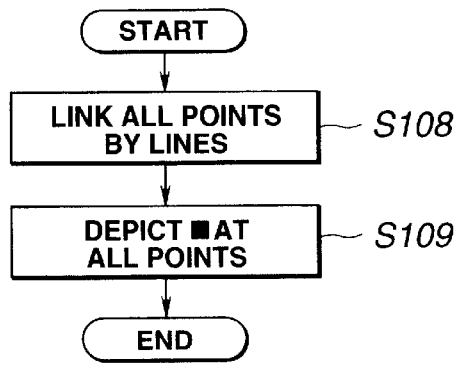
Figure 39:
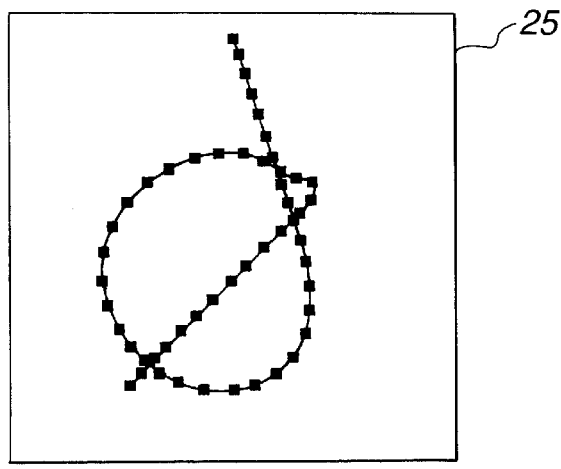

When the linear model is designated to display an image showing the shape of the endoscope, points in a coordinate system indicating the positions of all the source coils are linked by lines at step S108 in FIG. 38. A tiny blackened square is generated at all the points at step S109. The processing is then terminated. Consequently, an image representing the shape of the endoscope like in FIG. 39 is displayed on the monitor 25.

As described so far, according to the present embodiment, sense coils having outputs that permit estimation of the most precise spaces in which a source coil is present are selected from among a plurality of sense coils in a three-dimensional space. The three-dimensional position of the source coil is thus estimated. Consequently, the three-dimensional positions of all of the source coils can be estimated accurately.

The configuration of the second embodiment is identical to that of the first embodiment. A difference lies in a method of estimating the three-dimensional position of each source coil. The same reference numerals will therefore be assigned to the components identical to those of the first embodiment.

A circle on which a source coil is present and which is estimated using one sense coil is, as shown in FIGS. 15A and 15B, determined by solving an equation of a circle expressed using each point $(x_g, y_g)$. The point $(x_g, y_g)$ satisfies the two nonlinear equations (26) and (27) defined using the coordinates indicating the positions of any of the single-core coils $C_{s0}$ to $C_{s2}$ and any of the single-core coils $C_{s1}$ to $C_{s3}$. The point $(x_g, y_g)$ is determined according to Newton's method.

Figure 40:
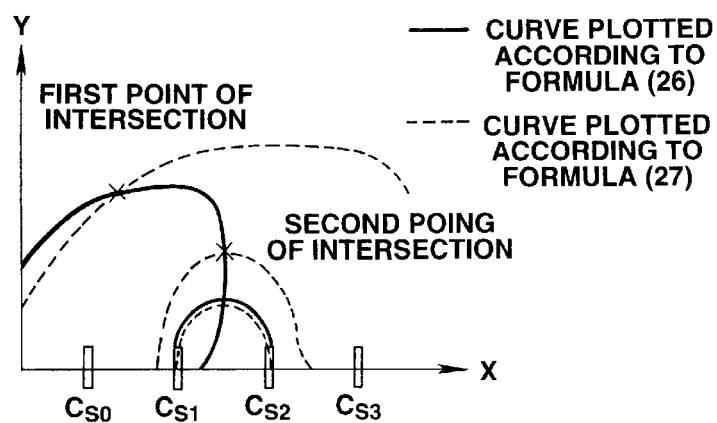
FIG. 40 to FIG. 42 relate to the second embodiment of the present invention.

When the source coils and sense coils approach each other, as shown in FIG. 40, a plurality of points of intersection satisfies the equations (26) and (27). One of the points of intersection is selected based on an estimated initial value $(x_g, y_g)$.

Assuming that the second point of intersection shown in FIG. 40 is selected, a circle on which a source coil is present is determined based on the coordinates of the second point of intersection.

Figure 18:
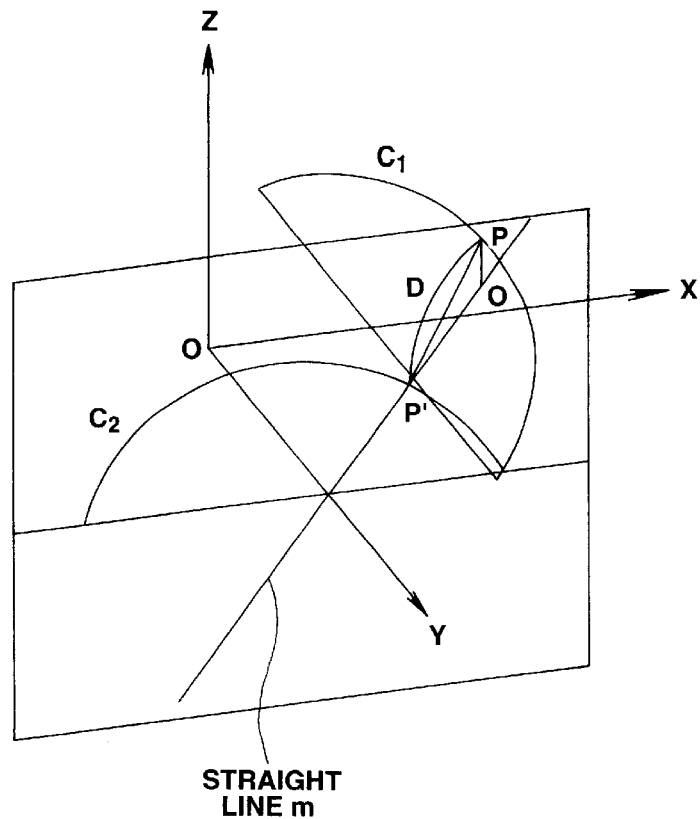

The determined circle $C_1$ is shown in FIG. 18. The circle $C_2$ is determined [using] in terms of another sense coil. The most closely located points P and P' on the two circumferences are obtained to determine the three-dimensional position of the source coil.

If the second point of intersection is correct, the distance between the points P and P' approaches zero. If the second point of intersection is incorrect, the distance between the points P and P' increases. A pair of sense coils permitting estimation of two circles, points on which being separated by the shortest distance, is selected to estimate the three-dimensional position of a source coil.

Figure 41:
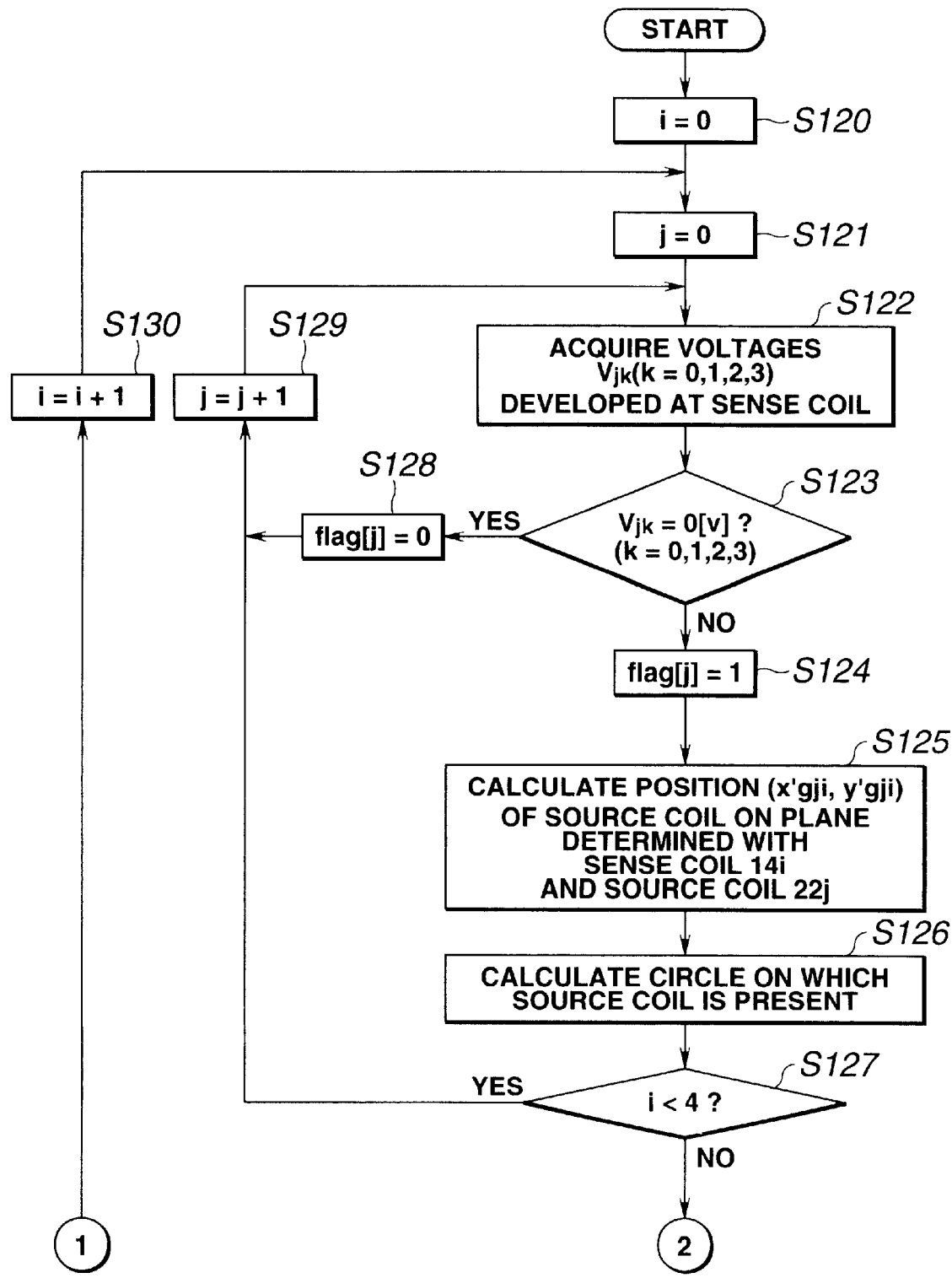
Figure 42:
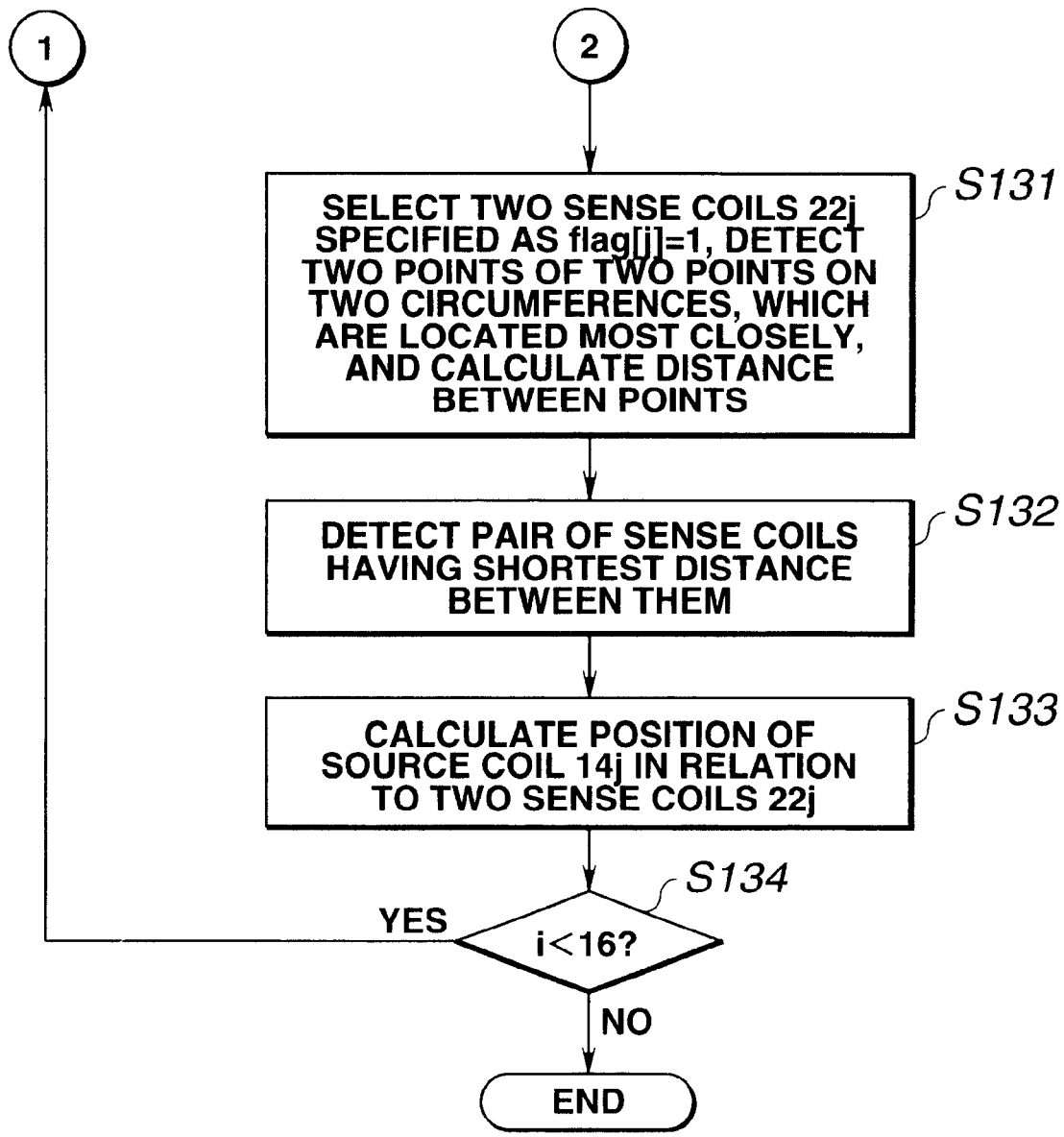

FIG. 41 and FIG. 42 are flowcharts describing estimation of the three-dimensional position of a source coil.

As described in FIG. 41, at steps S120 and S121, the serial numbers of the source coils 14$i$ and sense coils 22$j$ are initialized.

First, the O-th source coil and the O-th sense coil are selected. Voltages $V_{00}$, $V_{01}$, $V_{02}$, and $V_{03}$ developed at four single-core coils constituting the O-th sense coil are acquired at step S122. At step S123, the CPU 32 determines whether or not all the four voltages acquired at step S122 are 0 V.

At step S123, the CPU 32 determines that all the voltages are O V, a flag j associated with the O-th sense coil is reset to O at step S128. At step S129, j is incremented and control is returned to step S122. Control is thus passed to handling of the first sense coil.

At step S123, if the CPU 32 determines that all of the voltages are not O V, the flag j associated with the O-th sense coil is set to 1 at step S124.

The position $(x_{g00}, y_{g00})$ of the O-th source coil on a plane determined with the O-th sense coil and O-th source coil is obtained at step S125. A circle on which the source coil is present is estimated at step S126.

When it is found at step S127 that handling the O-th sense coil is completed, control is passed to step S129 where j is incremented.

A step S127, when the CPU 32 detects that handling all of the sense coils in relation to the O-th source coil is completed, control is passed to step S131 in FIG. 42.

As described in FIG. 42, sense coils having associated flags set to 1 are selected at step S131. Relative to all of the pairs of selected sense coils, most closely located points on two circumferences are detected and the distance between the two points is calculated.

A pair of sense coils found to have the shortest distance between them at step S131 is selected at step S132. The three-dimensional position of the source coil is estimated using the two selected sense coils.

At step S134, the CPU 32 determines whether the positions of all the source coils have been estimated. If not, i is incremented at step S130 in FIG. 41. Control is then returned to step S121. The processing is repeated until the positions of all the source coils have been estimated. When the three-dimensional positions of the sixteen source coils have been determined, the processing is terminated.

From the distance between points on two circles estimated using a pair of sense coils, whether the circles have been estimated correctly can be determined. Even if the sense coils and source coils approach each other, the three-dimensional position of each source coil can be estimated correctly.

The configuration of the third embodiment is identical to that of the first embodiment. A difference lies in a method of estimating the three-dimensional position of a source coil. The same reference numerals will be assigned to components identical to those of the first embodiment.

According to the present embodiment, from the conditions under which two curves intersect, the CPU 32 determines whether a circle estimated using a sense coil consisting of four single-core coils has been determined highly precisely. Two sense coils are selected to estimate the three-dimensional position of each source coil.

A circle estimated using one sense coil and having a source coil present thereon is determined by determining a point $(x_g, y_g)$ which satisfies two nonlinear equations (26) and (27), according to Newton's method. The nonlinear equations (26) and (27) are defined using the coordinates indicating the positions of any of the single-core coils $C_{s0}$ to $C_{s2}$ and any of the single-core coils $C_{s1}$ to $C_{s3}$ shown in FIGS. 15A and 15B.

The partial differentials of $V_{y0}$ and $V_{y3}$ determined according to the formulas (26) and (27) with respect to $x_g$ and $y_g$ are expressed as follows:

$$\frac{\partial V_{y0}}{\partial x_g}, \frac{\partial V_{y0}}{\partial y_g} \quad (54)$$

$$\frac{\partial V_{y3}}{\partial x_g}, \frac{\partial V_{y3}}{\partial y_g} \quad (55)$$

Assuming that $y_g$ is a function of $x_g$, the tangent vectors of the curves expressed as the formulas (26) and (27) which are observed at the point $(x_g, y_g)$ are provided as follows:

$$v_0 = \left(\frac{\partial V_{y0}}{\partial x_g}, -\frac{\partial V_{y0}}{\partial y_g}\right) = (x_0, y_0) \quad (56)$$

$$v_0 = \left(\frac{\partial V_{y3}}{\partial x_g}, -\frac{\partial V_{y3}}{\partial y_g}\right) = (x_3, y_3) \quad (57)$$

Assuming that the normalized vectors of the tangent vectors are given as follows:

$$v'_0 = (x'_0, y'_0) \quad (58)$$

$$v'_3 = (x'_3, y'_3) \quad (59)$$

an angle θ at which the curves expressed as the formulas (26) and (27) intersect is provided as follows:

$$\cos\theta = x'_0 x'_3 + y'_0 y'_3 \quad (60)$$

As shown in FIGS. 43A and 43B, when the angle θ is small, the point of intersection is susceptible to noise. For this reason, two sense coils that provide two curves defining the angle θ, which approximates an angle between orthogonal curves, are selected to estimate the three-dimensional position of a source coil.

Figure 44:
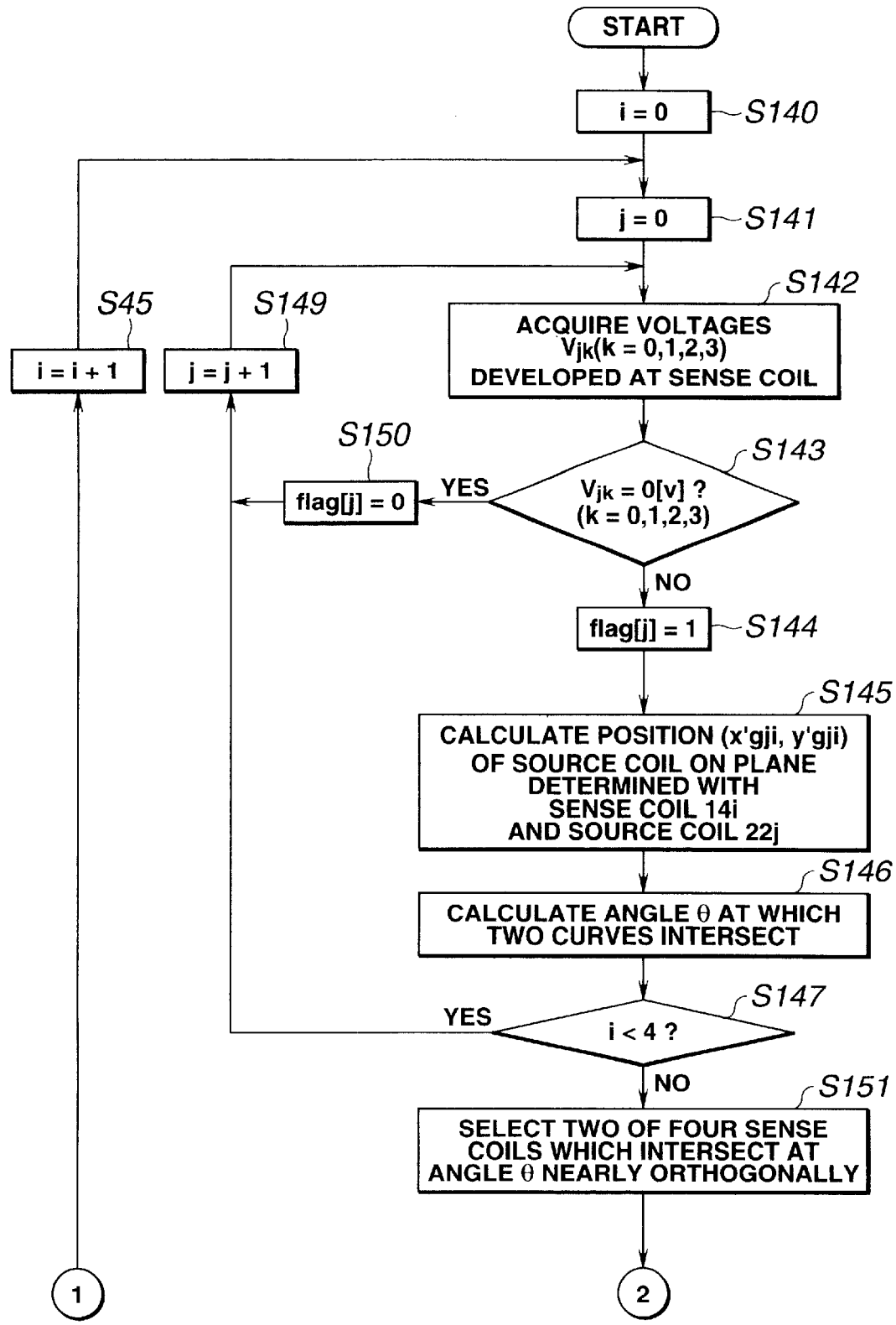
Figure 45:
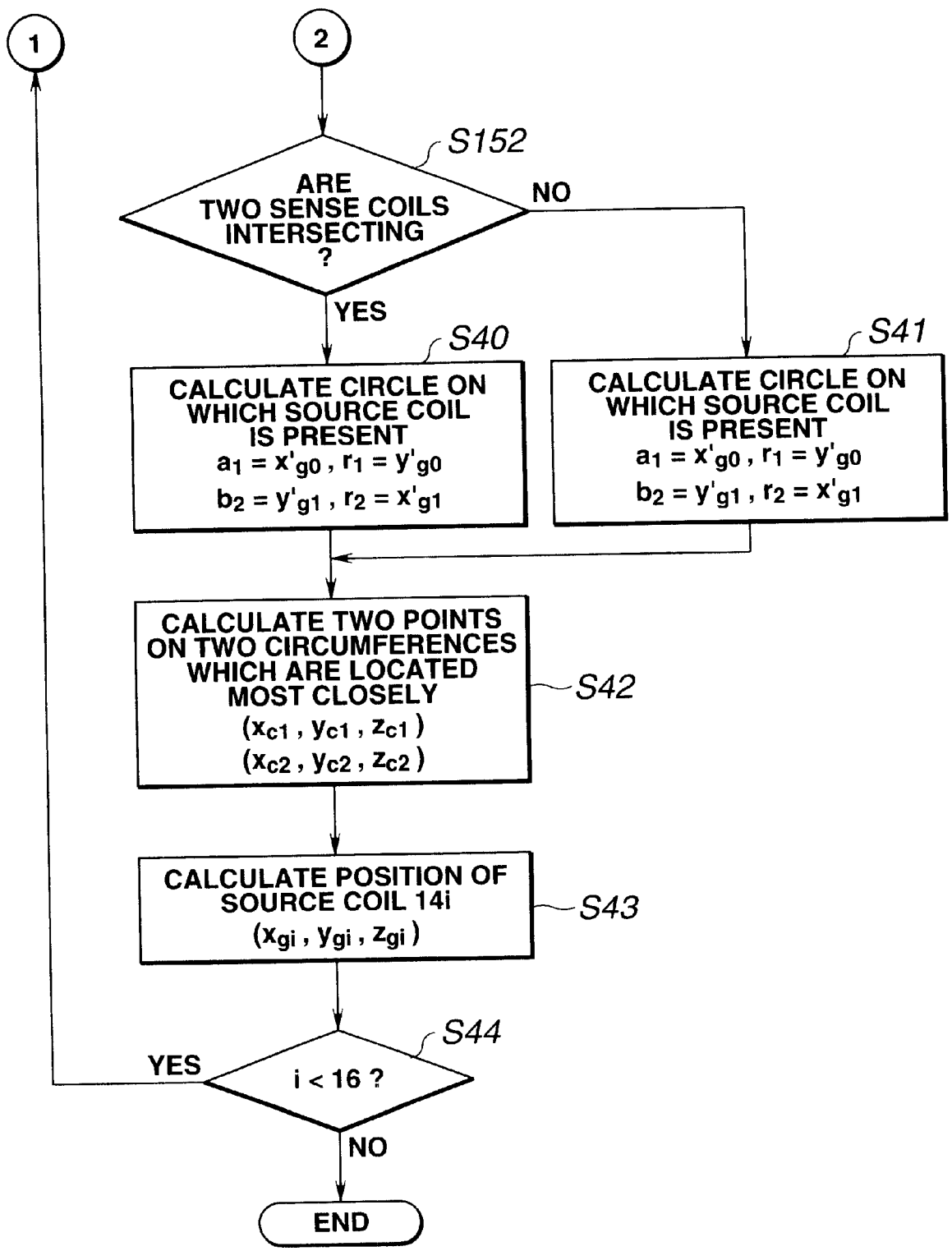

FIG. 44 and FIG. 45 are flowcharts describing estimation of the three-dimensional position of a source coil.

As described in FIG. 44, the serial numbers of the source coils 14i and sense coils 22j are initialized at step S140 and step S141.

First, the 0-th source coil and the 0-th sense coil are selected. Voltages $V_{00}$, $V_{01}$, $V_{02}$, and $V_{03}$ developed at four single-core coils of the 0-th sense coil are acquired at step S142. At step S143, the CPU 32 determines whether all of the four voltages acquired at step S142 are 0 V.

If it is found at step S143 that all the voltages are 0 V, a flag j associated with the 0-th sense coil is reset to 0 at step S150. At step S149, j is incremented and control is then returned to step S142 where the processing is carried out using the first sense coil.

If it is found at step S143 that all the voltages are not 0 V, the flag associated with the 0-th sense coil is set to 1 at step S144.

At step S145, the position $(x_{g00}, y_{g00})$ of the 0-th source coil on a plane determined with the 0-th sense coil and 0-th source coil is obtained. The angle H at which the two curves intersect at the point $(x_{g00}, y_{g00})$ is calculated at step S146.

If it is found at step S147 that the processing using the 0-th sense coil is completed, control is passed to step S149 where j is then incremented.

If it is found at step S147 that the processing performed on the 0-th source coil using all of the sense coils is completed, control is passed to step S151.

At step S151, sense coils having associated flags set to 1 are selected. Two out of the sense coils are selected under the condition that the angle θ between intersecting curves determined using the sense coils approximates the angle between orthogonal curves.

As described in FIG. 45, at step S152, the CPU 32 determines whether the two sense coils selected at step S151 are orthogonal to each other. If so, control is passed to step S40. Otherwise, control is passed to step S41.

Steps succeeding step S40, until the processing is terminated, are identical to those described in relation to the first embodiment (see FIG. 20 and FIG. 21).

According to the present embodiment, two sense coils not susceptible to noise or the like are selected from among a plurality of sense coils each composed of four single-core coils. The three-dimensional position of a source coil can be estimated highly precisely.

The configuration of the fourth embodiment is identical to that of the first embodiment. Differences lie in the number of sense coils and the placement thereof, and a method of estimating the three-dimensional position of a source coil. The same reference numerals will be assigned to the components identical to those of the first embodiment.

According to the present embodiment, the three-dimensional position of each source coil is not estimated using sense coils each composed of four single-core coils. Instead, a plurality of single-core coils is arranged in a three-dimensional space. The three-dimensional position and orientation of each source coil are estimated from voltages developed at the single-core coils.

Figure 46:
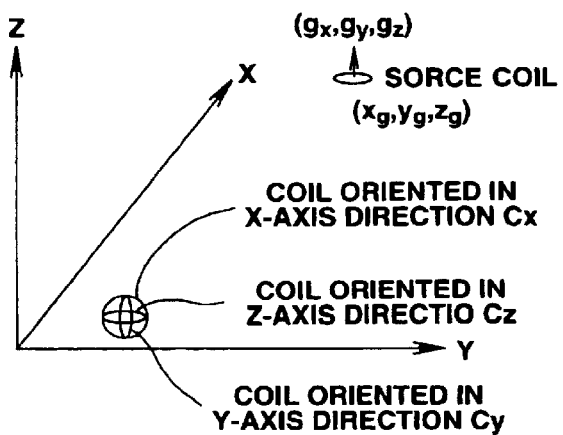
FIG. 46 and FIG. 47 relate to the fourth embodiment of the present invention.

As shown in FIG. 46, one source coil generating magnetic fields is placed with a gradient $(g_x, g_y, g_z)$ at a position $(x_g, y_g, z_g)$ in a three-dimensional space XYZ. Magnetic fields Hi, Hy' and H., or strictly speaking, components of a magnetic field developed at a proper position P(Xd' Yd'Zd) are expressed as follows:

$$\begin{pmatrix} H_x \\ H_y \\ H_z \end{pmatrix} = \frac{k_g}{r^5} \begin{pmatrix} 2(x_d - x_g)^2 - (y_d - y_g)^2 - (z_d - z_g)^2 & 3(y_d - y_g)(x_d - x_g) & 3(z_d - z_g)(x_d - x_g) \\ 3(x_d - x_g)(y_d - y_g) & 2(y_d - y_g)^2 - (z_d - z_g)^2 - (x_d - x_g)^2 & 3(z_d - z_g)(y_d - y_g) \\ 3(x_d - x_g)(z_d - z_g) & 3(y_d - y_g)(z_d - z_g) & 2(z_d - z_g)^2 - (y_d - y_g)^2 - (x_d - x_g)^2 \end{pmatrix} \begin{pmatrix} g_x \\ g_y \\ g_z \end{pmatrix} \quad (61)$$

where $k_g$ denotes a constant, and r denotes a distance between the source coil and the point P. The magnetic fields $H_x$, $H_y$, and $H_z$ are oriented in the same directions as the X, Y. and Z axes respectively.

Assuming that single-core coils $C_x$, $C_y$, and $C_z$ oriented in the same directions as the coordinate axes X, Y. and Z are placed at the point P. voltages $V_x$, $V_y$ and $V_z$ developed at the single-core coils $C_x$, $C_y$ and $C_z$ are expressed as follows:

$$\begin{pmatrix} V_x \\ V_y \\ V_z \end{pmatrix} = \frac{k_g}{r^5} \begin{pmatrix} 2(x_d - x_g)^2 - (y_d - y_g)^2 - (z_d - z_g)^2 & 3(y_d - y_g)(x_d - x_g) & 3(z_d - z_g)(x_d - x_g) \\ 3(x_d - x_g)(y_d - y_g) & 2(y_d - y_g)^2 - (z_d - z_g)^2 - (x_d - x_g)^2 & 3(z_d - z_g)(y_d - y_g) \\ 3(x_d - x_g)(z_d - z_g) & 3(y_d - y_g)(z_d - z_g) & 2(z_d - z_g)^2 - (y_d - y_g)^2 - (x_d - x_g)^2 \end{pmatrix} \begin{pmatrix} g_x \\ g_y \\ g_z \end{pmatrix} \quad (62)$$

The single-core coil $C_x$ oriented in the X-axis direction has an axis, about which a wire is wound, oriented in the same direction as the X axis. The same applies to the single-core coils $C_y$ and $C_z$ oriented in the same directions as the Y and Z axes respectively.

Herein, $k_s$ denotes a constant determined with the sizes of source coils and sense coils and the number of windings constituting a coil. r denotes a distance between a source coil and sense coil, and is obtained as follows:

$$r = \sqrt{(x_d - x_g)^2 + (y_d - y_g)^2 + (z_d - z_g)^2} \quad (63)$$

Figure 47:
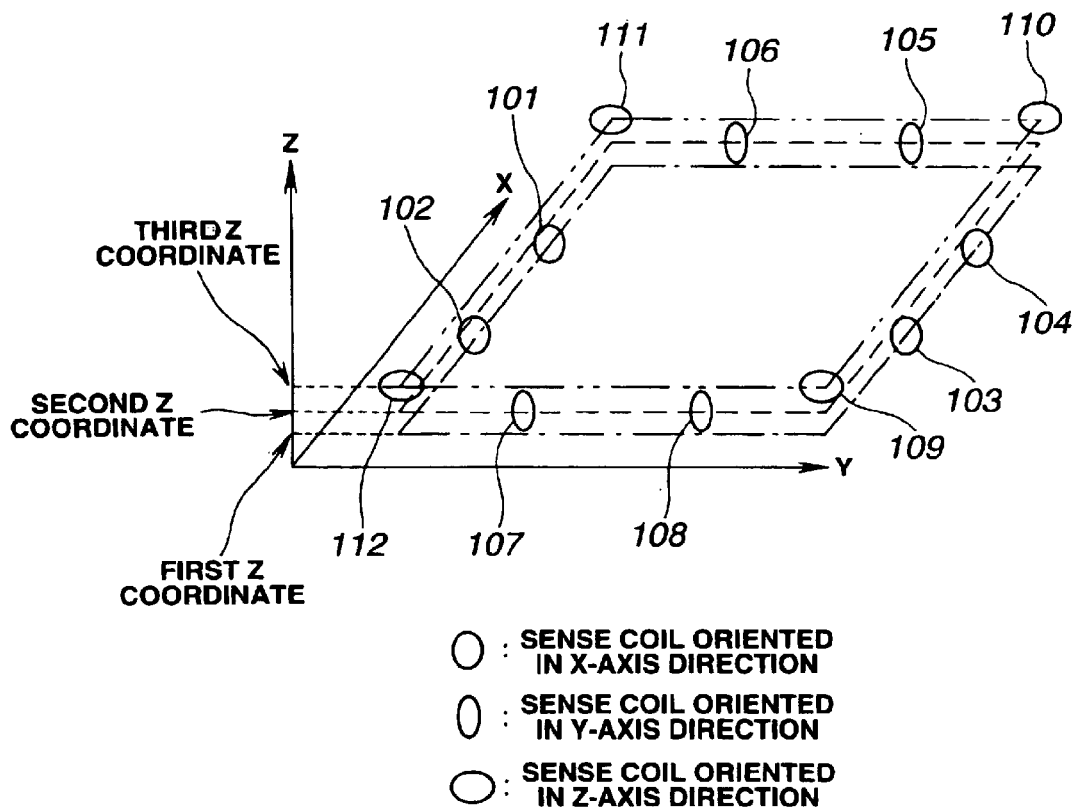

As shown in FIG. 47, according to the present embodiment, a plurality of single-core sense coils is arranged in a three-dimensional space. More particularly, twelve sense coils including sense coils 101, 102, 103, and 104, sense coils 105, 106, 107, and 108, and sense coils 109, 110, 111, and 112 are incorporated in the examining table 4. The sense coils 101, 102, 103, and 104 having centers that share the first z coordinate are oriented in the same direction as, for example, the X axis. The sense coils 105, 106, 107, and 108 having centers that share the second z coordinate different from the first z coordinate are oriented in the same direction as the Y axis. The sense coils 109, 110, 111, and 112 having centers that share the third z coordinate different from the first and second z coordinates are oriented in the same direction as the Z axis. Since the voltages, positions, and gradients of the twelve sense coils are known, twelve nonlinear equations in which the position ($x_g$, $y_g$, $z_g$) and gradient ($g_z$, $g_y$, $g_z$) of a source coil are specified as unknowns can be defined based on the formula (62).

The solutions of the twelve nonlinear equations are obtained, that is, the position and gradient of the source coil are obtained through iterative improvement (Gauss-Newton's method).

Assuming that x is a parameter specifying the position ($x_g$, $y_g$, $z_g$) and gradient ($g_z$, $g_y$, $g_z$) of the source coil and that an initial value of the parameter is $x^{(0)}$, a k-th order estimated value $x^{(k)}$ is obtained through iterative improvement. A function V(x) of a model of power induced in a sense coil is expanded as a Taylor' series in the neighborhood of $x^{(k)}$. The linear approximate expression of the function is provided as follows:

$$V(x) = V(x^{(k)}) + \left[\frac{\partial V(x)}{\partial x}\right]_{x = x^{(k)}} (x - x^{(k)}) \quad (64)$$

When Vm is regarded as a voltage measured at a sense coil, an observation equation is defined as follows:

$$Vm(x) = V(x^{(k)}) + \left[\frac{\partial V(x)}{\partial x}\right]_{x = x^{(k)}} (x - x^{(k)}) \quad (65)$$

Herein, the right side of the equation is nearly equal to the left side. This is because Vm contains an error occurring during measurement.

When the first term in the right side of the formula (65) is transposed to the left side, $$\Delta Vm^{(k)} = A^{(k)} \Delta k^{(k)} \quad (66)$$

Herein, the following relationship is established:

$$\Delta Vm^{(k)} = Vm - V(x^{(k)}) = Vm - Vm^{(k)} \quad (67)$$

$$\Delta k^{(k)} = x - x^{(k)} \quad (68)$$

$$A_{ij} = \left[\frac{\partial V_i(x)}{\partial x_j}\right]_{x = x^{(k)}} \quad (69)$$

where i denotes any of 1 to n and j denotes any of 1 to m. The number of elements constituting one row corresponds to the number of unknowns n, and the number of elements constituting one column corresponds to the number of sense coils m. By rewriting the formula (66), the solution $\Delta x^{(k)}$ is expressed as follows:

$$\Delta k^{(k)} = (B^{(k)} W A^{(k)})^{-1} B^{(k)} W \Delta Vm^{(k)} \quad (70)$$

where B denotes a transposed matrix of A, and W denotes a matrix serving as a weight.

An improved estimated value of the parameter is therefore expressed based on the formula (68) as follows:

$$x^{(k+1)} = x^{(k)} + \Delta k^{(k)} \quad (71)$$

When twelve single-core coils (sense coils) are arranged as shown in FIG. 47, a matrix A expressed as the formula (72) below is defined with the positions and gradients of the coils.

$$A = \begin{bmatrix} \frac{\partial V_{x0}}{\partial x_g} & \frac{\partial V_{x0}}{\partial y_g} & \frac{\partial V_{x0}}{\partial z_g} & \frac{\partial V_{x0}}{\partial g_x} & \frac{\partial V_{x0}}{\partial g_y} & \frac{\partial V_{x0}}{\partial g_z} \\ \frac{\partial V_{x1}}{\partial x_g} & \frac{\partial V_{x1}}{\partial y_g} & \frac{\partial V_{x1}}{\partial z_g} & \frac{\partial V_{x1}}{\partial g_x} & \frac{\partial V_{x1}}{\partial g_y} & \frac{\partial V_{x1}}{\partial g_z} \\ \vdots & \vdots & \vdots & \vdots & \vdots & \vdots \\ \frac{\partial V_{z11}}{\partial x_g} & \frac{\partial V_{z11}}{\partial y_g} & \frac{\partial V_{z11}}{\partial z_g} & \frac{\partial V_{z11}}{\partial g_x} & \frac{\partial V_{z11}}{\partial g_y} & \frac{\partial V_{z11}}{\partial g_z} \end{bmatrix} \quad (72)$$

The weight matrix W is expressed as follows:

$$W = \begin{bmatrix} \sigma_0^2 & 0 & 0 & \cdots & 0 \\ 0 & \sigma_1^2 & 0 & \cdots & 0 \\ 0 & 0 & \sigma_2^2 & \cdots & 0 \\ \vdots & \vdots & \vdots & \ddots & \vdots \\ 0 & 0 & 0 & \cdots & \sigma_{11}^2 \end{bmatrix} \quad (73)$$

Herein, $\sigma_i$ (i=0, 1, ..., 11) in the weight matrix W denotes a variation in voltage measured at each sense coil. The variation is attributable to environmental noise or the like.

The k-th $\Delta Vm$ is given as follows:

$$\Delta Vm = \begin{bmatrix} Vm_0 - V_{x0}(x^{(k)}) \\ Vm_1 - V_{x1}(x^{(k)}) \\ Vm_2 - V_{x2}(x^{(k)}) \\ \vdots \\ Vm_{11} - V_{z11}(x^{(k)}) \end{bmatrix} \quad (74)$$

Consequently, the position and gradient of each source coil are estimated by following step (1) to step (4) described below.

At step (1), k is initialized with 0. The initial values of the position and gradient of a source coil are specified as $(x_g, y_g, z_g)^{(0)}$ and $(g_x, g_y, g_z)^{(0)}$ respectively. For example, the initial values of the position and gradient are set to the center position in a space in which the position of the source coil is measured, and a gradient vector (0, 0, 1) having the same direction as the Z axis.

At step (2), the formulas (72), (73), and (74) are solved with the k-th parameter value [specified therein].

At step (3), the magnitude of update $\Delta x^{(k)}$ for the kth parameter value is calculated according to the formula (71).

At step (4), the steps (2) to (4) are repeated until the magnitude of update $\Delta x^{(k)}$ is minimized.

According to the present embodiment, sense coils oriented in the X, Y, and Z-axis directions are placed at the same height above the floor. The position of each source coil is estimated in this state. Alternatively, the sense coils may be placed at any [positions] position and oriented in any direction. As long as the positions and gradients of the sense coils are known, the position of each source coil can be estimated.

If a space in which source coils are present is limited, the initial value of the position of each source coil is, as mentioned previously, adopted as the position thereof. Thus, the position and gradient of each source coil can be obtained through iterative improvement. However, if the space is wide, the initial position must be determined according to an appropriate method.

For example, when sense coils are arranged in two rows and two columns as they are in the first embodiment, the technique described in relation to the first to third embodiments is employed. Specifically, a space (circle) in which each source coil is present is determined using sense coils each composed of four single-core coils. The position of each source coil is estimated using a plurality of sense coils. Thus, the position of each source coil can be estimated highly precisely according to the iterative improvement method.

When determination of a circle and iterative improvement are performed relative to all of the source coils 14i, the number of calculations is enormous. Determination of a circle and iterative improvement are performed relative to only the leading source coil 14a. Since the source coils are arranged continuously, the estimated position of the immediately preceding source coil may be adopted as an initial value, and iterative improvement may be carried out. For estimating the three-dimensional position of the source coil 14b, the estimated three-dimensional position of the source coil 14a is adopted as an initial value, and iterative improvement is carried out.

Since the source coils are continuously arranged, the three-dimensional position of a source coil to be estimated may be predicted from the estimated three-dimensional position of a preceding source coil. Iterative improvement may be carried out using the predicted position as an initial value.

Assume that the three-dimensional positions of the source coils 14a and 14b are expressed as follows:

$$P_a = \begin{bmatrix} x_a \\ y_a \\ z_a \end{bmatrix} \quad P_b = \begin{bmatrix} x_b \\ y_b \\ z_b \end{bmatrix} \quad (75)$$

The estimated three-dimensional position of the source coil 14a is adopted as an initial value used to estimate the three-dimensional position of the source coil 14b. The positions of the source coil 14c and subsequent source coils are predicted from the three-dimensional positions of the two preceding source coils.

For the source coil 14c, for instance, the position thereof is predicted according to the following formula:

$$P_c = P_b + (P_b - P_a) \quad (76)$$
$$= \begin{bmatrix} x_b \\ y_b \\ z_b \end{bmatrix} + \left( \begin{bmatrix} x_b \\ y_b \\ z_b \end{bmatrix} - \begin{bmatrix} x_a \\ y_a \\ z_a \end{bmatrix} \right)$$

Since the present embodiment is used to examine an organ in a body cavity, a temporal variation in the three-dimensional position of a source coil is presumably limited, that is, motions made in the body cavity by the source coils are limited. From this viewpoint, the iterative improvement method may be implemented by employing the previously estimated three-dimensional position as an initial position.

According to the present embodiment, the three-dimensional position and gradient of each source coil are estimated based on outputs of a plurality of sense coils according to the iterative improvement method. The adverse effect of noise or the like is alleviated and the precision in estimation can be improved.

When the three-dimensional position of each source coil is estimated through iterative improvement, if an initial position is determined according to an appropriate method, the number of calculations can be decreased.

The configuration of the endoscope shape detection system in accordance with the fifth embodiment of the invention is identical to that of the fourth embodiment. In the present embodiment, only the three-dimensional position of each source coil is estimated.

According to the present embodiment, the three-dimensional position of each source coil is not estimated using sense coils having four single-core coils. Similar to the fourth embodiment, a plurality of single-core coils is placed in a three-dimensional space. The three-dimensional position of each source coil is estimated from voltages developed at the single-core coils.

Assuming that a matrix of electromotive forces developed at the sense coils in the sense coil unit is V, that a matrix having a term in which the three-dimensional positions of a source coil and sense coils are specified is H, and that a term in which the gradient of the source coil is specified is G, the following relational expression is established:

$$V = HG \tag{77}$$

A transposed matrix $H^t$ of the matrix H is specified as a multiplicand in both sides of the formula (77) in order to delete the term in which the gradient of the source coil is specified.

$$H^t V = H^t H G \tag{78}$$

When an inverse matrix $[H^t H]^{-1}$ of $H^t H$ is specified as a multiplicand in both the sides of the formula (78), $$[H^t H]^{-1} H^t V = G \tag{79}$$

The formula (79) is assigned to the formula (77), thus defining the following formula devoid of the term in which the gradient of the source coil is specified.

$$V = H[H^t H]^{-1} H^t V \tag{80}$$

As shown in FIG. 47, according to the present embodiment, a plurality of sense coils that are single-core coils is arranged in a three-dimensional space. More particularly, twelve sense coils including the sense coils 101, 102, 103, and 104, the sense coils 105, 106, 107, and 108, and the sense coils 109, 110, 111, and 112 are incorporated in the examining table 4. The sense coils 101, 102, 103, and 104 having centers that share the first z coordinate are oriented in the same direction as, for example, the X axis. The sense coils 105, 106, 107, and 108 having centers that share the second z coordinate different from the first z coordinate are oriented in the same direction as the Y axis. The sense coils 109, 110, 111, and 112 having centers that share the third z coordinate different from the first and second z coordinates are oriented in the same direction as the Z axis. Since the voltages, positions, and gradients of the twelve sense coils are known, twelve nonlinear equations in which the position $(x_g, y_g, z_g)$ of a source coil is unknown are defined based on the formula (62).

The solutions of the twelve nonlinear equations are obtained, that is, the position of the source coil is estimated through iterative improvement (Gauss-Newton's method).

x is regarded as a parameter indicating the position $(x_g, y_g, z_g)$ of the source coil. The initial value of the parameter is $x^{(0)}$.

The k-th order estimated value, $x^{(k)}$, is obtained through iterative improvement. A function $V(x)$ of a model of power developed at a sense coil is expanded in the neighborhood of $x^{(k)}$ in order to produce a Taylor's series. The linear approximate expression of the function is given as the formula (64) employed in the fourth embodiment.

The formula (64) contains the term expressing the following partial differential:

$$\frac{d(x)}{d} \tag{81}$$

$V(x)$ in the term expressing partial differential is expressed in terms of a voltage Vm measured at a sense coil in the right side of the formula (80).

$$V(x) = H[H^t H]^{-1} H^t Vm \tag{82}$$

Assuming that the voltage Vm is the voltage measured at a sense coil, the observation equation of the voltage vm is provided as the formula (65) of the fourth embodiment. When the first term in the right side of the formula (65) is transposed to the left side, the formula (66) of the fourth embodiment ensues.

The solution $\Delta x^{(k)}$ is expressed based on the formula (66) as the formula (70) of the fourth embodiment.

Consequently, an improved estimated value of the parameter is provided based on $\Delta x^{(k)} = x - x^{(k)}$ as the formula (71) of the fourth embodiment.

When twelve single-core coils (sense coils) are arranged as shown in FIG. 47, a matrix A expressed as the formula (83) below is defined with the positions of the coils.

$$A = \begin{bmatrix} \frac{dx0}{dg} & \frac{dx0}{dg} & \frac{dx0}{dg} \\ \frac{dx1}{dg} & \frac{dx1}{dg} & \frac{dx1}{dg} \\ \vdots & \vdots & \vdots \\ \frac{dz11}{dg} & \frac{dz11}{dg} & \frac{dz11}{dg} \end{bmatrix} \tag{83}$$

A matrix of weights W is provided as the formula (73) of the fourth embodiment. In the weight matrix W, σ(i=0, 1, . . . , 11) denotes a variation in voltage measured at each sense coil. The variation is attributable to, for example, environmental noise.

ΔVm for the k-th parameter values is expressed as the formula (74) of the fourth embodiment. The position of each source coil is obtained by following steps (1)' to (4)' described below.

At step (1)', k is initialized with 0, and the initial value of the position of a source coil is set to $(x_g, y_g, z_d)$ that indicates, for example, the center in a space in which the position of the source coil is measured.

At step (2)', the formulas (83), (73), and (74) are solved with the k-th parameter value.

At step (3)', a magnitude of update $\Delta x^{(k)}$ for the k-th parameter value is calculated according to the formula (71).

At step (4)', the steps (2)' to (4)' are repeated until the magnitude of update $\Delta x^{(k)}$ is minimized.

According to the present embodiment, the sense coils oriented in the same directions as the X, Y, and Z axes are placed at the same height above the floor, and the position of each source coil is estimated. Alternatively, the sense coils may be arranged at any position and oriented in any direction. Nevertheless, as long as the positions and gradients of the sense coils are known, the position of each source coil can be estimated.

If a space in which the source coils are present is narrow, the initial value of the position of a source coil may be considered to indicate a proper position, and iterative improvement may then be carried out in order to estimate the position of the source coil. However, if the space is wide, the initial position must be determined according to an appropriate method.

For example, when sense coils are arranged in two rows and two columns as they are in the first embodiment, the technique described in conjunction with the first three embodiments should be adopted. Specifically, a space (circle) in which each source coil is present is determined using a plurality of sense coils each composed of four single-core coils. The position of each source coil is estimated using the plurality of sense coils. By performing iterative improvement, the position of each source coil can be estimated highly precisely.

If determination of a circle and iterative improvement were carried out in relation to each of the source coils 14$i$, the number of calculations would be enormous. Therefore, determination of a circle and iterative improvement should be carried out in relation to only the leading source coil 14$a$. For the other source coils, since the source coils are continuous, the estimated position of the immediately preceding source coil may be used as an initial value to carry out iterative improvement. For estimating the three-dimensional position of the source coil 14$b$, the estimated three-dimensional position of the source coil 14$a$ is used as an initial value to carry out iterative improvement.

Since the source coils are continuous, the three-dimensional position of each source coil to be estimated may be predicted from the previously estimated three-dimensional position of a source coil, and iterative improvement may be carried out with the predicted position as an initial value.

Similarly to the fourth embodiment, the three-dimensional positions of the source coils 14$a$ and 14$b$ are expressed as the formula (75) of the fourth embodiment. An initial value used to estimate the three-dimensional position of the source coil 14$b$ is the position of the source coil 14$a$. For the source coil 14$c$ and subsequent source coils, the position or each source coil is predicted from the three-dimensional positions of two preceding source coils. For example, the three-dimensional position of the source coil 14$c$ is estimated according to the formula (76) of the fourth embodiment.

The present embodiment is used for examinations of body cavities. A temporal variation in the three-dimensional position of each source coil is presumably limited because motions made in a body cavity by the source coils are limited. Accordingly, the previously estimated three-dimensional position may be adopted as an initial position for performing iterative improvement.

The present embodiment can provide the same advantage as the fourth embodiment. In addition, excluding the relational expression having the term in which the gradient of a source coil is specified and decreasing the number of unknowns can be used to estimate the three-dimensional position of each source coil.

The endoscope shape detection system 3 of the present sixth embodiment of the invention has, in addition to the same components as those of the first embodiment, a position memory means in which estimated positions of source coils are recorded time-sequentially. The other components are identical to those of the first embodiment. The present embodiment is different from the first embodiment in a method of estimating the three-dimensional position of each source coil.

According to the sixth embodiment, the method described in conjunction with the first five embodiments is employed in estimating the three-dimensional positions of the source coils 14$i$. The estimated three-dimensional positions are successively recorded in a position memory means (not shown).

The current estimated position of each source coil 14$i$ is expressed as follows:

$$P_{i,n} = \begin{pmatrix} x_{i,n} \\ y_{i,n} \\ z_{i,n} \end{pmatrix} \tag{84}$$

The past estimated position thereof is expressed as follows:

$$P_{i,n-1} = \begin{pmatrix} x_{i,n-1} \\ y_{i,n-1} \\ z_{i,n-1} \end{pmatrix} \tag{85}$$

The current position $P'_{i,n}$ of each source coil 14$i$ is calculated by weighting and summarizing the estimated positions.

Assuming that a weight to be applied to the current estimated position is $\alpha$, the current position $P'_{i,n}$ nof each source coil is obtained according to the following formula:

$$P'_{i,n} = \alpha P'_{i,n-1} + (1-\alpha) P'_{i,n} \tag{86}$$

Alternatively, intermediate values of x, y, and z coordinates may be extracted from the current position of each source coil and two past estimated positions. The intermediate values may be considered as the x, y, and z coordinates indicating the current position of each source coil (median filter).

The present embodiment suppresses uncertainty in the three-dimensional position of each source coil, which is observed when the source coils and sense coils are separated from each other.

The configuration of the endoscope shape detection system 3 of the seventh embodiment is identical to that of the sixth embodiment. A difference lies in a method of estimating the three-dimensional position of each source coil.

According to the seventh embodiment of the invention, the method described in relation to the first five embodiments is employed in estimating the three-dimensional positions of the source coils 14$i$. The estimated positions are successively recorded in a position memory means (not shown).

The time-sequentially recorded estimated positions of each source coil 14$i$ are provided as follows:

$$P_{i,0}, P_{i,1}, P_{i,2}, \ldots, P_{i,N} \tag{87}$$

The predicted positions of each source coil 14$i$ are provided as follows:

$$Q_{i,0}, Q_{i,1} Q_{i,2}, \ldots, Q_{1,N} \tag{88}$$

Herein, the N-th predicted position shall be a current position.

The sum of the squares of differences between the estimated positions and predicted positions of each source coil 14$i$ is expressed as follows:

$$f_{i,1} = \sum_{j=0}^{N} (P_{i,j} - Q_{i,j})^2 \tag{89}$$

The sum of the squares of differences in displacement between adjoining predicted positions is expressed as follows:

$$f_{i,2} = \sum_{j=2}^{N} \{(Q_{i,j} - Q_{i,j-1}) - (Q_{i,j-1} - Q_{i,j-2})\}^2 \quad (90)$$

$$= \sum_{j=2}^{N} (Q_{i,j} - 2Q_{i,j-1} + Q_{i,j-2})^2$$

$f_{i,1}$ and $f_{i,2}$ are summed with $f_{i,2}$ weighted by $\omega$ as follows:

$$f_i = f_{i,1} + \omega f_{i,2} \quad (91)$$

Herein, when the weight $\omega$ is small, the position of each source coil 14*i* approaches the estimated position. When the weight $\omega$ is large, the position of each source coil 14*i* approaches the predicted position.

For obtaining the predicted position $Q_{ij}$ that minimizes $f_i$, the partial differential of the formula f is calculated with respect to the predicted position $Q_{ij}$ and a predicted position $Q_{ij}$ satisfying $f'_i = 0$ is obtained.

The partial differential of $f_i$ is calculated with respect to the predicted position $Q_{ij}$, and 0 is specified as $f'_i$.

$$P = MQ \quad (92)$$

The formula (92) is rewritten using the inverse matrix of M as follows:

$$Q = M^{-1} P \quad (93)$$

The predicted position is calculated according to the formula (93).

For example, where seven previous three-dimensional estimated positions of each source coil 14*i* are recorded, the formula (94) below is defined based on the formula (92).

$$\begin{bmatrix} P_{i,0} \\ P_{i,1} \\ P_{i,2} \\ P_{i,3} \\ P_{i,4} \\ P_{i,5} \\ P_{i,6} \end{bmatrix} = \begin{bmatrix} 1+\omega & -2\omega & \omega & 0 & 0 & 0 & 0 \\ -2\omega & 1+5\omega & -4\omega & \omega & 0 & 0 & 0 \\ \omega & -4\omega & 1+6\omega & -4\omega & \omega & 0 & 0 \\ 0 & \omega & -4\omega & 1+6\omega & -4\omega & \omega & 0 \\ 0 & 0 & \omega & -4\omega & 1+6\omega & -4\omega & \omega \\ 0 & 0 & 0 & \omega & -4\omega & 1+5\omega & -2\omega \\ 0 & 0 & 0 & 0 & \omega & -2\omega & 1+\omega \end{bmatrix} \begin{bmatrix} Q_{i,0} \\ Q_{i,1} \\ Q_{i,2} \\ Q_{i,3} \\ Q_{i,4} \\ Q_{i,5} \\ Q_{i,6} \end{bmatrix} \quad (94)$$

The weight $\omega$ is set to a specified value and the determinant of the inverse matrix of the matrix M is calculated. The predicted positions are then obtained according to the formula (93).

According to the present embodiment, a motion made by each source coil is predicted from the past estimated positions of each source coil. The current position of each source coil is obtained based on the estimated positions and predicted positions. Uncertainty in the three-dimensional position of each source coil observed when the source coils and sense coils are separated from each other can be suppressed. Even when the source coils move, the position of each source coil can be determined on a more stable basis than according to the technique employed in the fifth embodiment.

In the subsequent embodiments, the shape of an endoscope is estimated using the estimation algorithm described in relation to the first seven embodiments.

According to the eighth embodiment of the invention, as shown in FIGS. 48A–C, examinations are conducted through endoscopic observation using an endoscope system 206 and an endoscope shape detection system 211. Specifically, the endoscope system 206 consists mainly of an endoscope 203, a camera control unit (hereinafter, a CCU) 204, and an observation monitor 205. The endoscope 203 is inserted into the body of a patient 202 lying down on an examination table 201. The CCU 204, having a light source device incorporated therein, processes a signal representing an endoscopic image sent from the endoscope 203. An endoscopic view is displayed on the observation monitor 205. The endoscope shape detection system 211 position detection system consists mainly of, for example, twelve source coils 203(1) to 203(12), a coil unit 208, a control unit 209, and a monitor 210. The twelve source coils 203(1) to 203(12) are incorporated in an insertion unit 207 of the endoscope 203, and generate magnetic fields. The coil unit 208 having, for example, sixteen sense coils 208(1) to 208(16) incorporated therein detects the magnetic fields generated by the source coils 203(1) to 203(12). The control unit 209 processes a signal output from the coil unit 208. Consequently, the shape of the endoscope is depicted on the monitor 210.

Hereinafter, the source coils 203(1) to 203(1.2) are represented by source coils 203(g) (g=1 to 12), and the sense coils 208(1) to 208(16) are represented by sense coils 208(h) (h=1 to 16).

Three markers 212 each having one source coil incorporated therein are fastened near the anus of the patient 202, on the left flank thereof, and on the right flank thereof. These markers 212 are connected to the control unit 209. An input unit 213 used to designate a magnification, modify setting, or enter various kinds of data is also connected to the control unit 209.

Figure 49:
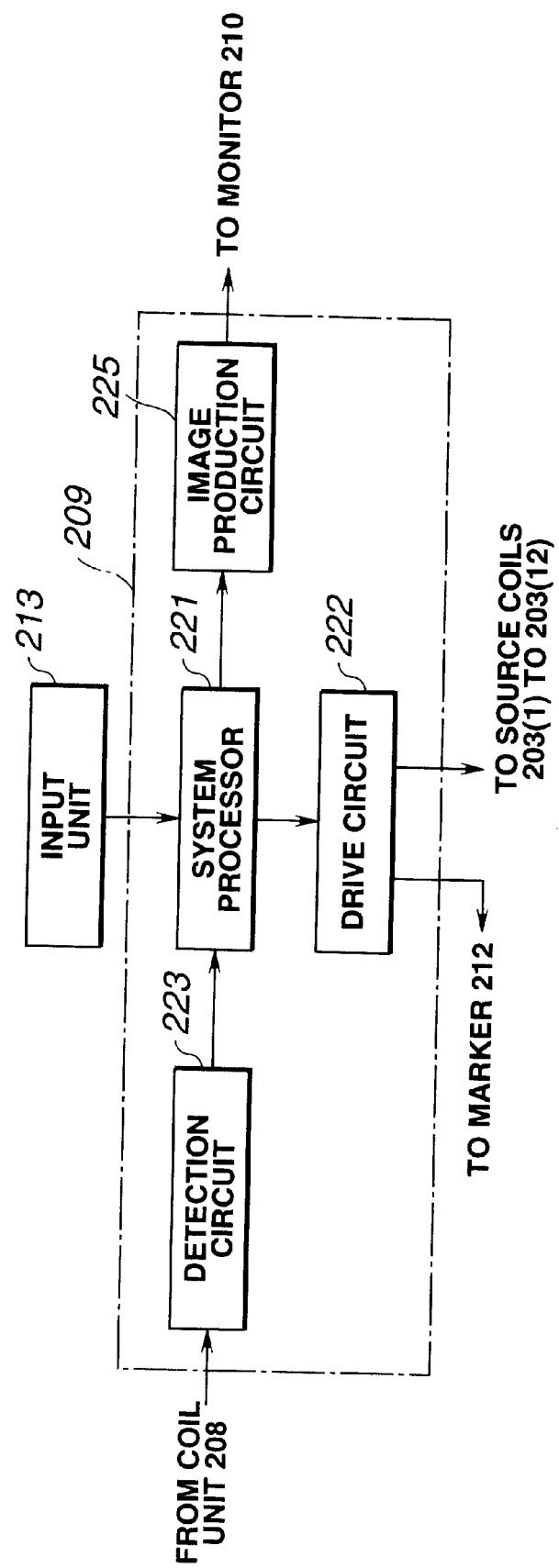

The control unit 209 consists, as shown in FIG. 49, of a system processor 221, a drive circuit 222, a detection circuit 223, and an image production circuit 225. The system processor 221 controls the components of the endoscope shape detection system 211, and carries out position estimation and other arithmetic operations using detection signals sent from the sense coils 208(h) and markers 212. The drive circuit 222 supplies a driving current to the source coils 203(g), which are incorporated in the insertion unit 207 of the endoscope 203, and the markers 212 in response to a control signal sent from the system processor 221. The driving current induces alternating gradients in the source coils and markers. The detection circuit 223 amplifies magnetic detection currents supplied from the sense coils 208(h) incorporated in the coil unit 208 and the markers 212, converts them into digital signals, and then outputs the digital signals to the system processor 221. The image production circuit 225 outputs the digital data produced by the system processor 221 into analog signals, and outputs the analog signals to the monitor 210. The digital data represents the shape of the endoscope 203 and the locations of the markers 212. The input unit 213 is connected to the system processor 221.

Operations of the present embodiment will be described in conjunction with FIG. 50 to FIG. 55.

The system processor 221 in the control unit 9 detects, as described in FIG. 50, the positions of the twelve source coils 203(g) incorporated in the endoscope 203 by manipulating digital data that represents magnetic detection currents supplied from the sense coils 208(h) at step S201.

Thereafter, as shown in FIGS. 51A and 51B, similarly to the positions of the source coils 203(g) in the endoscope 203, the positions of an anus marker 251, a left marker 252, and a right marker 253 are detected at step S202. The anus marker 251, left marker 252, and right marker 253 are the markers 212 fastened near the anus of the patient 202, on the left flank thereof, and on the right flank thereof. The outer product h of a vector M1 extending from the anus marker 251 to the left marker 252 by a vector M2 extending from the anus marker 251 to the right marker 252 is calculated (h=M1×M2).

Figure 52:
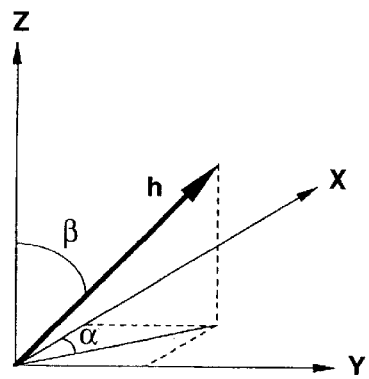

At step S203, a plane having the vector h as a normal vector is defined as a patient plane on which a patient lies down. The patient plane shifts along with a change in the posture of the patient 202, because the patient plane is defined using the markers 212 fastened to the patient 202. The vector h exhibits angles of rotation α and β relative to the X and Z axes of a coordinate system for detection, as shown in FIG. 52.

Figure 53:
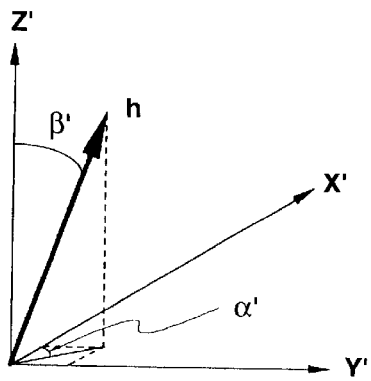
Figure 54:
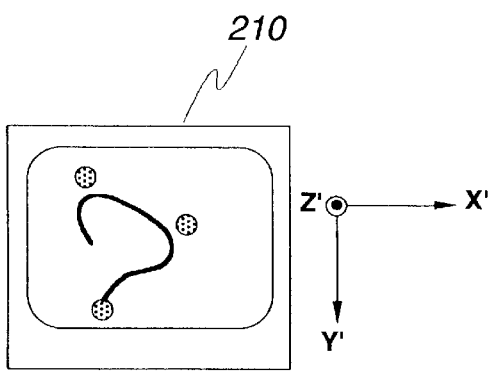
Figure 55:
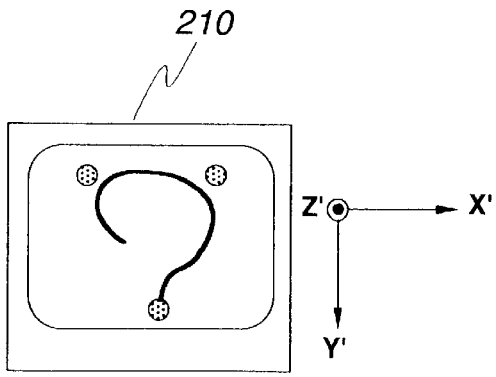

At step S204, angles of rotation α' and β' of the normal vector h, which is determined at step S203, relative to the X' and Z' axes of a coordinate system for display are calculated as shown in FIG. 53.

At step S205, based on the angles of rotation α' and β' calculated at step S204, coordinate transformation is performed on data representing the detected positions of the twelve source coils 203(g) incorporated in the endoscope 203 and data representing the detected positions of the anus marker 251, left marker 252, and right marker 253.

At step S206, due to the coordinate transformation, the previous image of a shape (FIG. 54) is changed to the image (FIG. 55) with the endoscope seen in the direction of the normal on the patient plane.

As mentioned above, according to the present embodiment, data representing a change in the posture of the patient 202 is removed from position information of each source coil 203(g). The shape of the endoscope is depicted with the relationship thereof relative to a user-designated line of sight held constant. Once a user sets his/her line of sight in an easy-to-see direction, even if the patient 202 changes his/her posture, the direction of the depicted shape of the endoscope remains constant.

The system configuration of the ninth embodiment of the invention is identical to that of the eighth embodiment. A difference lies in processing performed by the system processor 221 in the control unit 209.

Figure 56:
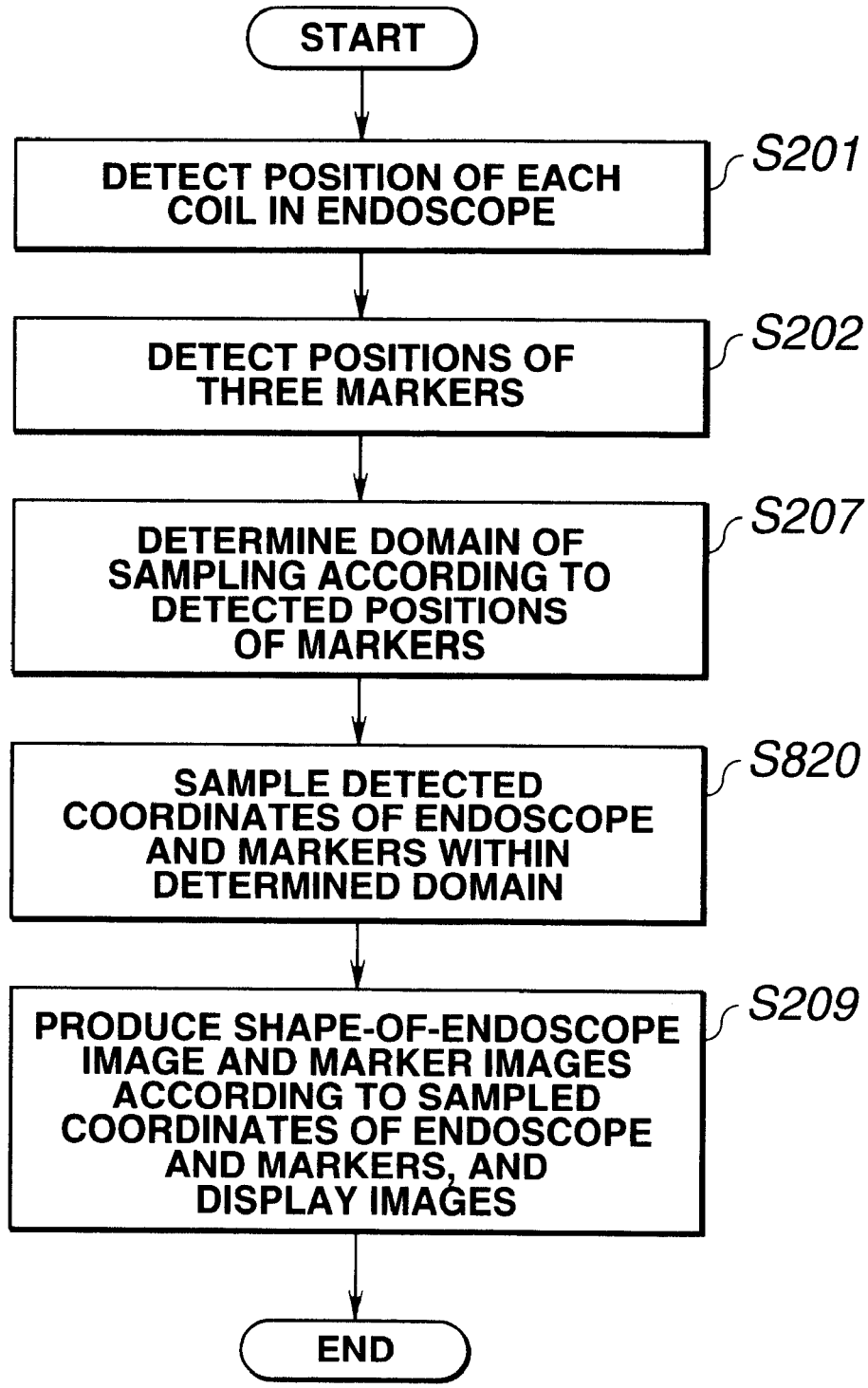
FIG. 56 to FIG. 58 relate to the sixth embodiment of the present invention.

According to the present embodiment, as described in FIG. 56, at step S201, the system processor 221 in the control unit 209 detects the positions of the twelve source coils 203(g) incorporated in the endoscope 203. At this time, the system processor 221 uses digital data of magnetic detection currents supplied from the sense coils 208(h).

Thereafter, similarly to the source coils 203(g) lying in the endoscope 203, the positions of the anus marker 251, left marketer 252, and right marker 253 are detected at step S202 (see FIGS. 51A and 51B). The anus marker 251, left marketer 252, and right marker 253 are the markers 212 fastened near the anus of the patient 202, on the left flank thereof, and on the right flank thereof.

Figure 57:
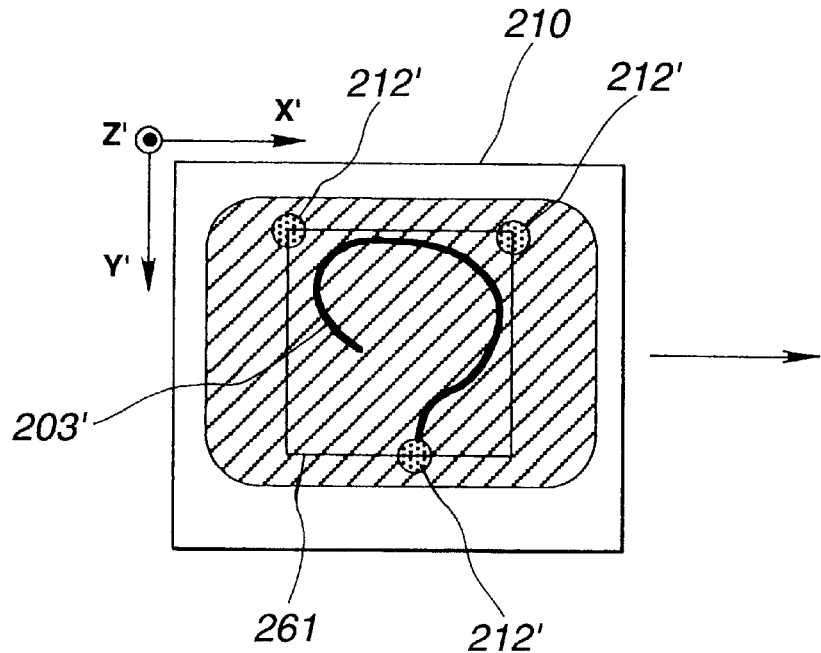

At step S207, a domain of sampling 261 shown in FIG. 57 is defined using the three markers of the anus marker 251, left marker 252, and right marker 253.

Thereafter, at step S208, data of the detected position of the endoscope 203 is sampled from the domain of sampling 261 defined at step S207.

Figure 58:
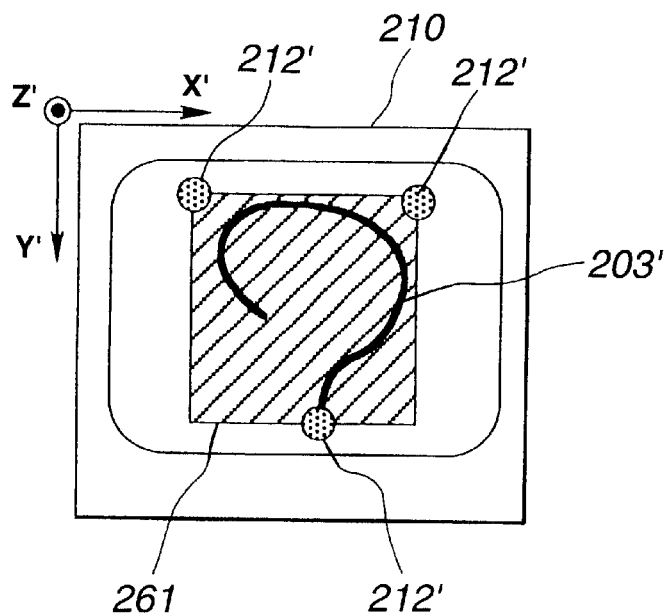

Finally, at step S209, an image 203a showing the shape of the endoscope and images 212a showing the markers are produced using the detected position data of the endoscope 203 and the detected position data of the three markers 212. The shape image depicted using the detected position data within the domain of sampling is solely displayed as shown in FIG. 58.

As mentioned above, according to the present embodiment, the shape of the endoscope is depicted using the detected position data within a domain of sampling defined using at least three source coils of the anus marker 251, left marker 252, and right marker 253. An image based on data outside of the user-designated domain can be eliminated. Consequently, the shape of an endoscope dwelling in a region of interest can be identified readily.

The tenth embodiment is nearly identical to the eighth embodiment. A difference alone will be described. The same reference numerals will be assigned to the identical components. The description of the components will be omitted.

As shown in FIGS. 59A–E, the outer surface of the observation monitor 205, a CRT, is covered with an isolation sheet 205a made of a non-conducting material, such as polyester. The outer side of the isolation sheet 205a is covered with a magnetic shielding plate 205b effective in blocking magnetic fields and made of an amorphous alloy or the like.

Similarly, the outer surface of the monitor 210 is covered with an isolation sheet 210a made of a non-conducting material, such as polyester. The outer side of the isolation sheet 210a is covered with a magnetic shielding plate 210b effective in blocking magnetic fields and made of an amorphous alloy or the like.

As shown in FIGS. 60A and 60B, a detection circuit 223 in the control unit 209 is electrically isolated from a magnetic shielding casing 271 by four spacers 272a, 272b, 272c, and 272d made of a non-conducting material, for example, polycarbonate, and locked in the magnetic shielding casing 271. The magnetic shielding casing 271 is electrically isolated from the control unit 209 by four spacers 273a, 273b, 273c, and 273d made of a non-conducting material, and locked in the control unit 209.

The other components are identical to those of the eighth embodiment.

Next, a description will be made of an operation of the present embodiment having the foregoing components. While the insertion unit 207 of the endoscope 203 is inserted into a body cavity, an endoscopic image of the interior of the body cavity is displayed on the observation monitor 205 by means of the CCU 204. Magnetic fields generated by the source coils 203(g) incorporated in the insertion unit 207 of the endoscope 203 are detected by the sense coils 208(h). Digital data of magnetic detection currents supplied proportionally to the detected magnetic fields are used to detect the positions of the twelve source coils 203(g) incorporated in the endoscope 203. The shape of the endoscope is depicted on the monitor 210.

Magnetic noise generated by the observation monitor 205 and monitor 210 are decayed by the magnetic shielding plate 205b and magnetic shielding plate 210b. The magnetic shielding plates 205b and 210b also are electrically isolated from the observation monitor 205 and monitor 210 owing to the isolation sheet 205a and isolation sheet 210a, respectively. This intensifies the effect of decay attributable to eddy-current losses occurring on the magnetic shielding plate 205b and magnetic shielding plate 210b.

In the control unit 209, magnetic noise generated by the drive circuit 222 for supplying a driving current that induces alternating gradients in the source coils 203(g) is decayed by the magnetic shielding casing 271. The magnetic shielding casing 271 is electrically isolated from the control unit 209 and detection circuit 222 by the spacers 272a, 272b, 272c, and 272d and the spacers 273a, 273b, 273c, and 273d, respectively. This intensifies the effect of decay attributable to an eddy-current loss occurring on the magnetic shielding casing 271.

The other operations are identical to those of the eighth embodiment.

According to the present embodiment, magnetic noise generated by the observation monitor 205 and monitor 210 are decayed by the magnetic shielding plate 205b and magnetic shielding plate 210b. Moreover, the magnetic shielding plate 205b and magnetic shielding plate 210b are electrically isolated from the observation monitor 205 and monitor 210 by means of the isolation sheet 205a and isolation sheet 210a, respectively. This intensifies the effect of decaying magnetic fields by utilizing eddy-current losses occurring on the magnetic shielding plate 205b and magnetic shielding plate 210b. The adverse effect of magnetic noise generated by the observation monitor 205 and monitor 210 can be suppressed effectively. The shape of an endoscope can be depicted on the monitor 210 in a more stable manner.

In the control unit 209, the magnetic shielding casing 271 decays magnetic noise generated by the drive circuit 22 for supplying a driving current with which alternating gradients are induced in the source coils 203(g). The spacers 272a, 272b, 272c, and 272d and the spacers 273a, 273b, 273c, and 273d electrically isolate the magnetic shielding casing 271 from the control unit 209 and detection circuit 222. This intensifies the effect of decaying magnetic fields by utilizing eddy-current losses occurring on magnetic shielding casing 271. The adverse effect of the magnetic noise generated by the drive circuit 222 can be suppressed effectively. Consequently, the shape of the endoscope can be depicted on the monitor 210 on a more stable basis.

As shown in FIGS. 61A–C, the observation monitor 205 may not be a CRT, but may be realized with a liquid crystal display 281. The observation monitor 205 also may be realized with a plasma display instead of the liquid crystal display 281. The monitor 210 similarly may be realized with a liquid crystal display or plasma display.

A liquid crystal display 281, in principle, creates little magnetic noise. Compared with a CRT, magnetic noise can be reduced, thus eliminating the need for magnetic shields.

The eleventh embodiment is nearly identical to the eighth embodiment. A difference alone will be described. The same reference numerals will be assigned to the identical components. The description of the components will be omitted.

As shown in FIGS. 62A–D, an endoscope 203a of the present embodiment has an insertion unit 301 that is elongated and flexible, an operation unit 302 located at the back end of the insertion unit 301, and a universal cable 303 extending from the operation unit 302. A connector attached to the end of the universal cable 303 is coupled to the CCU 204.

The operation unit 302 has a bending knob 304. The bending knob 304 is manipulated, whereby a bendable part 306 adjoining the distal part of the insertion unit 301 can be bent.

According to the present embodiment, no source coils are lying through the insertion unit. An inserted form detection probe 3Q7 is passed through a treatment appliance channel lying along the axis of the insertion unit 301. Twelve source coils 203(g) are incorporated at predetermined intervals along the axis of the inserted form detection probe (hereinafter, probe) 307.

The probe 307 is passed through the treatment appliance channel, and the distal end, or back end, of the probe is positioned and immobilized. The twelve source coils 304(g) are thus placed along the axis of the insertion unit 301 at predetermined intervals.

Four markers 212(1), 212(2), 212(3), and 212(4) (generically, 212(i)) are placed on th body surface of the patient 202, for example, near the anus and on the left flank and right flank, and on an operator's hand. The markers 212(i) each contain one magnetic generation device or marker coil 212a.

According to the present embodiment, the probe 307 having the source coils 203(g) incorporated therein is passed through the forceps channel lying through the endoscope 203a. The source coils 203(g) are thus incorporated in the insertion unit 301 of the endoscope 203a. Alternatively, the source coils 203(g) may be incorporated directly in the insertion unit 301 of the endoscope 203a.

Figure 63:
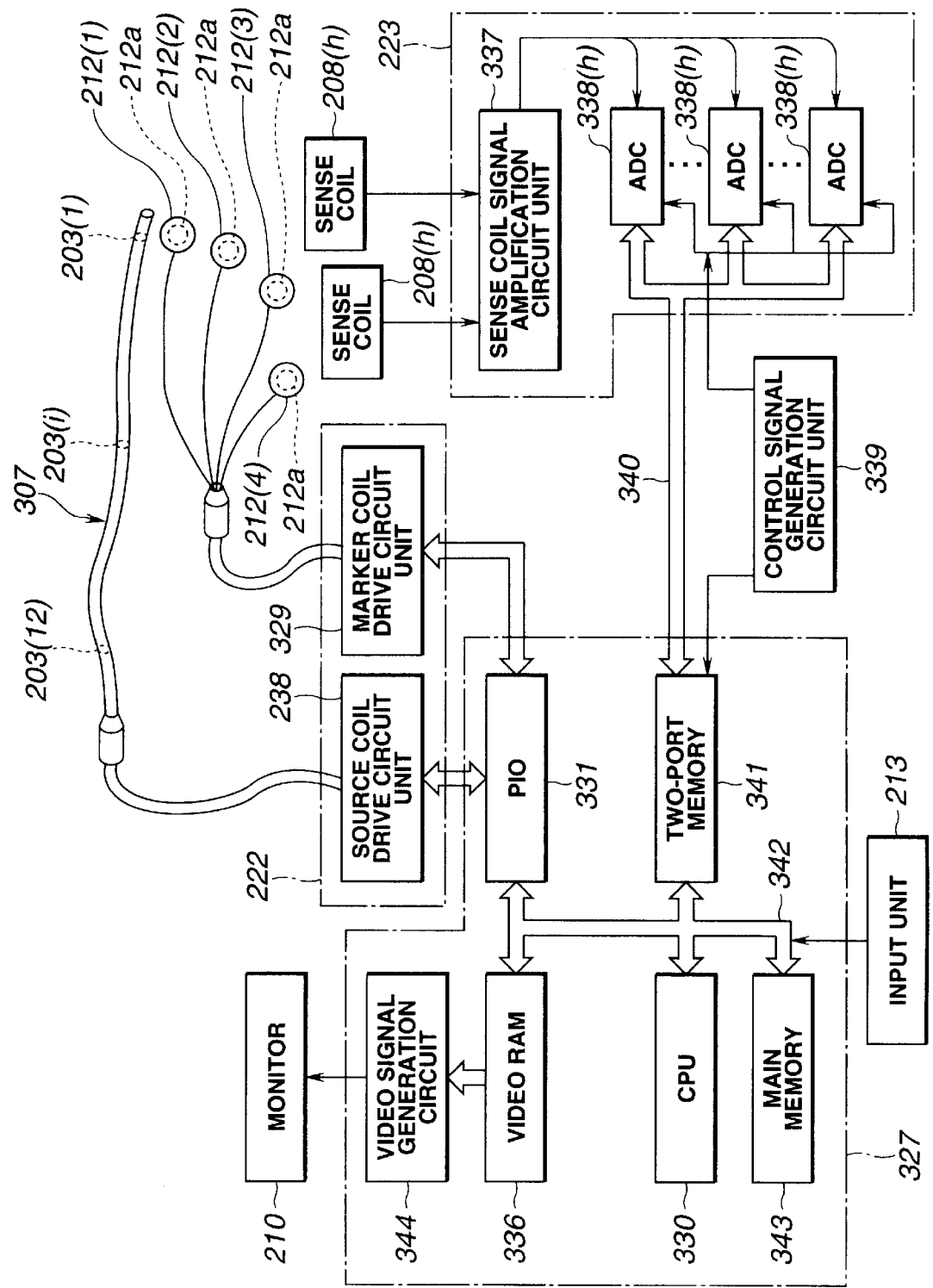

As shown in FIG. 63, the control unit 209 of the present embodiment consists of the drive circuit 222, the detection circuit 223, and a host processor 327. The drive circuit 222 drives the source coils 203(g) and marker coils 212a. The detection circuit 223 detects signals received by the sense coils 208th). The host processor 327 consists of a CPU 330 operating as the system processor 221 for processing signals detected by the drive circuit 222, and a video signal generation circuit 344 operating as the image production circuit 225.

As shown in FIG. 63, in the probe 307 lying through the insertion unit 301 of the endoscope 203a, the twelve source coils 203(g) for generating magnetic fields are placed at predetermined intervals. The source coils 203(g) are connected to a source coil drive circuit unit 32B for producing twelve driving signals of different radio frequencies. The source coil drive circuit unit 328 is included in the drive circuit 222.

The marker coils 212a are connected to a marker coil drive circuit unit 329 for producing four driving signals of different radio frequencies that are different from the radio frequencies of the source coil driving signals. The marker coil drive circuit unit 329 is included in the drive circuit 22.

In the drive circuit 222 in the control unit 209, the source coil drive circuit unit 328 drives the source coils 203(g) using currents of sine waves of different frequencies serving as driving signals. The marker coil drive circuit unit 329 drives the marker coils 212a using the currents serving as driving signal. Driving frequencies at which the coils are driven are set cased on driving frequency setting data,or driving frequency data, stored in a driving frequency setting data storage means or driving frequency setting data memory means (not shown). The driving frequency setting data storage means or driving frequency setting data memory means is included in the source coil drive circuit unit 328 and marker coil drive circuit unit 329 alike.

Data of the driving frequencies are stored in the driving frequency storage means (not shown) in the source coil drive circuit unit 328 and marker coil drive circuit unit 329 via a parallel input/output (PIO) circuit 331 by means of the central processing unit (CPU) 330 in the host processor 327. The CPU 330 is responsible for calculations needed to depict the shape of the endoscope.

The sense coils 208(h) are connected to a sense coil signal amplification circuit unit 337 included in the detection circuit 223.

The detection circuit 223 consists of the sense coil signal amplification circuit unit 337, and A/D converters 338(h). After weak signals detected by the sense coils 208(h) are amplified by the sense coil signal amplification circuit unit 337, the signals are converted into digital data readable by the host processor 327 by means of the A/D converters 338(h). The digital data are written in a twoport memory 341 over a local data bus 340 in response to a control signal sent from a control signal generation circuit unit 339.

The CPU 330 reads the digital data written in the two-port memory 341 over an internal bus 342 in response to a control signal sent from the control signal generation circuit unit 339. The CPU 330 uses a main memory 343 to perform frequency sampling (fast Fourier transform (FFT)) on the digital data. Magnetic detection information representing frequency components having frequencies that correspond to the driving frequencies at which the source coils 203(g) and marker coils 212a are driven are sampled and separated from other information. The digital data items of the separated magnetic field detection information are used to calculate the coordinates indicating the spatial positions of the source coils 203(g) that are lying through the insertion unit 301 of the endoscope 203a and those of the marker coils 212a.

The inserted state of the insertion unit 301 of the endoscope 203a is estimated from the data representing the calculated coordinates indicating the positions of the source coils 203(g). Display data based on which the shape of the endoscope is depicted [is] are output to a video RAM 336. Display data based on the marker coils 212a are produced using the data of the calculated coordinates indicating the positions of the marker coils 212a. The display data are then output to the video RAM 336.

Figure 64A:
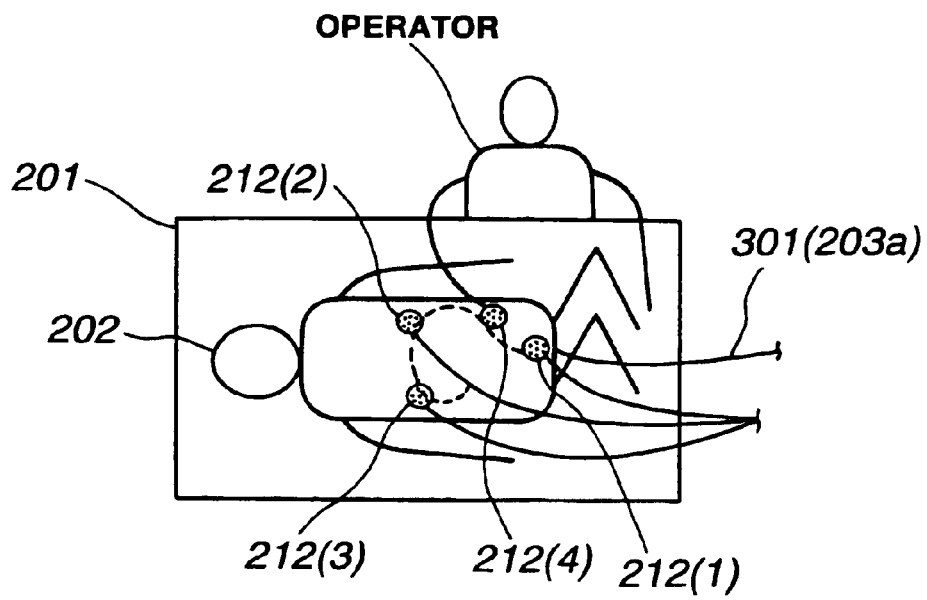
FIG. 64A is a diagrammatic view of an operator, a patient and the control unit shown in FIG. 63.
Figure 64B:
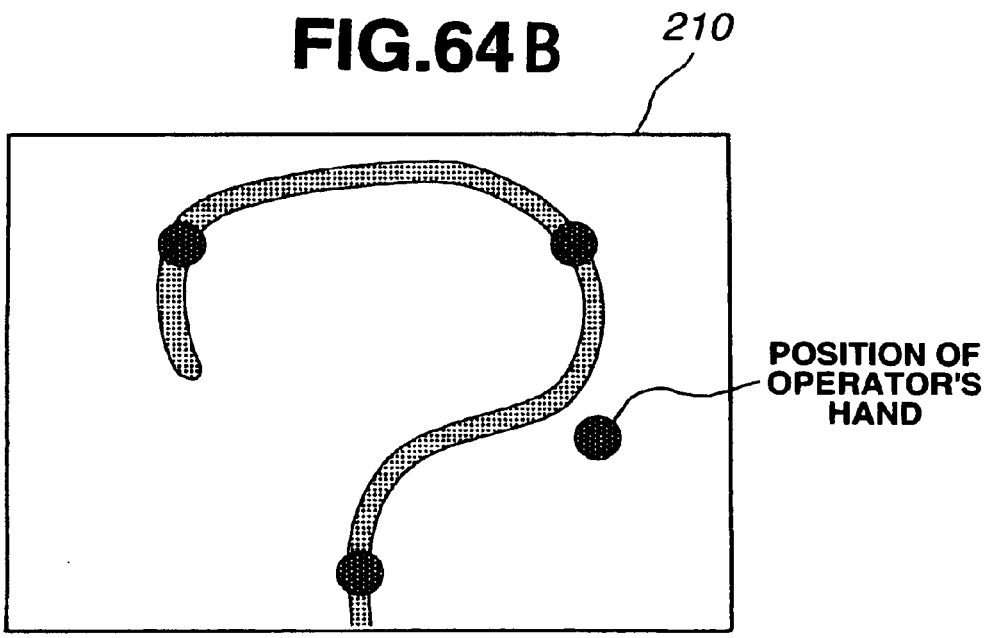

The data written in the video RAM 336 are read using the video signal generation circuit 344, converted into an analog video signal, and output to the monitor 210. With input of the analog video signal, the inserted form of the insertion unit 301 of the endoscope 203a and the positions of the markers are, as shown in FIGS. 64A–B, depicted on the display screen of the monitor 210.

According to the present embodiment, the positions of the markers are depicted together with the shape of the endoscope. The positional relationship between the insertion unit of the endoscope and a patient's body can therefore be ascertained. The marker 212a placed near the anus serves as an important index indicating a border between the interior of a patient's body and the exterior thereof.

One out of the plurality of markers is placed on an operator's hand, thus the position of the operators hand can be depicted on the monitor 210.

The configuration of the twelfth embodiment is identical to that of the eleventh embodiment. The twelfth embodiment is characterized by a method of displaying an image on a monitor.

Figure 65A:
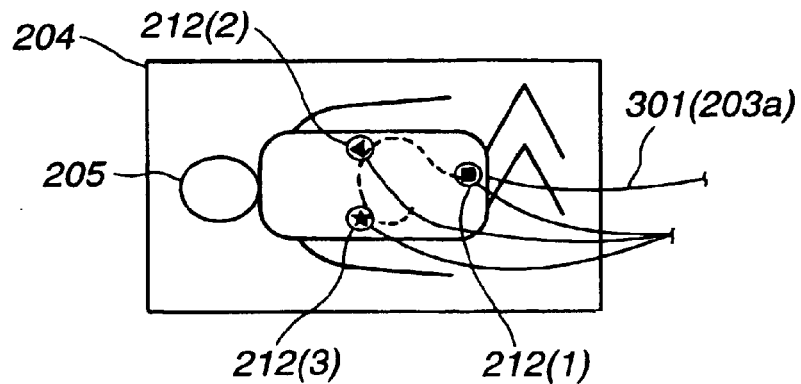
Figure 65B:
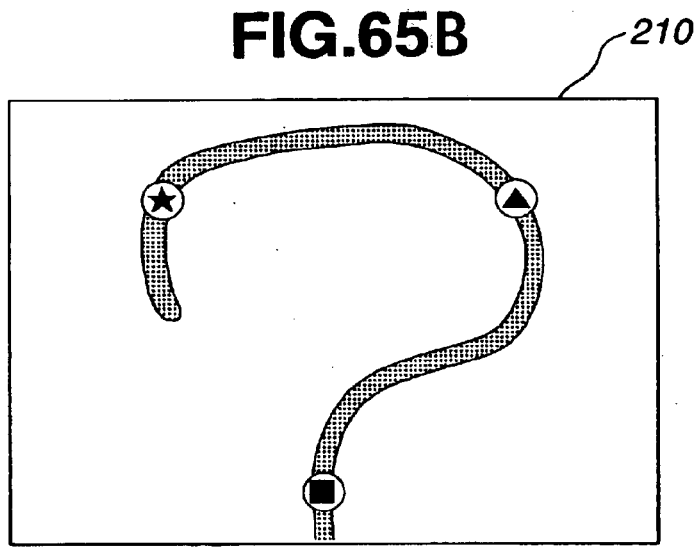
FIG. 65B is a diagrammatic view of endoscope shape modeling performed by the endoscope shape detection systems.

As shown in FIGS. 65A–B, a symbol is inscribed in each marker itself. For example, a blackened square is inscribed in the marker 212(1), a blackened triangle is inscribed in the marker 212(2), and a blackened star is inscribed in the marker 212(3). The same symbols are drawn in the images of the corresponding markers on the monitor 210. The other operations are identical to those exerted by the tenth embodiment.

The markers can be associated with the images of the markers on the monitor. This results in an easierto-see image showing the shape of the endoscope.

According to the present embodiment, the blackened square, blackened triangle, and blackened star are employed. The symbols are not limited to these ones. Any colors, numerals, or characters can be employed as long as they are discernible on the monitor. A combination of any of the colors, numerals, or characters, for example, colored characters may be used.

Figure 66:
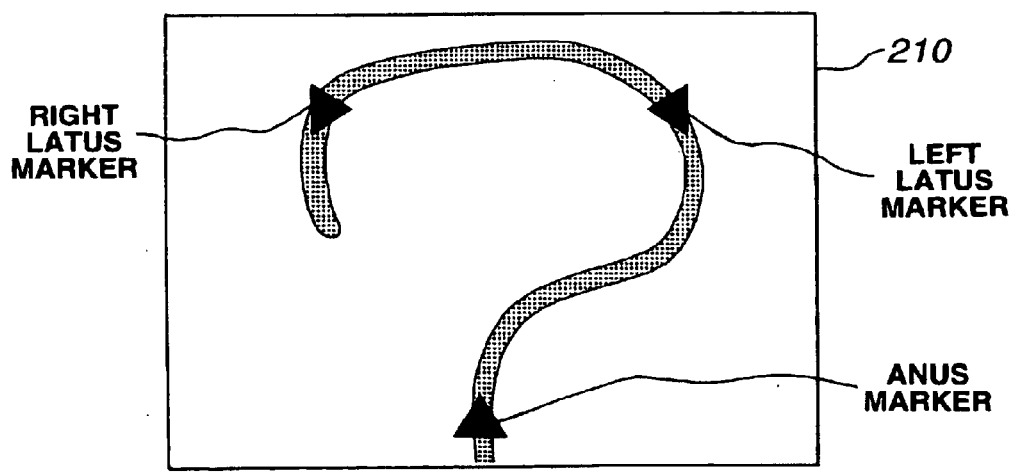

According to the present embodiment, the markers on the monitor are depicted as circles with the symbols drawn therein. Alternatively, as shown in FIG. 66, an upward triangle, a rightward triangle, and a leftward triangle may be displayed. Specifically, a blackened triangle may be depicted at the position of the anus, a blackened triangle tilted 90° rightwardly may be depicted at the position of the right flank, and a blackened triangle tilted 90° leftwardly may be depicted at the position of the left flank. In short, the images of the markers on the monitor may have any shapes. The images of the markers having any shapes may be displayed in combination with the foregoing symbols.

The configuration of the thirteenth embodiment is identical to that of the eleventh embodiment. The thirteenth embodiment is characterized in that the position information of markers can be stored.

When the marker 212(1) is placed at the anus of the patient 202, since the anus is unlikely to the abdomen, not planar, there is difficulty in placing the marker 212(1) There is a fear that the marker 212(1) may come off from the patient 202 during an examination.

Figure 67A:
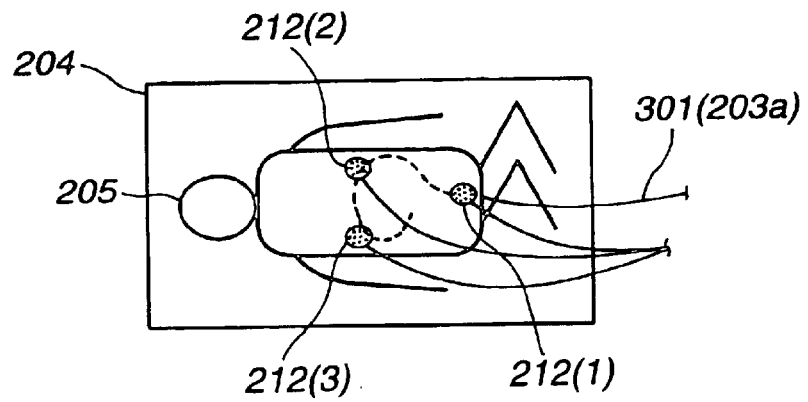
FIGS. 67A and 67B are schematic views of a patient undergoing operations of the endoscope shape detection system in accordance with the tenth embodiment of the present invention.
Figure 67B:
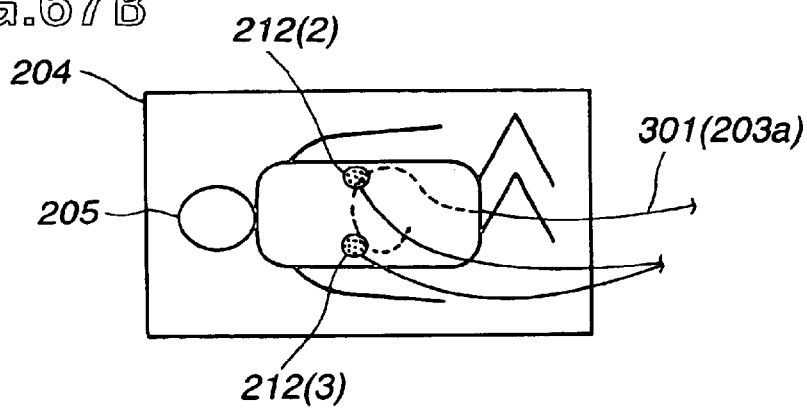
Figure 67C:
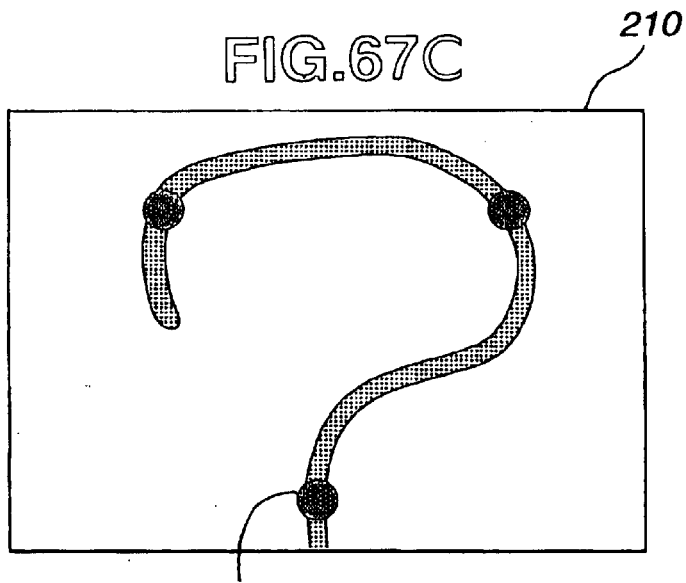
FIG. 67C is a diagrammatic view of endoscope shape modeling performed by the endoscope shape detection system of FIG. 67A.

As shown in FIGS. 67A–C, the marker 212(1) is placed at the anus of the patient 202 prior to an examination. The position data of the marker coil 212a are stored in a control unit 209a. A storage area may be preserved in the main memory 343 in the host processor 327 or in a newly included memory. A command instructing storage is issued from the input unit 213.

After the position data of the marker 212(1) is stored, the marker 212(1) is removed from the patient 202 and an examination is started.

In addition to the markers 212(2) and 212(3) actually placed on the patient 202, display data of the marker 212(1) is produced based on the stored position data of the marker coil 212a. The marker coil 212a is depicted together with the shape of the endoscope during the examination.

As mentioned in conjunction with the twelfth embodiment, the markers themselves and the images of the markers on the monitor may be associated with one another even in the thirteenth embodiment.

The positional relationship between the insertion unit of the endoscope and the patient' s body can be ascertained without the marker 212(1) detaching from the patient 202 during an examination.

The form of the fourteenth embodiment is identical to that of the eleventh embodiment. A difference lies in processing to be performed by the system processor 221. The same reference numerals will be assigned to the identical components. The description of the components will be omitted.

Figure 68:
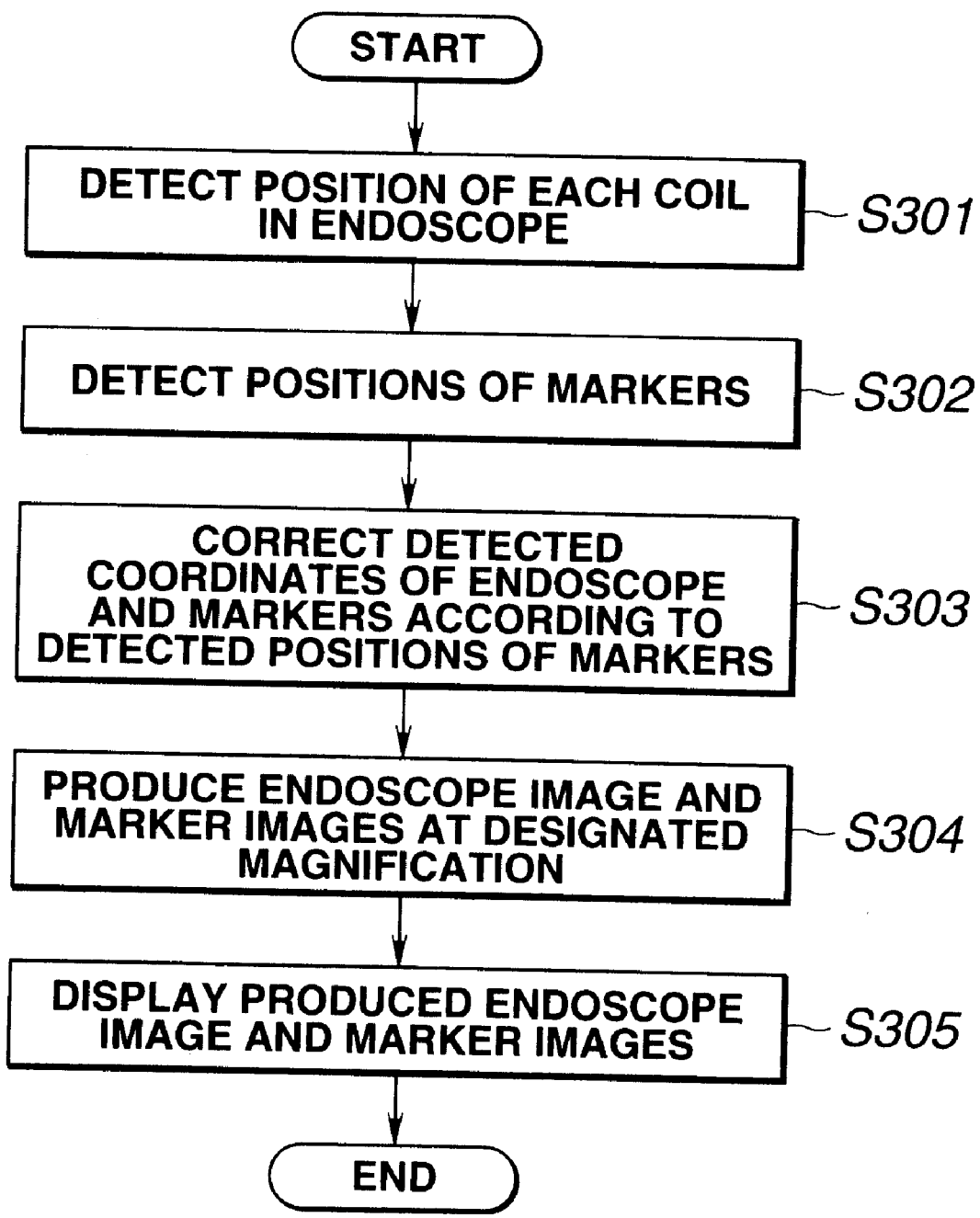
FIG. 68 to FIG. 71 relate to the eleventh embodiment of the present invention.

An operation of the fourteenth embodiment will be described in conjunction with FIG. 68.

Figure 69:
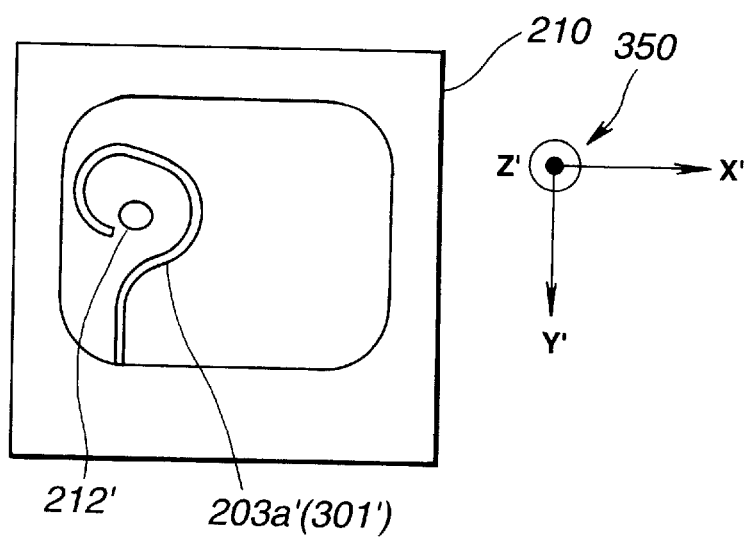

The system processor 221 in the control unit 209 detects the positions of the source coils 203(g) in the endoscope 203a at step S301 in FIG. 69.

Specifically, the system processor 221 controls the drive circuit 222, applies a driving signal of an alternating current sequentially to the source coils 203(g) (g=1 to 12) in the endoscope 203. Alternating gradients are therefore generated around the source coils 203(g). The sense coils 208(h) in the coil unit 208 detect the alternating gradients. Magnetic detection currents supplied from the sense coils are amplified by the detection circuit 223, and converted into digital data. The system processor 221 acquires the digital data, and detects the positions of the twelve source coils 203(g) incorporated in the endoscope 203a.

Similarly to the source coils 203(g) in the endoscope 203a, the reference position on the patient 205, or more particularly, the position of the marker 212 locked near the umbilicus of the patient 205 is detected using the sixteen sense coils 208(h) (step S302).

Figure 70:
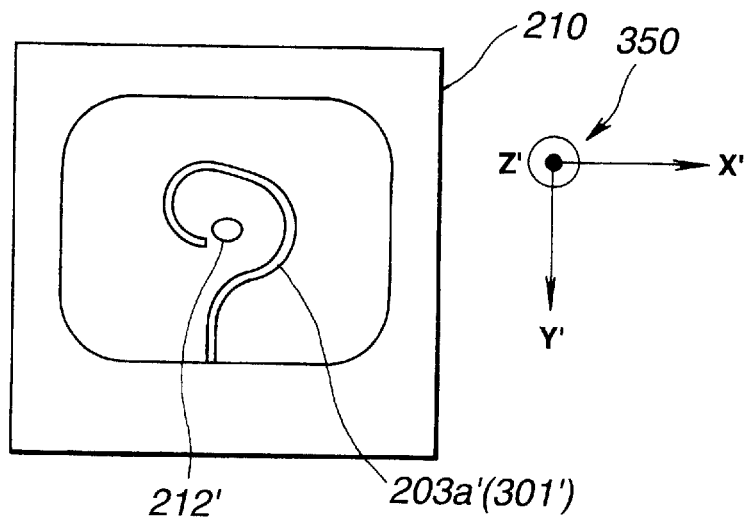

The system processor 221 detects the positions of the twelve source coils 203(g) and those of the markers 212. Consequently, an image 203a' of the endoscope an image 301' of the insertion unit 301 and an image 212' of the marker are, as shown in FIG. 70, displayed on the shape display monitor 210 via the image production circuit 225.

Thereafter, display position correction is input using the input unit 213, or an automatic display position correction mode for automatically correcting display positions is designated. The system processor 221 corrects the coordinates indicating the positions of the endoscope 203 and marker 212 according to the position of the marker 212 detected at step S303.

Prior to correction, the shape of the endoscope is depicted as shown in FIG. 69. The coordinates represented by data of twelve detected points in the endoscope 203a and data of the detected position of the marker 212 are corrected using offset values with the position information of the marker 212 as a reference. Consequently, the marker 212 is depicted in the center of the shape of the endoscope. The coordinates in the coordinate system for display are corrected accordingly. Consequently, the shape of the endoscope is depicted as shown in FIG. 70.

For example, a display position at which the marker image 212' is displayed may be an eccentric position (Xo'-A, Yo'-B, Zo'-C) deviated from the center (Xo', Yo', Zo') of the display surface of the shape display monitor 210. Herein, the eccentric position and the center are defined in the coordinate system 350 for display. The position of the marker image 212' and the positions of the source coils 203(g) are corrected by subtracting the offset value (A, B, C) from the coordinates (Xo'-A, Yo'-B, Zo'-c) and (Xsg', Ysg, Zsg') indicating the positions, respectively. Thereafter, the marker image 212' and others are displayed. Consequently, the image of the shape of the endoscope is, as shown in FIG. 70, displayed near the center of the display surface of the shape display monitor 210 with the marker image 212' located in the center.

When the shape of the endoscope is, as shown in FIG. 70, depicted near the center of the display surface, a user may, if necessary, designate or modify any magnification using the input unit 213. Consequently, the image 203a' of the shape of the endoscope and the image 212' of the marker are enlarged at the designated magnification according to the data of the detected position of the endoscope 203a and the data of the detected position of the marker 212 (see FIG. 71) (step S304).

Unless a magnification is input to be modified, the previously designated magnification is adopted as a newly designated magnification in order to produce the endoscope image 203a' and marker image 212'.

Figure 71:
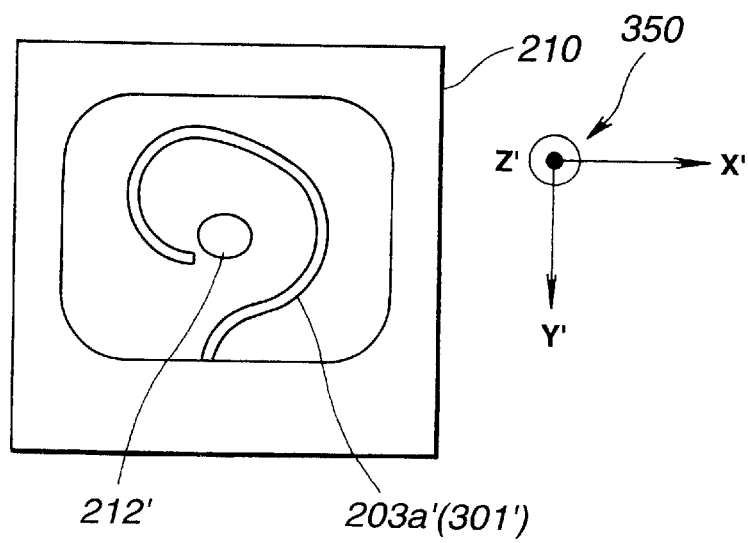

Finally, the endoscope image 203a' and marker image 212' produced at the previous step S304 are, as shown in FIG. 71, displayed on the shape display monitor 210 (step S305). Shape display is then terminated or control is returned to step S301.

According to the present embodiment, the marker 212 is placed at a reference position that should be depicted in the center of a display area on the monitor in which an inserted shape is depicted. The patient 202 may have a different body form and size from a previous patient or a positional deviation of the patient 202 on the examination table 201 may be different from that of the previous patient. Even so, the inserted shape can be developed near the center of a display range in the coordinate system for display and thus depicted.

Consequently, even when a magnification is modified, unless the magnification is excessively large, even if the patient 202 is different in size from the previous one, having the image of an inserted shape larger than a display area may be prevented. A user will therefore be freed or relieved from such a nuisance that he/she must reset the magnification.

When a proper magnification is set initially, even if patient 202 size differs from another, the magnification need not be modified. The image of an inserted shape can be displayed at a proper size and not partly come out of the display area. An operator will be free from a nuisance that a magnification must be modified or re-set. This results in an endoscope shape detection system that is user-friendly or offers good maneuverability.

As mentioned above, according to the present embodiment, the display position at which the shape of the endoscope is depicted is corrected by analyzing the position information of the source coils in relation to the position information of the marker 212. Consequently, the shape of the endoscope is depicted around the center of a display area. The shape of the endoscope can be enlarged, making the most of the display area. Even from patient to patient, the shape of the endoscope can be depicted with the display position hardly affected.

Unless a user-designated magnification is excessively large, part of an inserted shape will not come out of the display area and the shape of the endoscope can be depicted fully in the display area. In other words, when the shape of the endoscope is depicted at a size permitting a user to enjoy easy-to-see viewing, even if an object is different in size or the like from another, the shape of the endoscope can be depicted with any part thereof not coming out of the display area.

The fifteenth embodiment is identical to the fourteenth embodiment except that three markers 212(1), 212(2), and 212(3) (hereinafter, generically, 212(i)) are employed.

The three markers 212(i) each have one source coil incorporated therein. The markers 212(i) are fastened, for example, near the anus of the patient 202, on the right flank thereof, and on the left flank thereof, and connected to the drive circuit 222 in the control unit 209 over cables.

According to the present embodiment, the three markers 212(i) each have a source coil incorporated therein and are fastened at reference positions on the patient 202. A correcting means is included for correcting display positions and a magnification according to the detected positions of the source coils incorporated in the three markers 212(i). Position information unaffected by a change in the position of the patient 202 is retrieved from the position information of the source coils incorporated in the three markers 212(i). In addition, a magnification is set to a value permitting the shape of the endoscope to be depicted in the whole display surface. Consequently, the detected shape of the endoscope is depicted near the center of the display screen, and enlarged, making the most of the display screen.

Figure 72:
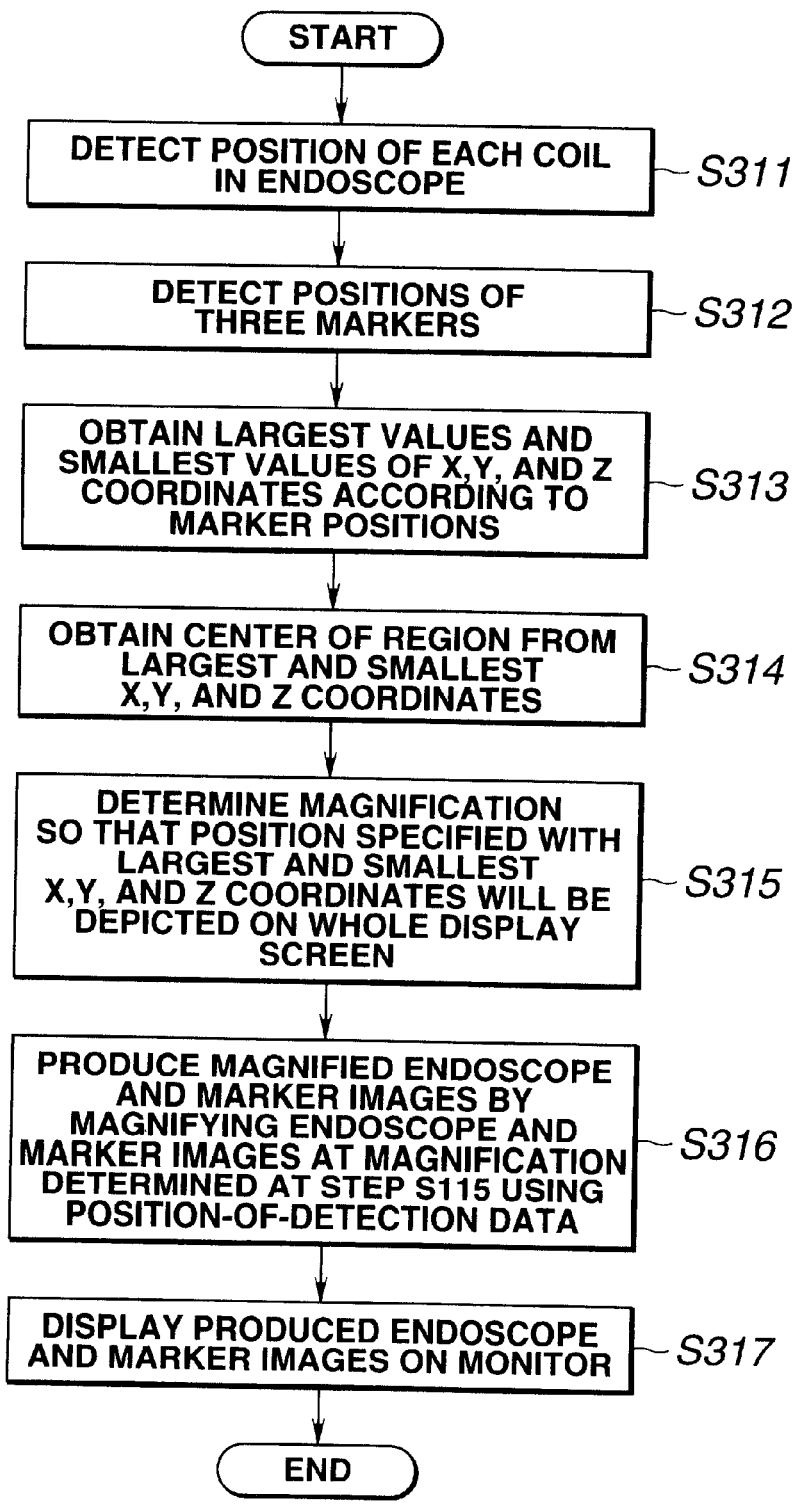
FIG. 72 to FIG. 74 relate to the twelfth embodiment of the present invention.

An operation of the fifteenth embodiment will be described in conjunction with FIG. 72.

The system processor 221 in the control unit 209 uses the digital data of magnetic detection currents supplied from the sense coils 208(h) to detect the positions of the twelve source coils 203(g) incorporated in the endoscope 203a (step S311).

Figure 73:
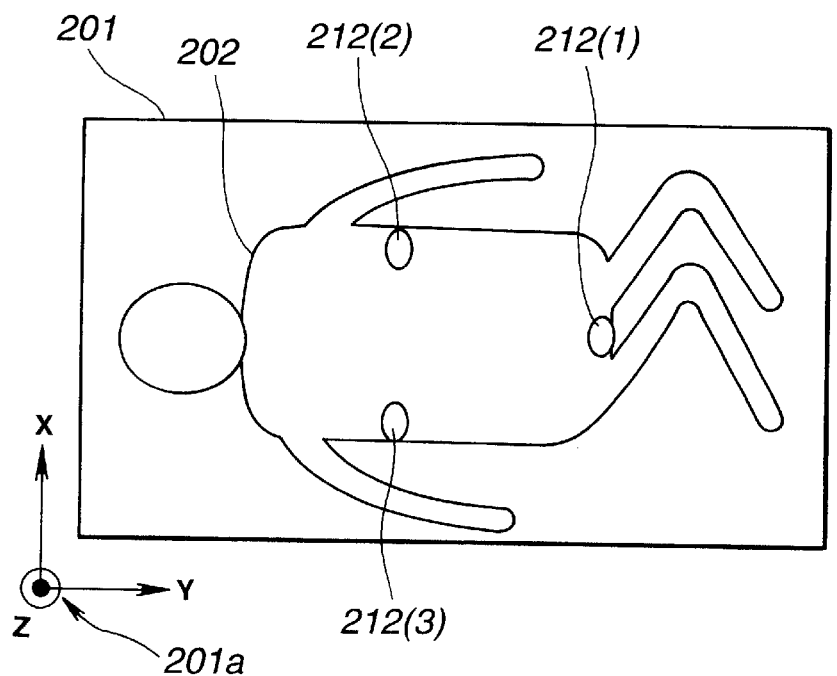

Thereafter, similarly to the source coils 203(g) in the endoscope 203a, the reference positions on the patient 202, or more particularly, the positions of the markers 212(i) are detected as shown in FIG. 73 (step S312). The markers 212(i) are fastened, for example, near the anus, on the left flank, and on the right flank. Maximum and minimum values of x, y, and z coordinates in the coordinate system for detection 201a, defined with regard to the examination table 201, are retrieved from the coordinates indicating the estimated positions of the three markers (step S313).

The center of the coordinate system for detection 201a is detected from the maximum and minimum values of the x, y, and z coordinates retrieved at step S312 (step S314). A magnification is set to a value permitting the positions indicated with the maximum and minimum values of the x, y, and z coordinates in the coordinate system for detection 201a to define the largest range of depiction on the whole display screen (step S315).

Figure 74:
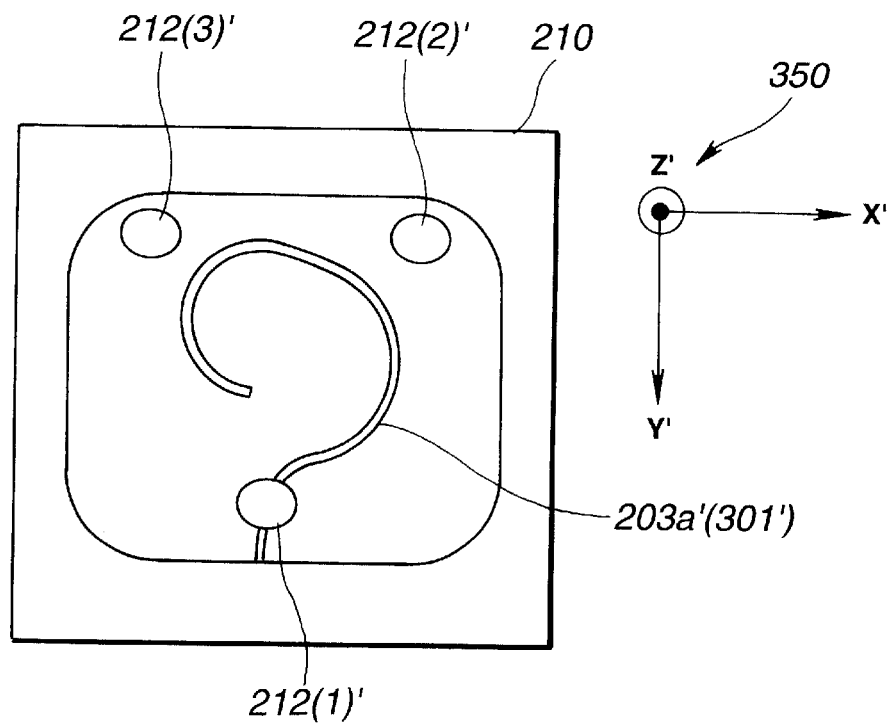

An image 203a' of the endoscope and images 212(i)' of the markers like the ones shown in FIG. 74 are produced based on the magnification set at step S315, the data of the detected position of the endoscope 203a, and the data of the detected positions of the markers 212(i). Finally, the endoscope image 203a' and marker images 212(i)' produced at the previous step S316 are, as shown in FIG. 74, displayed on the shape display monitor 210 (step S317). Shape display is then terminated.

According to the present embodiment, a magnification is automatically set according to the body size and form of a patient in relation to the positions of the three markers 212(i). In addition to the same advantage as that provided by the fourteenth embodiment, the image of the shape of the endoscope can be enlarged at a magnification matched with the patients body size and form by making the most of a display area.

The configuration of the sixteenth embodiment of the present invention is identical to that of the fifteenth embodiment. A difference lies in part of the processing of an inserted shape.

The present embodiment includes, in addition to the same components as the fifteenth embodiment, a depiction correcting means for correcting the thickness with which the shape of the endoscope is depicted or the size with which the markers are depicted. The present embodiment is characterized by a facility for enlarging an image of the shape of the endoscope not only in the same manner as in the fifteenth embodiment but also in such a manner that the shape will not be depicted too thickly and the markers will not be depicted too large in size.

Figure 75:
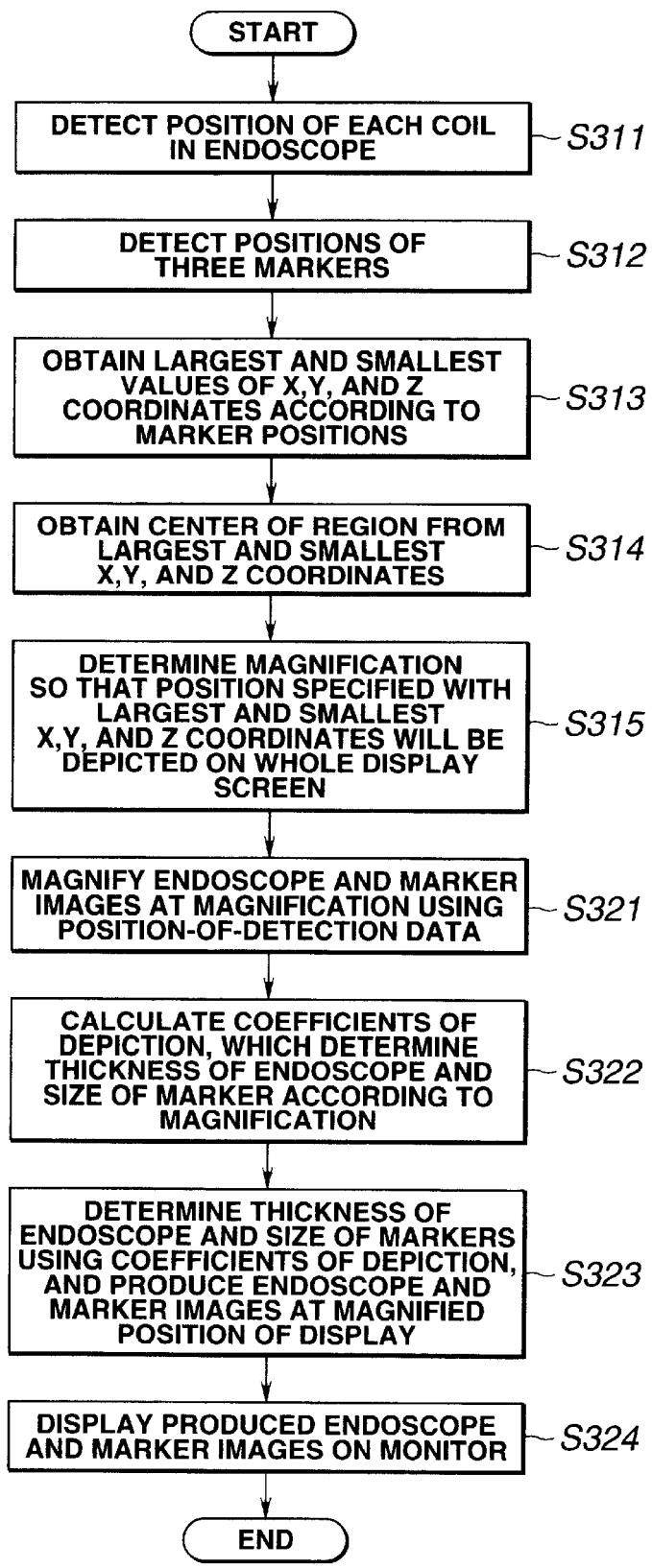

Next, an operation of by the sixteenth embodiment will be described in conjunction with FIG. 75. The flowchart of FIG. 75 is identical to that of FIG. 72 until step S315.

The system processor 221 in the control unit 209 uses the digital data of magnetic detection currents supplied from the sense coils Z08(h) to detect the positions of the twelve source coils 203(g) incorporated in the endoscope 203a (step S311).

Similarly to the source coils 203(g) in the endoscope 203a, the positions of the markers 212(i) located, as shown in FIG. 73, near the anus of the patient 202, on the left flank thereof, and on the right flank thereof are detected (step S312). Maximum and minimum values of x, y, and z coordinates in the coordinate system for detection 201a are retrieved from the coordinates indicating the estimated positions of the markers (step S313).

The center of the coordinate system is detected based on the maximum and minimum values of the x, y, and z coordinates in the coordinate system which are retrieved at step S313 (step S314). A magnification is set to a value permitting the positions indicated with the maximum and minimum values of the x, y, and z coordinates in the coordinate system for detection 201a, which are retrieved at step S314, to define the largest range of depiction in the whole display screen (step S315).

Figure 76A:
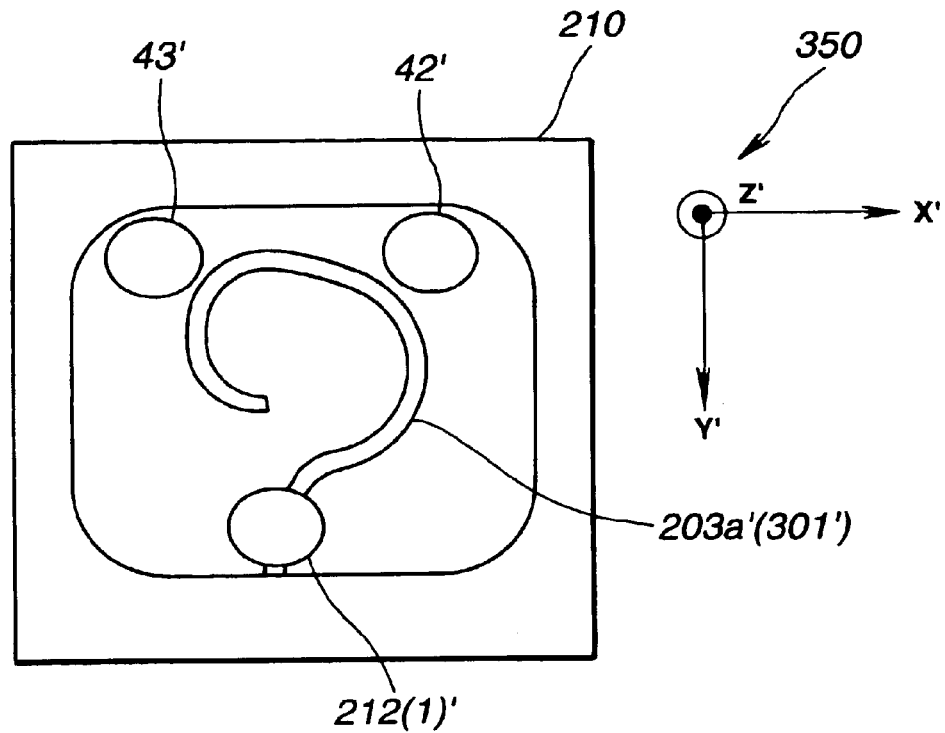
FIGS. 76A and 76B are display views of displays viewed during step S323 of FIG. 75.

An image of the endoscope 203a produced based on the data of the detected position thereof and images of the three markers 212(i) produced based on the data of the detected positions thereof are enlarged at the magnification set at step S315. Display positions at which the enlarged endoscope image 203a' and marker images 212(i)' are displayed are determined (step S321). At the magnification, as shown in FIG. 76A, the endoscope image 203a' and marker images 212(i)' are displayed by making the most of the whole display screen. The thickness of the endoscope image 203a' or the size of the marker images 212(i)' may become excessive.

The magnification set at step S315 is multiplied certain coefficient, thus calculating a compressive depiction coefficient. The depiction coefficient determines the thickness of an image of the endoscope and the size of images of the markers, as shown in FIG. 76B (step S322).

Thereafter, the thickness and size are determined according to the depiction coefficient calculated at step S322. The endoscope image 203a ' and marker images 212(i)' are produced with the determined thickness and size, and then displayed at the display positions determined at step S321 (step S323).

Figure 76B:
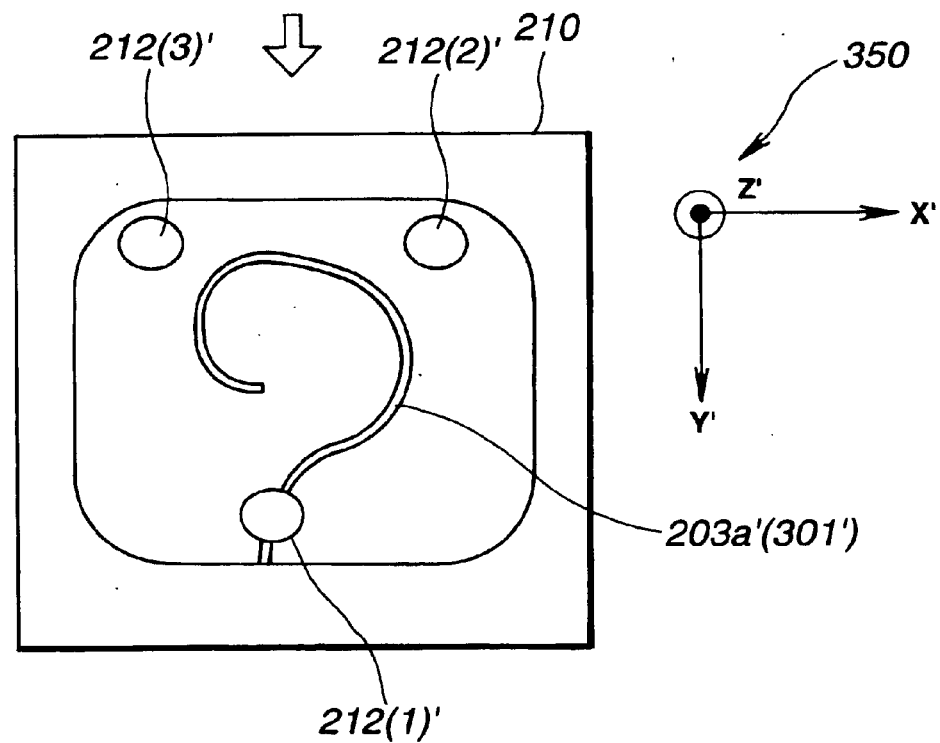

Finally, the endoscope image 203a' and marker images 212(i)' produced at step S323 are displayed as shown in of FIG. 76B (step S324). The processing is then terminated.

The present embodiment can provide the same advantage as the fifteenth embodiment. In addition, the thickness with which the shape of the endoscope is depicted and the size with which the markers are depicted are corrected. Therefore, when an image of the shape of the endoscope is enlarged, the thickness of the image of the shape of the endoscope and the size of the images of the markers will not become excessively large in conformity with the magnification. The image of the shape of the endoscope and the images of the markers can be displayed with a proper thickness and proper size. The image of the shape of the endoscope can always be enlarged and displayed at a size permitting a user to enjoy easy-to-see viewing.

The seventeenth embodiment of the invention has, in addition to the same components as those of the fourteenth embodiment, a pointing means such as a mouse. A user points out any area on a display screen to be enlarged. The image within the area is then enlarged.

An operation of the present embodiment will be described using the foregoing components.

Magnetic fields generated by applying a driving signal sequentially to the plurality of source coils 203(g) are detected by the sense coils 208(h) in order to obtain the positions of the source coils 203(g). The shape of the endoscope is then depicted on the shape display monitor 210.

Figure 77:
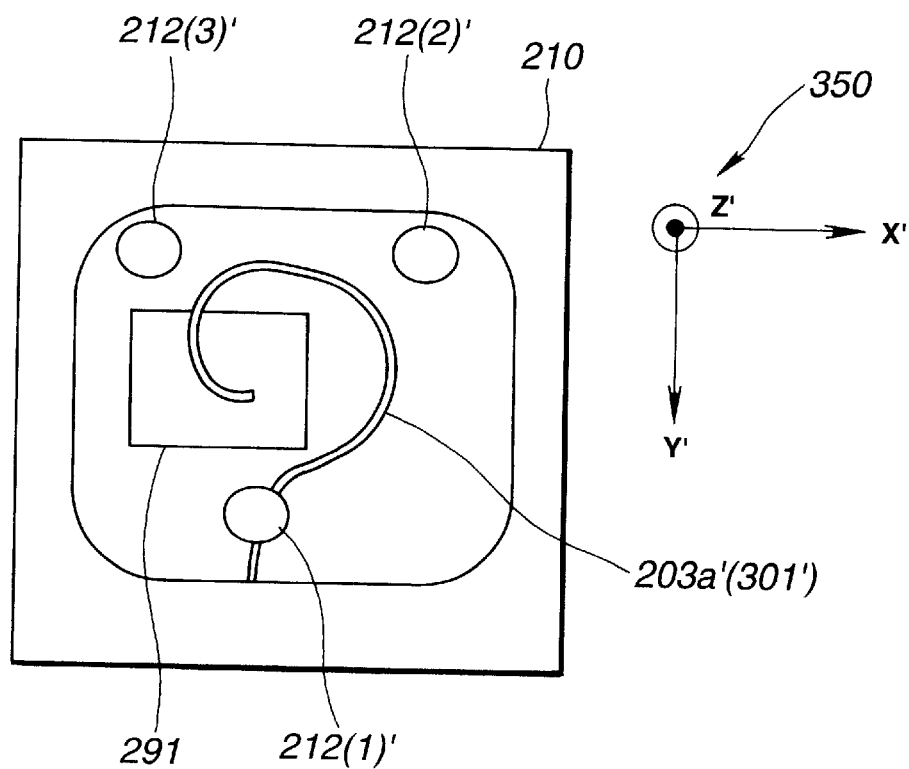
FIG. 77 and FIG. 78 relate to the fourteenth embodiment of the present invention.
Figure 78:
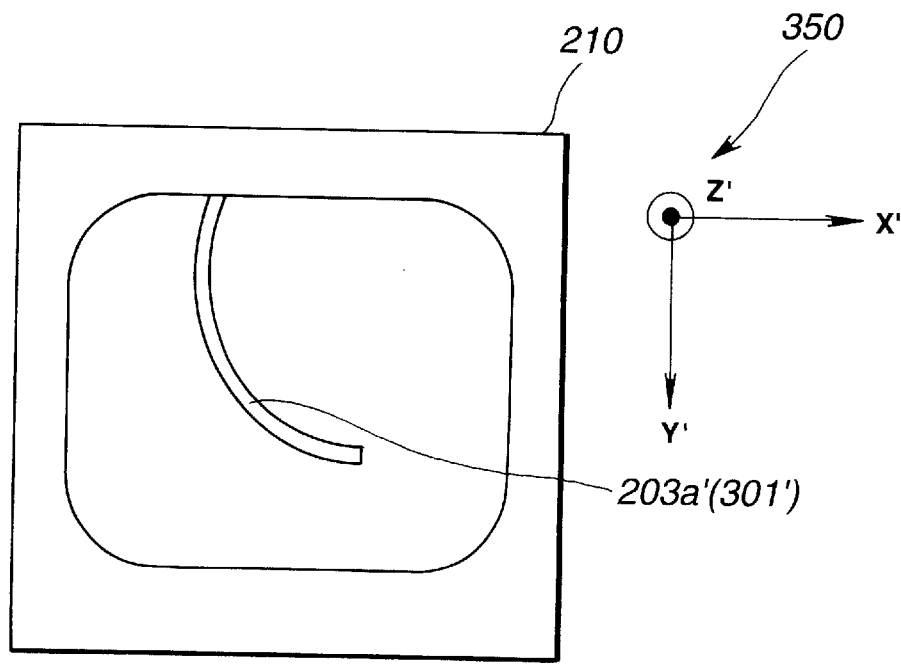

When the sixteenth embodiment endoscope image 203a' and marker images 212(i)' are displayed on the shape display monitor 210, as shown in FIG. 76B, and a user wants to enlarge part of the endoscope image 203a' displayed on the shape display monitor 210, the user uses the pointing means such as a mouse to point out an area 291 to be enlarged, as shown in FIG. 77. The control unit 209 enlarges the image within the area alone and displays it as shown in FIG. 78.

The present embodiment is not limited to the fifteenth embodiment and sixteenth embodiment but can also apply to the fourteenth embodiment.

The present embodiment can also apply to endoscope shape detection systems in accordance with related arts. For example, the marker 212 as well as the correcting means for correcting a display position by detecting the position of the marker 212 may be excluded from the configuration of the fourteenth embodiment. In this case, a user may use a mouse or the like of the input unit 213 to designate any area on the display screen to enlarge. An instruction for instructing enlargement of the image within the area may then be issued.

According to the present embodiment, a user designates a portion of an image, which shows the shape of the endoscope and appears on the monitor, which the user wants to enlarge. The designated portion alone, or in other words, the designated area on the display screen is then enlarged and displayed. Consequently, an image within an area which a user wants to scrutinize can be enlarged and observed.

The other advantages are identical to those provided by the fourteenth to sixteenth embodiments.

In the fourteenth embodiment, the plurality of source coils 203(g) is incorporated in the endoscope 203a. The plurality of sense coils 208(h) is placed at a known position outside the endoscope 203a. The marker 212 has a source coil. Alternatively, the plurality of sense coils 208(h) may be arranged in the endoscope at predetermined intervals. Each of the plurality of source coils 203(g) may be placed at known positions outside of the endoscope 203a. The marker 212 may have a sense coil.

In the fourteenth embodiment, for example, display control is achieved as described below. Namely, when an inserted form is depicted on the display means by detecting the position of the marker 212, if the image of the inserted form is enlarged while being positioned near the center of the display means, no part of the enlarged image of the inserted form will come out of a display area. A means for changing a reference position at which the inserted form is depicted may be employed.

For example, when the distal part of the insertion unit 301 is inserted through the anus, the system processor 221 determines the relative position information of the first source coil 203(1), located in the distal end of the insertion unit 301, with respect to a reference position at which the marker 212 is detected. The reference position (position of the marker) is positioned in the upper part of the display screen. The shape of the distal part of the insertion unit 301 that is located below the reference position is depicted with emphasis. Thus, the reference position for display and, if necessary, a magnification, may be varied depending on an actual inserted state or form that varies with the progress of insertion.

The fifteenth embodiment has the facility for automatically setting the size of an image of an inserted form to be displayed on the display means. Alternatively, the size of the image of an inserted form may be designated manually.

The eighteenth embodiment is nearly identical to the eleventh embodiment. A difference alone will be described. The same reference numerals will be assigned to the components identical to those of the eleventh embodiment.

The eleventh embodiment has the configuration including, as shown in FIG. 63, the four markers 212(i) and the marker coil drive circuit unit 329 which is incorporated in the drive circuit 222 in the control unit 209. The present embodiment does not use the four markers 212(i) or the marker coil drive circuit unit 329.

A light guide for transmitting light from a light source in the CCU 204, as shown in FIGS. 79A–D, extends through the endoscope 203a of the present embodiment. The transmitted illumination light is emitted through an illumination window (not shown) formed at the distal end of the insertion unit 301. A patient or the like is thus illuminated. Light reflecting from an illuminated object, such as a lesion, is converged on an imaging device 352 located on the image plane of an objective 351 [by means of the]. The objective 351 is locked in an observation window adjoining the illumination window. The imaging device 352 photoelectrically converts a formed optical image.

A video signal processor in the CCU 204 processes a signal resulting from photoelectric conversion and produces a standard video signal. An image is then displayed on the monitor 205 connected to the CCU 204. A control signal instructing a control unit 209a to read an image signal from the imaging device 352 is sent from the CCU 204 in the endoscope shape detection system 211.

As described in relation to the eleventh embodiment, the probe 307 is passed through and locked in the forceps channel 354 (see FIG. 79D) in the endoscope 203a. The forceps channel 354 is also used as a suction channel through which intracorporeal mucus or the like is withdrawn. When the probe 307 is passed through and locked in the forceps channel 354, the forceps channel 354 may not be able to be used as the suction channel.

Figure 80:
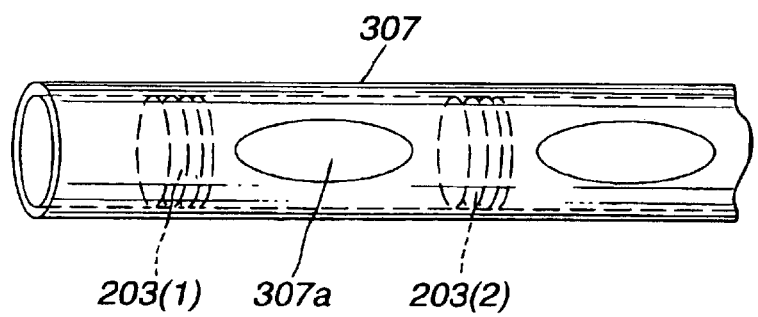

According to the present embodiment, the probe 307 in which the plurality of source coils 203(g) is placed at predetermined intervals is hollow, as shown in FIG. 80. A plurality of recesses 307a is formed in the lateral surface. Consequently, even when the probe 307 is passed through and locked in the forceps channel 304, the hollow probe 307 and recesses 307a can be used for suction. The forceps channel 354 can thus be used as the suction channel.

According to the present embodiment, as mentioned above, the probe 307 having the source coils 203(g) is passed through and locked in the forceps channel 354 of the endoscope 203a. The source coils 203(g) are thus incorporated in the insertion unit 301 of the endoscope 203a. Alternatively, the source coils 203(g) may be incorporated directly in the insertion unit 301 of the endoscope 203a.

Figure 81:
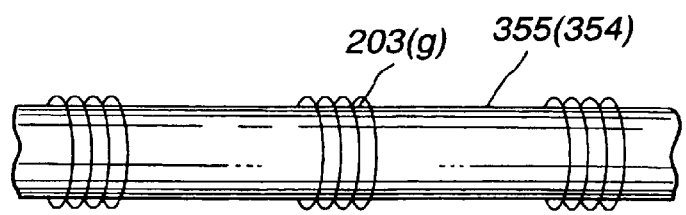

When the source coils 203(g) are incorporated directly in the insertion unit 301 of the endoscope 203a, the plurality of source coils 203(g), as shown in FIG. 81, circumscribe a tube 355, which forms the forceps channel 354, at predetermined intervals.

The other components are identical to those of the eleventh embodiment.

An operation of the present embodiment will be described below.

According to the present embodiment, a control signal instructing the control unit 209a to read of an image signal from the imaging device 352 in the endoscope 203 connected to the CCU 204 is sent by the CCU 204 in the endoscope shape detection system over a signal cable 353.

In response to the control signal sent from the CCU 204, the control unit 209a in the endoscope shape detection system 211 detects through the plurality of sense coils 208(h) placed in the coil unit 208 magnetic fields generated by the plurality of source coils 203(g) in the probe 307. The probe 307 is passed through and locked in the forceps channel 354 in the endoscope 203a. Detection signals output from the plurality of sense coils 208(h) in the coil unit 208 are analyzed in order to estimate the three-dimensional positions of the plurality of source coils 203(g) in the probe 307 passed through and locked in the forceps channel 354. Consequently, the shape of the endoscope is depicted on the monitor 210.

Figure 82:
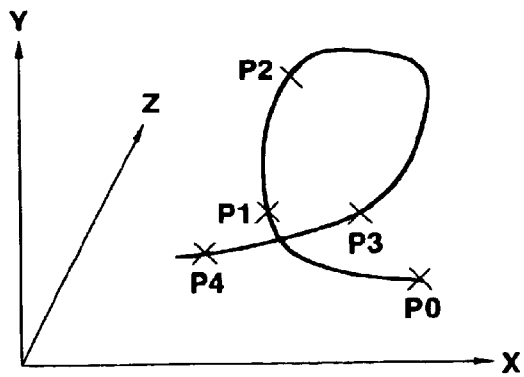

FIG. 82 shows an example of images of the shape of the insertion unit 301 produced by interpolating the three-dimensional positions of the source coils 203(g) estimated by the endoscope shape detection system 211.

Points Pk (k=0, 1, . . . , n−1) indicate the three-dimensional positions of the source coils 203(g). Herein, k denotes the serial number of each source coil starting with the source coil located at the probe tip.

Figure 83:
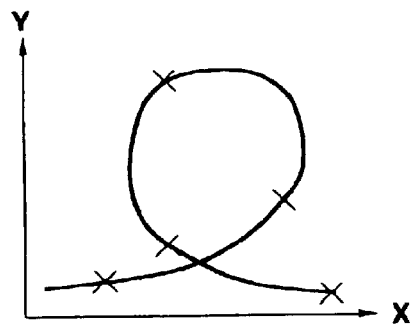
Figure 84:
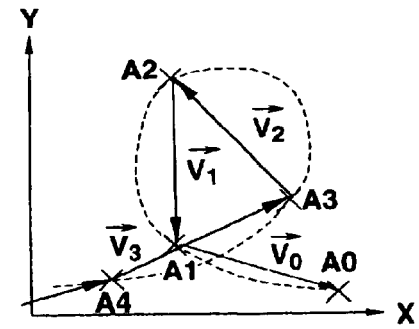

FIG. 83 and FIG. 84 show an image produced by projecting the inserted form shown in FIG. 83 on the XY plane. Points Ak(xk, yk) (k=0, 1, . . . , n−1) indicate the positions of the source coils on the XY plane, on which the inserted form is projected, associated with the three-dimensional positions Pk (k=0, 1, . . . , n−1). Vectors Vk t k=0, 1, . . . , n−2) are vectors exhibited by two most distal source coils 203(g) located in the distal part of the probe.

Overlapping of two vectors is assessed in order to ascertain whether the endoscope is looped.

Figure 85:
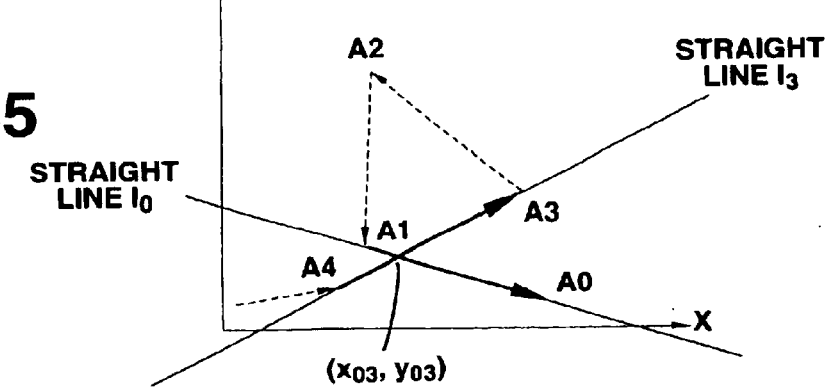

Referring to FIG. 85, method of detecting overlapping of, for example, vector V0 and vector V3 will be discussed. Specifically, a point of intersection (x03, yO3) between straight lines $l_0$ and $l_3$ along which the vectors are oriented is detected. Whether the point of intersection satisfies any one of the conditions listed below under which the point of intersection lies on two vectors is determined.

(1) when x1<x0 and y1<y0
x1<03<x0 and y1≦y03≦y0
(2) when x1<x0 and y0<y1
x1≦03≦x0 and y0≦y03≦y1
(3) when x0<x1 and y1<y0
x0≦03≦x1 and y1≦y03≦y0
(4) when x0<x1 and y0<y1
x0≦03≦x1 and y0≦y03≦y1
(5) when x4<x3 and y4<y3
x4≦03≦x3 and y4≦y03≦y3
(6) when x4<x3 and y3<y4
x3≦03≦x4 and y3≦y03≦y4
(7) when x3<x4 and y4<y3
x3≦03≦x4 and y4≦y03≦y3
(8) when x3<x4 and y3<y4
x3≦03≦x4 and y3≦y03≦y4 (conditional expression)
All pairs of vectors are assessed for overlapping.

First, the leading vector V0 is assessed for overlapping relative to vector V2 to vector Vn−1. Thereafter, vector V1 is assessed for overlapping relative to vector V3 to vector Vn−1. This operation is repeated until it is performed on vector Vn−4, whereby all pairs of vectors can be assessed in order to detect overlapping.

If overlapping of vectors is detected during processing, for example, a warning that looping has occurred may be displayed on the screen of the monitor 210 on which an inserted form of the endoscope is depicted. The endoscope shape detection system 211 also may issue a sound to attract a user's attention.

Figure 86:
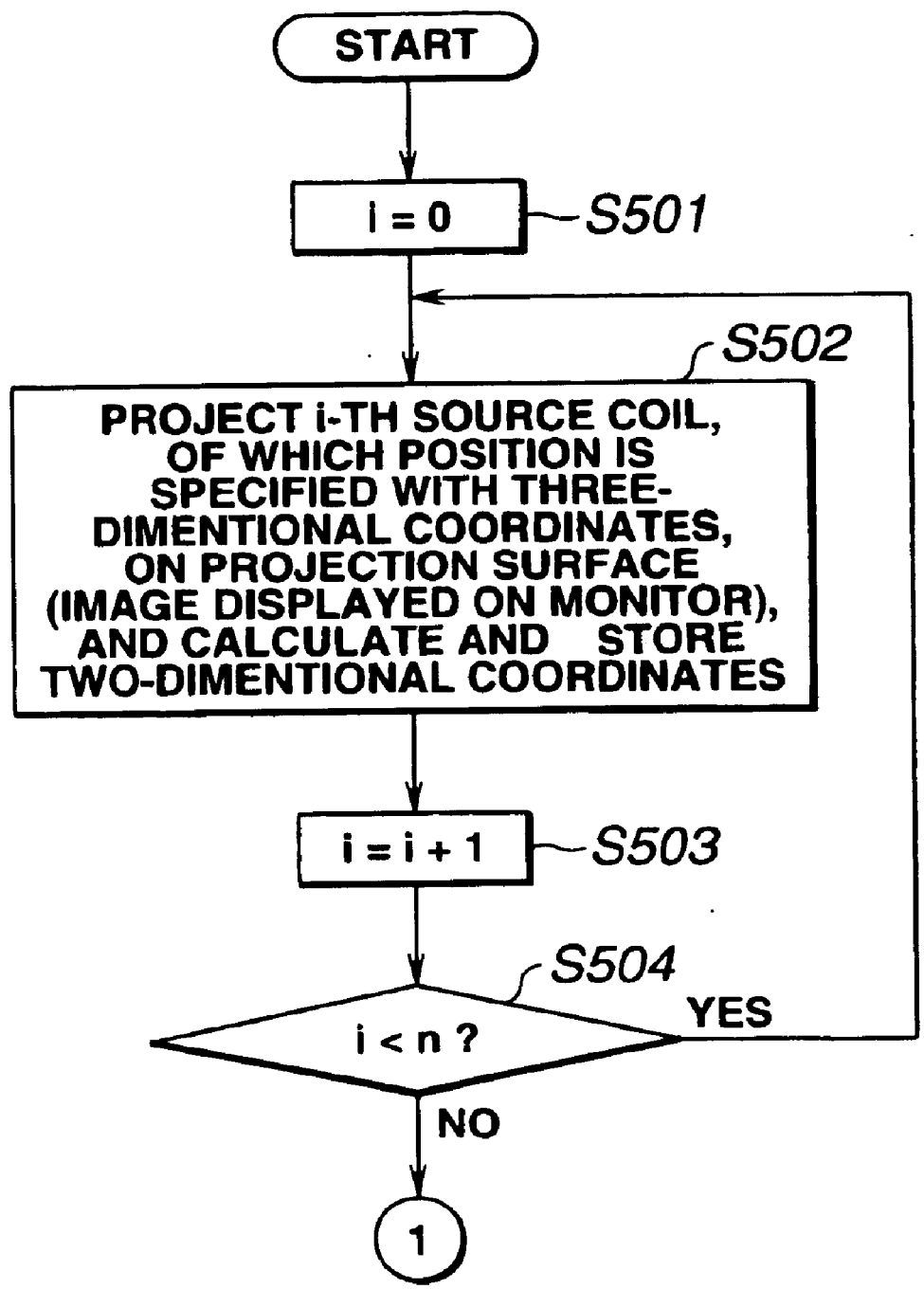

The foregoing processing will be described in conjunction with the flowcharts of FIG. 86 and FIG. 87. As described in FIG. 86, the identification number i of a source coil is initialized at step S501. A source coil is projected on a projection surface corresponding to the monitor 210 in order to transform the coordinates indicating the estimated three-dimensional position of the source coil into coordinates indicating a two-dimensional position. The coordinates indicating the two-dimensional position are then recorded at step S502. The identification number of a source coil is incremented by one in order to transform the coordinates indicating the three-dimensional position of the next source coil at step S503. At step S504, the system processor 211 determines whether the coordinates indicating the three-dimensional positions of all of the source coils have been transformed. If the coordinates indicating the three-dimensional positions of all of the source coils have been transformed, control is passed to step S505 in FIG. 87.

Figure 87:
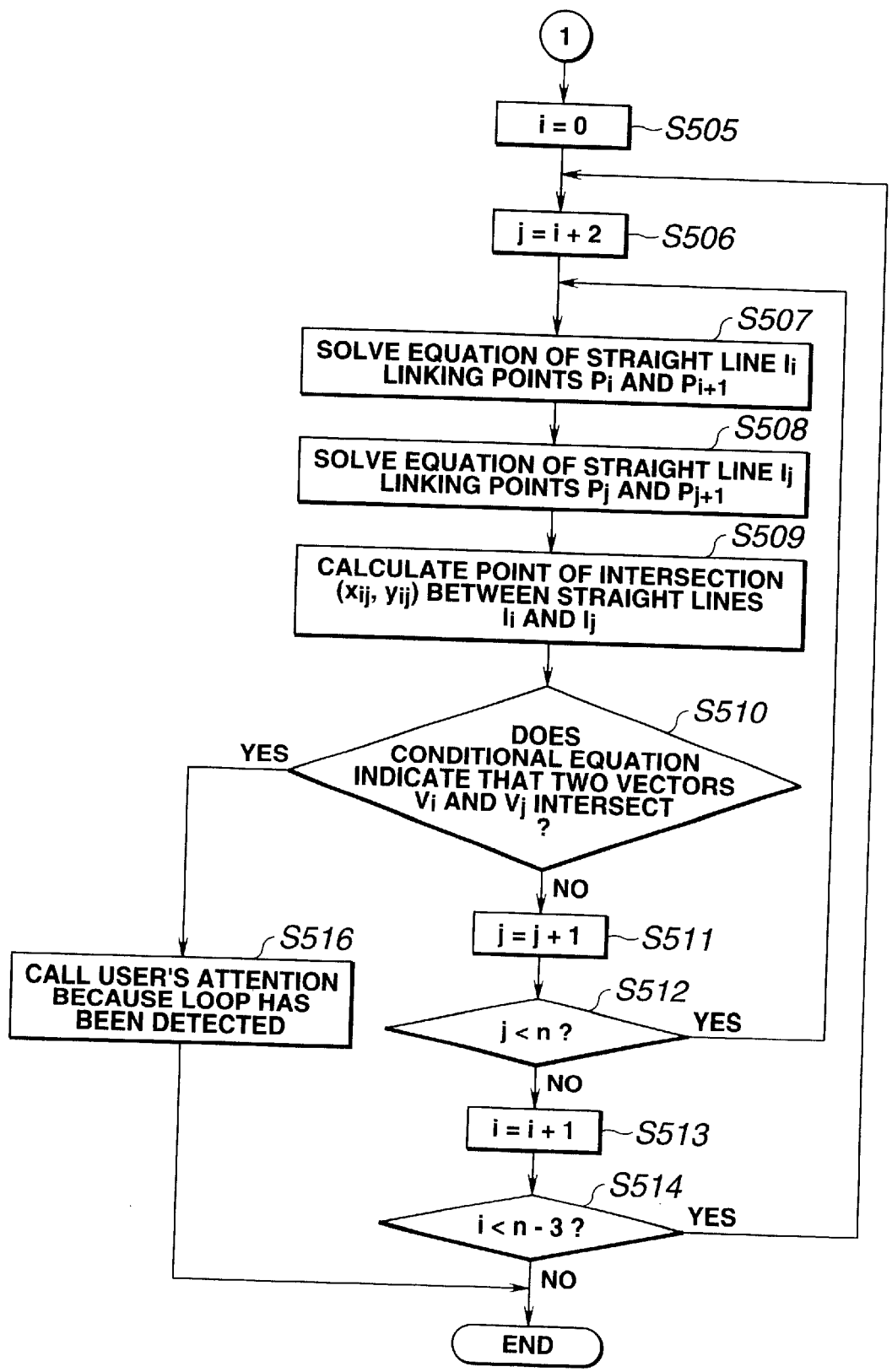

As described in FIG. 87, the identification numbers i and j of two vectors Vi and Vj are initialized, at steps S505 and S506, respectively. The equations of straight lines li and lj, having the same directions as the vectors Vi and Vj, are defined at steps S507 and S508. A point of intersection (xij, yij) between the two straight lines li and lj is determined at step S509. At step S510, the system processor 211 determines, according to discriminants for the equations, whether a point of intersection (xij, yij) is present on the two vectors Vi and Vj. At step S510, if the system processor 211 determines that a point of intersection is present on the two vectors, the two vectors intersect, indicating looping. A warning is given to a user manipulating the endoscope at step S516. If the two vectors are not intersecting, control is then passed to the next step S511.

At step S511, the identification number of vector Vj is incremented by one. At step S512, the system processor 211 determines whether vector Vj is intersecting vector Vi. If whether vector Vj is intersecting vector Vi is not determinable, control is returned to step S507. If vector Vj is intersecting vector Vi, control is passed to step S513.

At step S513, the identification number of vector Vi is incremented by one. At step S514, the system processor 211 determines whether vector Vj has been checked for intersection relative to all vectors Vi. If vector Vj has not been checked for intersection relative to all vectors Vi, control is returned to step S506. If vector Vj has been checked for intersection relative to all the vectors Vi, the program is terminated.

According to the present embodiment, a warning is displayed on the monitor 210 connected to the control unit 209a in the endoscope shape detection system 211. Alternatively, the warning may be displayed on the image observation monitor 205 connected to the CCU 204. The CCU 204 also may issue a sound so as to attract a user's attention.

As mentioned above, according to the present embodiment, it is possible to help a user recognize that the insertion unit of the endoscope is looping.

The nineteenth embodiment is nearly identical to the eighteenth embodiment. A difference alone will be described. The same reference numerals will be assigned to identical components. The description of the components will be omitted.

The CCU 204 in the present embodiment consists of, as shown in FIG. 88, a signal processing unit 204a, an image freeze controller 204b, a motion estimation circuit 204c, and a control circuit 204d. The signal processing unit 204a processes an image signal sent from the imaging device 352 in the endoscope 203a. The image freeze controller 204b outputs an image signal processed by the signal processing unit 204a to the image observation monitor 205, and switches between a motion picture and still picture. The motion estimation circuit $20^4c$ estimates a motion made by the distal part of the insertion unit 301 according to the three-dimensional position information of the distal part of the insertion unit 301 sent from the control unit 209a in the endoscope shape detection system 211 over the signal cable 353. The control circuit 204d controls the image freeze controller 204b according to a manipulation performed on a Freeze switch located on the operation unit 302 of the endoscope 203a, and the motion made by the distal part of the insertion unit 301 estimated by the motion estimation circuit 204c.

The other components are identical to those of the eighteenth embodiment.

An operation of the present embodiment having the foregoing components will be described below.

According to the present embodiment, a control signal instructing the control unit 209a to read an image signal from the imaging device 352 in the endoscope 203a connected to the CCU 204 is sent from the CCU 204 in the endoscope shape detection system 211 over the signal cable 353.

In response to the control signal sent from the CCU 204, the control unit 209a in the endoscope shape detection system 211 uses the plurality of sense coils 208th) placed in the coil unit 208 to detect magnetic fields generated by the plurality of source coils 203(g). The plurality of source coils 203(g) is placed in the probe 307 passed through and locked in the forceps channel 354 in the endoscope 203a. Detection signals supplied from the plurality of sense coils 208(h) in the coil unit 208 are analyzed to estimate the three-dimensional positions of the plurality of source coils 203(g) in the probe 307 passed through and locked in the forceps channel 354. Consequently, the shape of the endoscope is depicted on the monitor 210.

By manipulating the Freeze switch located on the operation unit 302 of the endoscope 203a, images to be displayed on the image observation monitor 205 can be switched from a motion picture to a still picture.

Figure 79A:
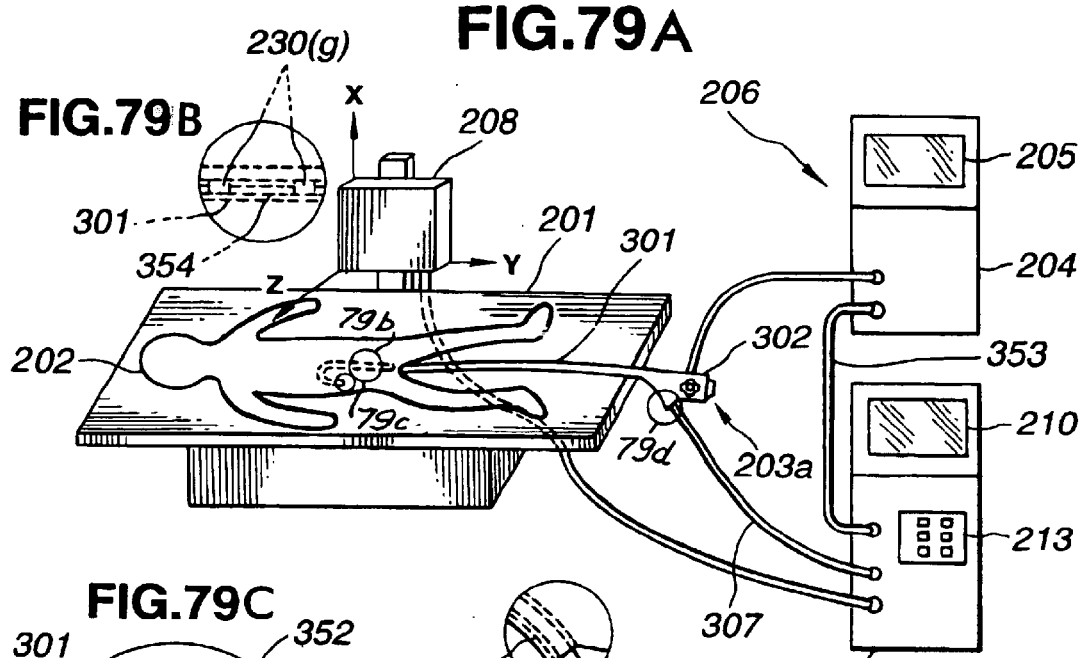
Figures 79B, 79C, 79D:
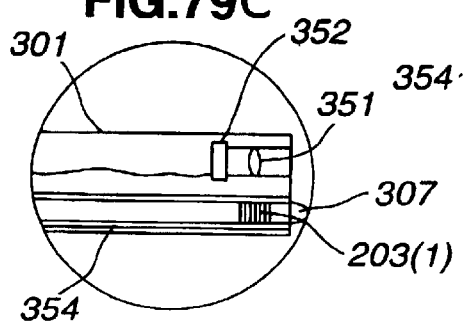
FIG. 79B is a partial schematic view, drawn to an enlarged scale, taken along line 79b in FIG. 79A.
FIG. 79C is a partial schematic view, drawn to an enlarged scale, taken along line 79c in FIG. 79A.
FIG. 79D is a partial schematic view, drawn to an enlarged scale, taken along line 79d in FIG. 79A.

As described in relation to the eighteenth embodiment, the plurality of source coils 203(g) is placed in the probe 307 at predetermined intervals. The probe 307 is passed through and locked in the forceps channel 354 in the endoscope 203a. Consequently, the plurality of source coils 203(g) is placed along the insertion unit 301 of the endoscope 203a. The distal source coil 203(1) is, as shown in FIG. 79C, located near the distal end of the insertion unit 301. The endoscope shape detection system 211 can detect the three-dimensional position of the distal end of the insertion unit 301 using the source coil 203(1).

According to the present embodiment, the control unit 209a supplies the information of the detected three-dimensional position of the insertion unit 301 to the CCU 204 over the signal cable 353. A motion made by the distal part of the insertion unit 301 is detected based on the three-dimensional position information of the distal part of the insertion unit 301. Freezing may be activated using the Freeze switch located on the operation unit 302 of the endoscope 203a.

Specifically, as shown in FIG. 89, the three-dimensional position information (xk, yk, zk) of the distal part of the insertion unit 301 is input from the control unit 209a to the CCU 204 over the-signal cable 353. The motion estimation circuit 204c stores the three-dimensional information (xk, yk, zk) of the distal part of the insertion unit 301.

Thereafter, the motion estimation circuit 204c reads the previously stored three-dimensional position information (xk−1, yk−1, zk−1) at step S522. A magnitude of motion mk made by the distal part of the insertion unit 301 is calculated based on the current three-dimensional position information (xk, yk, zk) and the previously stored three-dimensional position information (xk−1, yk−1, zk−1) according to the formula (95).

$$m_k = \sqrt{(x_{k-1} - x_k)^2 + (y_{k-1} - y_k)^2 + (z_{k-1} - z_k)^2} \qquad (95)$$

At step S524, the control circuit 204d in the CCU 204 determines whether a freeze signal has been input by manipulating the Freeze switch located on the operation unit 302 of the endoscope 203a. If the freeze signal has been input, at step S525, the control circuit 204d determines whether the magnitude of motion mk made by the insertion unit 301, which is calculated by the motion estimation circuit 204c at step S525, is smaller than a predetermined threshold mth. If the magnitude of motion mk is not smaller than the threshold mth, control is returned to step S524.

When the control circuit 204d determines that the magnitude of motion mk made by the distal part of the insertion unit 301 is smaller than the predetermined threshold mth, the control circuit 204d controls the image freeze controller 204b at step S526. Consequently, an ongoing endoscopic image (motion picture) having been processed by the signal processing circuit 204a is displayed in the form of a frozen or still image on the image observation monitor 205.

As mentioned above, according to the present embodiment, a motion made by the insertion unit 301 of the endoscope 203a can be estimated accurately. A frozen image devoid of a color mismatch can be displayed.

According to the present embodiment, the plurality of source coils 203(g) is placed in the probe 307 and the probe 307 is passed through and locked in the forceps channel 354 in the endoscope 203a. If the shape of the endoscope need not be depicted, only one sense coil may be embedded directly in the distal part of the insertion unit 301. the magnitude of motion mk made by the distal part of the insertion unit 301 may then be calculated using the sense coil in the distal part. Freezing may then be controlled accordingly.

As mentioned above, the three-dimensional positions of the plurality of source coils 203(g) lying through the probe 307 are estimated for calculating the magnitude of motion mk made by the distal part of the insertion unit 301. The probe 307 is passed through and locked in the forceps channel 354 in the endoscope 203a. The technique of estimating motion using a displayed image which is described in, for example, Japanese Examined Patent Publication No. 8-34577, may be adopted in combination with the technique of calculating the magnitude of motion in order to control freezing.

In this case, the image freeze controller 204d references both the magnitude of motion made by the distal part of the insertion unit 301, which is calculated using the source coils and sense coils according to the present embodiment, and the magnitude of motion calculated using an image according to the Japanese Examined Patent Publication No. 34577. If both the magnitudes of motion indicate no motion, a frozen image is displayed on the image observation monitor 205. If either of the magnitudes of motion indicates a motion, a normal motion picture is displayed on the image observation monitor 205.

Consequently, a motion made by the distal part of the insertion unit 301 can be detected accurately. When an object moves, movements shown by images can be detected. A frozen image showing a little motion also can be produced.

The twentieth embodiment has the same configuration as the nineteenth embodiment. The description of the configuration will be omitted.

According to the present embodiment, as shown in FIG. 90, a freeze instruction signal is sensed at step S531. When the freeze instruction signal is generated, magnitudes of motions by images produced from the time of generation until a predetermined time instant are calculated successively. An image showing the least magnitude of motion is displayed as a frozen image.

Specifically, at step S531, if a freeze instruction signal has been generated, a parameter j is initialized at step S532. A magnitude of motion mk by an image Ik is calculated according to the formula (95) at steps S521, S522, and S523. At step S533, whether the parameter j is 0 is determined. Since the parameter j is 0, the calculated magnitude of motion mk is recorded as the least magnitude of motion, hence mmin=mk. The image Ik is then displayed as a frozen image at step S535.

At step S536, the system processor 211 determines whether the parameter j exceeds a predetermined frequency S. If the parameter j does not exceed the predetermined frequency S. control is passed to step S537. The parameters j and k are incremented by one, and control is returned to step S521. The magnitude of motion mk+1 shown by the next image Ik+1 is calculated at steps S521 to S523. At step S533, the system processor 211 determines whether the parameterj is 0. If the parameter j is 1, control is passed to step S538. The magnitude of motion mk+1 shown by the image Ik+1 is compared with the least magnitude of motion main. If mk+1 <mmin, control is passed to step S534. The magnitude of motion mk+1 is recorded as the least magnitude of motion mmin=mk+1. The image Ik+1 is displayed as a frozen image at step S535. By contrast, if mmin<mk+1, the magnitude of motion and frozen image remain unchanged. Control is returned to step S537.

The above procedure is repeated. At step S536, if the parameter j exceeds the predetermined frequency S, a predetermined time has elapsed, an image showing the least motion among motions detected within the predetermined frequency or time is displayed as a frozen image.

As mentioned above, according to the present embodiment, an image showing the least motion among motions detected within the predetermined time can be displayed as a frozen image.

The configuration of the twenty-first embodiment is nearly identical to that of the eighth embodiment. The control unit 209 has, as shown in FIG. 91, a recording unit 224 for recording digital data produced by the system processor 221 for representing the shape of the endoscope 203 and the positions of the markers 212. Setting data used to reflect setting parameters in the digital data representing the shape of the endoscope 203 and the positions of the markers 212 is input from the input unit 213 to the system processor 221. The same reference numerals are assigned to the other identical components.

An operation of the twenty-first embodiment will be described in conjunction with FIG. 92 to FIG. 95.

As described in FIG. 92, based on digital data representing magnetic detection currents supplied from the sense coils 208(h), the system processor 221 in the control unit 209 detects the positions of the twelve source coils 203(g) and the positions of the markers 212 at step S401. The twelve source coils 203(g) are incorporated in the endoscope 203. The markers 212 are fastened near the anus of the patient 202, on the left flank thereof, and on the right flank thereof.

The current setting for a screen structure is acquired as setting parameters at step S402. At steps S403 and S404, if neither a recording request nor a reproduction request has been issued, the image production circuit 225 produces, at step S405, a display image according to the setting parameters for the screen structure acquired at step S402.

At step S403, if a recording request has been issued, control is passed to step S411 in FIG. 93. Position data of detected positions are recorded in the recording unit 224 at step S411. The setting for the screen structure is recorded in the recording unit 224 while associated with the position data produced at step S401 in relation to identification numbers or the like. Normal displaying is restarted at step S405 in FIG. 92.

Data recorded in the recording unit 224 are data composed of, as shown in FIG. 95, a header and a coordinate data division. The header includes a doctor name, a patient identification number, a date of examination, a start time of examination, and an end time thereof. The coordinate data division includes position data and setting data for a screen structure to be recorded.

At step S404 in FIG. 92, if a reproduction request has been issued, control is passed to step S421 in FIG. 94. Position data of detected positions are read from a user-designated record data block in the recording unit 224 at step S421. Thereafter, the setting data for a screen structure associated with the position data of detected positions read at step S421 are read from the recording unit 224 at step S422.

At step S423, the system processor 211 determines whether any parameter must be reflected in the setting data for a screen structure read by a user manipulating the data input unit 226. If any parameter should be reflected, the designated parameter is reflected at step S423 in the current setting data for a screen structure acquired at step S402. Control is then returned to normal displaying of step S405 in FIG. 92. If no parameter should be reflected, step S423 is skipped. Control is then returned to normal displaying of step S405 in FIG. 92.

As mentioned above, according to the present embodiment, the system processor 221 in the control unit 209 records position data of detected positions and setting parameters for display in the recording unit 224. The position data of detected positions is used to produce an image of a shape to be displayed during an examination under endoscopic observation. Not only the same image as that produced during an examination but also another image of the shape that cannot be seen during the examination can be displayed.

The system configuration of the twenty-second embodiment is the same as that of the twenty-first embodiment. A difference lies in part of processing performed by the system processor 221 in the control unit 209.

As described in FIG. 96, according to the present embodiment, at step S403, if no recording request has been issued, the system processor 221 in the control unit 209 determines whether an editing request has occurred at step S431 instead of determining whether a reproduction request has occurred at step S404 according to the twenty-first embodiment. At step S431, if no editing request has been issued, a display image is produced at step S405 according to the setting parameters for a screen structure acquired at step S402.

If an editing request has been issued, control is passed to step S421 in FIG. 97. Steps S421 to S424 are carried out in the same manner as those according to the twenty-first embodiment. Specifically, position data of detected positions are read from a user-designated record data block in the recording unit 224 at step S421. At step S422, the setting data for a screen structure associated with the position data of detected positions read at step S421 are read from the recording unit 224.

At step S423, the system processor 211 determines whether any parameter should be reflected in the read setting data for a screen structure that has been designated by a user. If any parameter should be reflected, the designated parameter is reflected at step S423 in the setting data for a screen structure acquired at step S402. Control is then passed to step S432. If no parameter should be reflected, step S423 is skipped and control is passed to step S432.

At step S432, control is passed to step S411 in FIG. 93 described in relation to the twenty-first embodiment. At step S411, position data of positions detected at step S401 are recorded in the recording unit 224. At step S412, the setting for a screen structure is recorded in the recording unit 224 while associated with the position data acquired at step S401 using identification numbers or the like (see FIG. 92). Control is then returned to normal displaying of step S405 in FIG. 96. At step S432 in FIG. 97, if no recording request has been issued, control is returned to normal displaying of step S405 in FIG. 96.

As mentioned above, the present embodiment provides the same advantage as the twenty-first embodiment. In addition, since a facility for editing record data is included, unnecessary data recorded during an examination can be deleted. Necessary minimum data can be preserved.

The twenty-third embodiment is concerned with a method of arranging the extracorporeal markers 212 of the eighth embodiment or eleventh embodiment. A difference alone will be described. The same reference numerals will be assigned to the identical components. The description of One components wile be omitted.

An object of the present embodiment is to provide an extracorporeal marker fastening device facilitating positioning of extracorporeal markers.

As shown in FIG. 98, an extracorporeal marker sheet 523 of the twenty-third embodiment is formed with a sheet made of a fabric that is soft enough to come into close contact with the patient 202 so as to cover the patient. Marker stowage pockets 522a, 522b, and 522c, serving as a means for positioning and fastening extracorporeal markers so that the extracorporeal markers can be freely mounted or dismounted, are formed at positions on the sheet that coincide with reference positions. Specifically, when the patient 202 is covered with the sheet 523, the positions of the marker stowage pockets 522a–c coincide with the reference positions near the anus of a patient and on both inferior sides of the ribs. Extracorporeal markers 212a, 212b, and 212c are stowed in the marker stowage pockets. Consequently, the extracorporeal markers 212i can be positioned and fastened at the positions of the stowage pockets 522i (i=a to c).

The extracorporeal markers 212i can be readily taken out of the stowage pockets 522i. Thereafter, when the extracorporeal markers 212i are stowed in the stowage pockets 522i again, the extracorporeal markers can be set at the positions nearly identical to the positions at which the markers had been set.

According to the present embodiment, when the posture of the patient 202 must be changed greatly in order to continue an examination under an endoscopic observation, the extracorporeal markers 212i may have to be taken out of the stowage pockets 522i. Even so, the extracorporeal markers 212i can be re-set at the same reference positions readily.

The size of the stowage pockets permits the extracorporeal markers 212i to be stowed in the stowage pockets 522i and remain nearly immobile in the stowage pockets 522i. The stowage pockets 522i may be made of an elastic material, such as a rubber that can stretch and contract.

A double-sided pressure sensitive adhesive tape 528 having both sides thereof coated with an adhesive is bonded to a plurality of positions on the lining of the extracorporeal marker sheet 523, including the positions of the linings of the marker stowage pockets 522a, 522b, and 522c. The extracorporeal marker sheet 523 can therefore be readily attached to or removed from the patient 202.

According to the twenty-third embodiment having the foregoing components, the extracorporeal marker sheet 523 can be mounted or fastened onto the patient 202 owing to the double-sided pressure sensitive adhesive tape 328 bonded to the lining of the extracorporeal marker sheet 523. The extracorporeal marker sheet 523 has the marker stowage pockets 522a, 522b, and 522c formed at predetermined positions thereon. Consequently, the extracorporeal markers 212i should merely be stowed in the stowage pockets 522i and can thus be readily fastened at the predetermined positions.

The patient 202 may change posture. Since the double-sided pressure sensitive adhesive tape 528 is bonded to the lining of the extracorporeal marker sheet 523 or at least the linings of the stowage pockets 522i, the extracorporeal markers 212i will not deviate from the reference positions on the patient 202.

Even if a patient changes his/her posture, it is nearly unnecessary to re-set the extracorporeal markers 212i, alleviating potential problems with examination.

The extracorporeal markers 212i may have to be removed from the stowage pockets 522i of the extracorporeal marker sheet 523 in order to allow a patient to change his/her posture significantly. Even so, the extracorporeal markers 212i should merely be stowed in the stowage pockets 522i and can thus be fastened at the predetermined positions again.

An extracorporeal marker sheet 523' of a variant like the one shown in FIG. 99 may be employed. The extracorporeal marker sheet 523' has Velcro tapes 542i (542a and 542c in FIG. 99) attached to the predetermined positions in place of the stowage pockets 5221. Mates 543i to the Velcro tapes 542i are bonded to the even parts of the outer surfaces of the extracorporeal markers 212i.

A belt-like double-sided pressure sensitive adhesive tape 544 is bonded to the lining of the extracorporeal marker sheet 523~. The extracorporeal marker sheet 523' can thus be fastened readily on the outer surface of the patient 202.

Instead of the double-sided pressure sensitive adhesive tape 544, a belt and buckle (not shown) may be adopted as a means for fastening the sheet on the outer surface of the patient 202. This variant operates nearly the same as the twenty-third embodiment, and provides nearly the same advantages.

The twenty-fourth embodiment of the present invention will be described with reference to FIG. 100. FIG. 100 shows an extracorporeal marker sheet in accordance with the twenty-fourth embodiment.

An object of the present embodiment is the same as that of the twenty-third embodiment.

As shown in FIG. 100, an extracorporeal marker sheet 551 of the twenty-fourth embodiment is realized with a sheet body having marker stowage pockets 522i. The sheet body is shaped like a running shirt that is long enough to reach the buttocks of the patient 202. The marker stowage pockets 522i are located at positions on the sheet body which coincide with the vicinity of the anus of the patient 202 and both inferior sides of the ribs thereof. The extracorporeal markers 212i are stowed in the marker stowage pockets 522i. Consequently, the extracorporeal markers 212i can be fastened at the positions of the marker stowage pockets.

The present embodiment provides the advantage described below.

The patient 202 is asked to wear the sheet 551 having the extracorporeal markers 212i stowed in the stowage portions that are the predetermined stowage pockets 522i. Consequently, a user is relieved from a nuisance of positioning the extracorporeal markers 212i.

The sheet body of the sheet 551 may be designed to open in the directions of the patient's waist. This obviates the necessity of asking the patient 202 to wear the sheet. The sheet can be mounted on the patient 202 merely by putting the sheet on the patient from above the patient.

The structure of the extracorporeal markers 212 employed in the aforesaid embodiments will be described below.

FIG. 101 and FIG. 102 are a sectional view and a left front view, respectively, showing the structure of an extracorporeal marker 212. The extracorporeal marker 212 shown in FIG. 101 and FIG. 102 has a cable 524 extending from a marker body 562. A coupling connector 563 is attached to the end of the cable 524. The coupling connector 563 can be freely detachably attached to the control unit 209 of the endoscope shape detection system 211 of, for example, the eighth embodiment.

A magnetic coil 564 is incorporated in the marker body 562, and coupled to a signal line (not shown) contained in the cable 524. The marker body 562 has a casing 565 that opens, for example, downwardly. The magnetic coil 564 is stowed in the opening of the casing 565. The opening of the casing 565 is covered with a casing 566 serving as a lid.

A portion of, for example, a signal line contained in the cable 524 coupled to the magnetic coil 564, which comes out of the marker body 562, is covered with an anti-breakage member 567. The anti-breakage member 567 secures the magnetic coil 564 and the proximal part of the cable 524 coupled to the magnetic coil 564.

The magnetic coil 564 is bonded and fixed to a concave part 568 in the center of the casing 565. The perimeter of the magnetic coil is filled with a filler 569 formed with an insulating non-magnetic member, for example, a silicon rubber. The filler 569 may be made of any material other than a rubber. A groove 571 is formed in the casing 565 where the casings 565 and 566 meet. An 0 ring 572 is received in the groove 571.

A screwing portion 573 of the casing 566 is sealed with an O ring 574. The casings 565 and 566 are secured using a screw 575, whereby the interiors of the casings 565 and 566 are held watertightly.

The anti-breakage member 567 has a convex part 576 formed at the end thereof. The convex part 576 is engaged with grooves 577 in the edges of the casings 565 and 566, and thus secured. The outer diameter of the convex part 576 is larger than the inner diameter of the groove 577. When the casings 565 and 566 are secured, the casings 565 and 566 and the anti-breakage member 567 are held watertightly.

The inner diameter of the anti-breakage member 567 is smaller than the outer diameter of the cable 524 extending from the magnetic coil 564. When the cable 524 is inserted, the cable 524 and anti-breakage member 567 are held watertightly.

The edges of the casings 565 and 566 are covered with a thermo-contractile tube 578 in order to prevent the casings from parting. The tube 578 may be any tube having a tightening force, for example, an elastic rubber tube. Members other than the magnetic coil 564 in the marker body 562 and the cable 524 are al made of a non-magnetic material.

A grip portion 579, shaped like a dorsal fin, is formed on the top of the outer surface of the casing 565. The grip portion 579 shown in FIG. 101 and FIG. 102 may be substituted for a grip portion 580 shaped like a capped pole as shown in FIG. 103.

Low grip portions 579a and 579b, shown in FIG. 104, also may be used. The low grip portions 579a and 579b will not be a hindrance when the marker sheet is mounted on a patient.

Since the extracorporeal markers 212 have the foregoing structure, the markers can be manipulated readily with the grip portions 579 formed on the outer surfaces of the extracorporeal markers 212. Consequently, the extracorporeal markers 212 can be readily attached or detached to or from the predetermined positions on the body surface or the like.

An extracorporeal marker 581 having an I-beam like cross-section, as shown in FIG. 105, may be used. The extracorporeal marker 581 has griping concave parts 583 formed on both sides of a maker body 582. The other structural features are identical to those shown in FIG. 101 and FIG. 102. This extracorporeal marker has the same advantage as the one shown in FIG. 101 and FIG. 102.

An extracorporeal marker having a fastening means for fastening the marker on a body surface will be described below.

An extracorporeal marker 585 shown in FIG. 106 is made by applying a bonding gel 586 to the bottom of the casing 566 of the marker body 562 of the extracorporeal marker 212 shown in FIG. 101 and FIG. 102. The bottom of the casing 566 to which the bonding gel 586 is applied comes into contact with the patient 202. The other structural features are identical to those shown in FIG. 101 and FIG. 102.

The extracorporeal marker 585 can be readily fastened on a body surface, alleviating the nuisance of time-consuming, tedious inspection.

A double-sided, pressure sensitive adhesive tape 587 may be, as shown in FIG. 107, attached to the bottom of the casing 566. In this case, a bonding and fastening means is placed on a contact surface of an extracorporeal marker 585' to be brought into contact with body surface. The extracorporeal marker can therefore be readily fastened on a body surface.

The structure shown in FIG. 108 or FIG. 109 may be used.

An extracorporeal marker 591 shown in FIG. 108 is made by boring an opening 592 in the grip portion 579 of the marker body 572 of the extracorporeal marker 212 shown in, for example, FIG. 99. A belt 595 is inserted into the opening 592. The belt 595 has a jut 593 at one end thereof and a plurality of holes 594, into which the jut 583 is received, in the other end thereof.

The belt 595 is long enough to be wound about the body of the patient 202. The belt 595 is wound about the patient 202 with the jut 593 received into any hole 594. The other structural features are identical to those shown in FIG. 101 and FIG. 102.

Like an extracorporeal marker 591' of a variant shown in FIG. 109, Velcro tapes 596a and 596b may be attached to the ends of the belt 595 and joined for fastening the extracorporeal marker 591'.

A buckle (not shown) may be employed.

The advantage provided by the extracorporeal marker 591 or 591' shown in FIG. 108 or FIG. 109, respectively, is substantially identical to that provided by the one shown in FIG. 106 or FIG. 107.

When the extracorporeal marker 591' has a low grip portion, a jut may be formed in order to prevent the Velcro tapes from becoming mismated.

According to the present invention, it is apparent that a wide range of embodiments can be constructed based on the invention without a departure from the spirit and scope of the invention. The present invention will be limited by the appended claims but not be restricted by any specific embodiments.

What is claimed is:

1. An endoscope shape detection system, comprising:
   a first coil to be inserted into a subject;
   a second coil placed at a predetermined position for sensing said first coil;
   at least one third coil placed at a predetermined position;
   a transmitting and receiving device for permitting transmission and reception of a first magnetic signal between said first coil and second coil, and transmission and reception of a second magnetic signal between said third coil and second coil; and
   an arithmetic unit for calculating first position information representing the position of said first coil to said second coil according to a first detection signal resulting from the transmission and reception of said first magnetic signal, and calculating second position information representing the position of said third coil relative to said second coil according to a second detection signal resulting from the transmission and reception of said second magnetic signal;
   wherein said second coil includes at least: a first magnetic detection unit made by arranging first, second, third, and fourth uniaxial origination coils along the same straight line to form a first line of sense coils while orienting them in the same direction; and a second magnetic detection unit made by arranging fifth, sixth, seventh, and eighth uniaxial origination coils along the same straight line to form a second line of sense coils, which is not parallel to the straight line along which said first, second, third, and fourth uniaxial origination coils of said first magnetic detection unit are arranged, while orienting them in the same direction.

2. An endoscope shape detection system according to claim 1, wherein said arithmetic unit includes a distance calculating unit for calculating a distance to said first coil or third coil with one of the first and second lines of sense coils as an axis.

3. An endoscope shape detection system according to claim 1, wherein said arithmetic unit includes a sampling unit for acquiring as a maximum output the largest output among outputs of said uniaxial origination coils and sampling said uniaxial origination coils in descending order of the maximum output; and a space estimating unit for estimating a location at which said first coil or third coil is present, using a uniaxial origination coil sampled by said sampling unit.

4. An endoscope shape detection system according to claim 1, further comprising a display control for depicting on a display position information of said first coil with a position, at which said third coil is placed, as a reference according to said first position information and second position information calculated by said arithmetic unit.

5. An endoscope shape detection system according to claim 1, wherein said third coil consists of a plurality of coils which can be placed at predetermined positions on said subject so that the coils will define a predetermined plane, further comprising a display control for depicting on a display position information of said first coil with said predetermined plane defined by said third coil as a reference according to said first position information and second position information calculated by said arithmetic unit.

6. An endoscope shape detection system according to claim 1, further comprising a display control for depicting on a display position information of said first coil according to said first position information, and for depicting on said display position information of said third coil as marker information, which is different from position information of said first coil, according to said second position information.

7. An endoscope shape detection system according to claim 6, wherein said display depicts the position of said third coil while being interlocked with an identifying unit for identifying said third coil.

8. An endoscope shape detection system according to claim 6, wherein said display control records the position of said third coil and depicts it on said display.

9. An endoscope shape detection system according to claim 1,
   wherein said third coil consists of a connection unit for connecting said third coil to said arithmetic unit, a coil body having a magnetic coil incorporated therein, and a cable linking said connection unit and coil body, and has a gripping irregular part formed on the outer surface of said coil body.

10. An endoscope shape detection system according to claim 9, wherein said coil body has a fastening unit for fastening said coil body on a body surface.

11. An endoscope shape detection system for use with an endoscope, comprising:
    at least one first coil to be inserted into a subject;
    at least one second coil placed at a predetermined position for sensing said first coil means;
    a third coil placed at a predetermined position;
    a transmitting and receiving unit for permitting transmission and reception of a first magnetic signal between said first coil and second coil, and transmission and reception of a second magnetic signal between said third coil and second coil; and
    an arithmetic unit for calculating first position information representing the position of said first coil relative to said second coil according to a first detection signal resulting from the transmission and reception of said first magnetic signal, and calculating second position information representing the position of said third coil relative to said second coil according to a second detection signal resulting from the transmission and reception of said second magnetic signal,
    wherein said first coil consists of a plurality of coils; and wherein said plurality of coils is incorporated in an insertion unit of the endoscope to be inserted into said subject; and
    further comprising an imaging unit, incorporated in the distal part of said insertion unit of said endoscope, for imaging an object in said subject; and a freezing unit for freezing an image projected by said imaging unit, wherein said arithmetic unit includes a motion estimating unit for estimating a motion made by the distal part of said insertion unit of said endoscope according to the three-dimensional position of a coil located in the distal part of said insertion unit of said endoscope; and a freezing controller, activated in response to a freeze instruction issued to said freezing unit, for controlling said freezing unit according to the results of motion estimation performed by said motion estimating unit.

12. An endoscope shape detection system according to claim 1, wherein said motion estimating unit has a magnitude-of-motion calculating unit for calculating a magnitude of motion from the three-dimensional positions of a coil located near the distal end of said insertion unit which are estimated at different time instants.

13. An endoscope shape detection system according to claim 1, wherein said freezing unit freezes an image when a magnitude of motion estimated by said motion estimating unit is smaller than a predetermined threshold.

14. An endoscope shape detection system according to claim 11, wherein said freezing unit freezes an image showing the least motion among motions estimated by said motion estimating unit within a predetermined time interval.

15. An endoscope shape detection system according to claim 11, wherein said arithmetic unit obtains the positions in a three-dimensional space of said plurality of coils being interlocked with said imaging unit.

16. An endoscope shape detection system, comprising:

at least one first coil to be inserted into a subject;

a second coil placed at a predetermined position for sensing said first coil means;

a third coil placed at a predetermined position;

a transmitting and receiving unit for permitting transmission and reception of a first magnetic signal between said first coil and second coil, and transmission and reception of a second magnetic signal between said third coil and second coil; and an arithmetic unit for calculating first position information representing the position of said first coil relative to said second coil according to a first detection signal resulting from the transmission and reception of said first magnetic signal, and calculating second position information representing the position of said third coil relative to said second coil according to a second detection signal resulting from the transmission and reception of said second magnetic signal, wherein said first coil consists of a plurality of coils; and wherein said plurality of coils is incorporated in an insertion unit of an endoscope to be inserted into said subject; and further comprising an imaging unit, incorporated in the distal part of said insertion unit of said endoscope, for imaging an object in said subject; a first motion estimating unit for estimating a motion shown by an image using an image projected by said imaging unit; and a freezing unit for freezing an image projected by said imaging unit, wherein said arithmetic unit includes a second motion estimating unit for estimating a motion made by the distal part of said insertion unit of said endoscope according to the three-dimensional position of a coil located in the distal part of said insertion unit of said endoscope; a freezing controller, activated in response to a freeze instruction issued to said freezing unit, for controlling said freezing unit according to the results of first motion estimation and second motion estimation performed by said first motion estimating unit and second motion estimating unit, respectively.

* * * * *